United States Patent
Zhu

(10) Patent No.: US 11,498,947 B2
(45) Date of Patent: Nov. 15, 2022

(54) STABILIZED BCL9 PEPTIDES FOR TREATMENT OF ABERRANT WNT SIGNALING

(71) Applicant: WntRx Pharmaceuticals Inc., Newton, MA (US)

(72) Inventor: David Zhu, Newton, MA (US)

(73) Assignee: WntRx Pharmaceuticals Inc., Newton, MA (US)

(*) Notice: Subject to any disclaimer, the term of this patent is extended or adjusted under 35 U.S.C. 154(b) by 0 days.

(21) Appl. No.: 17/215,698

(22) Filed: Mar. 29, 2021

(65) Prior Publication Data

US 2021/0292385 A1    Sep. 23, 2021

Related U.S. Application Data

(62) Division of application No. 15/766,268, filed as application No. PCT/US2016/055589 on Oct. 5, 2016, now Pat. No. 10,961,290.

(60) Provisional application No. 62/237,489, filed on Oct. 5, 2015.

(51) Int. Cl.
| | |
|---|---|
| A61K 38/00 | (2006.01) |
| C07K 14/47 | (2006.01) |
| A61K 45/06 | (2006.01) |
| C07K 14/82 | (2006.01) |
| A61P 35/00 | (2006.01) |
| A61K 38/17 | (2006.01) |

(52) U.S. Cl.
CPC ...... C07K 14/4705 (2013.01); A61K 38/1709 (2013.01); A61K 45/06 (2013.01); A61P 35/00 (2018.01); C07K 14/82 (2013.01); A61K 38/00 (2013.01)

(58) Field of Classification Search
None
See application file for complete search history.

(56) References Cited

U.S. PATENT DOCUMENTS

2014/0113857 A1    4/2014    Walensky et al.

FOREIGN PATENT DOCUMENTS

| CN | 101016332 | 8/2007 |
|---|---|---|
| CN | 101056886 | 10/2007 |
| CN | 103649113 | 3/2014 |
| CN | 104379821 | 2/2015 |
| WO | WO 2002083921 | 10/2002 |
| WO | WO 2017062518 | 4/2007 |
| WO | WO 2010115141 | 10/2010 |
| WO | WO 2013040142 | 3/2013 |
| WO | WO 2013143504 | 10/2013 |
| WO | WO 2019094733 | 5/2019 |

OTHER PUBLICATIONS

Azzarito et al., "Inhibition of α-helix-mediated protein-protein interactions using designed molecules," Nat Chem, Mar. 2013, 5(3):161-173.
Balkwill et al., "The tumor microenvironment at a glance," J Cell Sci, Dec. 2012, 125(Pt 23):5591-5596.
Belenkaya et al., "pygopus Encodes a nuclear protein essential for wingless/Wnt signaling," Development, Sep. 2002, 129(17): 4089-4101.
Bird et al., "Synthesis and biophysical characterization of stabilized alpha-helices of BCL-2 domains," Methods Enzymol, Jan. 2008, 446:369-386.
Clevers and Nusse, "Wnt/β-catenin signaling and disease," Cell, Jun. 2012, 149(6):1192-1205.
De la Roche et al., "The function of BCL9 in Wnt/beta-catenin signaling and colorectal cancer cells," BMC Cancer, Jul. 2008, 8:199.
Degorce et al., "HTRF: A technology tailored for drug discovery—a review of theoretical aspects and recent applications," Curr Chemical Genom, May 2009, 3, 22-32.
Grossmann et al. "Inhibition of oncogenic Wnt signaling through direct targeting of β-catenin," PNAS, Oct. 2012, 109(44):17942-17947.
International Preliminary Report on Patentability for International Application No. PCT/US2016/055589, dated Apr. 10, 2018, 7 pages.
International Search Report and Written Opinion for International Application No. PCT/US2016/055589, dated Feb. 2, 2017, 11 pages.
Kawamoto et al., "Analysis of the interaction of BCL9 with beta-catenin and development of fluorescence polarization and surface plasmon resonance binding assays for this interaction," Biochemistry, Oct. 2009, 48(40):9534-9541.
Kawamoto: "Targeting the BCL9/B9L binding interaction with beta-cateninas a potential anticancer strategy", Ph.D. Thesis, University of Michigan, 2010, pp. 20-22,43-46,53-56,71-72, XP008170299.
Kim et al., "Synthesis of all-hydrocarbon stapled α-helical peptides by ring-closing olefin metathesis," Nat Protocols, Jun. 2011, 6(6):761-771.
Kyi and Postow, "Checkpoint blocking antibodies in cancer immunotherapy," FEBS Letters, Jan. 2014, 588(2):368-376.
Liu et al., "Targeting Wnt-driven cancer through the inhibition of Porcupine by LGK974," Proc Nat Acad Sci USA, Dec. 2013, 110(50):20224-20229.
Sampietro et al., "Crystal structure of a beta-catenin/BCL9/Tcf4 complex," Molecular Cell, Oct. 2006, 24(2), 293-300.
Spranger et al., "Melanoma-intrinsic β-catenin signalling prevents anti-tumour immunity," Nature, Jul. 2015, 523(7559):231-235.
Thakur and Mishra, "Pharmacological modulation of beta-catenin and its applications in cancer therapy," J Cell Mol Med, Apr. 2013, 17(4):449-456.
Zhang et al., "AlphaScreen selectivity assay for β-catenin/B-cell lymphoma 9 inhibitors," Analytical Biochemistry, Jan. 2015, 469:43-53.

*Primary Examiner* — Thomas S Heard
(74) *Attorney, Agent, or Firm* — Fish & Richardson P.C.

(57) ABSTRACT

Methods for treating cancer with a stabilized BCL9 peptide are encompassed, wherein the stabilized peptide comprises a portion of the HD2 domain of the BCL9 protein containing a hydrocarbon crosslinker generated using α, α-disubstituted amino acids.

20 Claims, 64 Drawing Sheets

Specification includes a Sequence Listing.

```
                                   -  -++-+      +-  +
BCL9_HD2  #1    351LSQEQLEHRERSLQTLRDIQRMLF374

#2   LSQEQLE
          #3    SQEQLEH
          #4     QEQLEHR
          #5      EQLEHRE
          #6       QLEHRER
          #7        LEHRERS
          #8         EHRERSL
          #9          HRERSLQ
          #10          RERSLQT
          #11           ERSLQTL
          #12            RSLQTLR
          #13             SLQTLRD
          #14              LQTLRDI
          #15               QTLRDIQ
          #16                TLRDIQR
          #17                 LRDIQRB
          #18                  RDIQRBL
          #19                   DIQRBLF
          #20                  LRDIQRBL
```

FIG. 2A

*WX-024 WAS CONJUNCTED WITH BIOTIN IN THIS ASSAY

| PLASMA PK PARAMETERS | Cmax ng/mL | T1/2 hr | CL L/h/kg | Vz L | $AUC_{0-t}$ ng*hr/mL | $AUC_{0-INF}$ ng*hr/mL | BIOAVAILABILITY % |
|---|---|---|---|---|---|---|---|
| IV 5 mg/kg | 47354.5 | 2.44 | 0.047 | 0.005 | 105637 | 105709 | - |
| IP 5mg/kg | 10452 | 2.59 | 0.06 | 0.01 | 77618 | 77849 | 73.6 |
| IV 1mg/kg | 20950 | 2.51 | 0.026 | 0.0028 | 39024 | 39043 | - |

| PK PARAMETERS | UNIT | WX-024 5mg/kg, IV | WX-024 10mg/kg, IV | WX-024 15mg/kg, IV |
|---|---|---|---|---|
| CL | L/hr/kg | 0.0368 | 0.0428 | 0.0576 |
| $V_{SS}$ | L/kg | 0.0693 | 0.0788 | 0.0946 |
| TERMINAL $t_{1/2}$ | hr | 1.99 | 2.17 | 1.8 |
| $AUC_{last}$ | hr*ng/mL | 136000 | 233000 | 260000 |
| $AUC_{INF}$ | hr*ng/mL | 136000 | 233000 | 260000 |
| $MRT_{INF}$ | hr | 1.88 | 1.84 | 1.64 |
| CL | mL/min/kg | 0.613 | 0.713 | 0.96 |

*FIG. 10B*

| PK PARAMETERS | WX-024 10mg/kg, IP | WX-024 10mg/kg, SC | WX-024 5mg/kg, IM |
|---|---|---|---|
| $T_{max}$ | 4 | 8 | 4 |
| $C_{max}$ | 31000 | 7680 | 2430 |
| TERMINAL $t_{1/2}$ | 3.8 | 13 | 10.6 |
| $AUC_{last}$ | 279000 | 140000 | 44900 |
| $AUC_{INF}$ | 279000 | 146000 | 45300 |

*FIG. 10C*

| CT26.WT | IC50 (µM) | MIN | MAX | REP IC50 (µM) |
|---|---|---|---|---|
| WX-024 | 1.753 | 7.756 | 100.529 | 1.826 |
| DOXORUBICIN | 7.520 | 12.017 | 177.526 | 30.197 |

FIG. 16D

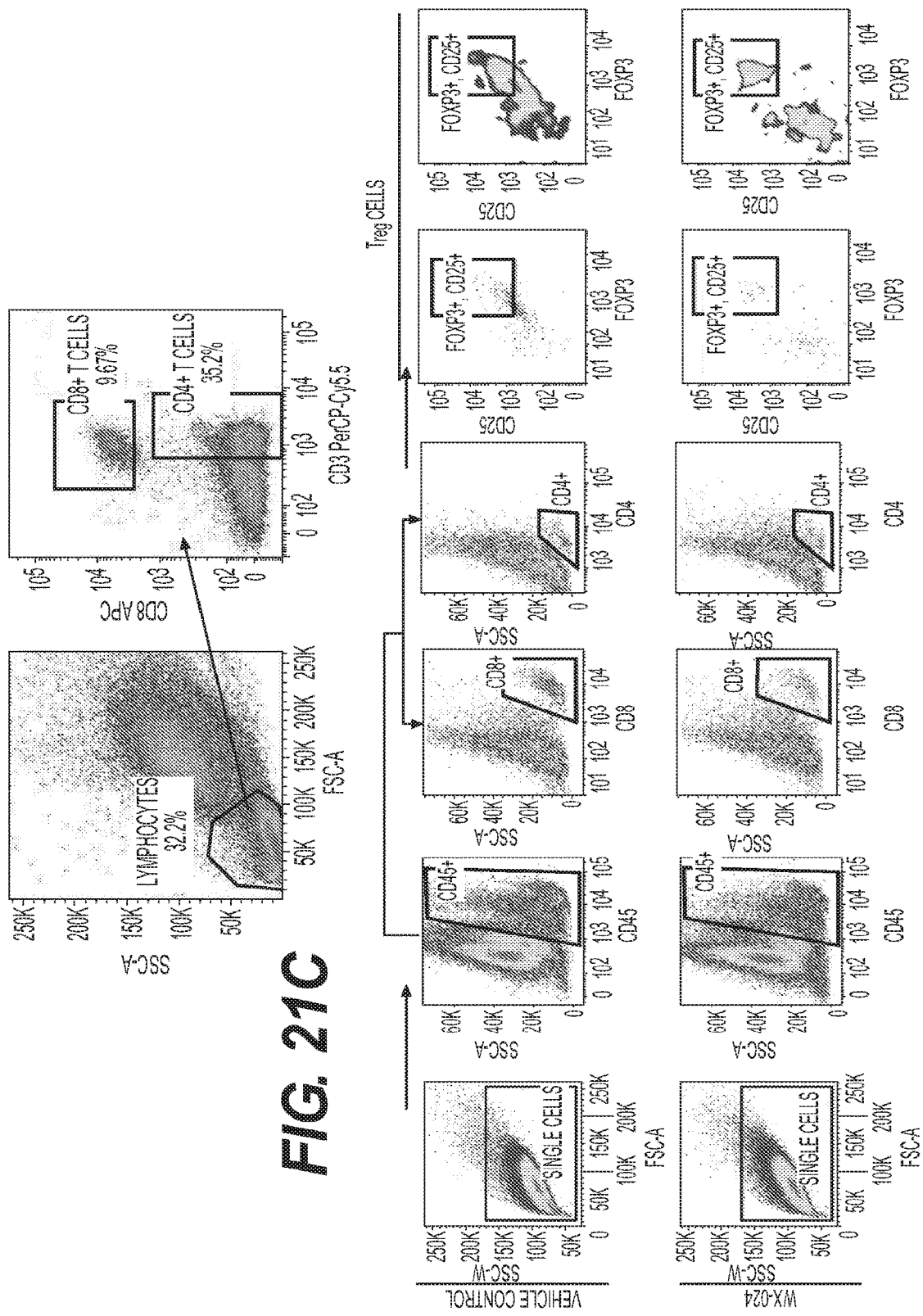

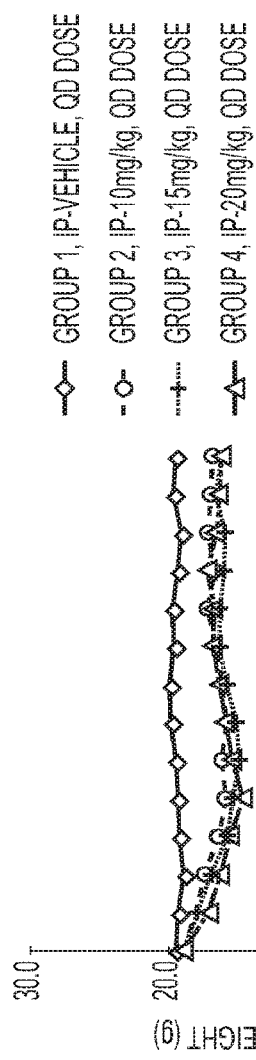
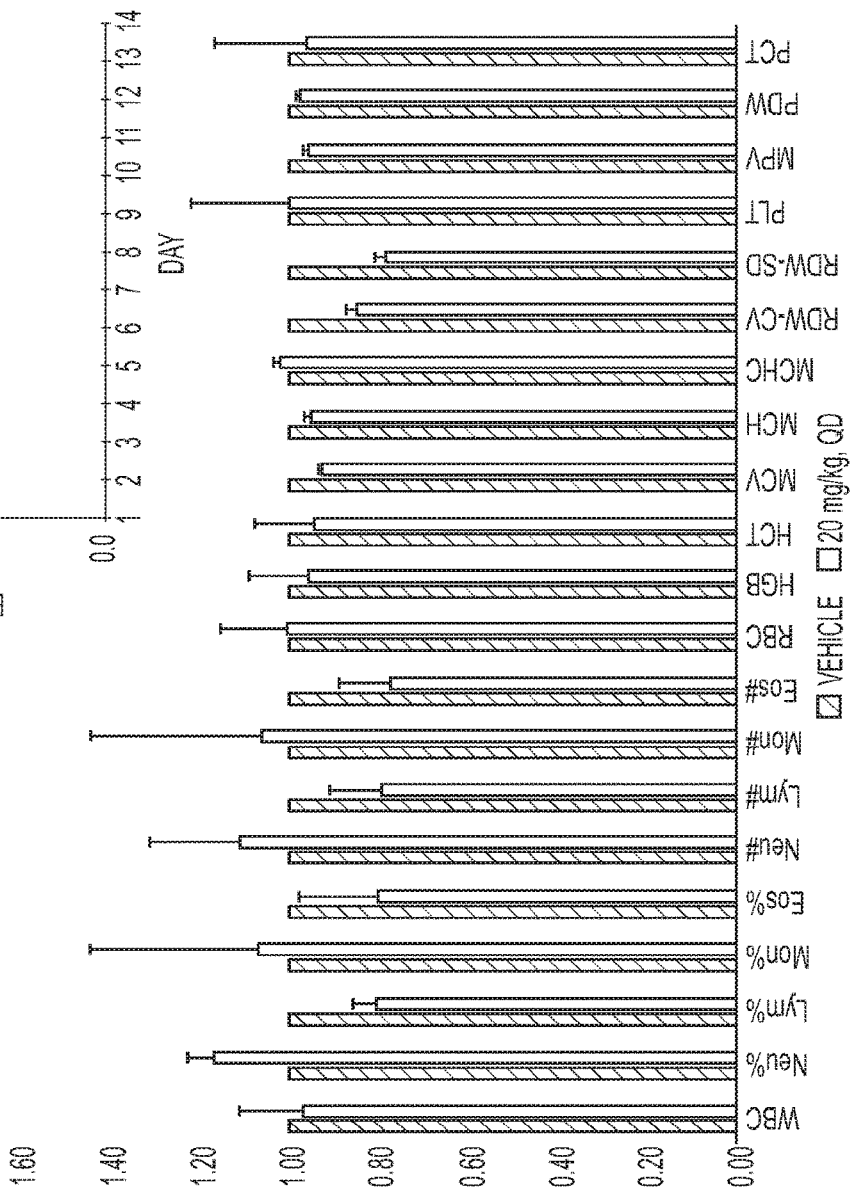
FIG. 30B
FIG. 30C

| PLASMA PK PARAMETERS | Cmax | T1/2 | CL | Vz | AUC0-t | AUC0-inf | F |
|---|---|---|---|---|---|---|---|
| | ng/mL | hr | L/h/kg | L | ng*hr/mL | ng*hr/mL | % |
| IV 1mg/kg | 17950 | 4.20 | 0.01 | 0.0019 | 95762 | 97416 | 100 |
| IV 5mg/kg | 35585 | 3.63 | 0.02 | 0.0031 | 250121 | 252912 | 100 |
| IP 5mg/kg | 11686 | 9.76 | 0.03 | 0.0116 | 144576 | 182817 | 72 |

| PK PARAMETERS | UNIT | ESTIMATED VALUE OF IP DOSE | ESTIMATED VALUE OF IV DOSE |
|---|---|---|---|
| $T_{MAX}$ | hr | 2.00 | - |
| $C_{MAX}$ | ng/mL | 102393 | - |
| TERMINAL $t_{1/2}$ | hr | 9.81 | 7.03 |
| $AUC_{last}$ | hr*ng/mL | 987148 | 996029 |
| $AUC_{INF}$ | hr*ng/mL | 996181 | 997708 |
| $MRT_{INF}$ | hr | - | 5.50 |
| Vss | L/kg | - | 0.166 |
| CL | L/hr/kg | - | 0.0301 |
| F | mL/min/kg | - | 5.50 |
|  | % | 100 | - |

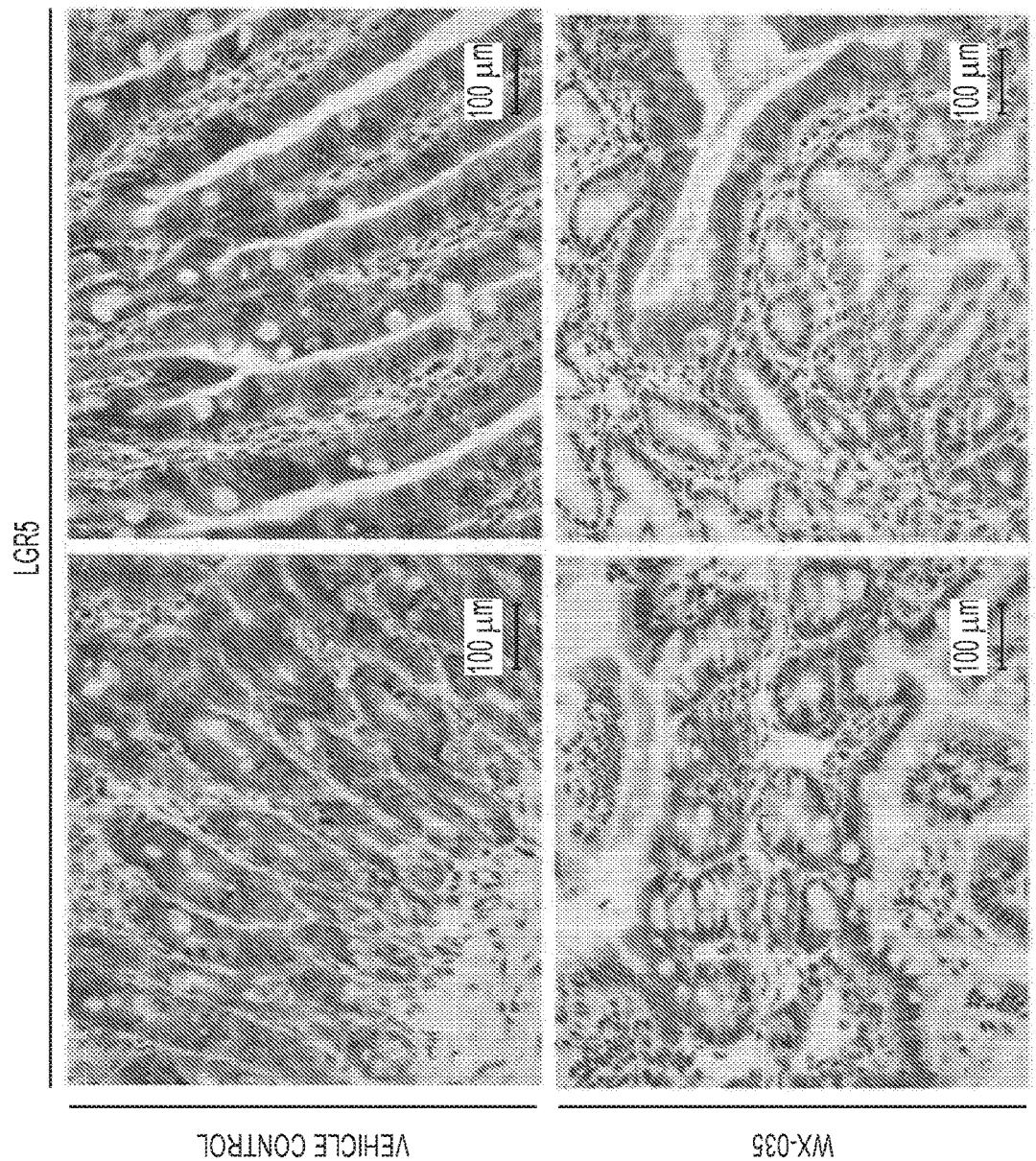

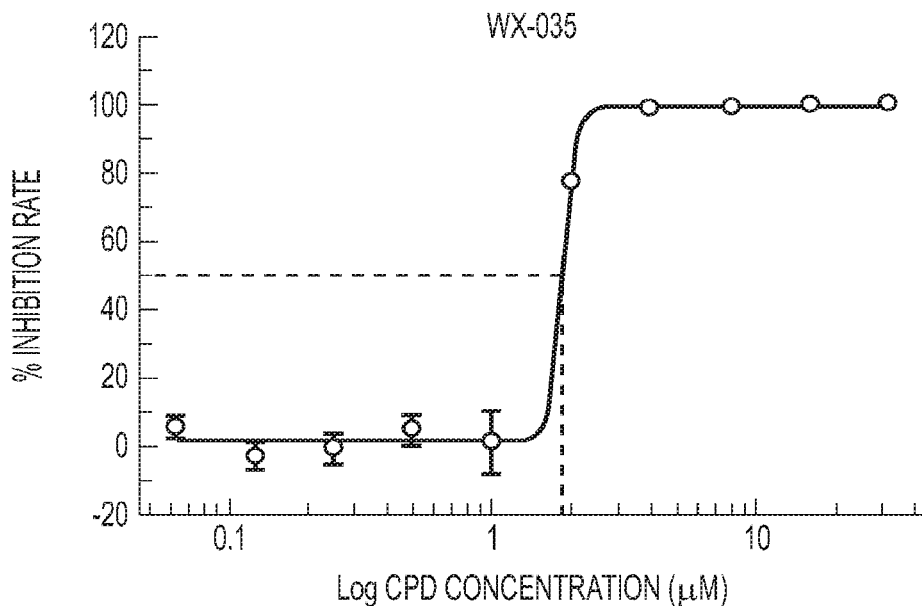
FIG. 38A
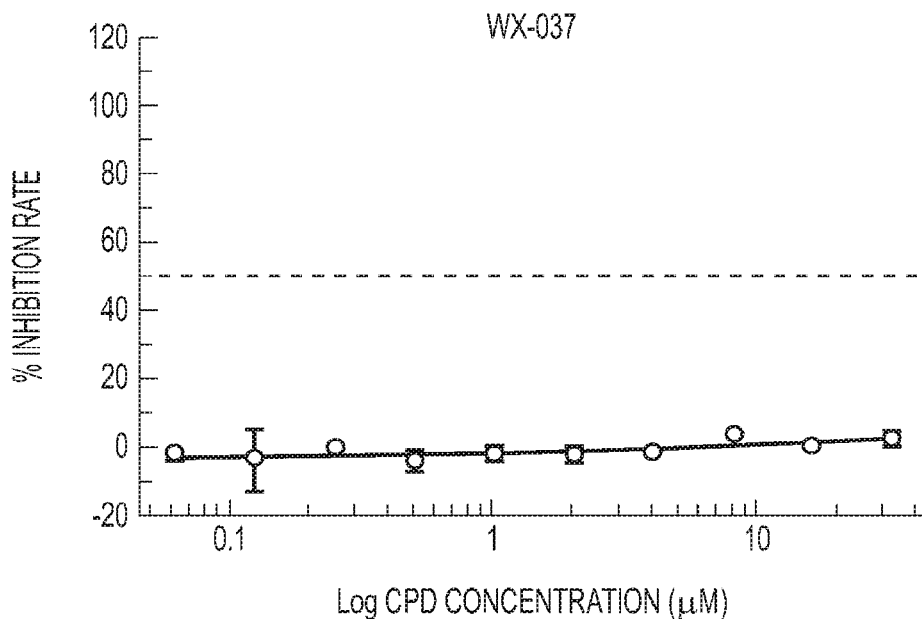
FIG. 38B
| TITLE | Ab IC50 (μM) |
|---|---|
| WX-037 | >32 |
| WX-035 | 1.858 |
FIG. 38C

| PLASMA PK PARAMETERS | Cmax | T1/2 | CL | Vz | AUC0-t | AUC0-inf | F |
|---|---|---|---|---|---|---|---|
| | ng/mL | hr | L/h/kg | L | ng*hr/mL | ng*hr/mL | % |
| IV 1mg/kg | 500.7 | 0.26 | 2.48 | 0.03 | 401.5 | 404.0 | 100 |

| PLASMA PK PARAMETERS | Cmax | T1/2 | CL | Vz | AUC0-t | AUC0-inf | F |
|---|---|---|---|---|---|---|---|
| | ng/mL | hr | L/h/kg | L | ng*hr/mL | ng*hr/mL | % |
| IV 1mg/kg | 738.1 | 1.26 | 1.65 | 0.09 | 527.9 | 605.0 | 100 |

| | IV DOSE OF 5 mg/kg | | IP DOSE OF 5 mg/kg | | SC DOSE OF 10 mg/kg | |
|---|---|---|---|---|---|---|
| | UNIT | ESTIMATED VALUE | UNIT | ESTIMATED VALUE | UNIT | ESTIMATED VALUE |
| CL | L/hr/kg | 0.0187 | $T_{max}$ | hr | 2.00 | $T_{max}$ | hr | 4.00 |
| $V_{ss}$ | L/kg | 0.0565 | $C_{max}$ | ng/mL | 34206 | $C_{max}$ | ng/mL | 5257 |
| TERMINAL $t_{1/2}$ | hr | 5.50 | TERMINAL $t_{1/2}$ | hr | 16.5 | TERMINAL $t_{1/2}$ | hr | 52.8 |
| $AUC_{last}$ | hr*ng/mL | 267725 | $AUC_{last}$ | hr*ng/mL | 296618 | $AUC_{last}$ | hr*ng/mL | 85107 |
| $AUC_{INF}$ | hr*ng/mL | 268028 | $AUC_{INF}$ | hr*ng/mL | 297506 | $AUC_{INF}$ | hr*ng/mL | 99581 |
| $MRT_{INF}$ | hr | 3.03 | F | % | 111 | F | % | 18.6 |
| CL | mL/min/kg | 0.311 | | | | |

*FIG. 41B*

| PK PARAMETERS | UNIT | ESTIMATED VALUE | PK PARAMETERS | UNIT | ESTIMATED VALUE |
|---|---|---|---|---|---|
| CL | L/hr/kg | 0.0301 | $T_{max}$ | hr | 2.00 |
| $V_{SS}$ | L/kg | 0.166 | $C_{max}$ | ng/mL | 102393 |
| TERMINAL $t_{1/2}$ | hr | 7.03 | TERMINAL $t_{1/2}$ | hr | 9.81 |
| $AUC_{last}$ | hr*ng/mL | 996029 | $AUC_{last}$ | hr*ng/mL | 987148 |
| $AUC_{INF}$ | hr*ng/mL | 997708 | $AUC_{INF}$ | hr*ng/mL | 996181 |
| $MRT_{INF}$ | hr | 5.50 | F | % | 100 |
| CL | mL/min/kg | 0.501 | | | |

FIG. 42B

SEQUENCE LISTING

```
<160> NUMBER OF SEQ ID NOS: 131

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 1

Leu Gln Thr Leu Arg Xaa Ile Gln Arg Xaa Leu
1               5                   10

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 2

Xaa Leu Gln Xaa Leu Arg Xaa Ile Gln Arg Xaa Leu
1               5                   10

<210> SEQ ID NO 3
<211> LENGTH: 30
<212> TYPE: PRT
```

<213> ORGANISM: Homo sapiens

<400> SEQUENCE: 3

Pro Asp Gly Leu Ser Gln Glu Gln Leu Glu His Arg Glu Arg Ser Leu
1               5                   10                  15
Gln Thr Leu Arg Asp Ile Gln Arg Met Leu Phe Pro Asp Glu
            20                  25                  30

<210> SEQ ID NO 4
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (22)..(22)
<223> OTHER INFORMATION: Norleucine
<220> FEATURE:
<221> NAME/KEY: source
<223> OTHER INFORMATION: /note="C-term NH2"

<400> SEQUENCE: 4

Leu Ser Gln Glu Gln Leu Glu His Arg Glu Arg Ser Leu Xaa Thr Leu
1               5                   10                  15
Arg Xaa Ile Gln Arg Xaa Leu Phe
            20

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 5

Leu Xaa Gln Glu Gln Xaa Glu
1               5

<210> SEQ ID NO 6
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 6

Ser Xaa Glu Gln Leu Xaa His
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 7

Gln Xaa Gln Leu Glu Xaa Arg
1               5

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 8
```

```
Glu Xaa Leu Glu His Xaa Glu
1               5

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 9

Gln Xaa Glu His Arg Xaa Arg
1               5

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 10

Leu Xaa His Arg Glu Xaa Ser
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
```

```
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 11

Glu Xaa Arg Glu Arg Xaa Leu
1               5

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 12

His Xaa Glu Arg Ser Xaa Gln
1               5

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 13

Arg Xaa Arg Ser Leu Xaa Thr
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 14

Glu Xaa Ser Leu Gln Xaa Leu
1               5

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 15

Arg Xaa Leu Gln Thr Xaa Arg
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 16

Ser Xaa Gln Thr Leu Xaa Asp
1               5
```

```
<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 17

Leu Xaa Thr Leu Arg Xaa Ile
1               5

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 18

Gln Xaa Leu Arg Asp Xaa Gln
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
```

```
<223> OTHER INFORMATION: /note="C-term NH2"

<400> SEQUENCE: 19

Thr Xaa Arg Asp Ile Xaa Arg
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Norleucine
<220> FEATURE:
<221> NAME/KEY: source
<223> OTHER INFORMATION: /note="C-term NH2"

<400> SEQUENCE: 20

Leu Xaa Asp Ile Gln Xaa Xaa
1               5

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 21

Arg Xaa Ile Gln Arg Xaa Leu
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: Any amino acid
<220> FEATURE:
<221> NAME/KEY: source
<223> OTHER INFORMATION: /note="C-term NH2"

<400> SEQUENCE: 22

Asp Xaa Gln Arg Xaa Xaa Phe
1               5

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: source
<223> OTHER INFORMATION: /note="C-term NH2"

<400> SEQUENCE: 23

Leu Arg Xaa Ile Gln Arg Xaa Leu
1               5

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: MOD_RES
<222> LOCATION: (10)..(11)
```

```
<223> OTHER INFORMATION: Beta-Ala
<220> FEATURE:
<221> NAME/KEY: source
<223> OTHER INFORMATION: /note="C-term NH2"

<400> SEQUENCE: 24

Leu Arg Xaa Ile Gln Arg Xaa Leu Xaa Ala Ala
1               5                   10

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(10)
<223> OTHER INFORMATION: Beta-Ala
<220> FEATURE:
<221> NAME/KEY: source
<223> OTHER INFORMATION: /note="C-term NH2"

<400> SEQUENCE: 25

Leu Arg Xaa Ile Gln Arg Xaa Leu Ala Ala
1               5                   10

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: source
<223> OTHER INFORMATION: /note="C-term NH2"

<400> SEQUENCE: 26

Leu Arg Xaa Ile Gln Arg Xaa Leu Xaa
1               5

<210> SEQ ID NO 27
<211> LENGTH: 12
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: source
<223> OTHER INFORMATION: /note="C-term NH2"

<400> SEQUENCE: 27

Leu Gln Thr Leu Arg Xaa Ile Gln Arg Xaa Leu Xaa
1               5                   10

<210> SEQ ID NO 28
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(14)
<223> OTHER INFORMATION: Beta-Ala

<400> SEQUENCE: 28

Leu Gln Thr Leu Arg Xaa Ile Gln Arg Xaa Leu Xaa Ala Ala Gly Arg
1               5                   10                  15

Lys Lys Arg Arg Gln Arg Arg Arg Pro Gln
            20                  25

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
```

```
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-Ala
<220> FEATURE:
<221> NAME/KEY: source
<223> OTHER INFORMATION: /note="C-term NH2"

<400> SEQUENCE: 29

Xaa Leu Gln Xaa Leu Arg Xaa Ile Gln Arg Xaa Leu Xaa Ala Ala
1               5                   10                  15

<210> SEQ ID NO 30
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-Ala

<400> SEQUENCE: 30

Xaa Leu Gln Xaa Leu Arg Xaa Ile Gln Arg Xaa Leu Xaa Ala Ala Gly
1               5                   10                  15

Arg Lys Lys Arg Arg Gln Arg Arg Pro Gln
                20                  25
```

```
<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(15)
<223> OTHER INFORMATION: Beta-Ala
<220> FEATURE:
<221> NAME/KEY: source
<223> OTHER INFORMATION: /note="C-term NH2"

<400> SEQUENCE: 31

Xaa Asp Gln Xaa Asp Arg Xaa Asp Gln Arg Xaa Asp His Ala Ala
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-Ala
<220> FEATURE:
<221> NAME/KEY: source
<223> OTHER INFORMATION: /note="C-term NH2"
```

<400> SEQUENCE: 32

Xaa Leu Glu Xaa Leu Arg Xaa Ile Glu Arg Xaa Leu Xaa Ala Ala
1               5                   10                  15

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: 2-Naphthylalanine
<220> FEATURE:
<221> NAME/KEY: MOD_RES
<222> LOCATION: (15)..(16)
<223> OTHER INFORMATION: Beta-Ala
<220> FEATURE:
<221> NAME/KEY: source
<223> OTHER INFORMATION: /note="C-term NH2"

<400> SEQUENCE: 33

Arg Xaa Leu Gln Xaa Leu Arg Xaa Ile Gln Arg Xaa Leu Xaa Ala Ala
1               5                   10                  15

<210> SEQ ID NO 34
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(14)
<223> OTHER INFORMATION: Beta-Ala

```
<220> FEATURE:
<221> NAME/KEY: source
<223> OTHER INFORMATION: /note="C-term NH2"

<400> SEQUENCE: 34

Leu Gln Xaa Leu Arg Asp Ile Gln Arg Xaa Leu Xaa Ala Ala
1               5                   10

<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 35

Leu Ala Gln Glu Gln Ala Glu
1               5

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 36

Ser Ala Glu Gln Leu Ala His
1               5

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 37

Gln Ala Gln Leu Glu Ala Arg
1               5
```

```
<210> SEQ ID NO 38
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 38

Glu Ala Leu Glu His Ala Glu
1               5

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 39

Gln Ala Glu His Arg Ala Arg
1               5

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 40

Leu Ala His Arg Glu Ala Ser
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 41

Glu Ala Arg Glu Arg Ala Leu
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 42

His Ala Glu Arg Ser Ala Gln
1               5

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 43

Arg Ala Arg Ser Leu Ala Thr
1               5

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 44

Glu Ala Ser Leu Gln Ala Leu
```

```
<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 45

Arg Ala Leu Gln Thr Ala Arg
1               5

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 46

Ser Ala Gln Thr Leu Ala Asp
1               5

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 47

Leu Ala Thr Leu Arg Ala Ile
1               5

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

```
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 48

Gln Ala Leu Arg Asp Ala Gln
1               5

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 49

Thr Ala Arg Asp Ile Ala Arg
1               5

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(7)
<223> OTHER INFORMATION: (S)-2-(4'-pentenyl)alanine

<400> SEQUENCE: 50

Leu Ala Asp Ile Gln Ala Xaa
1               5

<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine
```

```
<400> SEQUENCE: 51

Arg Ala Ile Gln Arg Ala Leu
1               5

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (5)..(6)
<223> OTHER INFORMATION: (S)-2-(4'-pentenyl)alanine

<400> SEQUENCE: 52

Asp Ala Gln Arg Xaa Ala Phe
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine

<400> SEQUENCE: 53

Leu Arg Ala Ile Gln Arg Ala Leu
1               5

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (S)-2-(4'-pentenyl)alanine
<220> FEATURE:
<221> NAME/KEY: MOD_RES
<222> LOCATION: (10)..(10)
<223> OTHER INFORMATION: (S)-2-(4'-pentenyl)alanine

<400> SEQUENCE: 54

Leu Gln Thr Leu Arg Ala Ile Gln Arg Ala Leu
1               5                   10

<210> SEQ ID NO 55
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 55

Ala Leu Gln Ala Leu Arg Ala Ile Gln Arg Ala Leu
1               5                   10

<210> SEQ ID NO 56
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 56

Ala Asp Gln Ala Asp Arg Ala Asp Gln Arg Ala Asp His
1               5                   10

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
```

```
<221> NAME/KEY: MOD_RES
<222> LOCATION: (11)..(11)
<223> OTHER INFORMATION: (S)-2-(4'-pentenyl)alanine

<400> SEQUENCE: 57

Ala Leu Glu Ala Leu Arg Ala Ile Glu Arg Ala Leu
1               5                   10

<210> SEQ ID NO 58
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (R)-2-(4'-pentenyl)alanine
<220> FEATURE:
<221> NAME/KEY: MOD_RES
<222> LOCATION: (5)..(5)
<223> OTHER INFORMATION: (S)-2-(4'-pentenyl)alanine
<220> FEATURE:
<221> NAME/KEY: MOD_RES
<222> LOCATION: (8)..(8)
<223> OTHER INFORMATION: (S)-2-(4'-pentenyl)alanine
<220> FEATURE:
<221> NAME/KEY: MOD_RES
<222> LOCATION: (12)..(12)
<223> OTHER INFORMATION: (S)-2-(4'-pentenyl)alanine

<400> SEQUENCE: 58

Arg Ala Leu Gln Ala Leu Arg Ala Ile Gln Arg Ala Leu
1               5                   10

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (R)-2-(7'-octenyl)alanine
<220> FEATURE:
<221> NAME/KEY: MOD_RES
<222> LOCATION: (10)..(10)
<223> OTHER INFORMATION: (S)-2-(4'-pentenyl)alanine

<400> SEQUENCE: 59

Leu Gln Ala Leu Arg Asp Ile Gln Arg Ala Leu
1               5                   10

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
```

```
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 60

Leu Ala Gln Glu Gln Ala Glu
1               5

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 61

Ser Ala Glu Gln Leu Ala His
1               5

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 62

Gln Ala Gln Leu Glu Ala Arg
1               5

<210> SEQ ID NO 63
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
```

-continued

```
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 63

Glu Ala Leu Glu His Ala Glu
1               5

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 64

Gln Ala Glu His Arg Ala Arg
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 65

Leu Ala His Arg Glu Ala Ser
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
```

```
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 66

Glu Ala Arg Glu Arg Ala Leu
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 67

His Ala Glu Arg Ser Ala Gln
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 68

Arg Ala Arg Ser Leu Ala Thr
1               5

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 69

Glu Ala Ser Leu Gln Ala Leu
1               5

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 70

Arg Ala Leu Gln Thr Ala Arg
1               5

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 71

Ser Ala Gln Thr Leu Ala Asp
1               5

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 72

Leu Ala Thr Leu Arg Ala Ile
1               5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 73

Gln Ala Leu Arg Asp Ala Gln
1               5

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 74

Thr Ala Arg Asp Ile Ala Arg
1               5

<210> SEQ ID NO 75
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"
<220> FEATURE:
<221> NAME/KEY: MISC_FEATURE
<222> LOCATION: (7)..(7)
<223> OTHER INFORMATION: Any amino acid

<400> SEQUENCE: 75

Leu Ala Asp Ile Gln Ala Xaa
1               5

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 76

Arg Ala Ile Gln Arg Ala Leu
1               5

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(6)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 77

Asp Ala Gln Arg Xaa Ala Phe
1               5
```

```
<210> SEQ ID NO 78
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (3)..(7)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: source
<223> OTHER INFORMATION: /note="May or may not be C-term NH2"

<400> SEQUENCE: 78

Leu Arg Ala Ile Gln Arg Ala Leu
1               5

<210> SEQ ID NO 79
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (6)..(10)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 79

Leu Gln Thr Leu Arg Ala Ile Gln Arg Ala Leu
1               5                   10

<210> SEQ ID NO 80
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 80

Ala Leu Gln Ala Leu Arg Ala Ile Gln Arg Ala Leu
1               5                   10

<210> SEQ ID NO 81
```

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 81

Ala Leu Gln Ala Leu Arg Ala Ile Gln Arg Ala Leu
1               5                   10

<210> SEQ ID NO 82
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 82

Ala Leu Gln Ala Leu Arg Ala Ile Gln Arg Ala Leu
1               5                   10

<210> SEQ ID NO 83
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 83
```

```
Ala Asp Gln Ala Asp Arg Ala Asp Gln Arg Ala Asp His
1               5                   10
```

```
<210> SEQ ID NO 84
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 84
```

```
Ala Asp Gln Ala Asp Arg Ala Asp Gln Arg Ala Asp His
1               5                   10
```

```
<210> SEQ ID NO 85
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 85
```

```
Ala Asp Gln Ala Asp Arg Ala Asp Gln Arg Ala Asp His
1               5                   10
```

```
<210> SEQ ID NO 86
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MOD_RES
<222> LOCATION: (7)..(7)
<223> OTHER INFORMATION: (S)-2-(4'-pentenyl)alanine
```

```
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 86

Ala Leu Glu Ala Leu Arg Ala Ile Glu Arg Ala Leu
1               5                   10

<210> SEQ ID NO 87
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(4'-pentenyl)alanine
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 87

Ala Leu Glu Ala Leu Arg Ala Ile Glu Arg Ala Leu
1               5                   10

<210> SEQ ID NO 88
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"

<400> SEQUENCE: 88

Ala Leu Glu Ala Leu Arg Ala Ile Glu Arg Ala Leu
1               5                   10

<210> SEQ ID NO 89
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (2)..(5)
<223> OTHER INFORMATION: /note="Hydrocarbon crosslinker (-CH2-CH2-CH2-
```

```
        CH=CH-CH2-CH2-CH2-) between residues, having an S-configuration on
        one end and an R-configuration on the other end"
<220> FEATURE:
<221> NAME/KEY: MOD_RES
<222> LOCATION: (8)..(8)
<223> OTHER INFORMATION: (S)-2-(4'-pentenyl)alanine
<220> FEATURE:
<221> NAME/KEY: MOD_RES
<222> LOCATION: (12)..(12)
<223> OTHER INFORMATION: (S)-2-(4'-pentenyl)alanine

<400> SEQUENCE: 89

Arg Ala Leu Gln Ala Leu Arg Ala Ile Gln Arg Ala Leu
 1               5                  10

<210> SEQ ID NO 90
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MOD_RES
<222> LOCATION: (2)..(2)
<223> OTHER INFORMATION: (R)-2-(4'-pentenyl)alanine
<220> FEATURE:
<221> NAME/KEY: MOD_RES
<222> LOCATION: (5)..(5)
<223> OTHER INFORMATION: (S)-2-(4'-pentenyl)alanine
<220> FEATURE:
<221> NAME/KEY: MISC_FEATURE
<222> LOCATION: (8)..(12)
<223> OTHER INFORMATION: /note="Hydrocarbon crosslinker (-CH2-CH2-CH2-
        CH=CH-CH2-CH2-CH2-) between residues, having an S-configuration at
        both ends"

<400> SEQUENCE: 90

Arg Ala Leu Gln Ala Leu Arg Ala Ile Gln Arg Ala Leu
 1               5                  10

<210> SEQ ID NO 91
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: MISC_FEATURE
<222> LOCATION: (2)..(5)
<223> OTHER INFORMATION: /note="Hydrocarbon crosslinker (-CH2-CH2-CH2-
        CH=CH-CH2-CH2-CH2-) between residues, having an S-configuration on
        one end and an R-configuration on the other end"
<220> FEATURE:
<221> NAME/KEY: MISC_FEATURE
<222> LOCATION: (8)..(12)
<223> OTHER INFORMATION: /note="Hydrocarbon crosslinker (-CH2-CH2-CH2-
        CH=CH-CH2-CH2-CH2-) between residues, having an S-configuration at
        both ends"

<400> SEQUENCE: 91

Arg Ala Leu Gln Ala Leu Arg Ala Ile Gln Arg Ala Leu
 1               5                  10

<210> SEQ ID NO 92
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MISC_FEATURE
<222> LOCATION: (3)..(10)
<223> OTHER INFORMATION: /note="Hydrocarbon crosslinker (-CH2-CH2-CH2-
      CH2-CH2-CH2-CH=CH- CH2-CH2-CH2-) between residues, having an
      R-configuration on one end and an S-configuration on the other
      end"

<400> SEQUENCE: 92

Leu Gln Ala Leu Arg Asp Ile Gln Arg Ala Leu
1               5                   10

<210> SEQ ID NO 93
<211> LENGTH: 12
<212> TYPE: PRT
<213> ORGANISM: Human immunodeficiency virus 1

<400> SEQUENCE: 93

Gly Arg Lys Lys Arg Arg Gln Arg Arg Arg Pro Gln
1               5                   10

<210> SEQ ID NO 94
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (3)..(7)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: MOD_RES
<222> LOCATION: (10)..(11)
<223> OTHER INFORMATION: Beta-Ala
<220> FEATURE:
<221> NAME/KEY: source
<223> OTHER INFORMATION: /note="C-term NH2"

<400> SEQUENCE: 94

Leu Arg Ala Ile Gln Arg Ala Leu Xaa Ala Ala
1               5                   10

<210> SEQ ID NO 95
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (3)..(7)
<223> OTHER INFORMATION: /note="Hydrocarbon crosslinker (-CH2-CH2-CH2-
      CH=CH-CH2-CH2-CH2-) between residues, having an S-configuration at
      both ends"
```

```
<220> FEATURE:
<221> NAME/KEY: MOD_RES
<222> LOCATION: (9)..(10)
<223> OTHER INFORMATION: Beta-Ala
<220> FEATURE:
<221> NAME/KEY: source
<223> OTHER INFORMATION: /note="C-term NH2"

<400> SEQUENCE: 95

Leu Arg Ala Ile Gln Arg Ala Leu Ala Ala
1               5                   10

<210> SEQ ID NO 96
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (3)..(7)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: source
<223> OTHER INFORMATION: /note="C-term NH2"

<400> SEQUENCE: 96

Leu Arg Ala Ile Gln Arg Ala Leu Xaa
1               5

<210> SEQ ID NO 97
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (6)..(10)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(14)
<223> OTHER INFORMATION: Beta-alanine

<400> SEQUENCE: 97

Leu Gln Thr Leu Arg Ala Ile Gln Arg Ala Leu Xaa Ala Ala Gly Arg
1               5                   10                  15

Lys Lys Arg Arg Gln Arg Arg Pro Gln
            20                  25
```

```
<210> SEQ ID NO 98
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-alanine

<400> SEQUENCE: 98

Ala Leu Gln Ala Leu Arg Ala Ile Gln Arg Ala Leu Xaa Ala Ala Gly
1               5                   10                  15

Arg Lys Lys Arg Arg Gln Arg Arg Pro Gln
            20                  25

<210> SEQ ID NO 99
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (14)..(15)
<223> OTHER INFORMATION: Beta-alanine
<220> FEATURE:
<221> NAME/KEY: source
<223> OTHER INFORMATION: /note="C-term NH2"

<400> SEQUENCE: 99

Ala Asp Gln Ala Asp Arg Ala Asp Gln Arg Ala Asp His Ala Ala
1               5                   10                  15
```

```
<210> SEQ ID NO 100
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-alanine
<220> FEATURE:
<221> NAME/KEY: source
<223> OTHER INFORMATION: /note="C-term NH2"

<400> SEQUENCE: 100

Ala Leu Glu Ala Leu Arg Ala Ile Glu Arg Ala Leu Xaa Ala Ala
1               5                   10                  15

<210> SEQ ID NO 101
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (2)..(5)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (8)..(12)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (14)..(14)
<223> OTHER INFORMATION: 2-Naphthylalanine
<220> FEATURE:
<221> NAME/KEY: MOD_RES
<222> LOCATION: (15)..(16)
<223> OTHER INFORMATION: Beta-alanine
<220> FEATURE:
<221> NAME/KEY: source
<223> OTHER INFORMATION: /note="C-term NH2"

<400> SEQUENCE: 101

Arg Ala Leu Gln Ala Leu Arg Ala Ile Gln Arg Ala Leu Xaa Ala Ala
```

```
<210> SEQ ID NO 102
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (3)..(10)
<223> OTHER INFORMATION: /note="Hydrocarbon crosslinker (-CH2-CH2-CH2-
      CH2-CH2-CH2-CH=CH- CH2-CH2-CH2-) between residues, having an
      R-configuration on one end and an S-configuration on the other
      end"
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: MOD_RES
<222> LOCATION: (13)..(14)
<223> OTHER INFORMATION: Beta-alanine
<220> FEATURE:
<221> NAME/KEY: source
<223> OTHER INFORMATION: /note="C-term NH2"

<400> SEQUENCE: 102

Leu Gln Ala Leu Arg Asp Ile Gln Arg Ala Leu Xaa Ala Ala
1               5                   10

<210> SEQ ID NO 103
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (6)..(10)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: source
<223> OTHER INFORMATION: /note="C-term NH2"

<400> SEQUENCE: 103

Leu Gln Thr Leu Arg Ala Ile Gln Arg Ala Leu Xaa
1               5                   10

<210> SEQ ID NO 104
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="May or may not be N-term Ac"
<220> FEATURE:
<221> NAME/KEY: MISC_FEATURE
<222> LOCATION: (1)..(4)
<223> OTHER INFORMATION: /note="Hydrocarbon crosslinker (-CH2-CH2-CH2-
      CH=CH-CH2-CH2-CH2-) between residues, having an S-configuration on
      one end and an R-configuration on the other end"
<220> FEATURE:
<221> NAME/KEY: MISC_FEATURE
<222> LOCATION: (7)..(11)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (13)..(13)
<223> OTHER INFORMATION: 2-Naphthylalanine
<220> FEATURE:
<221> NAME/KEY: MOD_RES
<222> LOCATION: (14)..(15)
<223> OTHER INFORMATION: Beta-alanine
<220> FEATURE:
<221> NAME/KEY: source
<223> OTHER INFORMATION: /note="C-term NH2"

<400> SEQUENCE: 104

Ala Leu Gln Ala Leu Arg Ala Ile Gln Arg Ala Leu Xaa Ala Ala
1               5                   10                  15

<210> SEQ ID NO 105
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="May or may not be N-term Ac"
<220> FEATURE:
<221> NAME/KEY: MISC_FEATURE
<222> LOCATION: (14)..(18)
<223> OTHER INFORMATION: /note="Hydrocarbon crosslinker (-CH2-CH2-CH2-
      CH=CH-CH2-CH2-CH2-) between residues, having an S-configuration at
      both ends"
<220> FEATURE:
<221> NAME/KEY: MOD_RES
<222> LOCATION: (22)..(22)
<223> OTHER INFORMATION: Norleucine
<220> FEATURE:
<221> NAME/KEY: source
<223> OTHER INFORMATION: /note="May or may not be C-term NH2"

<400> SEQUENCE: 105

Leu Ser Gln Glu Gln Leu Glu His Arg Glu Arg Ser Leu Ala Thr Leu
1               5                   10                  15

Arg Ala Ile Gln Arg Xaa Leu Phe
            20

<210> SEQ ID NO 106
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Norleucine
```

```
<400> SEQUENCE: 106

Leu Arg Asp Ile Gln Arg Xaa Leu
1               5

<210> SEQ ID NO 107
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Norleucine

<400> SEQUENCE: 107

Arg Asp Ile Gln Arg Xaa Leu
1               5

<210> SEQ ID NO 108
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: MOD_RES
<222> LOCATION: (10)..(11)
<223> OTHER INFORMATION: Beta-alanine
<220> FEATURE:
<221> NAME/KEY: source
<223> OTHER INFORMATION: /note="C-term NH2"

<400> SEQUENCE: 108

Leu Arg Ala Ile Gln Arg Ala Leu Xaa Ala Ala
1               5                   10

<210> SEQ ID NO 109
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: (S)-2-(4'-pentenyl)alanine
<220> FEATURE:
<221> NAME/KEY: MOD_RES
```

```
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (9)..(10)
<223> OTHER INFORMATION: Beta-alanine
<220> FEATURE:
<221> NAME/KEY: source
<223> OTHER INFORMATION: /note="C-term NH2"

<400> SEQUENCE: 109

Leu Arg Ala Ile Gln Arg Ala Leu Ala Ala
1               5                   10

<210> SEQ ID NO 110
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (3)..(3)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine
<220> FEATURE:
<221> NAME/KEY: MOD_RES
<222> LOCATION: (9)..(9)
<223> OTHER INFORMATION: 2-Naphthylalanine
<220> FEATURE:
<221> NAME/KEY: source
<223> OTHER INFORMATION: /note="C-term NH2"

<400> SEQUENCE: 110

Leu Arg Ala Ile Gln Arg Ala Leu Xaa
1               5

<210> SEQ ID NO 111
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (6)..(6)
<223> OTHER INFORMATION: (S)-2-(4'-pentenyl)alanine
<220> FEATURE:
<221> NAME/KEY: MOD_RES
<222> LOCATION: (10)..(10)
<223> OTHER INFORMATION: (S)-2-(4'-pentenyl)alanine
<220> FEATURE:
<221> NAME/KEY: MOD_RES
<222> LOCATION: (12)..(12)
<223> OTHER INFORMATION: 2-Naphthylalanine
<220> FEATURE:
<221> NAME/KEY: source
<223> OTHER INFORMATION: /note="C-term NH2"

<400> SEQUENCE: 111

Leu Gln Thr Leu Arg Ala Ile Gln Arg Ala Leu Xaa
```

```
1               5                  10
```

```
<210> SEQ ID NO 112
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Alpha, alpha-disubstituted amino acid
<220> FEATURE:
<221> NAME/KEY: MISC_FEATURE
<222> LOCATION: (6)..(10)
<223> OTHER INFORMATION: /note="Hydrocarbon crosslinker may or may not
      be present between residues"
<220> FEATURE:
<221> NAME/KEY: MOD_RES
<222> LOCATION: (10)..(10)
<223> OTHER INFORMATION: Alpha, alpha-disubstituted amino acid
<220> FEATURE:
<221> NAME/KEY: source
<223> OTHER INFORMATION: /note="See specification as filed for detailed
      description of substitutions and preferred embodiments"

<400> SEQUENCE: 112

Leu Gln Thr Leu Arg Xaa Ile Gln Arg Xaa Leu
1               5                  10

<210> SEQ ID NO 113
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Alpha, alpha-disubstituted amino acid
<220> FEATURE:
<221> NAME/KEY: MISC_FEATURE
<222> LOCATION: (1)..(4)
<223> OTHER INFORMATION: /note="Hydrocarbon crosslinker may or may not
      be present between residues"
<220> FEATURE:
<221> NAME/KEY: MOD_RES
<222> LOCATION: (4)..(4)
<223> OTHER INFORMATION: Alpha, alpha-disubstituted amino acid
<220> FEATURE:
<221> NAME/KEY: MOD_RES
<222> LOCATION: (7)..(7)
<223> OTHER INFORMATION: Alpha, alpha-disubstituted amino acid
<220> FEATURE:
<221> NAME/KEY: MISC_FEATURE
<222> LOCATION: (7)..(11)
<223> OTHER INFORMATION: /note="Hydrocarbon crosslinker may or may not
      be present between residues"
<220> FEATURE:
<221> NAME/KEY: MOD_RES
<222> LOCATION: (11)..(11)
<223> OTHER INFORMATION: Alpha, alpha-disubstituted amino acid
<220> FEATURE:
<221> NAME/KEY: source
<223> OTHER INFORMATION: /note="See specification as filed for detailed
      description of substitutions and preferred embodiments"

<400> SEQUENCE: 113

Xaa Leu Gln Xaa Leu Arg Xaa Ile Gln Arg Xaa Leu
1               5                  10
```

<210> SEQ ID NO 114
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Leu Ser Gln Glu Gln Leu Glu His Arg Glu Arg Ser Leu Gln Thr Leu
1               5                   10                  15

Arg Asp Ile Gln Arg Met Leu Phe
            20

<210> SEQ ID NO 115
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Leu Ser Gln Glu Gln Leu Glu
1               5

<210> SEQ ID NO 116
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Ser Gln Glu Gln Leu Glu His
1               5

<210> SEQ ID NO 117
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Gln Glu Gln Leu Glu His Arg
1               5

<210> SEQ ID NO 118
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Glu Gln Leu Glu His Arg Glu
1               5

-continued

```
<210> SEQ ID NO 119
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gln Leu Glu His Arg Glu Arg
1               5

<210> SEQ ID NO 120
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Leu Glu His Arg Glu Arg Ser
1               5

<210> SEQ ID NO 121
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Glu His Arg Glu Arg Ser Leu
1               5

<210> SEQ ID NO 122
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

His Arg Glu Arg Ser Leu Gln
1               5

<210> SEQ ID NO 123
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Arg Glu Arg Ser Leu Gln Thr
1               5

<210> SEQ ID NO 124
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 124

Glu Arg Ser Leu Gln Thr Leu
1               5

<210> SEQ ID NO 125
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Arg Ser Leu Gln Thr Leu Arg
1               5

<210> SEQ ID NO 126
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ser Leu Gln Thr Leu Arg Asp
1               5

<210> SEQ ID NO 127
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Leu Gln Thr Leu Arg Asp Ile
1               5

<210> SEQ ID NO 128
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Gln Thr Leu Arg Asp Ile Gln
1               5

<210> SEQ ID NO 129
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 129

Thr Leu Arg Asp Ile Gln Arg
1               5

<210> SEQ ID NO 130
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Norleucine

<400> SEQUENCE: 130

Leu Arg Asp Ile Gln Arg Xaa
1               5

<210> SEQ ID NO 131
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Norleucine

<400> SEQUENCE: 131

Asp Ile Gln Arg Xaa Leu Phe
1               5
```

STABILIZED BCL9 PEPTIDES FOR TREATMENT OF ABERRANT WNT SIGNALING

This application is a divisional of and claims priority to U.S. application Ser. No. 15/766,268, filed Apr. 5, 2018, which is a National Stage application under 35 U.S.C. § 371 of International Application No. PCT/US2016/055589, filed Oct. 5, 2016, which claims priority to U.S. Provisional Application No. 62/237,489, filed Oct. 5, 2015. The disclosures of the prior applications are incorporated by reference in their entirety.

SEQUENCE LISTING

This document includes a sequence listing submitted to the United States Patent and Trademark Office via the electronic filing system as an ASCII text file. The sequence listing, which is incorporated-by-reference herein, is titled "44574-0004002_SL.TXT," was created on Jun. 10, 2021, and has a size of 65.7 kilobytes.

FIELD

Disclosed here are polypeptides derived from the HD2 domain of human B-cell CLL/lymphoma 9 (BCL9) protein and variants thereof, as well as their use in the diagnosis, prevention, and/or treatment of a disease or disorder. Also disclosed are methods of generating such polypeptides and variants thereof.

BRIEF DESCRIPTION

β-catenin is a multifunctional protein of critical importance to cellular homeostasis and processes such as embryogenesis, epithelial cell growth, and organ regeneration. However, aberrant β-catenin signaling can lead to changes in transcriptional activation that can allow tumor growth and development. β-catenin is normally phosphorylated and targeted for degradation by the axin complex, but unphosphorylated β-catenin can accumulate if there is stimulation of the Wnt signaling pathway. Under conditions when the Wnt signaling pathway is activated, β-catenin binds to lymphoid enhancer factor/T cell factor (LEF/TCF) and is translocated into the nucleus to stimulate transcription of Wnt target genes (see Clevers and Nusse, Cell 149:1192-1205 (2012)), such as c-myc and CD44, that play roles in tumorigenesis.

Aberrant activation of the Wnt/β-catenin pathway has been shown in a variety of human cancers (see Thakur and Mishra, J Cell Mol Med 17(4):449-456 (2013)). Overactive β-catenin signaling can result in uncontrolled cellular proliferation within tumors, as well as affecting survival of cancer cells. In addition, β-catenin can support tumor metastasis by increasing the migratory and invasive capabilities of cancers cells. Up to 90% of all cases of sporadic colorectal cancers are associated with constitutive activation of Wnt signaling.

BCL9 is a protein known to be required for efficient β-catenin-mediated transcription in mammalian cells (see de la Roche et al., BMC Cancer 8:199 (2008)). BCL9 binds via its HD2 domain to β-catenin, and mutations in the HD2 domain disrupt the association of BCL9 with β-catenin.

Agents that selectively target β-catenin without impacting other Wnt signalling pathways are attractive targets for treatment of patients with cancer. Numerous approaches to develop agents that inhibit β-catenin activity have been employed (see Thakur and Mishra 2013). Many small molecule compounds targeted to inhibit β-catenin have shown promising efficacy in animal models, but more tailored and selective approaches to inhibiting β-catenin activation are needed.

One approach to selectively modulate β-catenin activity is the use of stabilized peptides comprising portions of proteins known to interact with and regulate the function of β-catenin. Stabilized peptides have numerous advantages over wild-type peptides as potential therapeutics, including increased helical content, proteolytic stability, and increased binding affinity for a target receptor (see Kim et al., Nat Protocols 6(6):761-771 (2011)). One β-catenin interactor for which stabilized peptides have been investigated is BCL9, which binds to β-catenin through its HD2 domain. However, attempts to use hydrocarbon linkers (i.e. "hydrocarbon stapling") to generate stabilized peptides comprising portions of the HD2 domain of BCL9 have been hampered by the expense of synthesis and low yield (see Kawamoto, PhD Dissertation in Medicinal Chemistry, Univ of Michigan (2010)). Other investigators have developed stabilized peptides of BCL9 wherein the α-helix of the HD2 domain of the BCL9 protein is stabilized via a hydrocarbon crosslinker(s) generated via ring-closing metathesis (RCM) (see US20140113857).

While these stabilized peptides have had some success in the art, there remains a need for stabilized peptides that are more capable of modulating immune response and therefore have improved in vivo efficacy in treating a tumor.

Disclosed herein are polypeptides derived from the HD2 domain of human B-cell CLL/lymphoma 9 (BCL9) protein. In some embodiments, the polypeptide has a length of 7-14 amino acids. In various embodiments, the polypeptide is stabilized via one or more hydrocarbon crosslinkers, resulting in a construct interchangeably referred as a "stabilized polypeptide" or "stapled polypeptide." In various embodiments, the polypeptide derived from the HD2 domain is capable of undergoing a reaction to form one or more hydrocarbon crosslinkers, and is referred as an "unstapled polypeptide."

In some embodiments, the polypeptide capable of undergoing a reaction to form one or more hydrocarbonds comprises any sequence selected from Table 1 or a variant thereof. In some embodiments, the $Xaa_1$, $Xaa_2$, $Xaa_3$ and/or $Xaa_4$ listed in Table 1 are each an α,α-disubstituted amino acid. In some embodiments, a hydrocarbon crosslinker is present between $Xaa_3$ and $Xaa_4$. In some embodiments, a hydrocarbon crosslinker is present between $Xaa_1$ and $Xaa_2$. In some embodiments, a hydrocarbon crosslinker is present between $Xaa_1$ and $Xaa_2$ and a hydrocarbon crosslinker is present between $Xaa_3$ and $Xaa_4$.

In some embodiments, the polypeptide comprises one or more hydrocarbonds, comprising any sequence selected from Table 1 or a variant thereof. In some embodiments, $Xaa_1$, $Xaa_2$, $Xaa_3$, and/or $Xaa_4$ are each alanine or an α,α-disubstituted alanine, a first hydrocarbon crosslinker is present between $Xaa_1$ and $Xaa_2$, and/or a second hydrocarbon crosslinker is present between $Xaa_3$ and $Xaa_1$.

In some embodiments, the polypeptide is capable of undergoing a reaction to form one or more hydrocarbon crosslinkers and comprises or consists of LQTLRX$aa_1$IQRX$aa_2$L (SEQ ID NO: 1) or a variant thereof. In some embodiments, $Xaa_1$ and $Xaa_2$ are each α,α-disubstituted amino acids.

In some embodiments, the polypeptide is capable of undergoing a reaction to form one or more hydrocarbon crosslinkers and comprises or consists of Xaa$_1$LQXaa$_2$LRXaa$_3$IQRXaa$_4$L (SEQ ID NO: 2) or a variant thereof. In some embodiments, Xaa$_1$, Xaa$_2$, Xaa$_3$, and Xaa$_4$ are each α,α-disubstituted amino acids. In some embodiments, Xaa$_1$ and Xaa$_2$ are each an α,α-disubstituted amino acid and a hydrocarbon crosslinker is present between Xaa$_3$ and Xaa$_4$. In some embodiments, Xaa$_3$ and Xaa$_4$ are each an α,α-disubstituted amino acid and a hydrocarbon crosslinker is present between Xaa$_1$ and Xaa$_2$.

In some embodiments, the polypeptide comprises a hydrocarbon crosslinker and comprises or consists of LQTLRXaa$_1$IQRXaa$_2$L (SEQ ID NO: 1) or a variant thereof. In some embodiments, Xaa$_1$ and Xaa$_2$ are each alanine and a hydrocarbon crosslinker is present between Xaa$_1$ and Xaa$_2$.

In some other embodiments, the polypeptide comprises a hydrocarbon crosslinker and comprises or consists of Xaa$_1$LQXaa$_2$LRXaa$_3$IQRXaa$_4$L (SEQ ID NO: 2) or a variant thereof. In certain embodiments, Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$.

In some embodiments, the α,α-disubstituted amino acid is an α-methyl, α-alkenyl amino acid. In some embodiments, the α-methyl, α-alkenyl amino acid is selected from (S)-2-(4'-pentenyl)alanine, (R)-2-(4'-pentenyl)alanine, (S)-2-(7'-octenyl)alanine, and (R)-2-(7'-octenyl)alanine.

In some embodiments, the hydrocarbon linker is selected from —CH2-CH2-CH2-CH=CH—CH2-CH2-CH2- and —CH2-CH2-CH2-CH2-CH2-CH2-CH=CH—CH2-CH2-CH2-. In some embodiments, the hydrocarbon crosslinker has an S-configuration on at least one end, or on both ends. In some embodiments, the hydrocarbon crosslinker has an R-configuration on at least one end, or on both ends. In some embodiments, the hydrocarbon crosslinker has an S-configuration on one end and an R-configuration on the other end.

In further embodiments, the N-terminus and/or C-terminus of the polypeptide or variant are further modified. In some embodiments, the N-terminus is modified with an acetyl group. In some embodiments, the C-terminus is modified with one, two, or more units of β-alanine, 2-Naphthylalanine, and/or 2-Naphthylalanine, and optionally linked to one, two, or more units of β-alanine, and wherein the carboxyl group of the C-terminus modification is optionally further modified with an NH$_2$ group. In some embodiments, the N-terminus and/or C-terminus modification further comprise a fluorenylmethyloxycarbonyl (Fmoc) group.

In some embodiments, the stapled polypeptide or variant described herein has one or more improved biological functions as compared to an unstapled wild-type human BLC9 HD2 domain or a fragment of a wild-type human BLC9 HD2 domain. When the stapled polypeptide or variant is administered to a subject and/or contacted with a target cell, the polypeptide or variant may be capable of exhibiting one or more improved biological functions selected from: inhibiting binding of BCL9 to β-catenin, inhibiting canonical Wnt/β-catenin signaling, decreasing regulatory T cell survival, decreasing expression of VEGF in a tumor, increasing CD4$^+$ T cell and/or CD8$^+$ T cell infiltration into a tumor, increasing T helper 17 (Th17) cell infiltration into a tumor, decreasing dendritic cells in a tumor, having a half-file (T$_{1/2}$) greater than at least 2 hours, inducing a tumor microenvironment favoring an immune reaction, and inhibiting tumor growth, cancer stem cell proliferation, and/or tumor metastasis.

Also disclosed herein are pharmaceutical compositions, comprising the stapled polypeptide or variant derived from the HD2 domain of human BLC9 protein and a pharmaceutically acceptable carrier. In some embodiments, the pharmaceutical composition comprises at least one additional agent, such as a checkpoint inhibitor, an EGFR inhibitor, a VEGF inhibitor, a VEGFR inhibitor, or an anti-cancer drug.

Also disclosed herein are methods of making and using the claimed stapled polypeptide or variant, e.g., in inhibiting, reducing, preventing, and/or treating a cancer in a subject. In some embodiments, the methods of using the claimed polypeptide or variant encompass inhibiting binding of BCL9 to β-catenin in a subject, as well as inhibiting canonical Wnt/β-catenin signaling in a subject.

Also disclosed herein are biomarkers used in monitoring treatment efficacy and/or selecting a subject to be treated with the claimed stapled polypeptide or variant. In some embodiments, the subject administered with the claimed polypeptide or variant is also treated with an additional therapeutic agent, radiation, and/or chemotherapy. A kit for making and using the claimed stapled polypeptide or variant is also disclosed.

BRIEF DESCRIPTION OF THE DRAWINGS

FIG. 2A depicts a domain mapping strategy that systematically walks through the HD2 domain of human BCL9 protein (SEQ ID NOS 114-130, 107, 131 and 106, respectively, in order of appearance).

FIG. 5A provides a schematic of the reporter assay where binding of BCL9 to β-catenin drives expression of a beta-lactamase (BLA) reporter gene in CellSensor™

LEF/TCF-bla HCT-116 cells (Invitrogen) (Abbreviations: β-cat, β-catenin; TF, transcription factor). A peptide corresponding to amino acids in the HD2 domain, such as WX-024, can inhibit binding of BCL9 to β-catenin. FIGS. 5B, 5C, and 5D depict results of the reporter assay using WX-021, WX-024, and ICG001, respectively. The $IC_{50}$ values of WX-021, WX-024, and ICG001 calculated from the results of this assay were 764 nM, 191 nM, and 1060 nM, respectively.

FIG. 6A provides a schematic of the HTRF assay, showing that the assay measures binding of a biotinylated BCL9 peptide (such as biotinylated WX-024) to β-catenin by assessing fluorescence resonance energy transfer (FRET) (Abbreviations: ab, antibody; SA, streptavidin). FIG. 6B shows the $K_D$ determination for binding of WX-024 to β-catenin based on the HTRF assay ($K_D$=4.21 nM).

FIG. 10B and FIG. 10C summarize the mean pharmacokinetic parameters calculated from this experiment.

As shown in FIG. 12A, tumor volumes (expressed in mm$^3$) were measured using calipers at days 0, 3, 5, 7, 9, 11, and 14 of the treatment period (*P<0.05, compared to vehicle group by Kruskal-Wallis analysis). FIG. 12B shows the average tumor mass of each treatment group at the conclusion of the study (day 22; *P<0.05, compared to vehicle group).

FIGS. 16A, 16B, 16C, and 16D depict results from a CellTiter Glo assay (Promega) measuring CT26 cell (ATCC) growth in vitro when treated with WX-024 or doxorubicin. FIG. 16A shows the growth rate of untreated cells from day 1 (D1) to day 5 (D5). FIG. 16B and FIG. 16C show the growth inhibition rate in WX-024 or doxorubicin-treated cells as measured in this assay, respectively. FIG. 16D summarizes the concentration of agents producing 50% inhibition of growth ($IC_{50}$), the minimum inhibition, the maximum inhibition, and the relative $IC_{50}$ that is the median value calculated based on each curve depicted in FIG. 16B and FIG. 16C.

FIG. 18A represents the tumor growth of each mouse treated with a vehicle while FIG. 18B represents the tumor growth of each mouse treated with WX-024.

FIG. 19A shows CD4$^+$ T cell counts presented as the percentage of total cells in each blood sample. FIG. 19B shows relative T cell count per total cells in each blood sample.

FIG. 20A shows CD8$^+$ T cell counts presented as the percentage of total cells in each blood sample. FIG. 20B shows relative T cell count per total cells in each blood sample.

FIG. 21C and FIG. 21D show representative FACS analysis of samples obtained from blood and tumor, respectively, tested in this experiment.

FIG. 25A shows CD4$^+$ T cell counts presented as a percentage of total tumor cells. FIG. 25B shows CD8$^+$ T cell counts presented as a percentage of total tumor cells. FIG. 25C represents CD4$^+$ or CD8$^+$ T cell counts presented as a percentage of total tumor cells.

FIG. 26A shows myeloid dendritic cells (mDC) count while FIG. 26B shows plastic dendritic cells (pDC) count. (*p<0.05; ***p<0.0001, compared to vehicle control group; One-Way ANOVA).

FIGS. 30A, 30B, and 30C depict the safety profile of WX-024 assessed in female balb/c mice. The mice were treated intravenously with vehicle, 10 mg/kg, 15 mg/kg, or 20 mg/kg WX-024 for 14 consecutive days (n=6). FIG. 30A shows H&E staining of major organs harvested from the mice treated with either vehicle or 10 mg/kg WX-024 at the conclusion of the experiment (day 14). FIG. 30B shows the average body weight of each treatment group throughout the experiment. FIG. 30C shows the complete blood cell count profiles of a vehicle treated group and a 20 mg/kg WX-024 treated group.

FIG. 31A shows the average WX-024 concentration in whole blood after the dosing on day 1. FIG. 31B shows the average WX-024 concentration in whole blood after the dosing on day 14.

FIG. 33A shows the concentration of WX-035 in the samples analyzed via liquid chromatography-mass spectrometry (LC-MS). From the concentration data, the maximum observed concentration ($C_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity (AUC$_{0-inf}$), and bioavailability were calculated, as shown in FIG. 33B.

FIG. 34A shows the concentration of WX-035 in the samples analyzed via liquid chromatography-mass spectrometry (LC-MS). From the concentration data, the time to reach the maximum concentration (T$_{max}$), the maximum observed concentration (C$_{max}$), terminal half-life (T$_{1/2}$), area under the curve from the time of dosing to the last measurable concentration (AUC$_{last}$), area under the curve from the time of dosing extrapolated to infinity (AUC$_{INF}$), and bioavailability (F) were calculated, as shown in FIG. 34B.

FIG. 36A shows total CD45$^+$ T cells as a percentage of total tumor cells. FIG. 36B shows total CD4$^+$ or CD8$^+$ T cells as a percentage of total tumor cells. FIG. 36C shows total CD25$^+$/Foxp3$^+$ T cells. FIG. 36D depicts the ratio between CD8$^+$ T cells and CD25$^+$/Foxp3$^+$ T cells in both treatment groups. FIG. 36E shows LGR5 staining of intestine samples collected in this experiment.

FIG. 38A and FIG. 38B show the effects of WX-035 and WX-037 in a cell viability assay using CT26.WT cells. FIG. 38C summarizes the in vitro profiles of each polypeptide. Ab IC$_{50}$ indicates the absolute concentration of an inhibitor where the cell viability is reduced by half.

FIG. 39A shows the plasma concentration measured after 15 min, 1, 2, or 4 hours of administration. FIG. 39B summarizes the pharmacokinetic profiles calculated using the plasma concentration results shown in FIG. 39A.

FIG. 40A shows the plasma concentration measured after 15 min, 1, 2, or 4 hours of administration. FIG. 40B summarizes the pharmacokinetic profiles calculated using the plasma concentration results shown in FIG. 40A.

FIG. 41A and FIG. 41B show PK data for WX-039 administered to female balb/c nude mice (N=2). WX-039 was administered to each mouse at 5 mg/kg intravenously, 5 mg/kg intraperitoneally, or 10 mg/kg subcutaneously. FIG. 41A shows the plasma concentration measured after 15 min, 1, 2, 4, 8, 24, 36, 48, and 72 hours of administration. FIG. 41B summarizes the pharmacokinetic profiles calculated using the plasma concentration results shown in FIG. 41A.

FIG. 42A and FIG. 42B show PK data for WX-036 administered to female balb/c nude mice (N=2). WX-040 was administered to each mouse at 30 mg/kg intravenously or 40 mg/kg intraperitoneally. FIG. 42A shows the plasma concentration measured after 15 min, 1, 2, 4, 8, 24, 36, 48, and 72 hours of administration. FIG. 42B summarizes the pharmacokinetic profiles calculated using the plasma concentration results shown in FIG. 42A.

DETAILED DESCRIPTION

A. BCL-9, β-Catenin, and Wnt Signaling

Figure 1A:
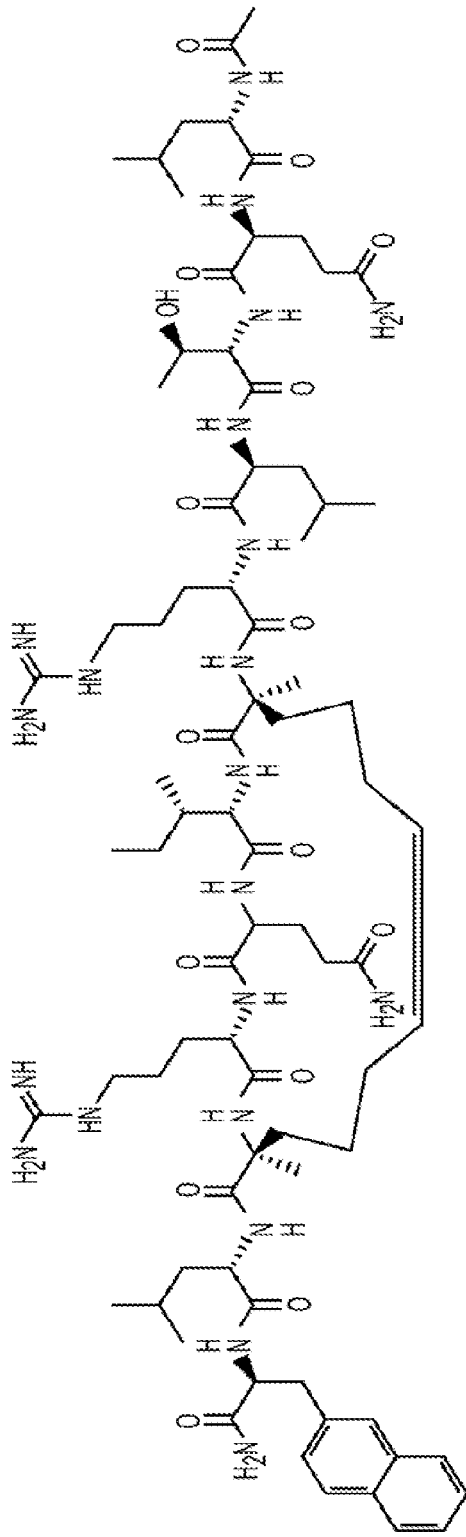
FIG. 1A and FIG. 1B show the structures of the stabilized peptide derived from the HD2 domain of BCL9 protein, corresponding to SEQ ID NO: 103 and SEQ ID NO: 104, respectively. The stabilized polypeptide of SEQ ID NO: 103, referred as "WX-024" in this application. The stabilized polypeptide of SEQ ID NO: 104 is referred as "WX-035" in this application. These peptides have an alkenyl linker(s) generated between α-methyl, α-alkenyl amino acids to stabilize the α-helix of the HD2 domain of the BCL9 protein.

Aberrant activation of Wnt signaling is implicated in a variety of cancers, as tumors can become dependent on Wnt signaling for growth and survival (see Grossmann et al. PNAS. 109(44):17942-17947 (2012)). Up to 90% of all cases of sporadic colorectal cancers are associated with constitutive activation of Wnt signaling.

β-catenin is a protein that can engage in protein-protein interactions that stimulate Wnt signaling leading to changes in transcriptional activation that can allow tumor growth and development. β-catenin is normally phosphorylated and targeted for degradation by the Axin complex. If there is stimulation of the Wnt signaling pathway, unphosphorylated β-catenin accumulates and binds to lymphoid enhancer factor/T cell factor (LEF/TCF) and is translocated into the nucleus to stimulate transcription of Wnt target genes (see Thakur 2013). Wnt target genes include c-myc and CD44, which are unregulated genes in tumor models. BCL9 is a protein required for efficient β-catenin-mediated transcription in mammalian cells (see de la Roche et al., BMC Cancer 8:199 (2008)).

"Canonical" Wnt/β-catenin signaling is a pathway activated by Wnt ligands binding to the Frizzled family of cell-surface receptors, which then regulate expression and intracellular localization of β-catenin. In the absence of Wnt ligands, β-catenin is phosphorylated and ubiquitinated within a destruction complex composed of adenomatous polyposis coli (APC), glycogen synthase kinase-3 (GSK-3), casein kinase-1 (CK1) and Axin, and targeted for degradation in a proteasome-dependent manner. In the presence of Wnt ligands, ubiquitination of β-catenin within the complex is suppressed, leading to saturation of phosphorylated β-catenin, which is then stabilized and translocated to the nucleus. There, phosphorylated β-catenin engages nuclear T-cell factor (TCF) transcription factors, such as Lymphoid Enhancer Factor/3 (LEF/TCF), to induce expression of genes that promote cell proliferation, migration, and survival, including c-Myc28 and Cyclin D.

Several molecules, including BCL9 and its homologue B-cell lymphoma 9-like (B9L), have been shown to be co-activators for Wnt/β-catenin transcription. The formation of a complex consisting of TCF, β-catenin, and BCL9 (or B9L) enhances β-catenin-dependent Wnt transcriptional activity. In normal cells, this transcriptional pathway is turned off when Wnt ligands uncouple from their receptors. However, a variety of loss-of-function mutations in APC and Axin, as well as activating mutations in β-catenin itself, enable β-catenin to escape the destruction complex and accumulate in the nucleus. Such inappropriate persistence of β-catenin promotes oncogenesis in a wide range of common human epithelial cancers, including hepatocellular, breast, colorectal, and hematological malignancies such as multiple myeloma. In addition, active β-catenin signaling results in T-cell exclusion, specifically CD8+ T-cells, which leads to therapy resistance and shorter patient survival times. Thus, blocking Wnt signaling by targeting β-cat may offer a powerful way to treat CRC, potentially preventing both tumor initiation and metastasis. See Spranger et al., Nature 523: 231-235 (2015).

Similar to other transcription factors, the development of selective, non-toxic β-catenin inhibitors and their translation to the clinic have proven to be a considerable challenge, as β-catenin interacts with the majority of its protein partners through the same binding surface. Thus, Wnt pathway inhibitors targeting this common binding surface have exhibited significant adverse effects in animal and clinical trials. There are only a few drugs targeting β-catenin in clinical trials, including PRI-724 (Eisai Pharmaceuticals; Phase II), LGK974 (Novartis; Phase I), and OMP-54F28 and OMP-18R5 (OncoMed/Bayer; Phase I). In addition, disruption of LEF/TCF interaction through small molecule and peptide inhibitors of β-cat can have serious side effects, including severe bone marrow hypoplasia, anemia, and generalized wasting of treated mice—likely a result of disrupting homeostatic Wnt signaling in normal hematopoietic and intestinal stem cells. Such therapeutic limitations may derive from disruption of β-catenin-TCF and β-catenin-E-cadherin interactions, which can affect epithelial tissue integrity. Furthermore, biological agents targeting the Frizzled receptor (OMP-54F28 and OMP-18R5) have shown significant bone marrow toxicity during clinical trials. The Wnt ligand is essential for Wnt/β-cat activation, but APC and β-catenin mutations in cancer cells could induce downstream transcription without Wnt ligand activation, so blocking Wnt secretion cannot inhibit endogenous oncogenic Wnt activity due to APC and β-catenin mutations induced downstream gene transcription. LGK974 only targets a small patient population, as identified by certain biomarkers. PRI-724, a small molecule inhibitor, is under phase II trials with daily infusion, but more than once-weekly intravenous (IV) dosing exhibits characteristics undesirable and untenable for clinical development.

Traditionally, Wnt signaling pathways include three different types of signaling: a canonical Wnt signaling pathway where Wnt regulates various transcriptional target genes through a β-catenin dependent manner; a noncanonical Wnt signaling pathway mainly involved in planer cell polarity, where Wnt may function independently of β-catenin; and a noncanonical Wnt/calcium pathway regulating an intracellular calcium level. In the present application, "canonical Wnt signaling" is interchangeably referred as "canonical Wnt/β-catenin signaling" or "Wnt signaling." As described herein, canonical Wnt/β-catenin signaling may refer to pathway components that control the amount of β-catenin in a patient or sample, e.g., by modulating the stability of β-catenin. In some embodiments, canonical Wnt/β-catenin signaling comprises pathway components that transcriptionally modulate one or more genes such as c-myc, ccnd1, cd44, LGR5, VEGFA, AXIN2, and LEF1. In some embodiments, canonical Wnt/β-catenin signaling comprises pathway components that are modulated by the interaction between β-catenin and BCL9. In some embodiments, canonical Wnt/β-catenin signaling comprises one or more genes that are transcriptionally controlled by the interaction between β-catenin and BCL9. The one or more genes controlled by the interaction between β-catenin and BCL9 may include c-myc, ccnd1, cd44, LGR5, VEGFA, AXIN2, and LEF1. In some embodiments, canonical Wnt/β-catenin signaling comprises one or more proteins, the transcriptional expressions of which are modulated by the interaction between β-catenin and BCL9. Those components may include, for example, c-Myc, Cyclin D1, CD44, LGR5, VEGFA, AXIN2, and LEF1.

B. Stabilized BCL-9 Peptides

Stabilized peptides have been shown to confer advantages such as increased helical content, proteolytic stability, and increased binding affinity for a target receptor (see Kim 2011). In particular, α-helix domains are known to be amenable to stabilization.

1. Polypeptide Derived from BCL9 HD2 Domain

The HD2 domain of BCL9 mediates the binding of BCL9 to β-catenin, and so far, the HD2 domain is the only domain of BLC9 shown to bind to β-catenin in cells (see de la Roche 2008). The HD2 domain forms an α-helix, and thus polypeptides derived from the HD2 domain of BCL9 in which the α-helix has been stabilized may be appropriate for inhibiting the interaction of BCL9 with β-catenin (Sampietro et al., Molecular Cell, 24, 293-300 (2006)).

In one embodiment, mapping the activity of portions of the HD2 domain of the BCL9 protein is done to determine active regions, which are interchangeably referred as core functional domains. In one embodiment, a peptide containing a portion of the HD2 domain of the BCL9 is structurally constrained. In certain embodiments, this structural constraint stabilizes an α-helix of the BCL9 peptide.

In some embodiments, a polypeptide described herein is derived from the HD2 domain of human BCL9 protein. As used herein, the terms "polypeptide," "peptide," and "protein" are used interchangeably and refer to a polymer comprising two or more amino acids bonded together to form a chain. The term "polypeptide derived from the HD2 domain of human BCL9 protein" encompasses the full-length HD2 domain of human BCL9 protein and fragments of such HD2 domain. Also encompassed here are variants of the full-length HD2 domain or the fragments. The sequence of the full-length HD2 domain of human BCL9 protein (SEQ ID NO: 3) is shown in Table 1. A polypeptide derived from the HD2 domain of human BCL9 protein, or a variant thereof, can be stapled or stabilized as disclosed herein.

In some embodiments, the polypeptide described herein comprises the full-length HD2 domain of human BCL9 protein. In some embodiments, the polypeptide described herein comprises a fragment and/or variant of the HD2 domain of human BCL9 protein. In a certain embodiment, the polypeptide derived from the HD2 domain of human BCL9 protein comprises a fragment of the HD2 domain of human BCL9 protein, which is further modified by substituting one or more amino acids with other naturally occurring amino acids or non-naturally occurring amino acids. In some embodiment, the polypeptide derived from the HD2 domain of human BCL9 protein is capable of undergoing a reaction to form one or more hydrocarbon crosslinkers. As used herein, the polypeptide capable of undergoing a reaction to form one or more hydrocarbon crosslinkers may be referred as an "unstapled polypeptide." In some embodiments, a polypeptide described herein comprises one or more non-naturally occurring amino acids. In some embodiments, the non-naturally occurring amino acid is norleucine. In some embodiments, the non-naturally occurring amino acid is an α,α-disubstituted amino acid. In some embodiments, the non-naturally occurring amino acid is an α-methyl, α-alkenyl amino acid. In some embodiment, the non-naturally occurring amino acid is a chiral molecule, comprising a chiral center with either S- or R-configuration. In some embodiment, the non-naturally occurring amino acid is selected from (S)-2-(4'-pentenyl)alanine, (R)-2-(4'-pentenyl)alanine, (S)-2-(7'-octenyl)alanine, and (R)-2-(7'-octenyl)alanine.

As used herein, a polypeptide derived from the HD2 domain of human BCL9 protein also encompasses a polypeptide that has undergone a reaction to form one or more hydrocarbon crosslinkers and thus comprises one or more hydrocarbon crosslinkers. As used herein, the polypeptide comprising one or more hydrocarbon crosslinkers may be referred as a "stabilized polypeptide" or a "stapled polypeptide." In some embodiments, the hydrocarbon crosslinker has a length of 2-15 carbons. In some embodiments, the hydrocarbon crosslinker has a length of 5-11 carbons. In some embodiments, the hydrocarbon crosslinker has a length of 7-11 carbons. In some embodiments, the hydrocarbon crosslinker has a length of 7-15 carbons. In some embodiments, the hydrocarbon crosslinker has a length of 8-11 carbons. In some embodiments, the hydrocarbon crosslinker has a length of 7 or 8 or 9 or 10 or 11 carbons, or more. In some embodiments, the hydrocarbon crosslinker is selected from —$CH_2$—$CH_2$—$CH_2$—$CH$=$CH$—$CH_2$—$CH_2$—$CH_2$— and —$CH_2$—$CH_2$—$CH_2$—$CH_2$—$CH_2$—$CH_2$—$CH$=$CH$—$CH_2$—$CH_2$—$CH_2$—.

In some embodiments, the stapled polypeptides described herein are capable of inhibiting the binding of BCL9 to β-catenin in vitro and/or in vivo. In some embodiments, a polypeptide derived from the HD2 domain of human BCL9 protein has one or more improved biological functions as compared to an unstapled wild-type HD2 domain of human BCL9 protein or as compared to a fragment of an unstapled wild-type HD2 domain. The one or more biological functions may be selected from one or more of: (1) inhibiting binding of BCL9 to β-catenin; (2) inhibiting canonical Wnt/β-catenin signaling; (3) decreasing regulatory T cell survival; (4) decreasing expression of VEGF in a tumor; (5) increasing CD4+ T cell and CD8+ T cell infiltration into a tumor; (6) increasing T helper 17 (Th17) cells in a tumor; (7) decreasing dendritic cells in a tumor; (8) having a half-life (T½) greater than at least 2 hours when administrated to a subject; (9) inducing a tumor microenvironment favoring an immune reaction; and (10) inhibiting tumor growth, cancer stem cell proliferation, and/or tumor metastasis.

The present disclosures encompass stapled peptides comprising a variant of a wild-type HD2 domain of human BCL9 protein, or a variant of a fragment of an unstapled wild-type HD2 domain, that retains one or more biological functions of the wild-type polypeptide. A "variant" as used herein in connection with the polypeptide described herein refers to a polypeptide that differs from a given polypeptide in amino acid sequence and/or chemical structure, but retains one or more biological functions of the given polypeptide (i.e., the polypeptide described herein). For instance, the variant may retain one or more biological functions of a polypeptide derived from the HD2 domain of human BCL9 protein such as e.g., the ability to bind β-catenin, inhibiting canonical Wnt/β-catenin signaling, and/or inhibit binding of BCL9 to β-catenin.

The variant polypeptide described herein may have one or more amino acid additions (e.g., insertion), deletions, and/or substitutions from the given polypeptide, as long as it retains the functional properties mentioned above. In some embodiments, the variant polypeptide described herein may have 1-30, 1-20, 1-10, 1-8, 1-5, 1-4, 1-3, or 1-2, or 1, 2, 3, 4, 5, 6, 7, 8, 9, 10, 15, 20, 25, or 30 amino acid additions (e.g., insertion), deletions, and/or substitutions from the wild-type polypeptide, including all integers in between these ranges.

In some embodiments, the variant comprises conservative substitution of one or more amino acids of a given polypeptide. A conservative substitution of an amino acid, i.e., replacing an amino acid with a different amino acid of similar properties (e.g., hydrophilicity, and degree and distribution of charged regions), typically involves a minor change and therefore does not significantly alter the biological activity of the polypeptide. These minor changes may be identified by considering the hydropathic index of amino acids based on a consideration of the hydrophobicity and charge of the amino acid. Amino acids of similar hydropathic indexes and hydrophilicity values can be substituted and still retain protein function. Both the hydrophobicity index and the hydrophilicity value of amino acids are influenced by the particular side chain of that amino acid. Consistent with that observation, amino acid substitutions that are compatible with biological function depend on the relative similarity of the amino acids, and particularly the side chains of those amino acids, as revealed by the hydrophobicity, hydrophilicity, charge, size, and other properties.

In some embodiments, the variant comprises substitution of one or more amino acids of a wild-type polypeptide or fragment by a non-naturally occurring amino acid. In some embodiments, the non-naturally occurring amino acid is norleucine. In some embodiments, the non-naturally occurring amino acid is an α,α-disubstituted amino acid. In some embodiments, the non-naturally occurring amino acid is an α-methyl, α-alkenyl amino acid. In some embodiment, the non-naturally occurring amino acid is a chiral molecule, comprising a chiral center with either an S- or R-configuration. In some embodiment, the non-naturally occurring amino acid is selected from (S)-2-(4'-pentenyl)alanine, (R)-2-(4'-pentenyl)alanine, (S)-2-(7'-octenyl)alanine, and (R)-2-(7'-octenyl)alanine.

The term "variant" also includes a polypeptide that has a certain percent homology, such as, e.g., at least about 50%, 60%, 70%, 80%, 85%, 90%, 95%, 96%, 97%, 98%, or 99% (or any percentage in between) to a wild-type polypeptide or fragment. As used herein, the term percent (%) homology defines the percentage of residues in the amino acid sequences of the variant and the given polypeptide that are identical after aligning the sequences and other spacing, e.g., using the BLAST alignment software.

In some embodiments, the variant comprises a polypeptide that is chemically and/or post-translationally modified in a manner different from the wild-type polypeptide or fragment, but retains one or more biological functions as described above. For instance, the variant may comprise one or more amino acids that are post-transitionally modified by e.g., phosphorylation, acetylation, methylation, ubiquitination, SUMOylation, or other post-translational modifications known in the art. The variant may also comprise one or more chemical modifications, e.g., one or more amino acid side chains that are modified or substituted with a different chemical moiety. As used herein, the term "variant" also encompasses a polypeptide that is identical to a given polypeptide in amino acid sequence, but having a different hydrocarbon crosslinker. The term "variant" may also refer to a polypeptide that is identical to a given polypeptide in amino acid sequence and chemical structure, but having a different chirality.

2. Structure of Polypeptide Derived from BCL9 HD2 Domain

In some embodiments, a polypeptide derived from the HD2 domain of human BCL9 protein has a length of 7-22 amino acids. In some embodiments, the polypeptide has a length of 7-14 amino acids. In some embodiments, the polypeptide has a length of 7 or 8 amino acids. In some embodiments, the polypeptide has a length of 10-14 amino acids. In some embodiments, the polypeptide has a length of 11 or 12 amino acids.

In some embodiments, a polypeptide derived from the HD2 domain of human BCL9 protein has a length of 7-14 amino acids and comprises any sequence selected from Table 1. In some embodiments, the polypeptide derived from the HD2 domain of human BCL9 protein has a length of 7 or 8 amino acids and comprises any sequence selected from Table 1. In some embodiments, a polypeptide derived from the HD2 domain of human BCL9 protein has a length of 10-14 amino acids and comprises any sequence selected from Table 1. In some embodiments, a polypeptide derived from the HD2 domain of human BCL9 protein has a length of 10 or 11 amino acids and comprises any sequence selected from Table 1. The polypeptides described herein also encompass variants of a polypeptide selected from Table 1 that retains one or more biological functions of the polypeptide. In various embodiments, the selected polypeptide is stabilized, e.g., by comprising one or more hydrocarbon cross-link. In Table 1, B indicates norleucine.

TABLE 1

Polypeptides derived from the HD2 domain of human BCL9 protein

| SEQ ID NO: | Generic Polypep ID | Amino Acid Sequence | Corresponding position within BCL9 | N-terminus Modification | C-terminus modificiation |
|---|---|---|---|---|---|
| 3 | HD2 | PDGLSQEQLEHRERSLQT LRDIQRMLFPDE | 348-377 | N/A | N/A |
| 4 | WX-001 | LSQEQLEHRERSLXaa$_1$T LRXaa$_2$IQRBLF | 351-374 | Ac | NH$_2$ |
| 5 | WX-002 | LXaa$_1$QEQXaa$_2$E | 351-357 | Ac | NH$_2$ |
| 6 | WX-003 | SXaa$_1$EQLXaa$_2$H | 352-358 | Ac | NH$_2$ |
| 7 | WX-004 | QXaa$_1$QLEXaa$_2$R | 353-359 | Ac | NH$_2$ |
| 8 | WX-005 | EXaa$_1$LEHXaa$_2$E | 354-360 | Ac | NH$_2$ |
| 9 | WX-006 | QXaa$_1$EHRXaa$_2$R | 355-361 | Ac | NH$_2$ |
| 10 | WX-007 | LXaa$_1$HRExaa$_2$S | 356-362 | Ac | NH$_2$ |
| 11 | WX-008 | EXaa$_1$RERXaa$_2$L | 357-363 | Ac | NH$_2$ |
| 12 | WX-009 | HXaa$_1$ERSXaa$_2$4 | 358-364 | Ac | NH$_2$ |
| 13 | WX-010 | RXaa$_1$RSLXaa$_2$T | 359-365 | Ac | NH$_2$ |
| 14 | WX-011 | EXaa$_1$SLQXaa$_2$L | 360-366 | Ac | NH$_2$ |
| 15 | WX-012 | RXaa$_1$LQTXaa$_2$R | 361-367 | Ac | NH$_2$ |
| 16 | WX-013 | SXaa$_1$QTLXaa$_2$D | 362-368 | Ac | NH$_2$ |
| 17 | WX-014 | LXaa$_1$TLRXaa$_2$I | 363-369 | Ac | NH$_2$ |
| 18 | WX-015 | QXaa$_1$LRDXaa$_2$Q | 364-370 | Ac | NH$_2$ |
| 19 | WX-016 | TXaa$_1$RDIXaa$_2$R | 365-371 | Ac | NH$_2$ |
| 20 | WX-017 | LXaa$_1$DIQXaa$_2$B | 366-372 | Ac | NH$_2$ |
| 21 | WX-018 | RXaa$_1$IQRXaa$_2$L | 367-373 | Ac | NH$_2$ |

TABLE 1-continued

Polypeptides derived from the HD2 domain of human BCL9 protein

| SEQ ID NO: | Generic Polypep ID | Amino Acid Sequence | Corresponding position within BCL9 | N-terminus Modification | C-terminus modification |
|---|---|---|---|---|---|
| 22 | WX-019 | DXaa$_1$QRBXaa$_2$F | 368-374 | Ac | NH$_2$ |
| 23 | WX-020 | LRXaa$_1$IQRXaa$_2$L | 366-373 | Ac | NH$_2$ |
| 24 | WX-021 | LRXaa$_1$IQRXaa$_2$L | 366-373 | Ac | 2-Nal-β-Ala-β-Ala-NH$_2$ |
| 25 | WX-022 | LRXaa$_1$IQRXaa$_2$L | 366-373 | Ac | β-Ala-β-Ala-NH$_2$ |
| 26 | WX-023 | LRXaa$_1$IQRXaa$_2$L | 366-373 | Ac | 2-Nal-NH$_2$ |
| 27 | WX-024 | LQTLRXaa$_1$IQRXaa$_2$L | 363-373 | Ac | 2-Nal-NH$_2$ |
| 28 | WX-029 | LQTLRXaa$_1$IQRXaa$_2$L | 363-373 | Ac | 2-Nal-β-Ala-β-Ala-GRKKRRQRRRPQ |
| 29 | WX-035 | Xaa$_1$LQXaa$_2$LRXaa$_3$IQRXaa$_4$L | 362-373 | Ac | 2-Nal-β-Ala-β-Ala-NH$_2$ |
| 30 | WX-036 | Xaa$_1$LQXaa$_2$LRXaa$_3$IQRXaa$_4$L | 362-373 | Ac | 2-Nal-β-Ala-β-Ala-GRKKRRQRRRPQ |
| 31 | WX-037 | Xaa$_1$DQXaa$_2$DRXaa$_3$DQRXaa$_4$DH | 362-374 | Ac | β-Ala-β-Ala-NH$_2$ |
| 32 | WX-038 | Xaa$_1$LEXaa$_2$LRXaa$_3$IERXaa$_4$L | 362-373 | Ac | 2-Nal-β-Ala-β-Ala-NH$_2$ |
| 33 | WX-039 | RXaa$_1$LQXaa$_2$LRXaa$_3$IQRXaa$_4$L | 361-373 | Ac | 2-Nal-β-Ala-β-Ala-NH$_2$ |
| 34 | WX-040 | LQXaa$_1$LRDIQRXaa$_2$L | 363-373 | Ac | 2-Nal-β-Ala-β-Ala-NH$_2$ |

In a certain embodiment, a polypeptide described herein is capable of undergoing a reaction to form one or more hydrocarbon crosslinkers. In some embodiments, the polypeptide comprises any sequence selected from Table 1 or variant thereof, wherein Xaa$_1$, Xaa$_2$, Xaa$_3$, and Xaa$_4$ are each an α, α-disubstituted amino acid. In some embodiments, the polypeptide described herein comprises any sequence selected from Table 1, wherein Xaa$_1$ and Xaa$_2$ are each an α,α-disubstituted amino acid and a hydrocarbon crosslinker is present between Xaa$_3$ and Xaa$_4$. In some embodiments, the polypeptide described herein comprises any sequence selected from Table 1, wherein Xaa$_3$ and Xaa$_4$ are each an α,α-disubstituted amino acid and a hydrocarbon crosslinker is present between Xaa$_1$ and Xaa$_2$. In some embodiments, the α,α-disubstituted amino acid is an α-methyl, α-alkenyl amino acid. In some embodiments, the α-methyl, α-alkenyl amino acid is an α-methyl, α-alkenyl alanine. In some embodiments, the α-methyl, α-alkenyl alanine is selected from (S)-2-(4'-pentenyl)alanine, (R)-2-(4'-pentenyl)alanine, (S)-2-(7'-octenyl)alanine, and (R)-2-(7'-octenyl)alanine.

In a certain embodiment, the polypeptide or variant thereof described herein is a stapled polypeptide comprising one or more hydrocarbon crosslinkers and comprises any sequence selected from Table 1 or variant thereof. In some embodiments, the polypeptide is a stapled polypeptide comprising one hydrocarbon crosslinker, wherein Xaa$_1$ and Xaa$_2$ are each alanine and the hydrocarbon crosslinker is present between Xaa$_1$ and Xaa$_2$. In other embodiments, the polypeptide is a stapled polypeptide comprising two hydrocarbon crosslinkers, wherein (1) Xaa$_1$, Xaa$_2$, Xaa$_3$, and Xaa$_4$ are each alanine, (2) a first hydrocarbon crosslinker is present between Xaa$_1$ and Xaa$_2$, and (3) a second hydrocarbon crosslinker is present between Xaa$_3$ and Xaa$_4$. In some embodiments, the hydrocarbon crosslinker has an S-configuration on both ends. In some embodiments, the hydrocarbon crosslinker has an R-configuration on both ends. In some embodiments, the hydrocarbon crosslinker has an S-configuration on one end and an R-configuration on the other end.

In some embodiments, a polypeptide described herein comprises or consists of an amino acid sequence of LXaa$_1$QEQXaa$_2$E (SEQ ID NO: 35), wherein Xaa$_1$ and Xaa$_2$ are each (S)-2-(4'-pentenyl)alanine.

In some embodiments, a polypeptide described herein comprises or consists of an amino acid sequence of SXaa$_1$EQLXaa$_2$H (SEQ ID NO: 36), wherein Xaa$_1$ and Xaa$_2$ are each (S)-2-(4'-pentenyl)alanine.

In some embodiments, a polypeptide described herein comprises or consists of an amino acid sequence of QXaa$_1$QLEXaa$_2$R (SEQ ID NO: 37), wherein Xaa$_1$ and Xaa$_2$ are each (S)-2-(4'-pentenyl)alanine.

In some embodiments, a polypeptide described herein comprises or consists of an amino acid sequence of EXaa$_1$LEHXaa$_2$E (SEQ ID NO: 38), wherein Xaa$_1$ and Xaa$_2$ are each (S)-2-(4'-pentenyl)alanine.

In some embodiments, a polypeptide described herein comprises or consists of an amino acid sequence of QXaa$_1$EHRXaa$_2$R (SEQ ID NO: 39), wherein Xaa$_1$ and Xaa$_2$ are each (S)-2-(4'-pentenyl)alanine.

In some embodiments, a polypeptide described herein comprises or consists of an amino acid sequence of LXaa$_1$HREXaa$_2$S (SEQ ID NO: 40), wherein Xaa$_1$ and Xaa$_2$ are each (S)-2-(4'-pentenyl)alanine.

In some embodiments, a polypeptide described herein comprises or consists of an amino acid sequence of EXaa$_1$RERXaa$_2$L (SEQ ID NO: 41), wherein Xaa$_1$ and Xaa$_2$ are each (S)-2-(4'-pentenyl)alanine.

In some embodiments, a polypeptide described herein comprises or consists of an amino acid sequence of HXaa$_1$ERSXaa$_2$Q (SEQ ID NO: 42), wherein Xaa$_1$ and Xaa$_2$ are each (S)-2-(4'-pentenyl)alanine.

In some embodiments, a polypeptide described herein comprises or consists of an amino acid sequence of RXaa$_1$RSLXaa$_2$T (SEQ ID NO: 43), wherein Xaa$_1$ and Xaa$_2$ are each (S)-2-(4'-pentenyl)alanine.

In some embodiments, a polypeptide described herein comprises or consists of an amino acid sequence of EXaa$_1$SLQXaa$_2$L (SEQ ID NO: 44), wherein Xaa$_1$ and Xaa$_2$ are each (S)-2-(4'-pentenyl)alanine.

In some embodiments, a polypeptide described herein comprises or consists of an amino acid sequence of RXaa$_1$LQTXaa$_2$R (SEQ ID NO: 45), wherein Xaa$_1$ and Xaa$_2$ are each (S)-2-(4'-pentenyl)alanine.

In some embodiments, a polypeptide described herein comprises or consists of an amino acid sequence of SXaa$_1$QTLXaa$_2$D (SEQ ID NO: 46), wherein Xaa$_1$ and Xaa$_2$ are each (S)-2-(4'-pentenyl)alanine.

In some embodiments, a polypeptide described herein comprises or consists of an amino acid sequence of LXaa$_1$TLRXaa$_2$I (SEQ ID NO: 47), wherein Xaa$_1$ and Xaa$_2$ are each (S)-2-(4'-pentenyl)alanine.

In some embodiments, a polypeptide described herein comprises or consists of an amino acid sequence of QXaa$_1$LRDXaa$_2$Q (SEQ ID NO: 48), wherein Xaa$_1$ and Xaa$_2$ are each (S)-2-(4'-pentenyl)alanine.

In some embodiments, a polypeptide described herein comprises or consists of an amino acid sequence of TXaa$_1$RDIXaa$_2$R (SEQ ID NO: 49), wherein Xaa$_1$ and Xaa$_2$ are each (S)-2-(4'-pentenyl)alanine.

In some embodiments, a polypeptide described herein comprises or consists of an amino acid sequence of LXaa$_1$DIQXaa$_2$B (SEQ ID NO: 50), wherein Xaa$_1$ and Xaa$_2$ are each (S)-2-(4'-pentenyl)alanine.

In some embodiments, a polypeptide described herein comprises or consists of an amino acid sequence of RXaa$_1$IQRXaa$_2$L (SEQ ID NO: 51), wherein Xaa$_1$ and Xaa$_2$ are each (S)-2-(4'-pentenyl)alanine.

In some embodiments, a polypeptide described herein comprises or consists of an amino acid sequence of DXaa$_1$QRBXaa$_2$F (SEQ ID NO: 52), wherein Xaa$_1$ and Xaa$_2$ are each (S)-2-(4'-pentenyl)alanine.

In some embodiments, a polypeptide described herein comprises or consists of an amino acid sequence of LRXaa$_1$IQRXaa$_2$L (SEQ ID NO: 53), wherein Xaa$_1$ and Xaa$_2$ are each (S)-2-(4'-pentenyl)alanine.

In some embodiments, a polypeptide described herein comprises or consists of an amino acid sequence of LQTLRXaa$_1$IQRXaa$_2$L (SEQ ID NO: 54), wherein Xaa$_1$ and Xaa$_2$ are each (S)-2-(4'-pentenyl)alanine.

In some embodiments, a polypeptide described herein comprises or consists of an amino acid sequence of Xaa$_1$LQXaa$_2$LRXaa$_3$IQRXaa$_4$L (SEQ ID NO: 55), wherein Xaa$_2$, Xaa$_3$ and Xaa$_4$ are each (S)-2-(4'-pentenyl)alanine whereas Xaa$_1$ is (R)-2-(4'-pentenyl)alanine.

In some embodiments, a polypeptide described herein comprises or consists of an amino acid sequence of Xaa$_1$DQXaa$_2$DRXaa$_3$DQRXaa$_4$DH (SEQ ID NO: 56), wherein Xaa$_2$, Xaa$_3$ and Xaa$_4$ are each (S)-2-(4'-pentenyl)alanine whereas Xaa$_1$ is (R)-2-(4'-pentenyl)alanine.

In some embodiments, a polypeptide described herein comprises or consists of an amino acid sequence of Xaa$_1$LEXaa$_2$LRXaa$_3$IERXaa$_4$L (SEQ ID NO: 57), wherein Xaa$_2$, Xaa$_3$ and Xaa$_4$ are each (S)-2-(4'-pentenyl)alanine whereas Xaa$_1$ is (R)-2-(4'-pentenyl)alanine.

In some embodiments, a polypeptide described herein comprises or consists of an amino acid sequence of RXaa$_1$LQXaa$_2$LRXaa$_3$IQRXaa$_4$L (SEQ ID NO: 58), wherein Xaa$_2$, Xaa$_3$ and Xaa$_4$ are each (S)-2-(4'-pentenyl)alanine whereas Xaa$_1$ is (R)-2-(4'-pentenyl)alanine.

In some embodiments, a polypeptide described herein comprises or consists of an amino acid sequence of LQXaa$_1$LRDIQRXaa$_2$L (SEQ ID NO: 59), wherein Xaa$_1$ is (R)-2-(7'-octenyl)alanine and Xaa$_2$ is (S)-2-(4'-pentenyl)alanine.

In some embodiments, a polypeptide described herein comprises or consists of an amino acid sequence of LXaa$_1$QEQXaa$_2$E (SEQ ID NO: 60), wherein Xaa$_1$ and Xaa$_2$ are each alanine and a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of SXaa$_1$EQLXaa$_2$H (SEQ ID NO: 61), wherein Xaa$_1$ and Xaa$_2$ are each alanine and a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of QXaa$_1$QLEXaa$_2$R (SEQ ID NO: 62), wherein Xaa$_1$ and Xaa$_2$ are each alanine and a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of EXaa$_1$LEHXaa$_2$E (SEQ ID NO: 63), wherein Xaa$_1$ and Xaa$_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $QXaa_1EHRXaa_2R$ (SEQ ID NO: 64), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $LXaa_1HRE Xaa_2S$ (SEQ ID NO: 65), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $EXaa_1RERXaa_2L$ (SEQ ID NO: 66), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $HXaa_1ERSXaa_2Q$ (SEQ ID NO: 67), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $RXaa_1RSLXaa_2T$ (SEQ ID NO: 68), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $EXaa_1SLQXaa_2L$ (SEQ ID NO: 69), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $RXaa_1LQTXaa_2R$ (SEQ ID NO: 70), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $SXaa_1QTLXaa_2D$ (SEQ ID NO: 71), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $LXaa_1TLRXaa_2I$ (SEQ ID NO: 72), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $QXaa_1LRDXaa_2Q$ (SEQ ID NO: 73), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $TXaa_1RDIXaa_2R$ (SEQ ID NO: 74), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $LXaa_1DIQXaa_2B$ (SEQ ID NO: 75), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $RXaa_1IQRXaa_2L$ (SEQ ID NO: 76), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $DXaa_1QRBXaa_2F$ (SEQ ID NO: 77), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises or consists of an amino acid sequence of $LRXaa_1IQRXaa_2L$ (SEQ ID NO: 78), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide described herein comprises and/or consists of an amino acid sequence of $LQTLRXaa_1IQRXaa_2L$ (SEQ ID NO: 79), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends.

In some embodiments, a polypeptide the polypeptide described herein comprises or consists of an amino acid sequence of $Xaa_1LQXaa_2LRXaa_3IQRXaa_4L$ (SEQ ID NO: 80), wherein (1) $Xaa_3$ and $Xaa_4$ are each (S)-2-(4'-pentenyl)alanine, (2) $Xaa_1$ and $Xaa_2$ are alanine, and (3) a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration on one end and having an R-configuration on the other end.

In some embodiments, a polypeptide described herein comprises or consists of an amino acid sequence of $Xaa_1LQXaa_2LRXaa_3IQRXaa_4L$ (SEQ ID NO: 81), wherein (1) $Xaa_1$ is (R)-2-(4'-pentenyl)alanine and $Xaa_2$ is (S)-2-(4'-pentenyl)alanine, (2) $Xaa_3$ and $Xaa_4$ are alanine, and (3) a hydrocarbon crosslinker is present between $Xaa_3$ and $Xaa_4$. In these embodiments, the hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of Xaa$_1$LQXaa$_2$LRXaa$_3$IQRXaa$_4$L (SEQ ID NO: 82), wherein Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of Xaa$_1$DQXaa$_2$DRXaa$_3$DQRXaa$_4$DH (SEQ ID NO: 83), wherein (1) Xaa$_3$ and Xaa$_4$ are each (S)-2-(4'-pentenyl)alanine, (2) Xaa$_1$ and Xaa$_2$ are alanine, and (3) a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration on one end and having an R-configuration on the other end.

In some embodiments, a polypeptide described herein comprises or consists of an amino acid sequence of Xaa$_1$DQXaa$_2$DRXaa$_3$DQRXaa$_4$DH (SEQ ID NO: 84), wherein (1) Xaa$_1$ is (R)-2-(4'-pentenyl)alanine and Xaa$_2$ is (S)-2-(4'-pentenyl)alanine, (2) Xaa$_3$ and Xaa$_4$ are alanine, and (3) a hydrocarbon crosslinker is present between Xaa$_3$ and Xaa$_4$. In these embodiments, the hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of Xaa$_1$DQXaa$_2$DRXaa$_3$DQRXaa$_4$DH (SEQ ID NO: 85), wherein Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of Xaa$_1$LEXaa$_2$LRXaa$_3$IERXaa$_4$L (SEQ ID NO: 86), wherein (1) Xaa$_3$ and Xaa$_4$ are each (S)-2-(4'-pentenyl)alanine, (2) Xaa$_1$ and Xaa$_2$ are alanine, and (3) a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration on one end and having an R-configuration on the other end.

In some embodiments, a polypeptide described herein comprises or consists of an amino acid sequence of Xaa$_1$LEXaa$_2$LRXaa$_3$IERXaa$_4$L (SEQ ID NO: 87), wherein (1) Xaa$_1$ is (R)-2-(4'-pentenyl)alanine and Xaa$_2$ is (S)-2-(4'-pentenyl)alanine, (2) Xaa$_3$ and Xaa$_4$ are alanine, and (3) a hydrocarbon crosslinker is present between Xaa$_3$ and Xaa$_4$. In these embodiments, the hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of Xaa$_1$LEXaa$_2$LRXaa$_3$IERXaa$_4$L (SEQ ID NO: 88), wherein Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of RXaa$_1$LQXaa$_2$LRXaa$_3$IQRXaa$_4$L (SEQ ID NO: 89), wherein (1) Xaa$_3$ and Xaa$_4$ are each (S)-2-(4'-pentenyl)alanine, (2) Xaa$_1$ and Xaa$_2$ are alanine, and (3) a hydrocarbon crosslinker is present between Xaa$_1$ and Xaa$_2$. In these embodiments, the hydrocarbon crosslinker is —CH2-CH2-CH2-CH=CH—CH2-CH2-CH2-, having an S-configuration on one end and having an R-configuration on the other end.

In some embodiments, a polypeptide described herein comprises or consists of an amino acid sequence of RXaa$_1$LQXaa$_2$LRXaa$_3$IQRXaa$_4$L (SEQ ID NO: 90), wherein (1) Xaa$_1$ is (R)-2-(4'-pentenyl)alanine and Xaa$_2$ is (S)-2-(4'-pentenyl)alanine, (2) Xaa$_3$ and Xaa$_4$ are alanine, and (3) a hydrocarbon crosslinker is present between Xaa$_3$ and Xaa$_4$. In these embodiments, the hydrocarbon crosslinker is —CH2-CH2-CH2-CH=CH—CH2-CH2-CH2-, having an S-configuration on both ends.

In some embodiments, a polypeptide described herein comprises or consists of an amino acid sequence of RXaa$_1$LQXaa$_2$LRXaa$_3$IQRXaa$_4$L (SEQ ID NO: 91), wherein Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends.

In some embodiments, a polypeptide described herein comprises and/or consists of an amino acid sequence of LQXaa$_1$LRDIQRXaa$_2$L (SEQ ID NO: 92), wherein Xaa$_1$ and Xaa$_2$ are each alanine and a hydrocarbon crosslinker is present between Xaa$_1$ and Xaa$_2$. In these embodiments, the hydrocarbon crosslinker is —CH$_2$—CH$_2$—CH$_2$—CH$_2$—CH$_2$—CH$_2$—CH=CH—CH$_2$—CH$_2$—CH$_2$—, having an R-configuration on one end and an S-configuration on the other end. In some embodiments, the polypeptide or variant described herein further comprises a chemical modification at the N-terminus and/or C-terminus. In some embodiment, the N-terminus of the polypeptide or variant described herein is further modified. In some embodiments, the N-terminus of the polypeptide or variant described herein is modified to an acetyl group. In some embodiments, the C-terminus of the polypeptide or variant described herein is further modified. In some embodiments, the C-terminus of the polypeptide or variant described herein is modified with NH$_2$. In some embodiments, the C-terminus of the polypeptide or variant described herein is modified with one, two, or more units of β-alanine, 2-Naphthylalanine, and/or 2-Naphthylalanine, optionally linked to one, two, or more units of β-alanine, wherein the carboxyl group of the C-terminus modification is optionally further modified with NH$_2$. In some embodiments, the N-terminus and/or the C-terminus of the polypeptide or variant described herein are further protected by fluorenylmethyloxycarbonyl group (Fmoc). In some embodiments, the polypeptide or variant is further conjugated to one or more chemical moieties that improve e.g., cell permeability, solubility, and stability of a polypeptide. In some embodiment, the polypeptide or variant is conjugated to a TAT polypeptide (GRKKRRQRRRPQ (SEQ ID NO: 93)).

In some embodiments, the polypeptide or variant consists of an amino acid sequence selected from Table 1, wherein the N-terminus of the polypeptide or variant is further modified with an acetyl group and the C-terminus of the polypeptide or variant is modified with $NH_2$.

In some embodiments, the polypeptide or variant consists of an amino acid sequence of $LRXaa_1IQRXaa_2L$ (SEQ ID NO: 94), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine, wherein the carboxyl group of the second β-alanine unit is modified with $NH_2$ (2-Nal-β-Ala-β-Ala-$NH_2$). This polypeptide may be referred as "WX-021" in this application.

In some embodiments, the polypeptide or variant consists of an amino acid sequence of $LRXaa_1IQRXaa_2L$ (SEQ ID NO: 95), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends. In these embodiments, the N-terminus of the polypeptide or variant may further be modified with an acetyl group. In these embodiments, the C-terminus of the polypeptide or variant may be further modified with two units of β-alanine, wherein the carboxyl group of the second β-alanine unit is modified with $NH_2$ (β-Ala-β-Ala-$NH_2$). This polypeptide may be referred as "WX-022" in this application.

In some embodiments, the polypeptide or variant consists of an amino acid sequence of $LRXaa_1IQRXaa_2L$ (SEQ ID NO: 96), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends. In these embodiments, the N-terminus of the polypeptide or variant may further be modified with an acetyl group. In these embodiments, the C-terminus of the polypeptide or variant may be further modified with 2-Naphthylalanine, wherein the carboxyl group of 2-Naphthylalanine is modified with $NH_2$ (2-Nal-$NH_2$). This polypeptide may be referred as "WX-023" in this application.

In some embodiments, the polypeptide or variant consists of an amino acid sequence of $LQTLRXaa_1IQRXaa_2L$ (SEQ ID NO: 97), wherein $Xaa_1$ and $Xaa_2$ are each alanine and a hydrocarbon crosslinker is present between $Xaa_1$ and $Xaa_2$. In these embodiments, the hydrocarbon crosslinker is —CH2-CH2-CH2-CH=CH—CH2-CH2-CH2-, having an S-configuration at both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine. In these embodiments, the polypeptide may be further conjugated to a TAT peptide (GRKKRRQRRRPQ (SEQ ID NO: 93)). This polypeptide may be referred as "WX-029" in this application.

In some embodiments, the polypeptide or variant consists of an amino acid sequence of $Xaa_1LQXaa_2LRXaa_3IQRXaa_4L$ (SEQ ID NO: 98), wherein $Xaa_1$, $Xaa_2$, $Xaa_3$ and $Xaa_4$ are each alanine and a first hydrocarbon crosslinker is present between $Xaa_1$ and $Xaa_2$ and a second hydrocarbon crosslinker is present between $Xaa_3$ and $Xaa_4$. In these embodiments, the first hydrocarbon crosslinker is —CH2-CH2-CH2-CH=CH—CH2-CH2-CH2-, having an S-configuration on one end and an R-configuration on the other end, whereas the second hydrocarbon crosslinker is —CH2-CH2-CH2-CH=CH—CH2-CH2-CH2-, having an S-configuration on both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine. In these embodiments, the polypeptide may be further conjugated to a TAT peptide (GRKKRRQRRRPQ (SEQ ID NO: 93)). This polypeptide may be referred as "WX-036" in this instant application.

In some embodiments, a polypeptide described herein consists of an amino acid sequence of $Xaa_1DQXaa_2DRXaa_3DQRXaa_4DH$ (SEQ ID NO: 99), wherein $Xaa_1$, $Xaa_2$, $Xaa_3$ and $Xaa_4$ are each alanine and a first hydrocarbon crosslinker is present between $Xaa_1$ and $Xaa_2$ and a second hydrocarbon crosslinker is present between $Xaa_3$ and $Xaa_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends. In these embodiments, the N-terminus of the polypeptide or variant may further be modified with an acetyl group. In these embodiments, the C-terminus of the polypeptide or variant may be further modified with two units of (β-alanine, wherein the carboxyl group of the second β-alanine unit is modified with $NH_2$ (β-Ala-β-Ala-$NH_2$). This polypeptide may be referred as "WX-037" in this application.

In some embodiments, a polypeptide described herein comprises or consists of an amino acid sequence of $Xaa_1LEXaa_2LRXaa_3IERXaa_4L$ (SEQ ID NO: 100), wherein $Xaa_1$, $Xaa_2$, $Xaa_3$ and $Xaa_4$ are each alanine and a first hydrocarbon crosslinker is present between $Xaa_1$ and $Xaa_2$ and a second hydrocarbon crosslinker is present between $Xaa_3$ and $Xaa_4$. In these embodiments, the first hydrocarbon crosslinker is —CH2-CH2-CH2-CH=CH—CH2-CH2-CH2-, having an S-configuration on one end and an R-configuration on the other end whereas the second hydrocarbon crosslinker is —CH2-CH2-CH2-CH=CH—CH2-CH2-CH2-, having an S-configuration on both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine, wherein the carboxyl group of the second β-alanine unit is modified with $NH_2$ (2-Nal-β-Ala-β-Ala-$NH_2$). This polypeptide may be referred as "WX-038" in this application.

In some embodiments, a polypeptide described herein comprises or consists of an amino acid sequence of $RXaa_1LQXaa_2LRXaa_3IQRXaa_4L$ (SEQ ID NO: 101), wherein $Xaa_1$, $Xaa_2$, $Xaa_3$ and $Xaa_4$ are each alanine and a first hydrocarbon crosslinker is present between $Xaa_1$ and $Xaa_2$ and a second hydrocarbon crosslinker is present between Xaa$_3$ and Xaa$_4$. In these embodiments, the first hydrocarbon crosslinker is —CH2-CH2-CH2-CH═CH—CH2-CH2-CH2-, having an S-configuration on one end and an R-configuration on the other end whereas the second hydrocarbon crosslinker is —CH2-CH2-CH2-CH═CH—CH2-CH2-CH2-, having an S-configuration on both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine, wherein the carboxyl group of the second β-alanine unit is modified with NH$_2$ (2-Nal-β-Ala-β-Ala-NH$_2$). This polypeptide may be referred as "WX-039" in this application.

In some embodiments, a polypeptide described herein comprises and/or consists of an amino acid sequence of LQXaa$_1$LRDIQRXaa$_2$L (SEQ ID NO: 102), wherein Xaa$_1$ and Xaa$_2$ are each alanine and a hydrocarbon crosslinker is present between Xaa$_1$ and Xaa$_2$. In these embodiments, the hydrocarbon crosslinker is —CH$_2$—CH$_2$—CH$_2$—CH$_2$—CH$_2$—CH$_2$—CH═CH—CH$_2$—CH$_2$—CH$_2$—, having an R-configuration on one end and an S-configuration on the other end. In these embodiments, the N-terminus of the polypeptide or variant may further be modified with an acetyl group. In these embodiments, the C-terminus of the polypeptide or variant may be further modified with 2-Naphthylalanine linked to two units of (β-alanine, wherein the carboxyl group of the second β-alanine unit is modified with NH$_2$ (2-Nal-β-Ala-β-Ala-NH$_2$). This polypeptide may be referred as "WX-040" in this application.

In some embodiments, the polypeptide or variant consists of an amino acid sequence of LQTLRXaa$_1$IQRXaa$_2$L (SEQ ID NO: 103), wherein Xaa$_1$ and Xaa$_2$ are each alanine and a hydrocarbon crosslinker is present between Xaa$_1$ and Xaa$_2$. In these embodiments, the hydrocarbon crosslinker is —CH2-CH2-CH2-CH═CH—CH2-CH2-CH2-, having an S-configuration at both ends. In these embodiments, the N-terminus of the polypeptide or variant may further be modified with an acetyl group. In these embodiments, the C-terminus of the polypeptide or variant may be further modified with 2-Naphthylalanine, wherein the carboxyl group of 2-Naphthylalanine is modified with NH$_2$ (2-Nal-NH$_2$). This polypeptide may be referred as "WX-024" in this application. The chemical structure of WX-024 is shown in FIG. 1A.

Figure 1B:
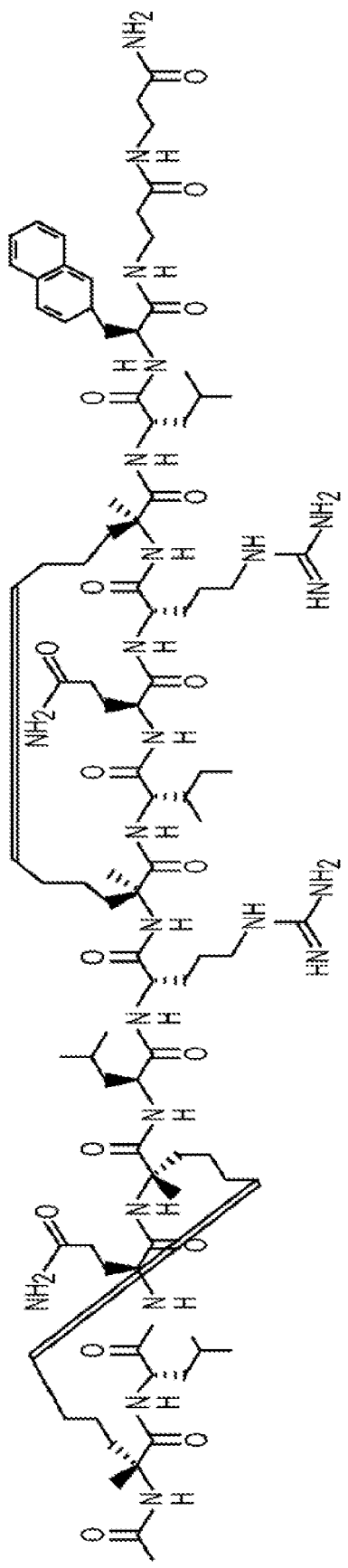

In some embodiments, the polypeptide or variant consists of an amino acid sequence of Xaa$_1$LQXaa$_2$LRXaa$_3$IQRXaa$_4$L (SEQ ID NO: 104), wherein Xaa$_1$, Xaa$_2$, Xaa$_3$ and Xaa$_4$ are each alanine and a first hydrocarbon crosslinker is present between Xaa$_1$ and Xaa$_2$ and a second hydrocarbon crosslinker is present between Xaa$_3$ and Xaa$_4$. In these embodiments, the first hydrocarbon crosslinker is —CH2-CH2-CH2-CH═CH—CH2-CH2-CH2-, having an S-configuration on one end and an R-configuration on the other end, whereas the second hydrocarbon crosslinker is —CH2-CH2-CH2-CH═CH—CH2-CH2-CH2-, having an S-configuration on both ends. In these embodiments, the N-terminus of the polypeptide or variant may further be modified with an acetyl group. In these embodiments, the C-terminus of the polypeptide or variant may be further modified with 2-Naphthylalanine linked to two units of β-alanine, wherein the carboxyl group of the second β-alanine unit is modified with NH$_2$ (2-Nal-β-Ala-β-Ala-NH$_2$). This polypeptide may be referred as "WX-035" in this instant application. The chemical structure of WX-035 is shown in FIG. 1B.

3. Hydrocarbon Crosslinkers

The polypeptides described herein can encompass a stabilized polypeptide having one or more hydrocarbon crosslinkers. The hydrocarbon crosslinker may confer a structural constraint(s) of the α-helix of the polypeptide derived from the HD2 domain of BCL9. In one embodiment, the α-helix of a polypeptide derived from the HD2 domain of the BCL9 peptide is stabilized by one or more hydrocarbon crosslinkers. As used herein, the terms "hydrocarbon crosslinker" and "crosslinker" (also known as a hydrocarbon staple, hydrocarbon linker, or a metathesized crosslinker) are used interchangeably and refer to a chemical linker between two amino acids, in which the linker significantly enhances and/or reinforces the secondary structure of a given polypeptide. The hydrocarbon crosslinker as described herein may be based on the incorporation of natural or non-natural amino acids that restrict the structural flexibility of the polypeptide compared to a wildtype (i.e. non-crosslinked) peptide.

For instance, the hydrocarbon crosslinker as used herein may enhance the stability of the α-helical structure of a polypeptide derived from the HD2 domain of human BCL9. The hydrocarbon crosslinker may extend across the length of one or more α-helical turns. As it is generally understood that one α-helical turn comprise about 3 to 4 amino acids, it will also be appreciated that amino acids positioned at e.g., i and i+3; i and i+4; or i and i+7 would be ideal positions for introducing a hydrocarbon crosslinker. For example, a polypeptide having a sequence of $X_1X_2X_3X_4X_5X_6X_7X_8X_9X_{10}$ may be crosslinked by a hydrocarbon crosslinker e.g., between $X_1$ and $X_4$, between $X_1$ and $X_5$, or between $X_1$ and $X_8$. However, other positions may also be considered with alternative intervals to enhance the stability of α-helical structure or other known structures (e.g., β-sheet structure) and/or to introduce a variation to the secondary structure by e.g., altering the number of amino acids per helical turn. Thus, any of the polypeptides derived from the HD2 domain of human BCL9 protein, as discussed herein, may be crosslinked at any suitable positions.

In some embodiments, a stabilized polypeptide described herein comprises a hydrocarbon crosslink at positions i and i+3, i and i+4, or i and i+7. In certain embodiments, the crosslink links a first amino acid (i) and a second amino acid (i+3) that occurs 3 amino acids downstream for the first amino acid. In certain embodiments, the crosslink links a first amino acid (i) and a second amino acid (i+4) that occurs 4 amino acids downstream from the first amino acid. In certain embodiments, the crosslink links a first amino acid (i) and a second amino acid (i+7) that occurs 7 amino acids downstream from the first amino acid.

In some embodiments, a polypeptide described herein comprises two or more hydrocarbon crosslinkers. In some embodiments, the peptide is stabilized with two hydrocarbon crosslinkers. In some embodiments, the peptide is stabilized with three crosslinkers. For example, three crosslinkers may be used for longer structures, such as those with 24 amino acids. The use of two or more hydrocarbon crosslinkers could be beneficial for enhancing and/or reinforcing the secondary structure of a given polypeptide as compared to a polypeptide comprising no hydrocarbon crosslinker or one hydrocarbon crosslinker. Multiple hydrocarbon crosslinks within a single peptide may confer additional stability to the alpha helix, such as better stability and an improved pharmacokinetic profile. In some embodiments, multiple crosslinks are present within a single polypeptide. In certain embodiments, these crosslinks may be sequential with the same distance between amino acids of the crosslink. In one embodiment, two crosslinks are present at positions i and i+3 and positions i' and i'+3. The position i' may reside between i and i+3 or reside after the position i+3. In one embodiment, two crosslinks are at positions i and i+4 and positions i' and i'+4 positions. The position i' may reside between i and i+4 or reside after the position i+4. In one embodiment, two crosslinks are at positions i and i+7 positions and positions i' and i'+7. The position i' may reside between i and i+7 or reside after the position i+7.

In certain embodiments, two crosslinks within a single peptide are at mixed positions, wherein one crosslink is at position i and i+3, i and i+4, or i and i+7; and the other crosslink has a different spacing between the amino acids that are linked. In some embodiments, the polypeptide described herein has two hydrocarbon crosslinkers wherein one crosslinker is at position i and i+3 and the other crosslinker at position i' and i'+4. In some embodiments, the position i' may reside between i and i+3 or reside after the position i+3. In some embodiments, the position i may reside between i' and i'+4 or reside after the position i'+4.

Various hydrocarbon crosslinkers are known in the art. (Azzarito et al., Nature Chemistry 5: 161-173 (2013)). In some embodiments, a hydrocarbon crosslinker disclosed herein is generated by connecting two α,α-disubstituted amino acids incorporated into a single polypeptide. In some embodiments, the hydrocarbon crosslinker is generated by a ring closing metathesis reaction connecting two α,α-disubstituted amino acids. A ring closing metathesis (also referred as a ring closing olefin metathesis) is known in the art (Kim et al., Nature Protocols 6: 761-771 (2011)).

The length of a hydrocarbon crosslinker as described herein may vary depending on the length of the substituents of the α,α-disubstituted amino acid. For instance, by using a suitable α,α-disubstituted amino acid, a hydrocarbon crosslinker generated by a ring closing metathesis reaction may have a length of 1, 2, 3, 4, 5, 6, 7, 8, 9, 10, 11, 12, 13, 14, or 15 carbons. In some embodiments, the hydrocarbon crosslinker has a length of 8-12 carbons. In some embodiments, the hydrocarbon crosslinker has a length of 8 or 11 carbons. In certain embodiments, the hydrocarbon linker is 8-carbons in length. In certain embodiments, the hydrocarbon linker is 11-carbons in length. The length of a hydrocarbon crosslinker may be adjusted depending on whether the hydrocarbon crosslinker would extend over one, two, three, or more helical turns. For instance, a hydrocarbon crosslinker having a length of 8 carbons may be used for connecting i and i+3 or i and i+4 positions. A hydrocarbond crosslinker having a length of 11 carbons may be used to connect i and i+7 positions.

In some embodiments, the hydrocarbon crosslinker is an alkenyl crosslinker. In some embodiments, a hydrocarbon crosslinker described herein is generated by connecting two α-alkyl, α-alkenyl amino acids. In some embodiments, the α-alkyl, α-alkenyl amino acid is an α-methyl, α-alkenyl amino acid. In some embodiments, the α-methyl, α-alkenyl amino acid is an α-methyl, α-alkenyl alanine. In some embodiments, the α-methyl, α-alkenyl alanine is selected from (S)-2-(4'-pentenyl)alanine, (R)-2-(4'-pentenyl)alanine, (S)-2-(7'-octenyl)alanine, and (R)-2-(7'-octenyl)alanine. In some embodiments, the hydrocarbon crosslinker is —CH$_2$—CH$_2$—CH$_2$—CH=CH—CH$_2$—CH$_2$—CH$_2$—. In some embodiments, the hydrocarbon crosslinker is —CH$_2$— CH$_2$—CH$_2$— CH$_2$—CH$_2$— CH$_2$—CH=CH— CH$_2$—CH$_2$—CH$_2$—.

In some embodiments, a hydrocarbon crosslinker described herein may have chirality at either end of the crosslinker. In some embodiments, the hydrocarbon cross linker has an S-configuration on both ends. In some embodiments, the hydrocarbon cross linker has an R-configuration on both ends. In some embodiments, the hydrocarbon cross linker has an S-configuration on one end and an R configuration on the other end. In some embodiments, the hydrocarbon crosslinker is —CH$_2$—CH$_2$—CH$_2$—CH=CH—CH$_2$—CH$_2$—CH$_2$—, having an S-configuration on both ends. In some embodiments, the hydrocarbon crosslinker is —CH$_2$—CH$_2$—CH$_2$—CH=CH—CH$_2$—CH$_2$—CH$_2$—, having an R-configuration on both ends. In some embodiments, the hydrocarbon crosslinker is —CH$_2$—CH$_2$—CH$_2$—CH=CH—CH$_2$—CH$_2$—CH$_2$—, having an S-configuration on one end and an R-configuration on the other end. In some embodiments, the hydrocarbon crosslinker is —CH$_2$—CH$_2$— CH$_2$—CH$_2$— CH$_2$—CH$_2$—CH=CH— CH$_2$—CH$_2$— CH$_2$—, having an S-configuration on both ends. In some embodiments, the hydrocarbon crosslinker is —CH$_2$—CH$_2$— CH$_2$—CH$_2$—CH$_2$—CH$_2$—CH=CH— CH$_2$—CH$_2$— CH$_2$—, having an R-configuration on both ends. In some embodiments, the hydrocarbon crosslinker is —CH$_2$—CH$_2$— CH$_2$—CH$_2$—CH$_2$— CH$_2$—CH=CH— CH$_2$—CH$_2$— CH$_2$—, having an S-configuration on one end and an R-configuration on the other end.

A variety of non-hydrocarbon linkers are known in the literature (see Azzarito et al., Nat Chem 5:161-173 (2013)). In some embodiments, the peptide is stabilized by a cross-linker that is a disulfide bridge, lactam bridge, hydrogen-bonding surrogate, or triazole staple.

4. Preparation and Purification of Peptides with Hydrocarbon Cross-Linkers

The present disclosures also provide methods to manufacture a polypeptide described herein. Such methods may comprise generating a polypeptide that is capable of undergoing a reaction to form one or more hydrocarbon cross-linkers, wherein the polypeptide comprises any sequence selected from Table 1 or a variant thereof. In some embodiments, the method comprises generating a polypeptide comprising LQTLRXaa$_1$IQRXaa$_2$L (SEQ ID NO: 1), Xaa$_1$LQXaa$_2$LRXaa$_3$IQRXaa$_4$L (SEQ ID NO: 2), or a variant thereof. In some embodiments, Xaa$_1$, Xaa$_2$, Xaa$_3$, and Xaa$_4$ are each an α, α-disubstituted amino acid; Xaa$_1$ and Xaa$_2$ are each an α, α-disubstituted amino acid and a hydrocarbon crosslinker is present between Xaa$_3$ and Xaa$_4$; or Xaa$_3$ and Xaa$_4$ are each an α, α-disubstituted amino acid and a hydrocarbon crosslinker is present between Xaa$_1$ and Xaa$_2$. In some embodiments, the α,α-disubstituted amino acid is an α-methyl, α-alkenyl amino acid.

In some embodiments, a method for manufacturing a polypeptide described herein comprises performing one or more chemical synthesis methods known to the skilled artisan and described herein. See, for example, Fields et al., Chapter 3 in Synthetic Peptides: A User's Guide, ed. Grant, W.H. Freeman & Co., New York, N.Y., 1992, p. 77; and Bird, G. H., et al., Methods Enzymol 446, 369-86 (2008). In some embodiments, a method for manufacturing a polypeptide described herein comprises using solid phase synthesis to generate the polypeptide. For instance, the polypeptide described herein may be manufactured by the automated Merrifield techniques of solid phase synthesis with the alpha-NH$_2$ protected by either t-Boc or Fmoc chemistry using side chain protected amino acids on, for example, an Applied Biosystems Peptide Synthesizer Model 430A or 431 or the AAPPTEC multichannel synthesizer APEX 396.

In some embodiments, the polypeptide described herein may also be manufactured in a high-throughput, combinatorial fashion, e.g., using a high-throughput multichannel combinatorial synthesizer. Other methods of synthesizing peptides are known in the art.

The methods to manufacture the polypeptides described herein may further comprise forming one or more hydrocarbon crosslinkers. The one or more hydrocarbon crosslinkers may be formed by subjecting the polypeptide described herein to metal-mediated ring-closing olefin metathesis. For instance, the synthetic strategy for generating hydrocarbon crosslinkers based on modified Ala residues (α-methyl, α-alkenyl amino acids) would be known to those of ordinary skill in the art. The hydrocarbon crosslinker connects adjacent turns of the α-helix, flanked on each end by an α-methyl group. The basis of the chemistry to generate this hydrocarbon crosslinker is incorporation of two α-methyl, α-alkenyl amino acids during synthesis of a peptide (see Kim 2011). A hydrocarbon crosslinker between these modified amino acids is then generated by use of a ruthenium-mediated ring-closing olefin metathesis. Following the ring closure, the polypeptide may be deprotected and released from such reaction, resulting in a polypeptide comprising one or more hydrocarbon crosslinkers.

The present disclosures also encompass methods of purifying a polypeptide manufactured according to the methods described herein. In some embodiments, the polypeptide is purified by high-performance liquid chromatograph (HPLC). In some embodiments, the purified polypeptide is substantially free of metal. As used herein, the term "substantially free of metal" refers to a composition comprising a polypeptide described herein and a metal at a concentration of less than about 0.5, 1, 2.5, 5, 10, 20, 30, 40, 50, 60, 70, 80, 90, or 100 ppm. In some embodiments, the purified polypeptide is substantially free of metal, comprising less than about 0.5 ppm. In some embodiments, the purified polypeptide comprises less than about 5 ppm. In some embodiments, the purified polypeptide comprises less than about 20 ppm.

A polypeptide manufactured according to the method disclosed herein may exist in various forms in the presence or absence of a solvent. For instance, the polypeptide may exist as powder, salt, liquid, crystal, or lyophilized composition. In some embodiments, the polypeptide described herein exists as a salt form or crystal. Examples of suitable salt forms include acetate, trifluoroacetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. The terms "crystal" and "crystallized" refer to a polypeptide that exists in the form of a crystal. Crystals are one form of the solid state of matter, which is distinct from other forms such as the amorphous solid state or the liquid crystalline state. The salt form or crystal of a polypeptide described herein retains one or more biological functions of the polypeptide that is manufactured in a different form (e.g., a powder form). In some embodiments, the salt form is trifluoroacetic salt, acetic salt, or hydrochloric salt. In some embodiments, the polypeptide described herein exists in a salt form and is stable at room temperature for at least one month. In some embodiment, the polypeptide described herein is stable at 2-8° C. for at least one month.

A polypeptide described herein may be conjugated to one or more chemical moieties that are known to improve e.g., cell permeability, solubility, and stability of a given polypeptide. The term "conjugate" refers to a polypeptide that is chemically linked to a second chemical moiety. In some embodiments, the polypeptide is conjugated to one or more modifications e.g., a cell-permeability increasing moiety and a cell targeting moiety. Various modifications in these categories are known in the art. For instance, the polypeptide described herein may be PEGylated, a modification known to facilitate cellular uptake, increases bioavailability, increases blood circulation and half-life, alters pharmacokinetics, decreases immunogenicity and/or decreases the needed frequency of administration. In some embodiments, the polypeptide described herein is conjugated to Ant8 (Antennapedia 8-mer peptide), TAT peptide (GRKKRRQRRRPQ (SEQ ID NO: 93)), or one or more units of β-alanine.

In various embodiments, a polypeptide described herein may also be conjugated to an agent. In some embodiment, the agent is an immunoadhesion molecule, an imaging agent, a therapeutic agent, or a cytotoxic agent. In an embodiment, the imaging agent is a radiolabel, an enzyme, a fluorescent label, a luminescent label, a bioluminescent label, a magnetic label, or biotin. In another embodiment, the radiolabel is $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$. In yet another embodiment, the therapeutic or cytotoxic agent is an anti-metabolite, an alkylating agent, an antibiotic, a growth factor, a cytokine, an anti-angiogenic agent, an anti-mitotic agent, an anthracycline, toxin, or an apoptotic agent, anti-cancer agent, an immunosuppressive agent, or an immune reaction stimulatory agent.

In various embodiments, an isolated nucleic acid encoding a polypeptide disclosed herein is also provided. Also provided is a vector (e.g., an expression vector) comprising the isolated nucleic acid disclosed herein.

In another aspect, a host cell is transformed with the vector disclosed herein. In an embodiment, the host cell is a prokaryotic cell, for example, E. coli. In another embodiment, the host cell is a eukaryotic cell, for example, a protist cell, an animal cell, a plant cell, or a fungal cell. In an embodiment, the host cell is a mammalian cell including, but not limited to, CHO, COS, NS0, SP2, PER.C6, or a fungal cell, such as *Saccharomyces cerevisiae*, or an insect cell, such as Sf9.

In various embodiments, a polypeptide disclosed herein can be prepared by culturing any one of the host cells disclosed herein in a culture medium under conditions sufficient to produce the polypeptide.

5. Pharmaceutical Composition

In various embodiments, pharmaceutical compositions comprising one or more of the polypeptides disclosed herein, either alone or in combination with other prophylactic agents, therapeutic agents, and/or pharmaceutically acceptable carriers, are provided. In some embodiments, the pharmaceutical composition may comprise one, two, three, or more polypeptides described herein. The pharmaceutical compositions comprising polypeptides provided herein are for use in, but not limited to, diagnosing, detecting, or monitoring a disorder, in preventing, treating, managing, or ameliorating a disorder or one or more symptoms thereof, and/or in research.

A "pharmaceutically acceptable carrier" refers to e.g., any and all solvents, solids, semisolids, liquid fillers, diluents, encapsulating materials, formulation auxiliaries, media, isotonic and absorption delaying agents, for use with a polypeptide described herein to comprises a "pharmaceutical composition" suitable for administration to a subject. The use of such media and agents for pharmaceutically active substances is well known in the art. Supplementary active compounds can also be incorporated into the compositions.

The pharmaceutically acceptable carrier may be selected based on the use and/or administration route of the composition.

The pharmaceutical compositions may be formulated into any of many possible dosage forms, such as, e.g., tablets, capsules, gel capsules, powders, or granules. The pharmaceutical compositions may also be formulated as solutions, suspensions, emulsions, or mixed media. In some embodiments, the pharmaceutical compositions may be formulated as lyophilized formulations or aqueous solutions.

In some embodiments, a pharmaceutical composition may be formulated as a solution. For example, the polypeptides described herein may be administered in an unbuffered solution, such as, e.g., in saline, in water, or in dimethyl sulfoxide (DMSO). In some embodiments, the polypeptides may also be administered in a suitable buffer solution. For example, the buffer solution may comprise acetate, citrate, prolamine, carbonate, or phosphate, or any combination thereof. In some embodiments, the buffer solution may be phosphate buffered saline (PBS). The pH and osmolality of the buffer solution containing the polypeptides can be adjusted to be suitable for administering to a subject.

In some embodiments, the pharmaceutical compositions may be formulated as suspensions in aqueous, non-aqueous, or mixed media. In some embodiments, the pharmaceutical composition is formulated in mixed media comprising water and DMSO. Aqueous suspensions may further contain substances which increase the viscosity of the suspension including, for example, sodium carboxymethylcellulose, sorbitol and/or dextran. The suspension may also contain stabilizers.

In some embodiments, the pharmaceutical composition is used for in vivo administration and may be sterile. Sterility may be readily accomplished, e.g., by filtration through sterile filtration membranes.

In various embodiments, a pharmaceutical composition comprising a polypeptide described herein may further comprise at least one additional agent. In some embodiments, the at least one additional agent is selected from one or more of a checkpoint inhibitor, an EGFR inhibitor, a VEGF inhibitor, a VEGFR inhibitor, and an anti-cancer drug.

In some embodiments, the pharmaceutical composition described herein comprises a checkpoint inhibitor. In an embodiment, the checkpoint inhibitor is an anti-PD-1 antibody, an anti-PD-L1 antibody, or an anti-CTLA4 antibody. In an embodiment, the checkpoint inhibitor targets a stimulatory checkpoint molecule such as e.g., CD27, CD40, OX40, GITR, or CD138. In yet another embodiment, the checkpoint inhibitor targets an inhibitory checkpoint molecule such as e.g., A2AR, B7-H3, B7-H4, B and T lymphocyte attenuator (BTLA), indoleamine 2,3-dioxygenase (IDO), Killer-cell immunoglobulin-like receptor (KIR), Lymphocyte Activation Gene-3 (LAG3), T-cell Immunoglobulin domain and Mucin domain 3 (TIM-3), VISTA (C10 or f54), or V-domain Ig suppressor of T cell activation.

In some embodiments, a pharmaceutical composition described herein comprises an EGFR inhibitor. In an embodiment, the EGFR inhibitor is erlotinib, gefitinib, lapatinib, panitumumab, vandetanib, or cetuximab.

In some embodiments, a pharmaceutical composition described herein comprises a VEGF or VEGFR inhibitor. In an embodiment, the VEGF or VEGFR inhibitor is pazopanib, bevacizumab, sorafenib, sunitinib, axitinib, ponatinib, regorafenib, vandetanib, cabozantinib, ramucirumab, lenvatinib, or ziv-aflibercept.

In some embodiments, a pharmaceutical composition described herein comprises an anti-cancer drug. The anti-cancer drug may be selected from: cyclophosphamide, methotrexate, 5-fluorouracil (5-FU), doxorubicin, mustine, vincristine, procarbazine, prednisolone, dacarbazine, bleomycin, etoposide, cisplatin, epirubicin, capecitabine, folinic acid, actinomycin, all-trans retinoic acid, azacitidine, azathioprine, bortezomib, carboplatin, chlorambucil, cytarabine, daunorubicin, docetaxel, doxifluridine, fluorouracil, gemcitabine, hydroxyurea, idarubicin, imatinib, irinotecan, mechlorethamine, mercaptopurine, mitoxantrone, paclitaxel, pemetrexed, teniposide, tioguanine, topotecan, valrubicin, vinblastine, vindesine, vinorelbine, and oxaliplatin.

C. Biological Function of Polypeptides Derived from the HD2 Domain of BCL9

The present disclosures encompass a polypeptide derived from the HD2 domain of human BCL9 protein or a variant thereof, including stabilized peptides, wherein the polypeptide exhibits favorable biological functions in one or more of the following categories: (a) the binding kinetics (on-rate, off-rate and affinity) of a polypeptide to BCL9, (b) potencies in various biochemical and cellular bioassays, (c) in vivo efficacies in relevant tumor models, (d) pharmacokinetic and pharmacodynamics properties, and (e) toxicological properties.

In some embodiments, a polypeptide described herein exhibits favorable biological functions in some or each of the categories listed above, e.g., potencies in various biochemical and cellular bioassays including a cell-based Wnt and/or β-catenin transcription assay. The term "biological function" refers the measured in vitro or in vivo action of a polypeptide described herein. In some embodiments, the polypeptide described herein has one or more improved biological functions as compared to an unstapled wild-type human BCL9 HD2 domain or a wild-type fragment, selected from: (1) inhibiting binding of BCL9 to β-catenin; (2) inhibiting canonical Wnt/β-catenin signaling; (3) decreasing regulatory T cell survival; (4) decreasing expression of VEGF in a tumor; (5) increasing CD4+ T cell and CD8+ T cell infiltration into a tumor; (6) increasing T helper 17 (Th17) cell numbers in a tumor; (7) modulating dendritic cells in a tumor; (8) having a half-life (T½) greater than at least 2 hours when administrated to a subject; (9) inducing a tumor microenvironment favoring an immune reaction; and (10) inhibiting tumor growth, cancer stem cell proliferation, and/or tumor metastasis. Various assays are known in the art for measuring these properties and can be used herein.

In some embodiments, WX-024 has one or more improved biological functions as compared to another stapled peptide, an unstapled wild-type human BCL9 HD2 domain, or a wild-type fragment, wherein the biological function is selected from the biological functions described herein. In some embodiments, the improved biological function is one or more of activity (e.g., as measured in vitro and/or in vivo) and pharmacokinetics. In some embodiments, WX-035 has one or more improved biological functions as compared to another stapled peptide, an unstapled wild-type human BCL9 HD2 domain, or a wild-type fragment, wherein the biological function is selected from the biological functions described herein. In some embodiments, the improved biological function is one or more of activity (e.g., as measured in vitro and/or in vivo) and pharmacokinetics.

The present disclosures also encompass a variant of the polypeptide, where the variant differs from the wild-type polypeptide in amino acid sequences and/or chemical structure, but retains one or more biological functions of the polypeptide.

As used herein, the terms "improve," "increase," "enhance," "elevate," "upregulate," and "promote" one or more biological functions are all used interchangeably, and mean that the levels or activities of one or more biological functions or readouts of the functions from in vitro and/or in vivo assays are increased above levels or activities observed in the absence of the polypeptide described herein and/or higher than a vehicle or control polypeptide (e.g., an unstapled wild-type human BCL9 HD2 domain, a polypeptide that does not comprise the core functional domain mediating the interaction between BCL9 and β-catenine, or a control polypeptide comprising a sequence not derived from the HD2 domain of human BCL9 etc.). For instance, without being bound to any theory, the polypeptide described herein may have an improved biological function in inhibiting binding of BCL9 to β-catenin, as assessed in various in vitro assays e.g., in a homogenous time resolved fluorescence (HTRF) assay, as compared to a control polypeptide, e.g., an unstapled wild-type human BCL9 HD2 domain. In this context, a polypeptide described herein may have an improved $K_D$ value as compared to that of the control polypeptide or the polypeptide described herein may bind to β-catenin in presence of the control polypeptide, indicating that the polypeptide described herein has an improved ability to inhibit binding of BCL9 to β-catenin as compared to the control polypeptide.

In some embodiments, the assay used to assess the biological function of the polypeptide described herein provides quantitative readout(s), and the readouts observed with a disclosed polypeptide are at least 30%, 40%, 50%, 60%, 70%, 80%, 90%, 100%, 200%, 300%, or more changed/improved as compared to those observed with a vehicle control polypeptide (e.g., an unstapled wild-type human BCL9 HD2 domain).

Various assays are known in the art for measuring biological activity/function, several of which are described herein as non-limiting examples described for illustrative purpose only.

1. Binding of BCL9 to β-Catenin

In some embodiments, a polypeptide or variant described herein inhibits binding of BCL9 to β-catenin in vitro and/or in vivo. In some embodiments, the polypeptide or variant disclosed herein inhibits the interaction between Pygo and BCL9 or the formation of a Pygo/BCL9/β-catenin complex. Pygopus (Pygo) and Legless (Lgs) were discovered in *Drosophila* as new Wnt signaling components that are essential for Armadillo-mediated transcription during normal development (Belenkaya et al., Development (2002) 129(17): 4089-4101). Pygo and BCL9/Legless transduce the Wnt signal by promoting the transcriptional activity of beta-catenin/Armadillo in normal and malignant cells. The ability of a polypeptide to inhibit binding of BCL9 to β-catenin can be assessed in various assays known in the art. In some embodiments, the polypeptide described herein inhibits binding of BCL9 to β-catenin when assessed in a Homogeneous Time Resolved Fluorescence (HTRF) binding assay. In this assay, a polypeptide is conjugated to a tag that can recognize another tag attached to its target protein (i.e., β-catenin). When the polypeptide is bound to the target protein and therefore the two tags are in proximity, a signal is generated and can be quantitatively read to calculate the binding affinity of the polypeptide. In some embodiments, the binding affinity of the polypeptide in this assay is compared against that of a control polypeptide (e.g., an unstapled wild-type HD2 domain human BCL9) to detect improved binding affinity as compared to that of the control polypeptide, indicating that the polypeptide likely would inhibit binding of BCL9 to β-catenin more efficiently than the control polypeptide. The assay may be conducted in the presence or absence of an untagged control polypeptide. The assay may also be conducted by tagging a control polypeptide (e.g., an unstapled wild-type HD2 domain human BCL9) in the presence or absence of an untagged polypeptide described herein (e.g., WX-024).

In some embodiments, a polypeptide described herein inhibits binding of BCL9 to β-catenin when assessed in an Amplified Luminescence Proximity Homogeneous Assay (ALPHA). In this assay, a polypeptide is conjugated to a donor bead and its target protein (i.e., β-catenin) is attached to an acceptor bead. When the two beads are in proximity due to the binding of the polypeptide to the target protein, a signal is generated and the binding affinity of the polypeptide can be quantitatively calculated. In some embodiments, the binding affinity of the polypeptide in this assay is compared against that of a vehicle or control polypeptide (e.g., an unstapled wild-type HD2 domain human BCL9) to detect improved binding affinity as compared to that of the vehicle or control polypeptide, indicating that the polypeptide likely would inhibit binding of BCL9 to β-catenin more efficiently than the control polypeptide. The assay may be conducted in the presence or absence of an unconjugated control polypeptide. The assay may also be conducted by conjugating the control polypeptide in the presence or absence of an unconjugated polypeptide described herein (e.g., WX-024).

In various embodiments, a polypeptide described herein inhibits binding of BLC9 to β-catenin when assessed in a Wnt transcription assay. In some embodiments, the Wnt transcription assay is a cell-based assay. In some embodiments, the cell-based Wnt transcription assay is a GeneBLAzer® beta-lactamase (bla) reporter assay. Various cell lines, transformed cell lines or primary cells derived from a healthy subject or subject suffering from a disease can be used in this assay. A cell line known to be dependent on canonical Wnt/β-catenin signaling for its survival may also be used. In some embodiments, CellSensor™ LEF/TCF-bla HCT-116 cells are used in this reporter assay. These cells contain a beta-lactamase (BLA) reporter gene under the control of a β-catenin/LEF/TCF response element stably integrated into HCT-116 cells. As the cells constitutively express beta-lactamase, adding a polypeptide that inhibits binding of BCL9 to β-catenin in this assay leads to reduced production of beta-lactamase. The efficiency of the polypeptide in suppressing Wnt transcription can therefore be quantitavely calculated in this assay. In some embodiments, a polypeptide described herein suppresses the Wnt transcription as measured in a GeneBLAzer® beta-lactamase (bla) reporter assay, which is indicative of the ability of the polypeptide to inhibit binding of BCL9 to β-catenin. In some embodiments, a polypeptide tested in this assay shows an improved $IC_{50}$ in suppressing Wnt transcription as compared to that of a vehicle or control polypeptide (e.g., an unstapled wild-type HD2 domain human BCL9), indicating that the disclosed polypeptide likely inhibits binding of BCL9 to β-catenin more efficiently than the vehicle or control polypeptide.

In some embodiments, a polypeptide described herein inhibits binding of BLC9 to β-catenin when assessed in a cell-viability assay. In some embodiments, the cell-viability assay is a CellTiterGlo luminescent assay, wherein the viability of cells is quantitatively measured. Various cell lines, transformed cell lines or primary cells derived from a healthy subject or subject suffering from a disease can be used in this assay. In some embodiments, a polypeptide described herein suppresses cell growth in this assay more efficiently than a vehicle or control polypeptide (e.g., an unstapled wild-type HD2 domain human BCL9), indicating that the disclosed polypeptide likely inhibits binding of BCL9 to β-catenin more efficiently than the vehicle or control polypeptide.

2. Canonical Wnt/β-Catenin Signaling

In certain embodiments, the polypeptides described herein can inhibit canonical Wnt/β-catenin signaling. Canonical Wnt/β-catenin signaling can be assessed in various in vitro and/or in vivo assays. In some embodiments, the effect of the polypeptide described herein on canonical Wnt/β-catenin signaling is assessed in a cell-based Wnt transcription assay, e.g., a GeneBLAzer® beta-lactamase (bla) reporter assay. The GeneBLAzer® beta-lactamase (bla) reporter assay measures the strength of canonical Wnt/β-catenin signaling by its ability to control the β-catenin/LEF/TCF response element and therefore can be used to assess whether a test agent can attenuate or increase the strength of canonical Wnt/β-catenin signaling control of its transcription targets. In some embodiments, a polypeptide described herein suppresses the Wnt transcription as measured in a GeneBLAzer® beta-lactamase (bla) reporter assay, indicating that the polypeptide can inhibit canonical Wnt/β-catenin signaling. In some embodiments, the polypeptide in this assay shows an improved $IC_{50}$ in suppressing Wnt transcription as compared to that of a vehicle or control polypeptide (e.g., an unstapled wild-type HD2 domain human BCL9), indicating that the polypeptide described herein has an improved ability to inhibit canonical Wnt/β-catenin signaling as compared to the vehicle or control polypeptide.

The ability of a polypeptide described herein to inhibit canonical Wnt/β-catenin signaling may also be assessed by measuring the gene expression and/or protein expression of target genes that are transcriptionally controlled by canonical Wnt/β-catenin signaling. The expression of target genes may be assessed in transformed cells contacted with a polypeptide described herein or a subject administered with such polypeptide. The target genes include e.g., c-myc, ccnd1, cd44, LGR5, VEGFA, AXIN2, and LEFT. The expression level of one or more target genes associated with canonical Wnt/β-catenin signaling may be analyzed using known methods in the art, e.g., cell staining, flow cytometry, western-blotting, and/or real-time quantitative PCR (rt-qPCR) analysis. In some embodiments, a polypeptide described herein reduces the expression of one or more target genes in a cell. In some embodiments, the polypeptide described herein reduces the expression of one or more target gene more efficiently than a vehicle or control polypeptide (e.g., an unstapled wild-type HD2 domain human BCL9).

3. Regulatory T Cell Survival

In some embodiments, a polypeptide described herein decreases regulatory T cell survival. In some embodiments, when administered to a subject, the polypeptide decreases regulatory T cell survival locally (e.g., in a tumor) and/or systemically (e.g., in blood). In some embodiments, when administered to a subject, the polypeptide decreases regulatory T cell survival as compared to a control polypeptide. Various markers, e.g., CD4, FOXP3, and CD25, are known to be expressed on regulatory T cells. The ability of a polypeptide disclosed herein to decrease regulatory T cell survival may be assessed by counting the total number of regulatory T cells present in blood and/or a specific tissue such as a tumor. For instance, samples obtained from a subject contacted with a polypeptide described herein may be stained with antibodies that detect markers associated with regulatory T cells. The samples may also be processed and labeled with antibodies that detect such markers and analyzed by flow cytometry. Gene and/or protein expression of such markers may be determined in a sample and analyzed by e.g., western-blotting and/or rt-qPCR.

In some embodiments, a polypeptide described herein reduces the number of regulatory T cells in blood and/or a tumor when administered to a subject. In some embodiments, the polypeptide reduces the expression of one or more markers associated with regulatory T cells in one or more samples obtained from a subject administered with the polypeptide. In some embodiments, the polypeptide further reduces the expression of the one or more markers as compared to a vehicle or control polypeptide (e.g., an unstapled wild-type HD2 domain human BCL9), when assessed in vivo.

4. VEGF Expression in a Tumor

In certain embodiments, a polypeptide described herein decreases the expression of VEGF in a tumor when administered to a subject bearing the tumor. Various assays to measure the gene expression and/or protein expression of VEGF in a tumor sample can be employed. For instance, after contacting the subject with the polypeptide, tumor cells may be collected and stained with an anti-VEGF antibody to detect VEGF protein. The cells may also be analyzed by e.g., rt-qPCR to determine the gene expression of VEGF. Other assays that indicate the change of VEGF expression can be employed. For instance, tumor samples from a subject contacted with a polypeptide described herein may be analyzed to detect various angiogenic markers controlled by VEGF. In some embodiments, a polypeptide described herein decreases the expression of VEGF more effectively than a vehicle or control polypeptide (e.g., an unstapled wild-type HD2 domain human BCL9).

5. CD4+ and/or CD8+ T Cell Infiltration into Tumor

In some embodiments, a polypeptide described herein increases CD4+ T cell and/or CD8+ T cell infiltration into a tumor when administered to a subject bearing the tumor. The infiltration of CD4+ T cells and/or CD8+ T cells into a tumor may be assessed by counting the total number of CD4+ T cells and/or CD8+ T cells present in a tumor or a sample (e.g., a biopsy) from the tumor. In some embodiments, a polypeptide described herein increases CD4+ T cell and/or CD8+ T cell infiltration into a tumor when administered to a subject bearing the tumor more effectively than a vehicle or control polypeptide (e.g., an unstapled wild-type HD2 domain human BCL9). Various markers, e.g., CD4 and CD45, are known to be expressed on CD4+ T cells, also referred as helper T cells. Various markers, e.g., CD8 and CD45, are known to be expressed on CD8+ T cells, also referred as cytotoxic T cells. The ability of the polypeptide to increase CD4+ and/or CD8+ T cell infiltration into a tumor may be assessed in vivo, by administering the polypeptide to a subject having a tumor. A tumor sample can be collected from the subject and stained with antibodies that detect markers associated with CD4+/CD8+ T cells. The samples may also be processed and labeled with, e.g., antibodies that detect such markers and analyzed by, e.g., flow cytometry. Gene and/or protein expression of such markers may also be determined in a sample and analyzed by e.g., western-blotting and/or rt-qPCR. In some embodiments, a polypeptide described herein increases the total amount of CD4+ T cells and/or CD8+ T cells in a tumor as compared to a vehicle or control polypeptide (e.g., an unstapled wild-type HD2 domain human BCL9).

In some embodiments, a polypeptide described herein increases the total number of CD4+ T cells and/or CD8+ T cells in blood when administered to a subject. The systemic increase of CD4+ T cells and/or CD8+ T cells may indicate increased CD4+ T cell and/or CD8+ T cell infiltration into a specific tissue as well, e.g., a tumor. In some embodiments, a polypeptide described herein increases the amount of circulating CD4+ T cells and/or CD8+ T cells in vivo as compared to a vehicle or control polypeptide (e.g., an unstapled wild-type HD2 domain human BCL9).

6. T Helper 17 Cell Infiltration into Tumor

In some embodiments, a polypeptide described herein increases T helper 17 cell infiltration into a tumor when administered to a subject bearing the tumor. The infiltration of T helper 17 cells into a tumor may be assessed by counting the total number of T helper 17 cells present in the tumor. In some embodiments, a polypeptide described herein increases T helper 17 cell infiltration into a tumor when administered to a subject bearing the tumor as compared to a vehicle or control polypeptide (e.g., an unstapled wild-type HD2 domain human BCL9). Various markers, e.g., IL-17, are known to be expressed on T helper 17 cells. The ability of the polypeptide to increase T helper 17 cell infiltration into a tumor may be assessed in vivo, by administering the polypeptide to a subject having a tumor. A tumor sample can be collected from the subject and stained with, e.g., antibodies that detect markers associated with T helper 17 cells. The samples may also be processed and labeled with antibodies that detect such markers and analyzed by flow cytometry. Gene and/or protein expression of such markers may also be determined in a sample and analyzed by e.g., western-blotting and/or rt-qPCR. The samples may be analyzed to detect the amount of IL-17 present in the samples.

In some embodiments, a polypeptide described herein increases the total amount of T helper 17 cells in blood when administered to a subject. The systemic increase of T helper 17 cells may indicate increased T helper 17 cells infiltration into a specific tissue, e.g., a tumor. The systemic increase of T helper 17 cells may be assessed by measuring the amount of IL-17 present in blood samples collected from a subject. In some embodiments, the polypeptide increases the amount of circulating T helper 17 cells in a subject as compared to a vehicle or control polypeptide (e.g., an unstapled wild-type HD2 domain human BCL9). In some embodiments, a polypeptide described herein increases the amount of circulating IL-17 in a subject as compared to a control polypeptide.

7. Dendritic Cells in Tumor

In some embodiments, a polypeptide described herein modulate dendritic cells present in a tumor when administered to a subject bearing the tumor. The number of dendritic cells present in a tumor may be assessed, e.g., by staining the tumor with antibodies that recognize one or more markers associated with dendritic cells. In some embodiments, a polypeptide described herein decreases dendritic cells present in a tumor when administered to a subject bearing the tumor more effectively than a vehicle or control polypeptide (e.g., an unstapled wild-type HD2 domain human BCL9). In some embodiments, a polypeptide described herein increases dendritic cells present in a tumor when administered to a subject bearing the tumor more effectively than a vehicle or control polypeptide (e.g., an unstapled wild-type HD2 domain human BCL9). Various markers, e.g., CD11c, are known to be expressed on dendritic cells. The ability of the polypeptide to decrease dendritic cells in a tumor may be assessed in vivo, by administering the polypeptide to a subject. A tumor sample can be collected from the subject and stained with antibodies that detect markers associated with dendritic cells. The samples may also be processed and labeled, e.g., with antibodies that detect such markers and analyzed by, e.g., flow cytometry. Gene and/or protein expression of such markers and analyzed by e.g., western-blotting and rt-qPCR.

In some embodiments, a polypeptide described herein decreases the total amount of dendritic cells in blood when administered to a subject. In some embodiments, a polypeptide described herein increases the total amount of dendritic cells in blood when administered to a subject. The systemic decrease of dendritic cells may indicate that the amount of dendritic cells in a specific tissue, e.g., a tumor, has also decreased. In some embodiments, a polypeptide described herein decreases the amount of circulating dendritic cells in a subject as compared to a vehicle or control polypeptide (e.g., an unstapled wild-type HD2 domain human BCL9). In some embodiments, a polypeptide described herein increases the amount of circulating dendritic cells in a subject as compared to a vehicle or control polypeptide (e.g., an unstapled wild-type HD2 domain human BCL9).

8. Half-Life in a Subject

In various embodiments, a polypeptide described herein has one or more improved pharmacokinetic parameters as compared to a vehicle or control polypeptide (e.g., an unstapled wild-type HD2 domain human BCL9). Such pharmacokinetic parameters may include e.g., a maximum observed concentration ($C_{max}$), time to reach the maximum concentration ($T_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity ($AUC_{0-inf}$), and bioavailability.

Methods for assessing pharmacokinetics of an agent are known in the art. For instance, blood samples from a subject administered with a polypeptide described herein may be obtained at 5 min, 1, 2, 4, 6, 8, 12, and 24 hours post-dose. The concentration of the polypeptide in the blood samples can be analyzed by various analytical tools, e.g., LC/MS. Based on the concentration of the polypeptide at each time point, pharmacokinetic parameters are calculated. As used herein, the term "maximum observed concentration ($C_{max}$)" refers to the maximum serum concentration that a polypeptide achieves after administration. Related to the concept of $C_{max}$, the time to reach the maximum concentration ($T_{max}$) is the time that it takes for a polypeptide to reach the maximum serum concentration. The terms "terminal half-life ($T_{1/2}$)" and "half-life ($T_{1/2}$)" are used interchangeably and refer to the time that a polypeptide takes to lose half of its serum concentration. Total body clearance (CL) represents the volume of blood completely cleared of a polypeptide per unit time. The term "volume of distribution ($V_z$)" refers to a theoretically calculated volume that would be required to contain the total amount of a polypeptide administered to a subject at the same concentration observed in the blood. The term "bioavailability" refers to the degree and rate at which a drug is absorbed into a living system or is made available at the site of physiological activity. Bioavailability can be a function of several of the previously described properties, including stability, solubility, immunogenicity and pharmacokinetics, and can be assessed using methods known to one skilled in the art.

In some embodiments, a polypeptide described herein has an improved half-life in a subject as compared to a control polypeptide. In some embodiments, the polypeptide has a half-life greater than at least 0.5, 1, 2, 3, 5, or 8 hours when administered to a subject, or any time period in between. In some embodiments, the polypeptide described herein has a half-life greater than at least 2 hours when administered to a subject. Pharmacokinetic parameters of the polypeptide may be assessed in a mammal including e.g., a mouse, a rat, or a human. The parameters may also be assessed using various administration routes, e.g., intravenous, intraperitoneal, subcutaneous, and intramuscular administration routes. In some embodiments, the pharmacokinetic parameters of the polypeptide described herein are assessed in mice. In some embodiments, the pharmacokinetic parameters of the polypeptide described herein are assessed in mice administered with the polypeptide subcutaneously. In some embodiments, the pharmacokinetic parameters of the polypeptide described herein are assessed in humans. In some embodiments, the pharmacokinetic parameters of the polypeptide described herein are assessed in humans after subcutaneous administration.

9. Tumor Microenvironment Favoring Immune Reaction

In various embodiments, a polypeptide described herein induces a tumor microenvironment favoring an immune reaction. In various embodiments, a polypeptide described herein induces a tumor microenvironment more favorable to an immune reaction than a vehicle or control polypeptide (e.g., an unstapled wild-type HD2 domain human BCL9).

As used herein, the term "tumor microenvironment" means a cellular microenvironment in and/or around a tumor, including various cells recruited to the tumors, blood vessels, immune cells, signaling molecules, and extracellular matrix. See e.g., Balkwill et al., *J Cell Sci* (2012) 125: 5591-5596. The polypeptide described herein may alter the composition of immune cells and/or signaling molecules in and/or around a tumor, thereby eliciting an immune reaction in the microenvironment around the tumor.

Various parameters may be used to assess a tumor microenvironment. For instance, an increased ratio between cytotoxic T cells and regulatory T cells in and/or around tumor tissues may indicate that a tumor microenvironment favors an immune reaction. A decreased amount of dendritic cells and/or regulatory T cells in and/or around tumor tissue may also indicate that a tumor microenvironment favors an immune reaction. Other parameters include increased circulating T cells in peripheral blood and an increased ratio between T helper 17 cells and regulatory T cells in and/or around tumor tissues. These parameters may indicate that a tumor microenvironment favors an immune reaction.

In some embodiments, a polypeptide described herein may increase the ratio between the amount of cytotoxic T cells and the amount of regulatory T cells in a tumor microenvironment. In some embodiments, the ratio change caused by the polypeptide is greater than that caused by a vehicle or control polypeptide (e.g., an unstapled wild-type HD2 domain human BCL9).

In some embodiments, a polypeptide described herein may increase the ratio between T helper 17 cells and regulatory T cells in a tumor microenvironment. In some embodiment, the ratio change caused by the polypeptide is greater than that caused by a vehicle or control polypeptide (e.g., an unstapled wild-type HD2 domain human BCL9).

10. Tumor Growth, Cancer Stem Cell Proliferation, and/or Tumor Metastasis

As Wnt signaling is a regulator of tumor growth, the efficacy of treatments that affect the binding of BCL9 to β-catenin, such as the stabilized peptides of the HD2 domain of the BCL9 peptide described herein, may be assessed in animal models.

The in vivo efficacy of stabilized BCL9 peptides may be assessed in models of human cancers using, e.g., BALB/c nude mice, since xenografts of human cancer cells will grow into tumors in these mice. For example, subcutaneous inoculation with Colo320DM tumor cells, a commercially available cell line derived from human colon cancer tissue, can be used to form a tumor in BALB/c nude mice. Additional in vivo models are also available to assess the in vivo efficacy of a polypeptide disclosed herein. For instance, Human DLD-1 colon cancer cells can be implanted into nude mice to assess tumor growth. The CT26 syngeneic mouse model of colon cancer may also be used, as it allows for assessment of tumor growth in the background of an intact immune system. Other types of cancer cells, e.g., B16 melanoma, 4T1 breast cancer, Renca renal cancer, and Lewis Lung Cell lung cancer cells, may also be used in these known animal models to assess the in vivo efficacy of the polypeptide disclosed herein.

By administering a polypeptide described herein to one or more animal models, the effect of the polypeptide in decreasing tumor growth in vivo may be assessed. In some embodiments, the polypeptide inhibits tumor growth in vivo more effectively than a vehicle or control polypeptide (e.g., an unstapled wild-type HD2 domain human BCL9). In some embodiments, the tumor mass/volume of a subject administered with the polypeptide described herein is at least 10%, 20%, 30%, 40%, 50%, 60%, 70%, 80%, 90%, 95%, or 99% smaller than that of a subject administered with the control polypeptide. From animal data on treatment with stabilized BCL9 peptides, the ability of the peptide to inhibit Wnt signaling can be assessed by e.g., staining of tissue samples with markers of Wnt signaling. These downstream markers of Wnt signaling include e.g., Axin2 and CD44.

Orthotopic mouse models may be used to assess the effects of a polypeptide described herein on tumor metastasis. For instance, an orthotropic animal model may be injected with cells carrying luciferase construct and then administered with its assigned treatment. The presence of the injected cells can be detected by administering luciferin substrate to each treated animal. The intensity of the bioluminescent signal can be quantitatively measured and used as an indicator of cell growth. In some embodiments, a polypeptide described herein suppresses tumor metastasis more effectively than the control polypeptide, when assessed in an orthotopic mouse model. In some embodiments, the polypeptide reduces tumor growth in an orthotopic mouse model at least 10%, 20%, 30%, 40%, 50%, 60%, 70%, 80%, 90%, 95%, or 99% as compared to a vehicle or control polypeptide (e.g., an unstapled wild-type HD2 domain human BCL9).

In some embodiments, the effects of a polypeptide described herein on cancer stem cell proliferation may be assessed by measuring biomarkers of various cancer stem cells. For instance, the expression level of CD44 and/or LGR5 may indicate the amount of cancer stem cells present in a sample. A tumor sample can be collected from a subject and stained with antibodies that detect markers associated with cancer stem cells. The samples may also be processed and labeled, e.g., with antibodies that detect such markers and analyzed by, e.g., flow cytometry. Gene and/or protein expression of such markers can be detected and analyzed by e.g., western-blotting and rt-qPCR. In some embodiments, the polypeptide described herein reduces the expression level of CD44 and/or LGR5 in a tumor when administered to a tumor bearing subject. In some embodiments, a polypeptide described herein more effectively reduces the expression level of CD44 and/or LGR5 than that of a vehicle or control polypeptide (e.g., an unstapled wild-type HD2 domain of human BCL9 protein).

D. Methods of Treatment with Stabilized BCL9 Peptides

1. Diseases with Aberrant Wnt/β-Catenin Signaling

Aberrant Wnt/β-catenin signaling has been implicated in the malignant transformation of normal cells into cancerous cells (see Thakur 2013). Activation of Wnt signaling and β-catenin nuclear localization has been linked to a tumor phenotype in multiple models.

The present disclosure encompasses compositions for use and methods of using the stapled polypeptides disclosed herein to inhibit binding of BCL9 to β-catenin in a subject by administering the polypeptide or a pharmaceutical composition comprising the polypeptide to the subject. The present disclosure also encompasses inhibiting canonical Wnt/β-catenin signaling in a subject by administering a polypeptide or pharmaceutical composition disclosed herein. The present disclosures further encompass methods of treating a disease in a subject by administering a polypeptide or pharmaceutical composition described herein to the subject. The disease may be a cancer or other tumorous disease associated with aberrant canonical Wnt/β-catenin signaling.

As used herein, "patient" and "subject" may interchangeably refer to an animal, such as a mammal or a human, being treated or assessed for a disease, disorder, or condition, at risk of developing a disease, disorder, or condition, or having or suffering from a disease, disorder, or condition. In some embodiments, the subject is a mammal. In some embodiments, the subject is a human.

In some embodiments, such disease, disorder, or condition may be a disease associated with aberrant canonical Wnt/β-catenin signaling, and/or which could benefit from inhibiting canonical Wnt/β-catenin signaling. In some embodiments, such disease, disorder, or condition is a cancer. In some embodiments, the cancer is a cancer where BCL9 and/or β-catenin are highly expressed. In some embodiments, the cancer is a cancer where BCL9 and β-catenin are co-localized in the nucleus of a cancer cell. In some embodiments, the cancer is selected from: familial adenomatous polyposis (FAP), ocular cancer, rectal cancer, colon cancer, colorectal cancer, cervical cancer, prostate cancer, breast cancer, bladder cancer, oral cancer, benign and malignant tumors, stomach cancer, liver cancer, pancreatic cancer, lung cancer, corpus uteri, ovarian cancer, prostate cancer, testicular cancer, renal cancer, brain/CNS cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, gastric cancer, ovarian cancer, hepatocellular carcinoma, and lymphangiogenesis. In some embodiments, the cancer is colorectal cancer. In some embodiments, the cancer is gastric cancer. In some embodiments, the cancer is ovarian cancer. In some embodiments, the cancer is Hepatocellular carcinoma. In some embodiments, the cancer is breast cancer. In some embodiments, the cancer is prostate cancer. In some embodiments, the cancer is skin melanoma. In some embodiments, the cancer is lung cancer.

In some embodiments, any of the polypeptide or variant disclosed herein or a pharmaceutical composition comprising such polypeptide can be used to treat a disease, e.g., a cancer, listed above. In some embodiment, the polypeptide or variant is WX-024. In some embodiments, the polypeptide or variant is WX-035.

In some embodiments, a tumor volume in a subject is reduced by more than 10%, 20%, 30%, 40%, or 50% (or any percentage inbetween) after administration of one or more dosages of a polypeptide described herein or a pharmaceutical composition comprising the polypeptide, as compared to that of a subject treated with a vehicle or an unstapled peptide. In certain embodiments, the reduction is achieved after 1 week, 2 weeks, 3 weeks, or more of administration (or any time period in between). In some embodiments, the tumor volume of a subject is reduced by more than 50%, as compared to that of a subject treated with a vehicle or unstapled peptide, after 2 weeks of administration. A suitable dosage and/or formulation of a pharmaceutical composition for administration to a subject could be determined by one of skill in the art as the materials and techniques necessary for the various methods of administration are available and known in the art. See e.g., Formulation and delivery of peptides and proteins, $1^{st}$ edition, Washington, ACS, pp. 22-45 and Peptide and protein drug delivery, $1^{st}$ edition, New York, Marcel Dekker, Inc., pp. 247-301. In some embodiment, the tumor volume of a subject administered with WX-024 or a pharmaceutical composition comprising the polypeptide is reduced by more than 50%, as compared to that of a subject treated with a vehicle or unstapled polypeptide, after 2 weeks of administration. In some embodiment, the tumor volume of a subject administered with WX-035 or a pharmaceutical composition comprising the polypeptide is reduced by more than 10%-50%, as compared to that of a subject treated with a vehicle or unstapled polypeptide, after 2 weeks of administration.

In various embodiments, the term "treatment" includes treatment of a subject (e.g. a mammal, such as a human) or a cell to alter the current course of the subject or cell. Treatment includes the alteration of one or more disease parameter, e.g., reduction in tumor volume or any other oncologic measurement known to one of skill in the art. Treatment includes, e.g., administration of a polypeptide described herein or a pharmaceutical composition comprising such polypeptide, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition or the associated symptoms. In various embodiments, the term "treatment" may include relieving, slowing, or reversing the pathological processes or symptoms in a subject suffering from a cancer. In some embodiments, the term "treatment" may include decreasing tumor burden in a subject suffering from a cancer. In some embodiments, the term "treatment" may include improving at least one symptom or measurable parameter of a cancer. It will be apparent to one of skill in the art which biological and/or physiological parameters can be used to access the pathological process of the malignant disease.

Treatment, and the measured parameters of treatment, can be assessed after administration of the polypeptide or pharmaceutical composition alone or in combination with one or more additional therapeutic agents, e.g., as a single bolus or separate sequential administrations. The additional agent may be any of the additional therapeutic agents mentioned herein or known to the skilled artisan. The polypeptide or pharmaceutical composition comprising the polypeptide, and/or the additional agent, may be administered once or multiple times, depending on the chosen regimen.

The present disclosures also encompass a polypeptide or pharmaceutical composition disclosed herein for use in treating a disease in a subject. In some embodiment, the disease may benefit from suppressing canonical Wnt/β-catenin signaling. In some embodiments, the disease is a cancer.

The present disclosures further encompass uses of a polypeptide or pharmaceutical composition disclosed herein in the manufacture of a medicament for treating a disease in a subject. In some embodiment, the disease may benefit from suppressing canonical Wnt/β-catenin signaling. In some an embodiment, the disease is a cancer.

In another embodiment, the disease treated is not cancer. In certain embodiments, the disease is a bone density defect, vascular defect of the eye, familial exudative vitreoretinopathy, early coronary disease, Alzheimer's disease, autosomal-dominant oligodontia, retinal angiogenesis, osteogenesis imperfecta, Tetra-Amelia syndrome, Mullerian-duct regression and virilization, SERKAL syndrome, Type II diabetes, Fuhrmann syndrome, odonto-onycho-dermal dysplasia, obesity, split hand/foot malformation, caudal duplication, tooth agenesis, skeletal dysplasia, focal dermal hypoplasia, autosomal recessive anonychia, neural tube defects, or sclerosteosis and Van Buchem disease.

2. Administration of Stabilized BCL9 Peptides

As non-crosslinked (i.e. wildtype) peptides are normally metabolized very rapidly in vivo, peptide stabilization may improve the pharmacokinetic profile of these peptides, when administered to a subject. As used herein, the terms "administering," or "administer" include delivery of the polypeptide described herein to a subject either by local or systemic administration. Administration may be by topical (including ophthalmic and to mucous membranes including vaginal and rectal delivery), pulmonary (e.g., by inhalation or insufflation of powders or aerosols, including by nebulizer, intratracheal, intranasal), epidermal, transdermal, oral, or parenteral. Parenteral administration includes intravenous, subcutaneous, intraperitoneal, or intramuscular injection or infusion; or intracranial, e.g., intrathecal or intraventricular, administration. Combinations of administration routes are also contemplated. The stapled peptide may be administered in a therapeutically-effective amount.

In some embodiments, a polypeptide or pharmaceutical composition described herein is administered intravenously. In some embodiments, a polypeptide or pharmaceutical composition described herein is administered intraperitoneally. In some embodiments, a polypeptide or pharmaceutical composition described herein is administered daily, weekly, monthly, or any suitable interval that can be used for treating a disease in a subject.

In some embodiments, administration of the stabilized peptide inhibits Wnt signaling in a subject. In some embodiments, administering of a stabilized BCL9 peptide inhibits binding of BCL9 to β-catenin. In some embodiments, administering administration of a stabilized BCL9 peptide inhibits canonical Wnt/β-catenin signaling. In some embodiments, administering administration of a stabilized BCL9 peptide treat a disease in a subject.

3. Combination Therapy with Stabilized BCL9 Peptides

In certain embodiments, a polypeptide or pharmaceutical composition disclosed herein is administered with at least one additional agent. In some embodiments, the at least one additional agent is selected from a checkpoint inhibitor, an EGFR inhibitor, a VEGF inhibitor, a VEGFR inhibitor, an anti-cancer drug. The additional agent may be administered in the same pharmaceutical composition as the stapled peptide, or they may be administered sequentially. The stapled peptide and the additional agent may be administered in a therapeutically-effective amount.

In certain embodiments, the additional agent is a checkpoint inhibitor. Checkpoint inhibitors, such as checkpoint blocking antibodies, block normal negative regulators of T cell immunity, thereby increasing the immune system's ability to control cancer in some patients (see Kyi and Postow, FEBS Letters 588: 368-376 (2013)). In certain embodiments, the checkpoint inhibitor administered with a polypeptide or pharmaceutical composition described herein inhibits PD1, PDL-1, and/or CTLA-4. In an embodiment, the checkpoint inhibitor is an anti-PD-1 antibody, an anti-PD-L1 antibody, and/or an anti-CTLA4 antibody. In certain embodiments, the checkpoint inhibitor is a checkpoint blocking antibody e.g., ipilimumab, nivolumab, or MK-3475. In an embodiment, the checkpoint inhibitor targets a stimulatory checkpoint molecule such as e.g., CD27, CD40, OX40, GITR, or CD138. In yet another embodiment, the checkpoint inhibitor targets an inhibitory checkpoint molecule such as, e.g., A2AR, B7-H3, B7-H4, B and T lymphocyte attenuator (BTLA), indoleamine 2,3-dioxygenase (IDO), Killer-cell immunoglobulin-like receptor (KIR), Lymphocyte Activation Gene-3 (LAG3), T-cell Immunoglobulin domain and Mucin domain 3 (TIM-3), VISTA (C10 or f54), or V-domain Ig suppressor of T cell activation.

Epidermal growth factor receptor (EGFR) inhibitors have shown efficacy in non-small cell lung cancer, as well as other types of cancer, especially in patients with genetic mutations in the EGFR or ALK (anaplastic lymphoma receptor tyrosine kinase) genes. In certain embodiments, the additional therapeutic agent administered with a polypeptide or pharmaceutical composition described herein is an EGFR inhibitor. In certain embodiments, the EGFR inhibitor is erlotinib, gefitinib, lapatinib, panitumumab, vandetanib, or cetuximab. In certain embodiments, a polypeptide or pharmaceutical composition described herein is administered together with an EGFR inhibitor in patients who have been determined to have molecular abnormalities in the EGFR or ALK genes.

In an embodiment, a VEGF and/or VEGFR inhibitor is administered as the second agent. In some embodiments, the VEGF and/or VEGFR inhibitor is one or more of pazopanib, bevacizumab, sorafenib, sunitinib, axitinib, ponatinib, regorafenib, vandetanib, cabozantinib, ramucirumab, lenvatinib, and ziv-aflibercept.

In some embodiments, an anti-cancer drug is administered as the second agent. In some embodiments, the anti-cancer drug is selected from one or more of: cyclophosphamide, methotrexate, 5-fluorouracil (5-FU), doxorubicin, mustine, vincristine, procarbazine, prednisolone, dacarbazine, bleomycin, etoposide, cisplatin, epirubicin, capecitabine, folinic acid, actinomycin, all-trans retinoic acid, azacitidine, azathioprine, bortezomib, carboplatin, chlorambucil, cytarabine, daunorubicin, docetaxel, doxifluridine, fluorouracil, gemcitabine, hydroxyurea, idarubicin, imatinib, irinotecan, mechlorethamine, mercaptopurine, mitoxantrone, paclitaxel, pemetrexed, teniposide, tioguanine, topotecan, valrubicin, vinblastine, vindesine, vinorelbine, and oxaliplatin.

In certain embodiments, a subject administered with a polypeptide or pharmaceutical composition disclosed herein is also treated with radiation therapy and/or chemotherapy before, after, or at the same time as the polypeptide or pharmaceutical composition administration. Further combination therapies with the additional agents disclosed herein are also contemplated.

4. Biomarkers

The present disclosures also encompass methods of measuring at least one biomarker to monitor treatment efficacy of a polypeptide or pharmaceutical composition described herein or to select a subject for treatment with such polypeptide or pharmaceutical composition. In some embodiments, the biomarker is one or more of BCL9, CD44, Axin2, cMyc, LGR5, VEGFA, Sox2, Oct4, Nanog, and/or active β-catenin. As used herein, active β-catenin refers to non-phosphorylated form of β-catenin.

Various known methods can be used to measure the gene expression level and/or protein level of such biomarkers. For instance, a sample from a subject treated with the polypeptide or pharmaceutical composition can be obtained, such as biopsy of a tumor, blood, plasma, serum, urine, amniotic fluid, synovial fluid, endothelial cells, leukocytes, monocytes, other cells, organs, tissues, bone marrow, lymph nodes, or spleen. In some embodiments, the sample is a biopsy of a tumor in a subject. The sample obtained from a subject may be stained with one or more antibodies or other detection agents that detect such biomarkers. The samples may also or alternatively be processed for detecting the present of nucleic acids, such as mRNAs, encoding the biomarkers via e.g., rt-qPCR methods.

In some embodiments, a reduced gene expression level and/or protein level of BCL9, CD44, Axin2, cMyc, LGR5, VEGFA, Sox2, Oct4, Nanog, and/or active β-catenin indicates treatment efficacy of a polypeptide or pharmaceutical composition described herein. The expression level of such biomarker may be measured after e.g., 1 day, 2 days, 3 days, 4 days, 5 days, one week, or two week of administration of the polypeptide or pharmaceutical composition, or any time period inbetween. In some embodiments, a method is disclosed comprising measuring the level of one or more of the biomarkers after one or more rounds of administration of a polypeptide or pharmaceutical composition described herein. In some embodiments, the method further comprises continuing to administer the polypeptide or pharmaceutical composition if the biomarker levels are reduced. In some embodiments, the method further comprises administering an increased dosage of a polypeptide or pharmaceutical composition described herein if the biomarker levels are not reduced, or increasing the frequency of subsequent administrations. In some embodiments, treatment is discontinued if biomarker levels are not reduced after the initial administration. In various embodiments, biomarker levels are also measured before a first administration of the polypeptide or pharmaceutical composition described herein, and compared to levels after one or more rounds of administration, wherein treatment efficacy and continued treatment steps are determined based on the change in biomarker level(s) from the level(s) prior to administration.

In some embodiments, an increased gene expression level and/or protein level of BCL9, CD44, Axin2, cMyc, LGR5, VEGFA, Sox2, Oct4, Nanog, and/or active β-catenin indicates that a subject would benefit from treatment with a polypeptide or pharmaceutical composition described herein, than a subject who does not have increased gene expression levels and/or protein levels. In some embodiments, methods of treatment are disclosed, comprising selecting patients having increased biomarker levels and administering a polypeptide or pharmaceutical composition described herein.

In certain embodiments, a subject having elevated level of gene and/or protein expression of BCL9, CD44, Axin2, cMyc, LGR5, VEGFA, Sox2, Oct4, Nanog, and/or active β-catenin is selected for treatment with a polypeptide or pharmaceutical composition described herein. In some embodiments, a subject suffering from a tumor is selected for treatment after obtaining a tumor sample from the subject and identifying an elevated gene and/or protein expression of BCL9, CD44, Axin2, cMyc, LGR5, VEGFA, Sox2, Oct4, Nanog, and/or active β-catenin. In some embodiments, a subject suffering from a tumor is selected for treatment after obtaining a tumor sample from the subject and identifying an elevated gene and/or protein level of BCL9. In some embodiments, a subject suffering from a tumor is selected for treatment after obtaining a tumor sample from the subject and identifying an elevated gene and/or protein level of CD44. In some embodiments, a subject suffering from a tumor is selected for treatment after obtaining a tumor sample from the subject and identifying an elevated gene and/or protein level of active β-catenin.

5. Dosage

Dosage regimens may be adjusted to provide an optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms provided herein are dictated by and directly dependent on (a) the unique characteristics of the active compound and the particular therapeutic or prophylactic effect to be achieved, and (b) the limitations inherent in the art of compounding such an active compound for the treatment of sensitivity in individuals. An exemplary, non-limiting range for a therapeutically or prophylactically effective amount of a binding protein provided herein is 0.1-20 mg/kg, for example, 1-10 mg/kg. It is to be noted that dosage values may vary with the type and severity of the condition to be alleviated. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

6. Kit

Also disclosed herein are kits for performing methods described herein. In various embodiments, a kit for manufacturing a polypeptide described herein is provided. In some embodiments, the kit comprises a polypeptide that is capable of undergoing a reaction to from one or more hydrocarbon crosslinkers. In some embodiments, the kit comprises a metal catalyst for performing metal-mediated ring-closing olefin metathesis.

In various embodiments, a kit for treating a disease in a subject is also provided. In some embodiments, the kit is for treating cancer in a subject. In some embodiments, the kit comprises a polypeptide or pharmaceutical composition disclosed herein. In some embodiments, the polypeptide in the kit is capable of undergoing a reaction to from one or more hydrocarbon crosslinkers. In some embodiments, the polypeptide in the kit has one or more hydrocarbon crosslinkers. In some embodiments, the kit further comprises at least one additional agent that can be administered to a subject.

In various embodiments, a kit for detecting and/or treating a subject having a tumor exhibiting elevated gene and/or protein expression of BCL9, CD44, Axin2, cMyc, LGR5, VEGFA, Sox2, Oct4, Nanog, and/or active β-catenin in a subject is provided. In some embodiments, the kit comprises agents for detecting the gene and/or protein expression of BCL9, CD44, Axin2, cMyc, LGR5, VEGFA, Sox2, Oct4, Nanog, and/or active β-catenin. In some embodiments, the kit further comprises a polypeptide or pharmaceutical composition disclosed herein. In some embodiments, the polypeptide in the kit is capable of undergoing a reaction to from one or more hydrocarbon crosslinkers. In some embodiments, the polypeptide in the kit has one or more hydrocarbon crosslinkers. In some embodiments, the kit further comprises at least one additional agent that can be administered to a subject.

Unless defined otherwise, all technical and scientific terms used herein have the same meaning as commonly understood by those of ordinary skill in the art to which the disclosure belongs.

The articles "a" and "an" refer to one or to more than one (i.e., to at least one) of the grammatical object of the article. For example, "an element" means one element or more than one element.

The term "or" means, and is used interchangeably with, the term "and/or," unless context clearly indicates otherwise. In this application, the use of the singular includes the plural unless specifically stated otherwise. Furthermore, the use of the term "including," as well as other forms, such as "includes" and "included," are not limiting. Any range described herein will be understood to include the endpoints and all values between the endpoints.

To the extent that the term "contain," "include," "have," or grammatical variants of such term are used in either the disclosure or the claims, such term is inclusive in a manner similar to the term "comprising" as "comprising" is interpreted when employed as a transitional word in a claim. The term "including" or its grammatical variants mean, and are used interchangeably with, the phrase "including but not limited to."

The term "about" means a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight or length. When the term "about" is used in conjunction with a numerical range, it modifies that range by extending the boundaries above and below the numerical values set forth. In general, the term "about" is intended to modify a numerical value above and below the stated value by a variance of ≤10%.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1. Generation of Stabilized BCL9 Peptides

Methods of synthesizing hydrocarbon crosslinkers using modified Ala residues (α,α-disubstituted amino acids such as α-methyl, α-alkenyl amino acids) are known in the art. See e.g., US20140113857 and Kim 2011. Each stabilized peptide used in the following examples was generated by a one on-resin synthesis method. Peptide elongation was performed on resin to generate each polypeptide, followed by a ring closing metathesis.

Hydrocarbon crosslinkers with different lengths, such as an 8-carbon crosslinker and an 11-carbon crosslinker, can be generated using an α-methyl, α-alkenyl amino acid with an alkenyl chain of suitable length. For instance, (S)2-(4'pentenyl)Ala was incorporated into a polypeptide to construct a stabilized polypeptide having an 8-carbon crosslinker with an S-configuration on both ends. (R)2-(4'-pentenyl)Ala was incorporated into a polypeptide to construct a stabilized polypeptide having an 8-carbon crosslinker with an R-configuration on both ends. For a stabilized polypeptide having an 8-carbon crosslinker with an S-configuration on one end and an R-configuration on the other end, (S)2-(4'-pentenyl) Ala and (R)2-(4'-pentenyl)Ala were used, respectively. To construct a stabilized polypeptide having an 11-carbon crosslinker with an S-configuration on one end and an R-configuration on the other end, (R)2-(7'-octenyl)Ala and (S)2-(4'-pentenyl)Ala were used, respectively.

Each polypeptide was purified using standard high-performance liquid chromatography (HPLC) protocols. A Zorbax C18 reverse-phase column, 9.4×250 mm (Agilent, pore size 80 Å, particle size 3.5 μm) was used. The solvents used were A: water, 0.1% (vol/vol) TFA; B: acetonitrile, 0.1% (vol/vol) TFA. The flow rate was 4 ml/min. The gradient was 10-100% (vol/vol) B over 30 min; 100% B over 5 min; 100-10% (vol/vol) B over 4 min; 10% (vol/vol) B over 1 min. The injection volume was 100-400 μl. The wavelength (nm) was 280 (for Fmoc-, Trp- or Tyr-containing peptides), or 220 (for others).

Example 2. Mapping of Functional Domains of the HD2 Domain of BCL9

As the Wnt signaling pathway impacts signaling in cancer and other diseases, stabilized peptides containing the HD2 domain of the BCL9 peptide were investigated. A BLAST search indicated that the HD2 domain of human BCL9 protein is unique and therefore peptides derived from this domain should be specific for inhibiting the effects of BCL9.

To further identify the core functional domain of the HD2 domain of BCL9 protein that binds to β-catenin, multiple lead optimization studies were performed in a series of three steps: (i) domain mapping of the full-length HD2 domain of human BCL9 protein; (ii) point mutations within the potential core functional domain; and (iii) terminal modification and staple site optimization. Two biochemical assays for detecting the binding between polypeptides and β-catenin were developed. The first assay was a Homogeneous Time Resolved Fluorescence (HTRF) binding assay (Cisco), in which a biotinylated polypeptide was conjugated with streptavidin-XL655 fluorescence and the histidine tag of β-catenin protein was conjugated with Eu-labeled monoclonal antibody (mAb). The second assay was an Amplified Luminescence Proximity Homogeneous Assay (ALPHA) screening assay (Perkin Elmer), in which a biotinylated polypeptide was conjugated with streptavidin coated donor beads and β-catenin protein was conjugated to protein A-coated acceptor beads through an anti-β-catenin antibody. In this binding assay, a PEG linker was used to conjugate the biotinylated peptide to the beads, allowing more room for BCL9 derived polypeptides to bind to β-catenin. As assessed in the ALPHA screen assay, the $K_D$ of the full-length HD2 domain of human BCL9 protein to β-catenin was 20 nM, with a 180-fold signal versus background ratio, resulting in a significant improvement over other known methods of detecting binding affinity. See e.g., Zhang et al., Analytical Biochemistry 469: 43-53 (2015) and Kawamoto et al., Biochemistry 48(40):9534-9541 (2009).

Domain mapping was done by constructing twenty overlapping stapled polypeptides (7 or 8-mers) spanning the HD2 domain of human BCL9. Polypeptides having a length of 8-20 amino acids are typically used as inhibitors of protein interactions as they have an additional advantage of being low-cost. As shown in FIG. 2A, this process involved the generation of small stabilized polypeptides and the use of point mutations of selected amino acids of the HD2 domain to verify the smallest functional domain of the HD2 domain. As seven amino acids is the shortest sequence to form a single i, i+4 staple, sequential stabilized peptides with a length of seven or eight amino acids were generated from amino acids 351 to 374 of human BCL9 protein. Table 2 below summarizes each polypeptide generated for domain mapping and indicates which amino acid residues were substituted with (S)2-(4'pentenyl)Ala to further generate an 8-carbon crosslinker. $Xaa_1$ and $Xaa_2$ in Table 2 represent (S)2-(4'pentenyl)Ala. Each polypeptide listed in Table 2 was constructed and crosslinked according to Example 1. All the polypeptides have an 8-carbon crosslinker ($—CH_2—CH_2—CH_2—CH=CH—CH_2—CH_2—CH_2—$) with an S-configuration on both ends. The N-terminus of each polypeptide is modified with an acetyl group while the C-terminus of the polypeptide is modified with an $NH_2$ group. B in Table 2 represents norleucine.

TABLE 2

Polypeptides generated for domain mapping

| SEQ ID NO: | Amino Acid Sequence (WX No.) | Corresponding position within BCL9 |
|---|---|---|
| 60 | LXaa$_1$QEQXaa$_2$E (WX-002) | 351-357 |
| 61 | SXaa$_1$EQLXaa$_2$H (WX-003) | 352-358 |
| 62 | QXaa$_1$QLEXaa$_2$R (WX-004) | 353-359 |
| 63 | EXaa$_1$LEHXaa$_2$E (WX-005) | 354-360 |
| 64 | QXaa$_1$EHRXaa$_2$R (WX-006) | 355-361 |
| 65 | LXaa$_1$HREXaa$_2$S (WX-007) | 356-362 |
| 66 | EXaa$_1$RERXaa$_2$L (WX-008) | 357-363 |
| 67 | HXaa$_1$ERSXaa$_2$Q (WX-009) | 358-364 |
| 68 | RXaa$_1$RSLXaa$_2$T (WX-010) | 359-365 |
| 69 | EXaa$_1$SLQXaa$_2$L (WX-011) | 360-366 |
| 70 | RXaa$_1$LQTXaa$_2$R (WX-012) | 361-367 |
| 71 | SXaa$_1$QTLXaa$_2$D (WX-013) | 362-368 |
| 72 | LXaa$_1$TLRXaa$_2$I (WX-014) | 363-369 |
| 73 | QXaa$_1$LRDXaa$_2$Q (WX-015) | 364-370 |
| 74 | TXaa$_1$RDIXaa$_2$R (WX-016) | 365-371 |
| 75 | LXaa$_1$DIQXaa$_2$B (WX-017) | 366-372 |
| 76 | RXaa$_1$IQRXaa$_2$L (WX-018) | 367-373 |
| 77 | DXaa$_1$QRBXaa$_2$F (WX-019) | 368-374 |
| 78 | LRXaa$_1$IQRXaa$_2$L (WX-020) | 366-373 |
| 105 | LSQEQLEHRERSLXaa$_1$TLRXaa$_2$IQRBLF (WX-001) | 351-374 |

Figure 2B:
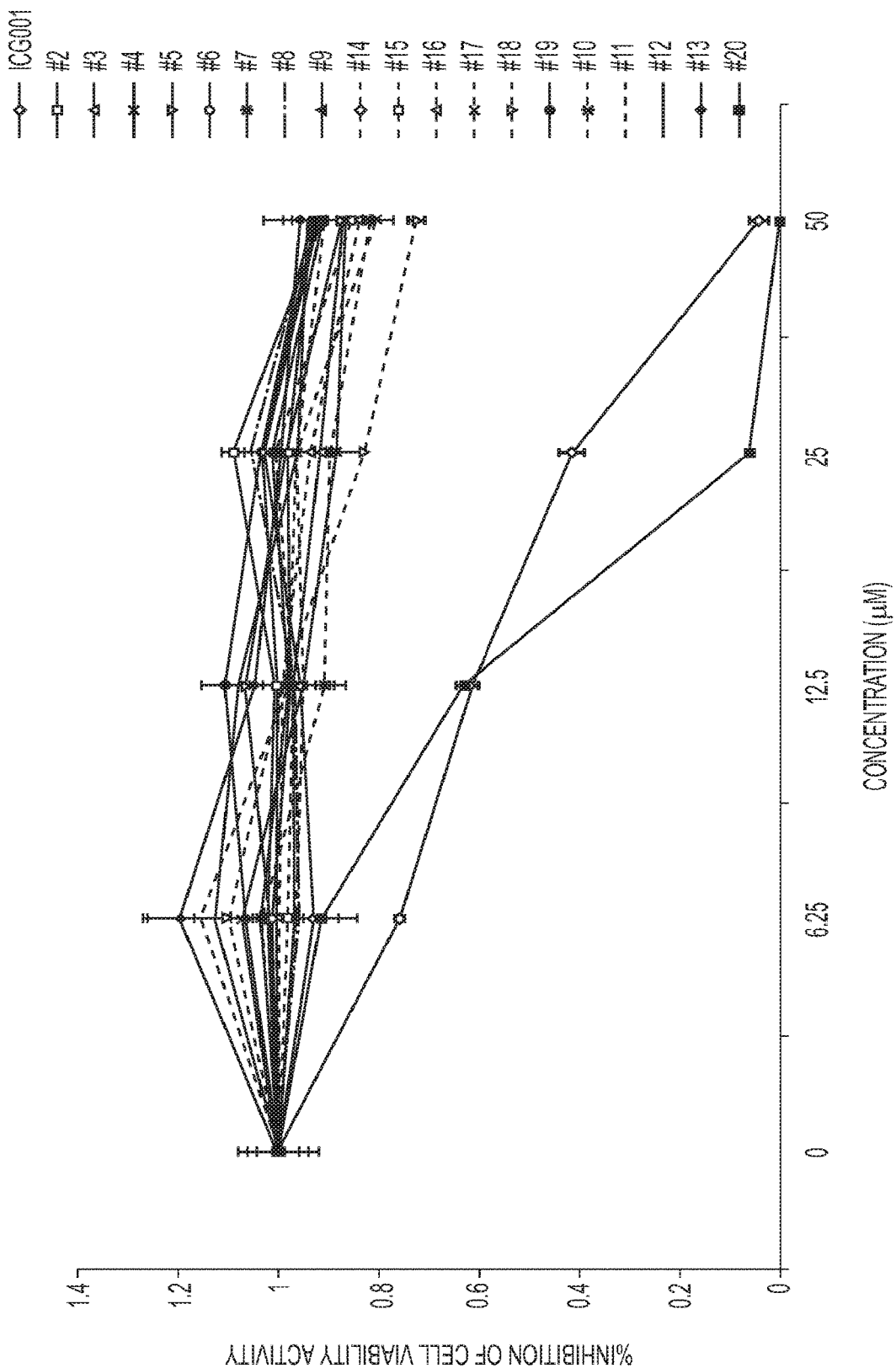
FIG. 2B shows results of a cell viability assay using increasing amounts of each domain fragment generated based on the domain mapping strategy depicted in FIG. 2A. ICG001, a known small molecule inhibitor of canonical Wnt/β-catenin signaling, was used as a positive control. The cell viability assay was performed using CellTiterGlo assay (Promega) with Colo320DM cells.

As shown in FIG. 2B, all the stabilized polypeptides listed in Table 2 were simultaneously tested in a cell viability assay. Colo320DM cells were selected for this assay as the proliferation of this particular cell line is dependent on BCL9 and β-catenin. ICG001, a known Wnt/β-catenin small molecule inhibitor, was used as a positive control. The cell viability at each treatment condition was analyzed using CellTiterGlo luminescent cell viability assay (Promega) according to the manufacturer's protocols.

Figure 2C:
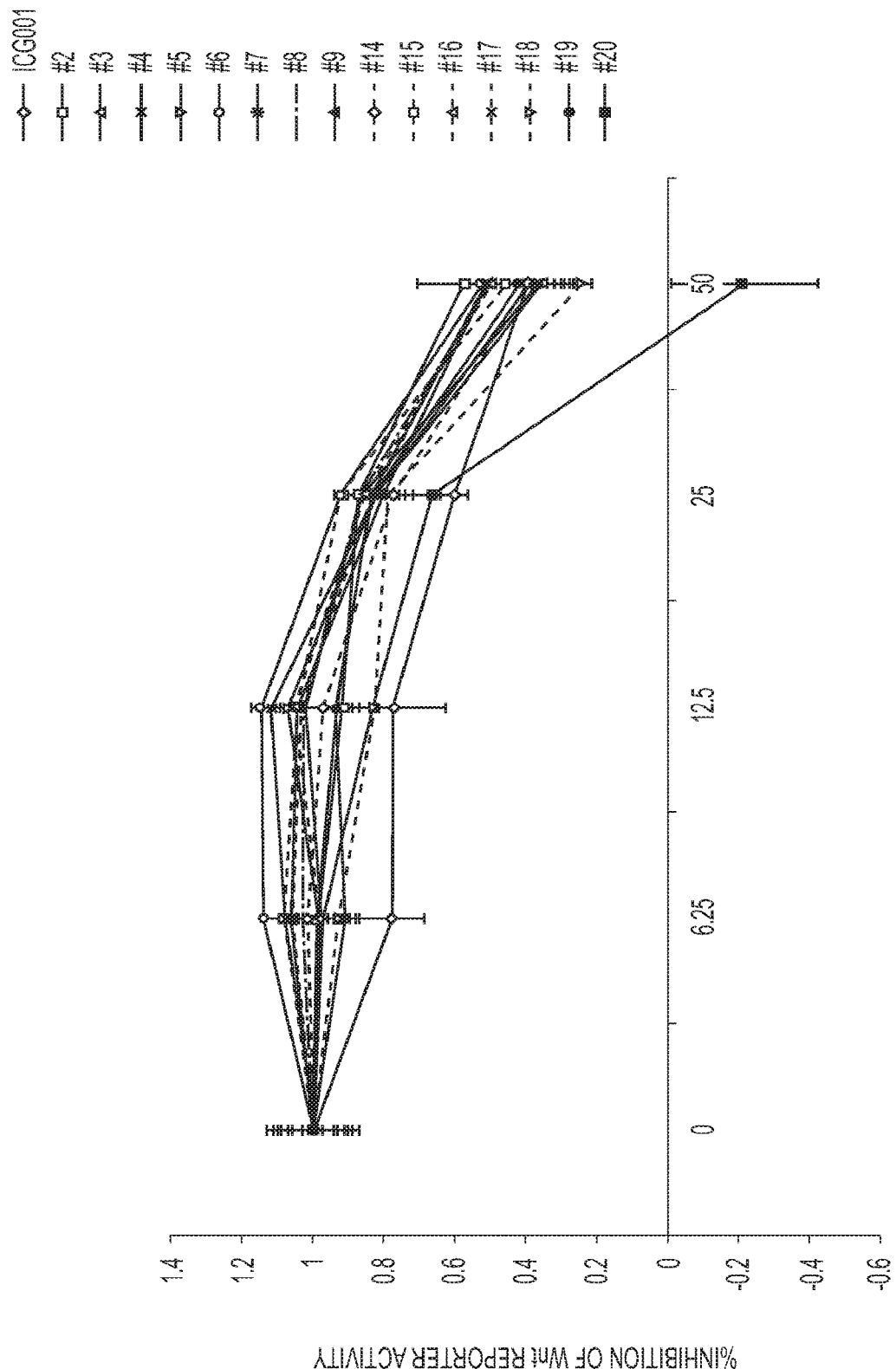
FIG. 2C shows results of a Wnt transcription assay using increasing amounts of each domain fragment generated in FIG. 2A. ICG001 was used as a positive control. The Wnt transcription assay was performed using GeneBlazer Wnt Reporter Assay (Invitrogen) with HCT116 cells.

As shown in FIG. 2B, ICG001 was capable of inducing cell death in a dose dependent manner. WX-020, comprising the distal portion of the HD2 domain, was also efficient in inhibiting cell growth, comparable to ICG001. The $IC_{50}$ value of WX-020 in this assay was 12.4 μM. The effect of WX-020 (comprising LRDIQRBL (SEQ ID NO: 106)) was superior to WX-018 (comprising RDIQRBL (SEQ ID NO: 107)), which does not have Leu at the N-terminus, suggesting that the core functional domain that binds to β-catenin involves the stretch of 8 amino acid residues encompassed by WX-020. Also, this improved potency of WX-020 indicates that a short stabilized polypeptide derived from the distal portion of the HD2 domain is sufficient to retain the ability to bind β-catenin and therefore block the interaction between BCL9 and β-catenin. The polypeptides were also tested in a cell-based Wnt transcription inhibition assay using GeneBLAzer® beta-lactamase (bla) reporter assay (invitrogen), as described in Example 4.1. In this assay, HCT116 cells were selected because the cells are known to have aberrant Wnt signaling activation due to the presence of a β-catenin mutation. Consistent with the results from the cell viability assay, WX-020 was the most effective polypeptide in inhibiting the Wnt transcription (FIG. 2C).

Figure 3:
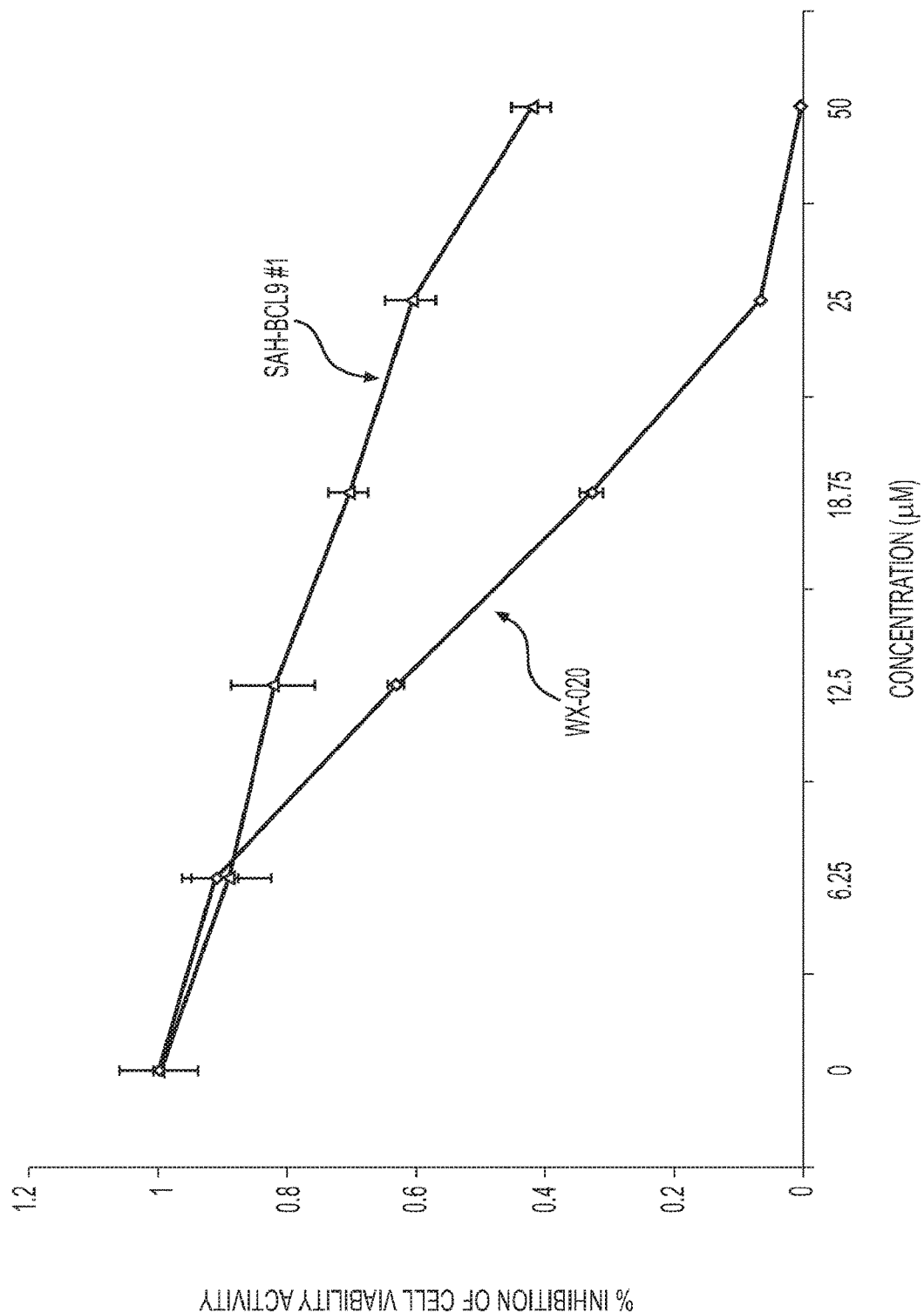
FIG. 3 depicts results of a cell viability assay comparing WX-020 and SAH-BCL9 #1. The cell viability assay was performed using CellTiterGlo assay (Promega) with Colo320DM cells.

Furthermore, as shown in FIG. 3, when tested in the same cell viability assay, the effect of WX-020 exceeded that of full length HD2 domain (WX-001; "SAH-BCL9 #1"), indicating that not all polypeptides comprising the core functional domain are necessary equally effective in blocking the interaction between BCL9 and β-catenin, dependent on the presence of other sequence elements or chain modifications. WX-020 was also tested in the ALPHA screen as described above and shown to have a $K_D$ value of 80 nM. WX-020 was tested in a Wnt transcription assay following the procedures described in Example 4.1 and shown to have an $IC_{50}$ value of 1580 nM.

Point mutations altering amino acids of the distal portion of the HD2 domain also reduced the efficacy of stabilized peptides, indicating that the distal region of the HD2 domain contains motifs of BCL9 involved in binding to β-catenin. In particular, Structure Activity Relationships (SAR) evaluation of the WX polypeptides indicated that the hydrophobic amino acids on the WX polypeptides mediate the binding to β-catenin.

Example 3. Stabilized Polypeptides Comprising the Core Functional Domain

Four additional stapled polypeptides with varying lengths of amino acids were generated, comprising the core functional domain identified in Example 2. The stapled polypeptides were further modified by adding known peptide tags or terminal modifications to improve permeability and solubility, such as Ant8, TAT, (β Ala)-(β Ala). Four additional stabilized polypeptides corresponding to SEQ ID NOs: 108-111 were generated using the standard peptide synthesis protocol set forth in Example 1 (Table 3; see also Table 1). See also Kim 2011. For instance, to construct WX-024 as shown in FIG. 1A, a hydrocarbon crosslinker was generated between the two Xaa amino acids of SEQ ID NO: 103 using ruthenium-mediated ring-closing olefin metathesis. Following the ring closure metathesis, the polypeptide was deprotected and released. The resulting stabilized polypeptide comprises a hydrocarbon crosslinker of —$CH_2$—$CH_2$—$CH_2$—CH=CH—$CH_2$—$CH_2$—$CH_2$— with an S-configuration on both ends. WX-024 contains an acetyl-group at the N-terminus and 2-Naphthylalanine at the C-terminus. The carboxyl group of the 2-Naphthylalanine at the C-terminus is further modified with $NH_2$. WX-021, WX-022, and WX-023 share the same sequence as WX-020, but modified with a different chemical moiety at the C-terminus (2-Naphthylalanine and two units of β-alanines with $NH_2$ at the C-terminus, two units of (β-alanines with $NH_2$ at the C-terminus, and 2-Naphthylalanine with $NH_2$ at the C-terminus, respectively). All the polypeptides were further purified according to the protocol described in Example 1.

Table 3 summarizes the four polypeptides comprising the core functional domain and indicates which amino acid residues were substituted with (S)2-(4'pentenyl)Ala to further generate an 8-carbon crosslinker ($Xaa_1$ and $Xaa_2$=(S) 2-(4'pentenyl)Ala).

TABLE 3

Additional stabilized polypeptides derived from the HD domain of BCL9 protein

| SEQ ID NO: | Amino Acid Sequence (WX No.) | Corresponding position within BCL9 | N-terminus Modification | C-terminus Modification |
|---|---|---|---|---|
| 108 | LRXaa$_1$IQRXaa$_2$L (WX-021) | 366-373 | Ac | 2-Nal-β-Ala-β-Ala-NH$_2$ |
| 109 | LRXaa$_1$IQRXaa$_2$L (WX-022) | 366-373 | Ac | β-Ala-β-Ala-NH$_2$ |
| 110 | LRXaa$_1$IQRXaa$_2$L (WX-023) | 366-373 | Ac | 2-Nal-NH$_2$ |
| 111 | LQTLRXaa$_1$IQRXaa$_2$L (WX-024) | 363-373 | Ac | 2-Nal-NH$_2$ |

Figure 4A:
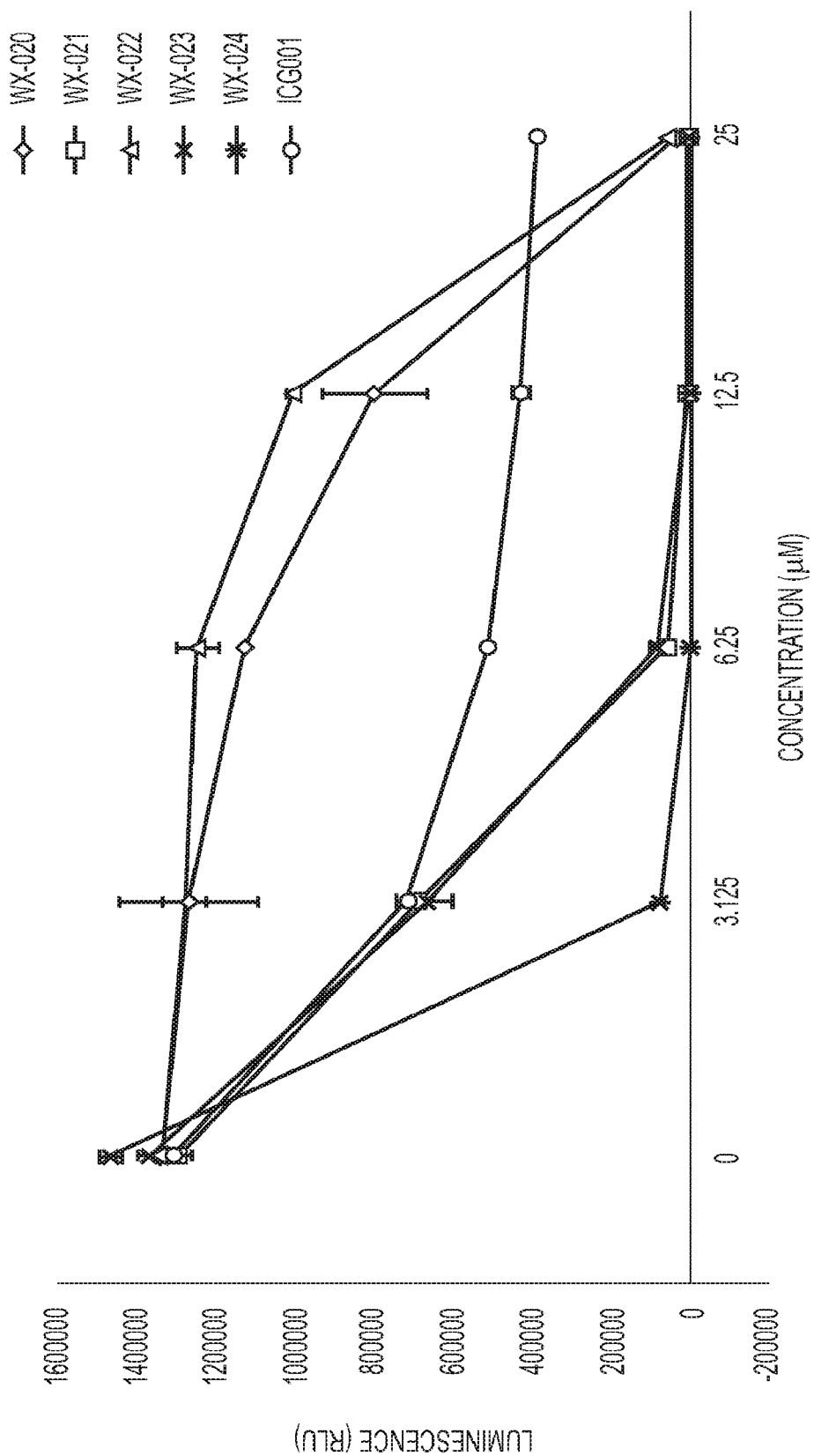
FIG. 4A depicts results of a cell viability assay comparing WX-020 and four different stabilized polypeptides derived from WX-020, including WX-024. The cell viability assay was performed using a CellTiterGlo assay (Promega) with HCT116 cells. ICG001 was used as a positive control.

The additional polypeptides were tested in a CellTiterGlo luminescent cell viability assay (Promega). ICG001 was used as a positive control in this assay. As shown in FIG. 4A, while all the tested polypeptides including WX-020 were capable of inhibiting cell growth in a dose dependent manner, WX-024 (and WX-021) was particularly effective in this assay. In particular, the $IC_{50}$ value of WX-024 in this assay was largely improved as compared to WX-020, demonstrating that WX-024 comprising the core functional domain is particularly effective in inhibiting cell viability and Wnt transcription as compared to other polypeptides comprising the same core functional domain.

Figure 4B:
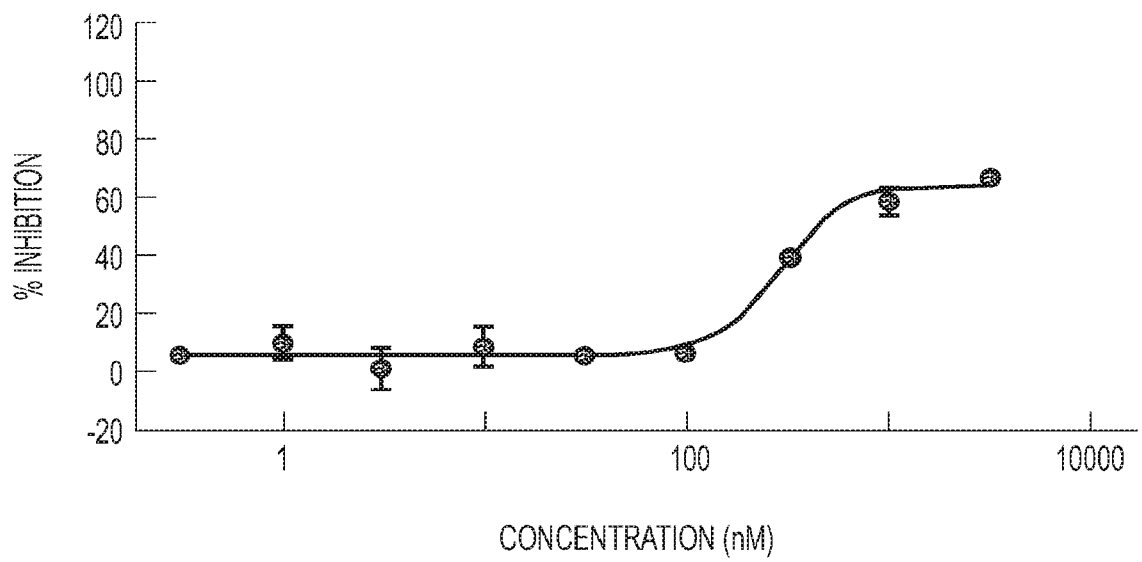
FIG. 4B depicts results of the acetate salt form of WX-024 tested in a cell-based Wnt transcription inhibition assay (IC$_{50}$=292 nM).
Figure 4C:
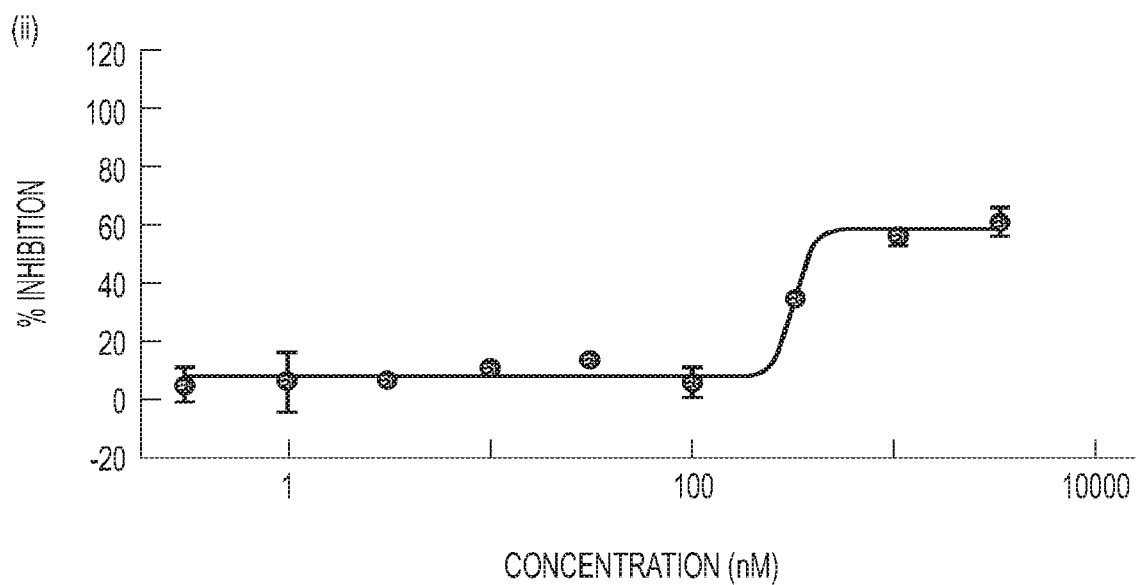
FIG. 4C shows the effect of the hydrochloric salt also tested in the same Wnt transcription inhibition assay (IC$_{50}$=313 nM).

Some preliminary studies on solubility, stability and salt selection were performed with WX-024 in collaboration with ChemPartner. As shown in FIG. 4B, the acetate salt form of WX-024 was tested in a cell-based Wnt transcription inhibition assay and effectively inhibited Wnt transcription ($IC_{50}$=292 nM). Likewise, FIG. 4C shows that the hydrochloric salt also effectively inhibited Wnt transcription in the same assay ($IC_{50}$=313 nM). WX-024 was soluble in water, DMSO, and PBS at 1 mg/mL, and the trifluroacetic acid salt form of WX-024 was stable at 2-8° C. and at room temperature for at least one month. In addition, the salt form of WX-024 was active in various in vitro cell viability assays.

Example 4. In Vitro Profile of Stabilized Polypeptides

Binding of BCL9 to β-catenin is known to activate Wnt signaling. Because Wnt/β-catenin activity regulates a large range of cell signals, a variety of assays can be used to measure activity of this pathway. WX-021 and WX-024 were assessed in a variety of cellular assays to assess its in vitro capability of modulating Wnt/β-catenin signaling.

Example 4.1. Cellular Activity of Stabilized Polypeptides

Figure 5A:
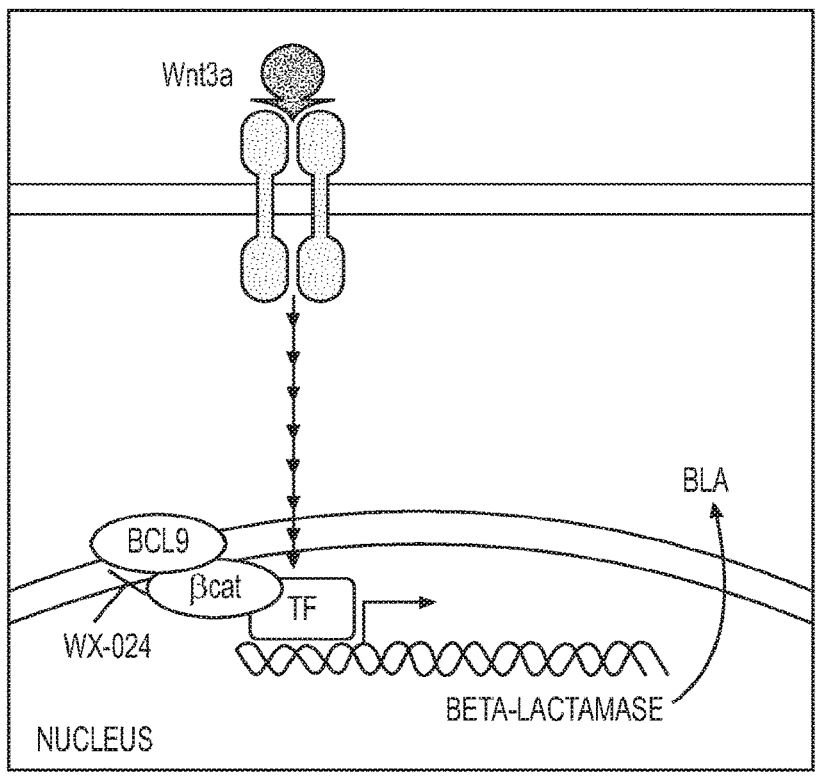
FIGS. 5A, 5B, 5C, and 5D show results of a GeneBlazer Wnt Reporter Assay (Invitrogen) testing WX-021, WX-024, and ICG001.

The cellular activity of WX-021 and WX-024 were measured via a GeneBLAzer® beta-lactamase (bla) reporter assay (invitrogen). ICG001 was used as a comparison. The GeneBLAzer uses CellSensor™ LEF/TCF-bla HCT-116 cells that contain a beta-lactamase (BLA) reporter gene under the control of the β-catenin/LEF/TCF response element stably integrated into HCT-116 cells, as shown in FIG. 5A. These cells constitutively express beta-lactamase and can be used to detect agonists and antagonists of the Wnt/β-catenin signaling pathway. The GeneBLAzer assay provides a ratiometric reporter response involving a two-color (blue/green) readout of stimulated and unstimulated cells.

LEF/TCF-bla HCT-116 cells were plated in assay medium (Invitrogen) on clear-bottom plates and incubated overnight at 37° C. Cells were then treated with a vehicle control (0.05% DMSO in water) or a range of doses of WX-021, WX-024, or ICG001 up to 10 µM for 5 hours. Cells were next incubated with the Wnt agonist, mWnt3a (provided in the GeneBLAzer kit) for 5 hours at 37° C. Substrate mixture (containing LiveBLAzer™ B/G substrate that employs CCF4-AM, a FRET substrate for beta-lactamase) was added to the wells, and the plate was incubated for 2.5 hours at room temperature in the dark. Black-walled, clear-bottom, 384-well plates (Corning Costar) were used with scanning done with a Spectramax M2. Plates were scanned first (Scan 1 in the blue channel) with excitation filter 409/20 nm and emission filter 460/40 nm. Plates were then scanned (Scan 2 in the green channel) with excitation filer 409/20 nm and emission filter 530/30 nm. Fluorescence emission values at 460 nm and 530 nm were obtained, and inhibition of the 460/530 ratios was used to determine the percent inhibition (% inhibition) of Wnt/β-catenin signaling by WX-024 using data analysis protocols from the manufacturer (Life Technologies).

Figure 5B:
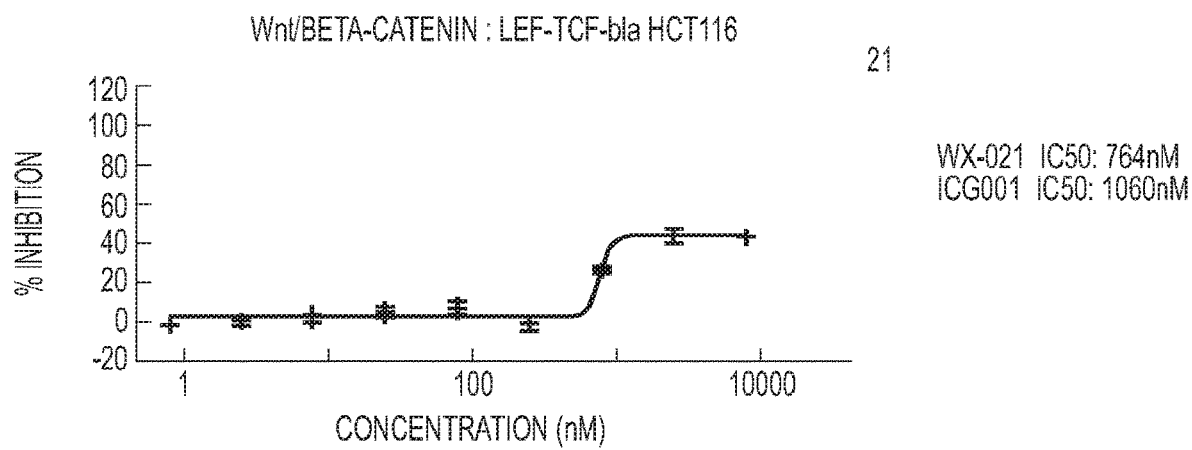
Figure 5C:
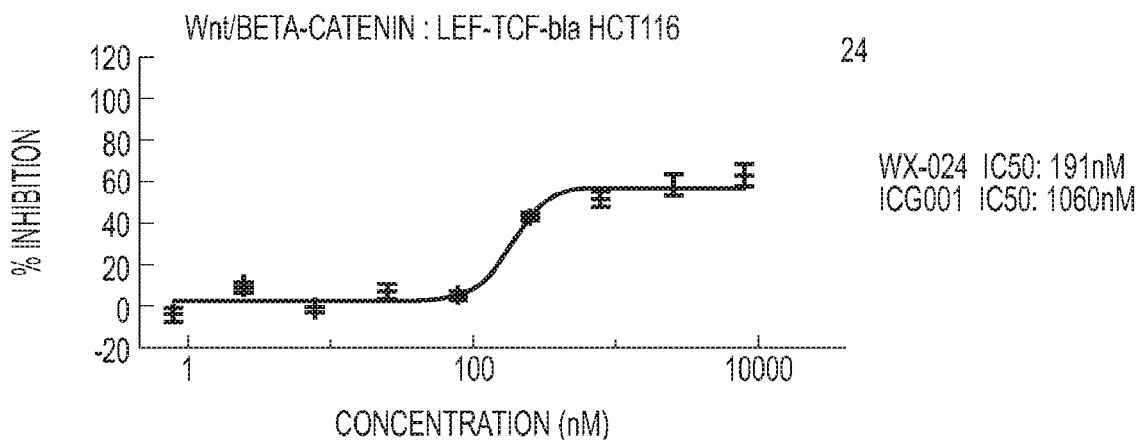
Figure 5D:
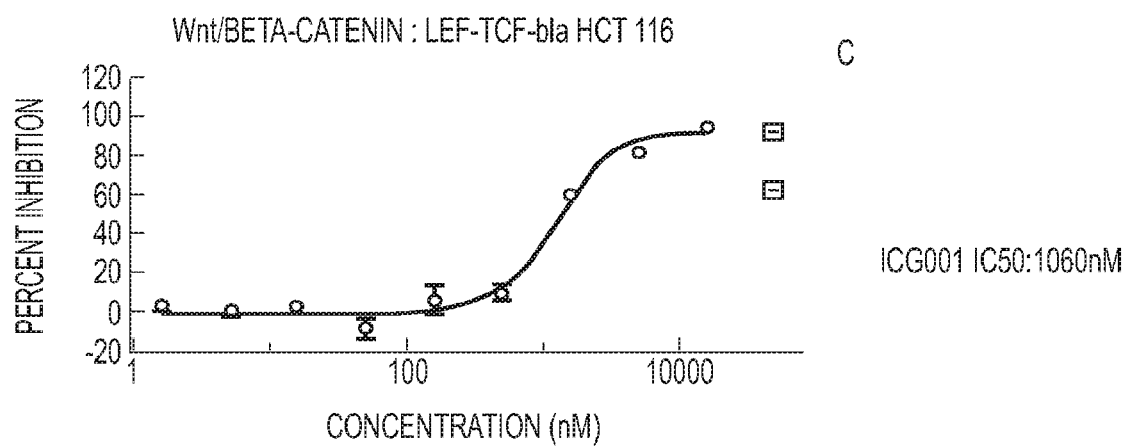
Figure 5E:
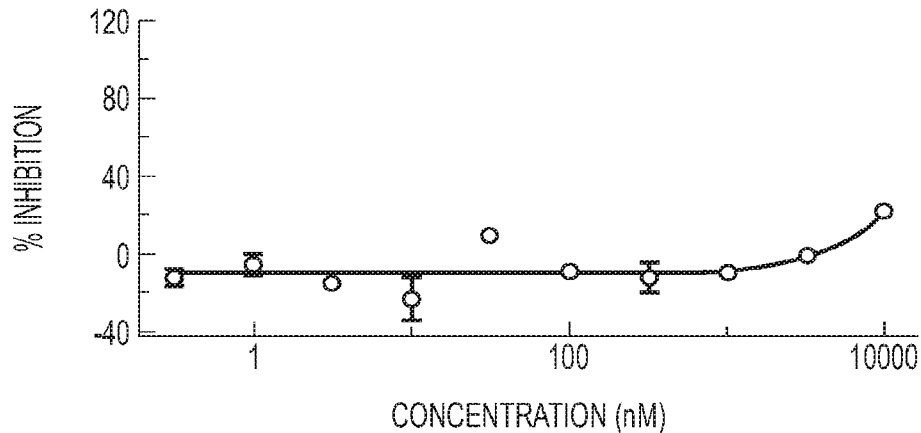
FIG. 5E shows that WX-024 also showed better in vitro potency targeting Wnt/β-catenin transcription than LGK-974 ($IC_{50}$>10 μM), which was expected, since LGK-974 targets extracellular Wnt signaling and does not directly inhibit β-cat transcription.

As shown in FIGS. 5B-5D, increasing concentrations of WX-021 and WX-024 produced greater inhibition of Wnt signaling in this reporter assay, as compared to ICG001. The $IC_{50}$ of WX-021 and WX-024 calculated from this assay were 764 nM and 191 nM, respectively. These stabilized polypeptides were more potent inhibitors of Wnt/β-catenin signaling than the known Wnt inhibitor, ICG001 ($IC_{50}$=1060 nM). Another Wnt inhibitor, LGK-974 (also known as Porcupine inhibitor), was tested in the same assay. LGK-974 inhibits Porcupine, a membrane bound O-acyltransferase that mediates palmitoylation of Wnt family proteins, which is required for secretion and functional activation of Wnt protein. Liu et al., *Proc Natl Acad Sci USA* (2013) 110: 20224-20229. WX-024 also showed better in vitro potency targeting Wnt/β-catenin transcription than LGK-974 ($IC_{50}$>10 µM), which was expected, since LGK-974 targets extracellular Wnt signaling and does not directly inhibit β-cat transcription (FIG. 5E).

Overall, while WX-021 and WX-024 were both effective in suppressing Wnt signaling pathway, the effect of WX-024 showed improved functional properties in both cell viability assay (FIG. 4) and Wnt transcription assay (FIG. 5) as compared to WX-021. Thus, WX-024 was selected for further characterization in subsequent in vitro and in vivo studies.

Example 4.2. Binding Affinity of WX-024 to B-Catenin

The ability of WX-024 to bind β-catenin was evaluated in a homogenous time resolved fluorescence (HTRF) assay (Cisbio). HTRF assays provide a means of assaying protein-protein interactions in a high-throughput format, as discussed in Degorce et al., *Curr Chemical Genom.* 3, 22-32 (2009). In an HTRF assay to measure a protein-protein interaction, binding of 2 proteins brings an HTRF donor and acceptor fluorophore into close proximity and generates the fluorescence energy transfer (FRET) signal. Each protein of the interaction is associated with the donor or the acceptor by an antibody reaction.

Figure 6A:
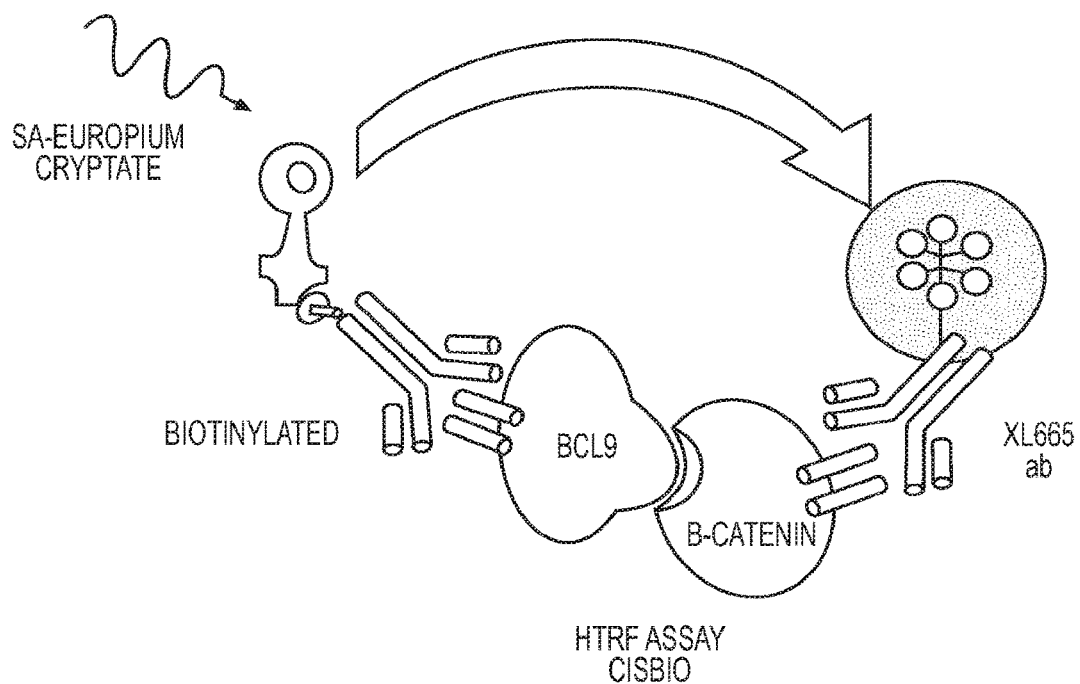
FIG. 6A and FIG. 6B show results of a homogenous time resolved fluorescence (HTRF) assay (Cisbio) measuring WX-024 (conjugated with biotin) binding to β-catenin.

FIG. 6A provides a schematic to depict the basis of the HTRF assay. In the HTRF assay for β-catenin (Cisbio), β-catenin is bound by an XL665-coupled antibody (ab) against β-catenin. See Degorce (2009). β-catenin bound to an XL665-coupled antibody can interact with its binding partners, such as BCL9 or BCL9 peptides.

For the HTRF assay, the β-catenin binding partner, WX-024, was coupled to biotin. After incubation of β-catenin and WX-024, the reaction was then incubated with streptavidin (SA) bound to europium cryptate (SA-europium cryptate). SA is a high-affinity binding partner to biotin and will tightly bind the SA-europium cryptate to the biotinylated stabilized polypeptides. Europium cryptate is an energy donor for an HTRF reaction. When not closely bound, there is no energy transfer between europium cryptate and XL665. However, when europium cryptate and XL-66 are in close proximity, such as when there is successful binding of biotinylated WX-024 to the β-catenin that is bound by the XL665 antibody, there is an energy transfer that can be measured.

Histidine-tagged β-catenin, BCL9 peptide labeled with biotin, europium (Eu) labeled monoclonal antibody for histidine tag, and SA-XL665 were used in the HTRF assay. Buffer for the assay contained 50 mM MES pH 6.5, 150 mM NaCl; 0.1% BSA, 1 mM DTT, and 0.1% Tween 20. Five µL of His-tag protein was added to plate. Five µL of the biotin-labeled peptide at various concentrations was added to the same well. Ten µL of Eu-labeled monoclonal antibody and SA-XL644 detection mixture were added. The reaction was incubated at room temperature for 1 hour and then the plate was read.

Figure 6B:
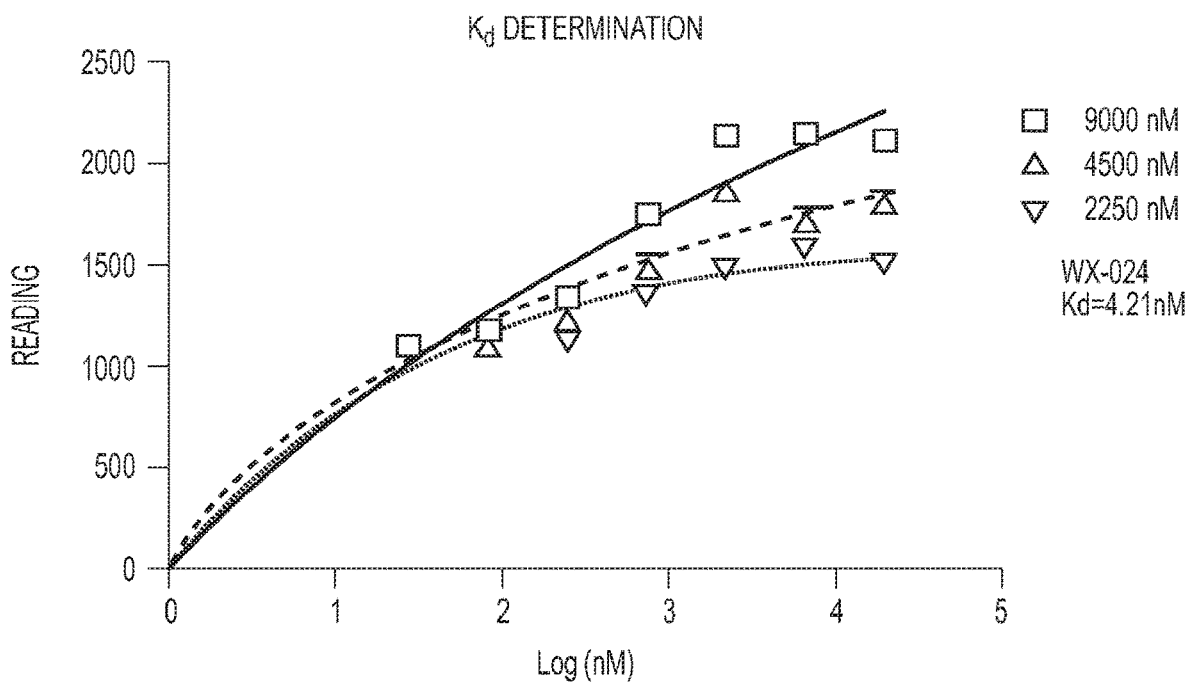

The results obtained from WX-024 are shown in FIG. 6B. The $K_D$ value of WX-024 calculated from the results was 4.21 nM.

Example 4.3. Comparison of WX-024 and ICG001 in a Cell Viability Assay

Figure 7:
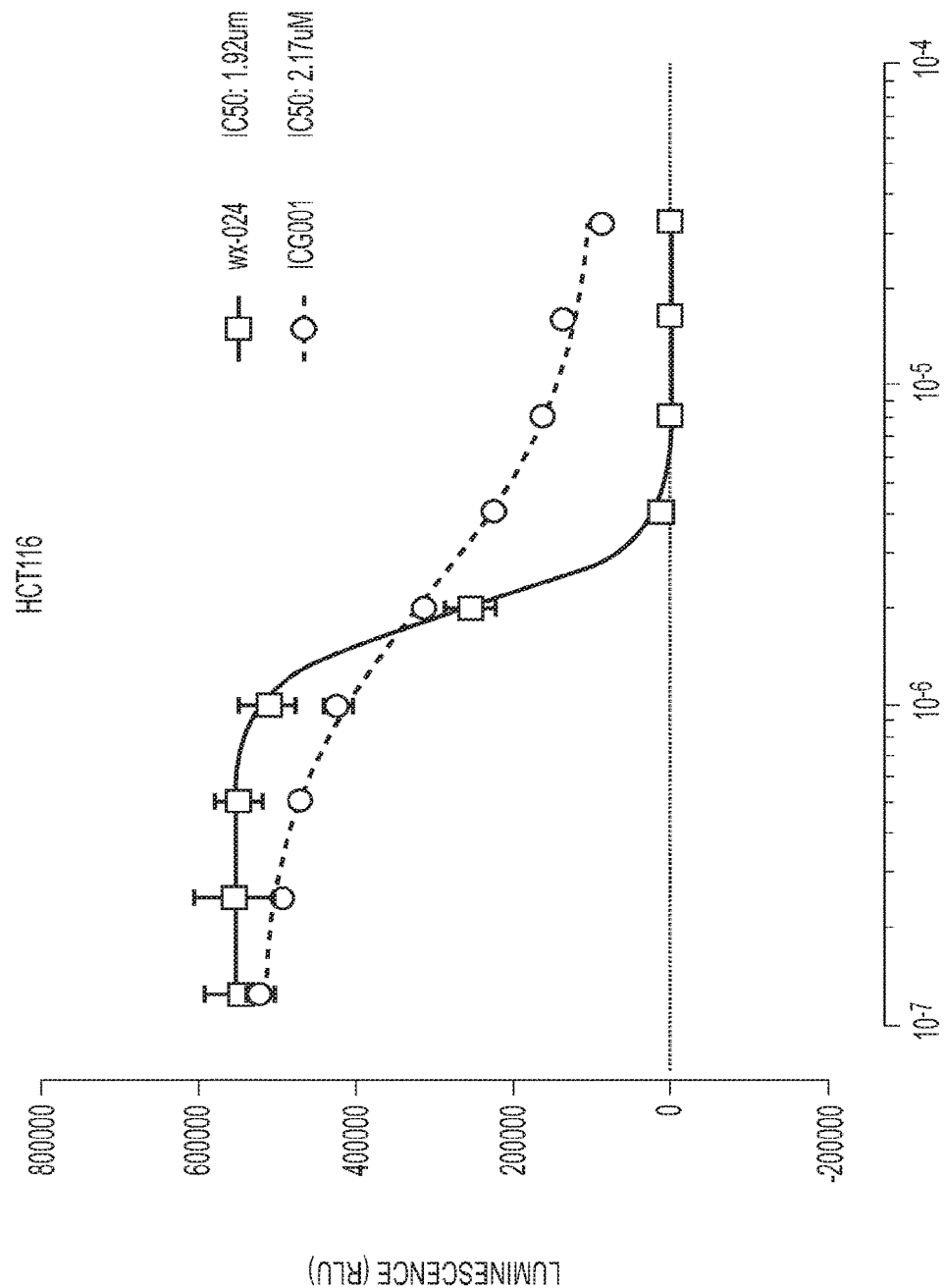
FIG. 7 shows cell viability data comparing WX-024 with ICG001 (a Wnt/β-catenin pathway inhibitor) using a CellTiterGlo assay (Promega) in HCT116 cells. The $IC_{50}$ values of WX-024 and ICG001 calculated based on this assay were 1.92 μM and 2.17 μM, respectively.

FIG. 7 presents the data on viability of HCT116 cells treated with increasing concentrations of either WX-024 or ICG001 using a CellTiterGlo luminescent cell viability assay (Promega) using standard manufacturer's procedures. Both WX-024 and ICG001 were able to inhibit cell growth as measured by the viability assay. In particular, the $IC_{50}$ value of WX-024 calculated from this assay was 1.92 µM, lower than that of ICG001 ($IC_{50}$=2.17 µM).

Overall, the data indicate that WX-024 has a robust in vitro profile consistent with inhibition of the Wnt signaling pathway.

Example 4.4. Comparison of WX-024 and Other Known Chemotherapeutic Agents

Figure 8A:
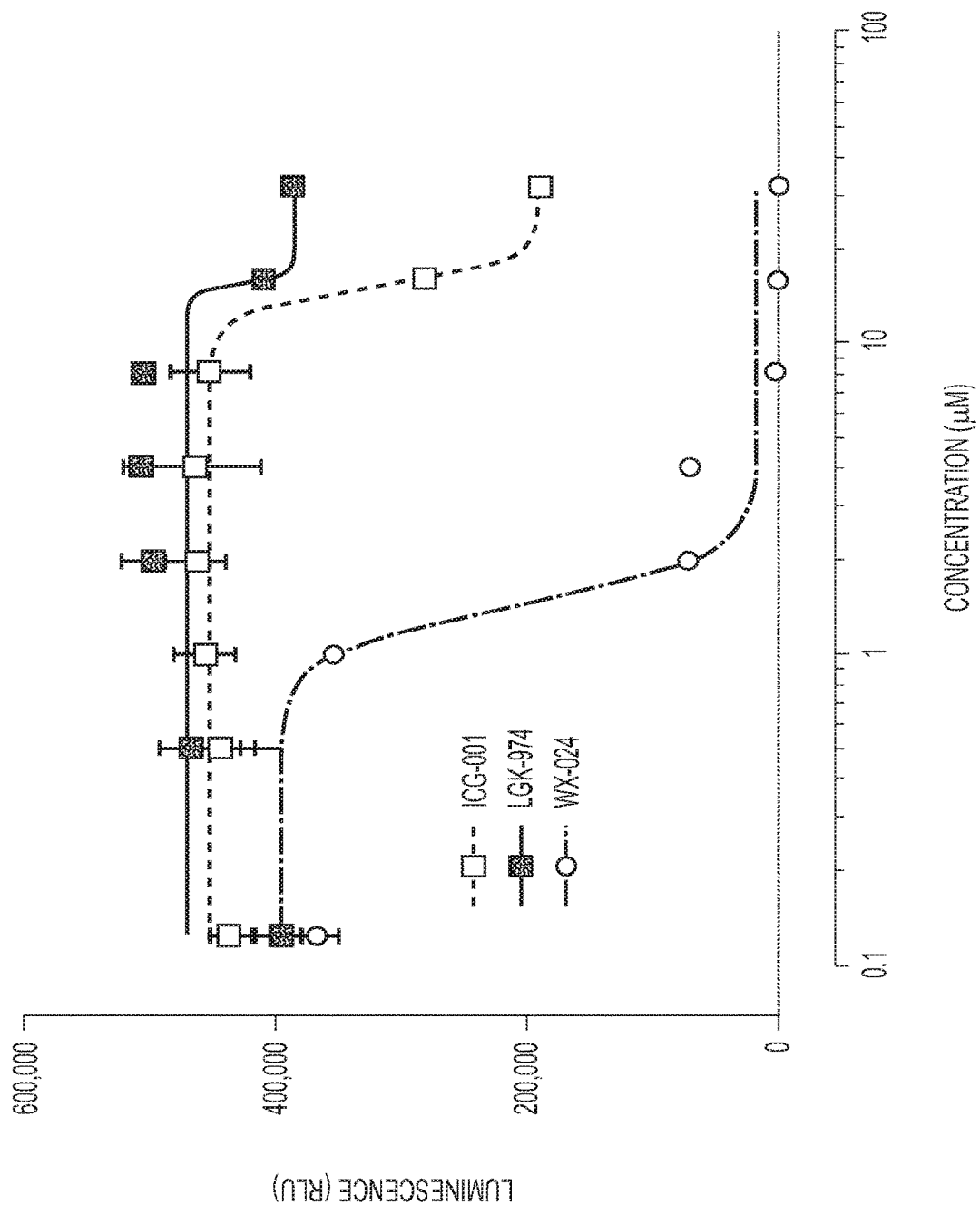
FIG. 8A shows results of a cell viability assay testing WX-024, ICG001, and LGK-974 (*P<0.05, WX-024 vs ICG001, LGK-974). Colo320DM cells were used in this cell viability assay.
Figure 8C:
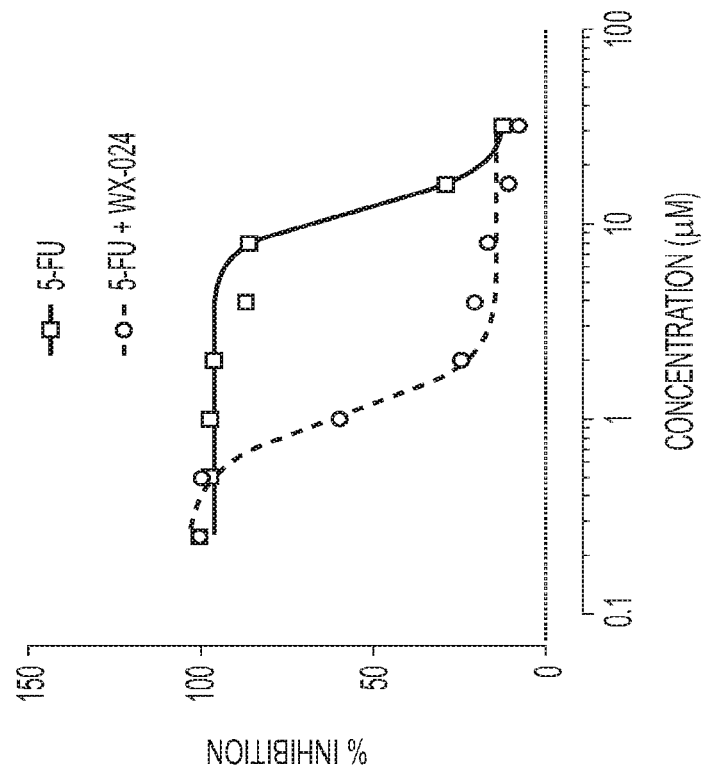
FIG. 8C shows results of the same cell viability assay comparing 5-FU treatment alone and a combination of 5-FU and WX-024 (*P<0.05).
Figure 8B:
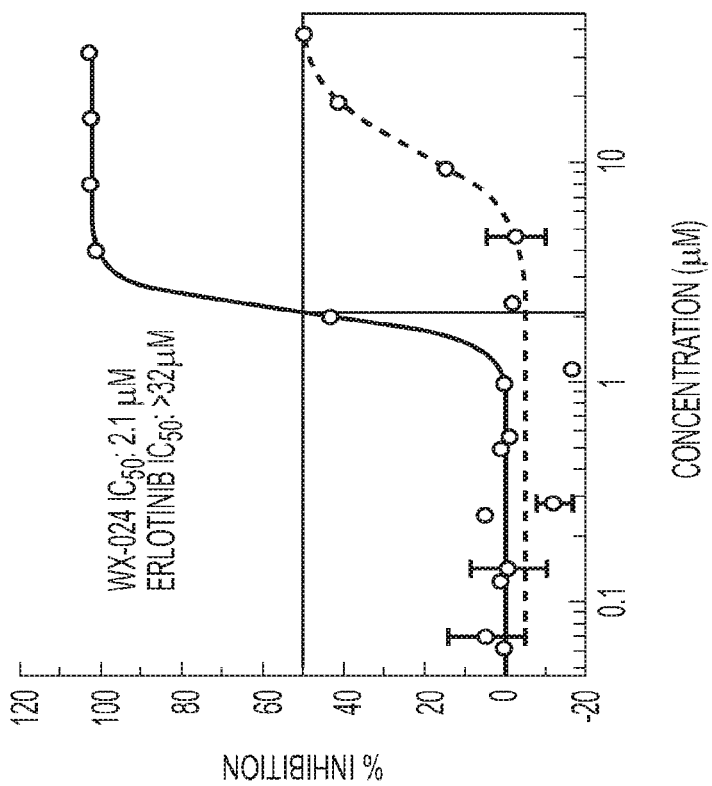
FIG. 8B shows results of the same cell viability assay testing WX-024 and Erlotinib.

WX-024 was also tested in a Colo320DM cell viability assay and compared to other chemotherapeutic agents. WX-024 was approximately 12-fold more effective in inhibiting cell growth of a BCL9/β-catenin dependent cell line than ICG001, LGK-974 (FIG. 8A) or Erlotinib (FIG. 8B).

WX-024 also offered benefits and improvements when used in combination with other known chemotherapeutic agents. In particular, as shown in FIG. 8C, WX-024 was tested in combination with a widely used chemotherapy drug in a colorectal cancer, 5-fluorouracil (5-FU), and showed that the combination therapy showed a significantly improved ability to inhibit cell growth ($IC_{50}$=1 µM) as compared to 5-FU treatment alone ($IC_{50}$=12.1 µM).

Example 4.5. Specificity of WX-024

As discussed in Example 4.1, WX-024 inhibited Wnt transcription in a cell-based assay. However, WX-024 did not produce any significant inhibition in other transcription assays, such as JAK/STAT (SIE-bla ME-180 cell line), PI3K/AKT/FOXO (TREx FOXO3-DBE-bla HeLa cell line), TGF-beta (SBE-bla HEK 293T cell line), or TNF-alpha/JNK (AP1-bla ME-180 cell line) pathways (Life Technologies), showing an $IC_{50}$ value greater than 10 µM in all these transcription assays. In these assays, the trifluoroacetic salt form of WX-024 was used. The data, summarized in Table 4 below, demonstrate that WX-024 is an inhibitor that specifically targets the Wnt/β-catenin pathway.

TABLE 4

Evaluation of WX-024 in additional pathways

| Pathway | Cell Line Tested | Stimulation | IC50 (nM) |
| --- | --- | --- | --- |
| JAK/STAT | SIE-bla ME-180 | IL-6 | >3160 |
| PI3K/AKT/FOXO3 | TREx FOXO3-DBE-bla HeLa | Insulin | >1000 |
| TGF-beta | SBE-bla HEK 293T | TGF-beta 1 | >3160 |
| TNF-alpha/JNK | AP1-bla ME-180 | TNF-alpha | >1000 |
| Wnt/Beta-Catenin | LEF-TCF-bla HCT116 | None | 191 nM |

Example 5. In Vivo Profile of Stabilized Polypeptide

Based on the robust in vitro profile of WX-024, experiments were performed in mice to determine the plasma pharmacokinetic parameters. In addition, WX-024 was evaluated in a mouse xenograft model to test for efficacy in inhibiting tumor growth.

Example 5.1. Pharmacokinetic Profile of WX-024 in Mice

The pharmacokinetic (PK) profile of WX-024 was assessed following intravenous (i.v.) and intraperitoneal (i.p.) injections in male ICR mice (an outbred strain). The tail vein was used for i.v. injections. The doses of WX-024 assessed with 1 mg/kg (i.v.) and 5 mg/kg (i.p. and i.v.). Following injections, blood samples were obtained via the retro-orbital vein at 5 min, 1, 2, 4, 6, 8, 12, and 24 hours postdose. Plasma was obtained from the blood samples following mixing with sodium heparin and centrifugation.

Figures 9A, 9B:
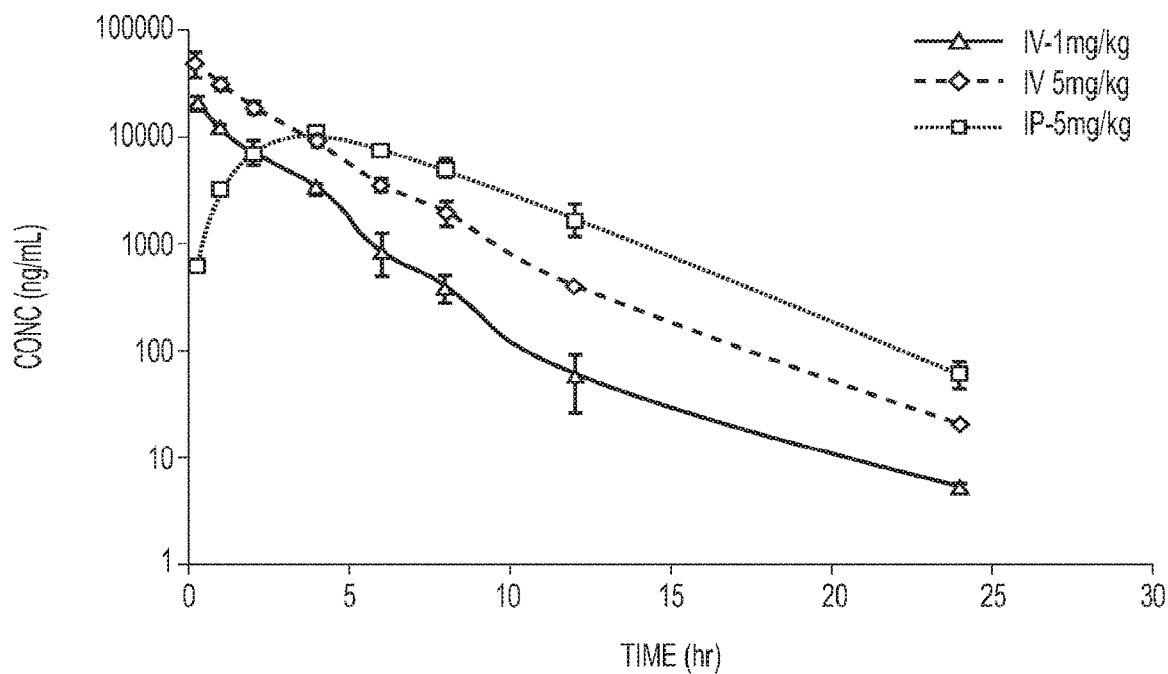
FIG. 9A and FIG. 9B show pharmacokinetic (PK) data for WX-024 with intravenous (i.v.) administration at 1 mg/kg or 5 mg/kg and intraperitoneal (i.p.) administration at 5 mg/kg to male ICR mice (an outbred strain). Blood samples were collected at 15 min, 1, 2, 4, 6, 8, 12, and 24 hours post-dosing and analyzed via liquid chromatography-mass spectrometry (LC-MS), as shown in FIG. 9A. From the plasma concentration data shown in FIG. 9A, the maximum observed concentration ($C_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity ($AUC_{0-inf}$), and bioavailability were calculated. These pharmacokinetic parameters are summarized in FIG. 9B.

The concentration of WX-024 (ng/ml) was determined using a LC/MS. LC analysis was done using an Agilent 100 HPLC. MS analysis was done using an AB Sciex API 4000. Calibration standards were prepared by serial dilution. The concentrations of WX-024 (ng/ml) over time are shown in FIG. 9A.

The maximum observed concentration ($C_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity ($AUC_{0-inf}$), and bioavailability were calculated using non-compartmental analysis modules in the FDA-certified pharmacokinetic program WinNonlin Professional v5.2 (Pharsight). These values are summarized in FIG. 9B. Of note, 5 mg/kg administered intravenously produced the greatest $C_{max}$ for WX-024 with a value of 47354 ng/ml. This is equivalent to greater than 30 µM, which is 15 times greater than the in vitro $IC_{50}$ calculated in Example 4, indicating that physiological relevant concentrations of WX-024 can be achieved in the plasma.

The $T_{1/2}$ of WX-024 with all dosing regimens was between 2.4-2.5 hours, which indicates that there is a substantial period wherein active WX-024 is present in the plasma. The bioavailability of WX-024 following i.p. dosing is 73.6%. This value is not provided for i.v. dosing as all of the compound enters the plasma so the bioavailability is 100%. The values for Cmax, Cl, $V_z$, $AUC_{0-t}$, and $AUC_{0-inf}$ are all also consistent with a profile that indicates adequate exposure to WX-024 following i.p. and i.v. dosing to potentially modulate Wnt signaling.

Figure 10A:
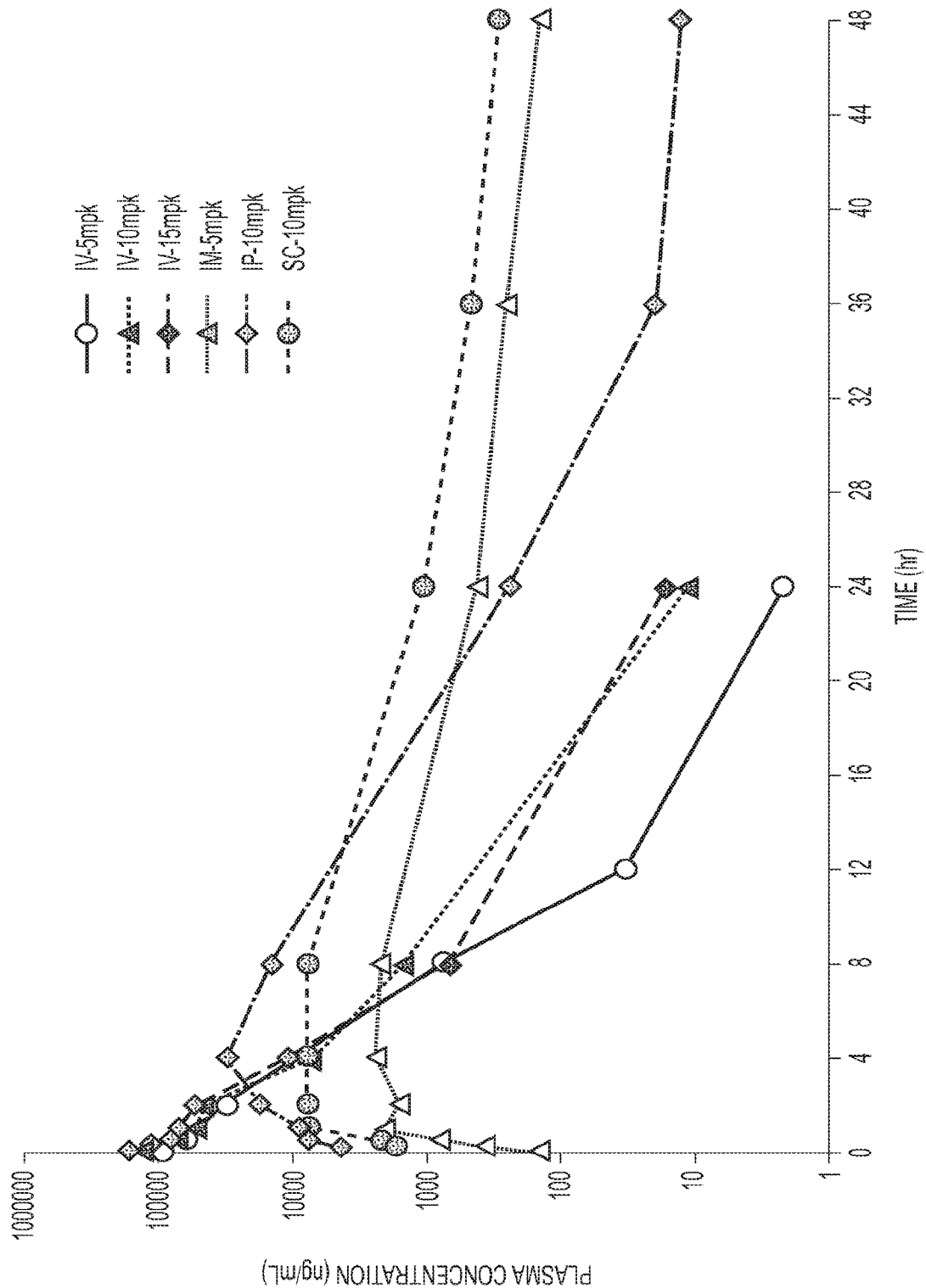
FIG. 10A shows PK data for WX-024 measured in female Balb/c mice. Each data point represents N=2. Mice were administered 5 mg/kg, 10 mg/kg, or 15 mg/kg intravenously, 5 mg/kg intramuscularly, 10 mg/kg intraperitoneally, or 10 mg/kg subcutaneously. Blood samples were collected at 15 min, 1, 2, 4, 6, 8, 12, and 24 hours (and 36 and 48 hours post-dose for intramuscular, subcutaneous, and intraperitoneal routes) post-dosing and analyzed via liquid chromatography-mass spectrometry (LC-MS).

A similar pharmacokinetic study of WX-024 was performed with a different mouse strain (female balb/c mice, n=2 per treatment) and additional administration routs, including intramuscular and subcutaneous routes. Briefly, a mixed solvent of 10% DMSO and 90% deionized $H_2O$ was used to dissolve WX-024. The peptide solution was prepared at the fixed concentration of 0.5 mg/ml, and then suitable amounts were administered according to the dose. The same mixed solvent was used as a vehicle treatment. Blood samples (300 µL) were collected periodically from the retro-orbital vein at 0.25, 1, 2, 4, 6, 7, 12, and 24-hours post-dose (and 36 and 48 hours post-dose for intramuscular, subcutaneous, and intraperitoneal routes), followed by plasma separation for pending bioanalysis by LC-MS/MS. Standard PK parameters were calculated by non-compartmental analysis modules in WinNonlin Professional (v5.2, Pharsight, FDA-certified). As shown in FIG. 10A, the plasma concentrations of WX-024 followed a similar trend to what was shown in FIG. 9A. The mean pharmacokinetic parameters calculated from this experiment are shown in FIG. 10B and FIG. 10C. Good bioavailability and a long half-life were observed for WX-024, indicating that daily dosing of WX-024 is feasible. Of note, the plasma concentrations of WX-024 remained stable for a long period when administered via intraperitoneal, intramuscular, subcutaneous routs, demonstrating that WX-024 can achieve physiologically relevant concentrations in vivo when administered in various routes.

Overall, these data indicate that WX-024 has a PK profile suitable for studying the in vivo effect of inhibiting the interaction of BCL9 and β-catenin.

Example 5.2. Efficacy of WX-024 in a Mouse Xenograft Model of Cancer

Based on the favorable PK profile of WX-024 in mice, described above, the efficacy of WX-024 was investigated in a mouse xenograft colon cancer model. The Colo320DM colon cancer model in BALB/c nude mice was employed, in which Colo320DM cells are injected subcutaneously into BALB/c nude mice. Tumors form from the Colo320DM cells as the nude mice do not mount a sufficient immune response to clear these tumors.

Colo320DM tumor cells (ATCC) were cultured in RPMI1640 medium (GIBCO, Cat #31800022) supplemented with 10% heat-inactivated fetal bovine serum at 37° C. Harvesting of Colo320DM cells was done when cells were growing in an exponential growth phase. Female BALB/c nude mice (Shanghai Laboratory Animal Center) were used for the study at 6-8 weeks of age. Animals had free access to water and irradiation sterilized food throughout the study period. Each mouse (n=16) was inoculated subcutaneously in the right flank region with $5\times10^6$ Colo320DM tumor cells in 0.1 mL of PBS. Tumors were allowed to develop for 14 days after inoculation, at which time the mean tumor size was 156.78 $mm^3$. During the study, the care and use of animals was conducted in accordance with the Association for Assessment and Accreditation of Laboratory Animal Care (AAALAC). Following inoculation of tumor cells, animals were checked daily for morbidity and mortality. The body weight of each animal was monitored throughout the study.

After the 14-day period for tumor development, the mice were divided into 4 treatment groups: 5, 10, and 15 mg/kg WX-024 and vehicle control groups. 4% ethanol+8% Tween 80+88% 10 mM PBS was used as a vehicle. All treatments were administered once daily. The WX-024 solution was dissolved in pure DMSO and then diluted with sterile water. The dosing volume was adjusted for body weight such that the dosing volume for each animal was 0.05 mL/10 g of body weight for i.v. dosing. The treatment period was 14 days.

Figure 11:
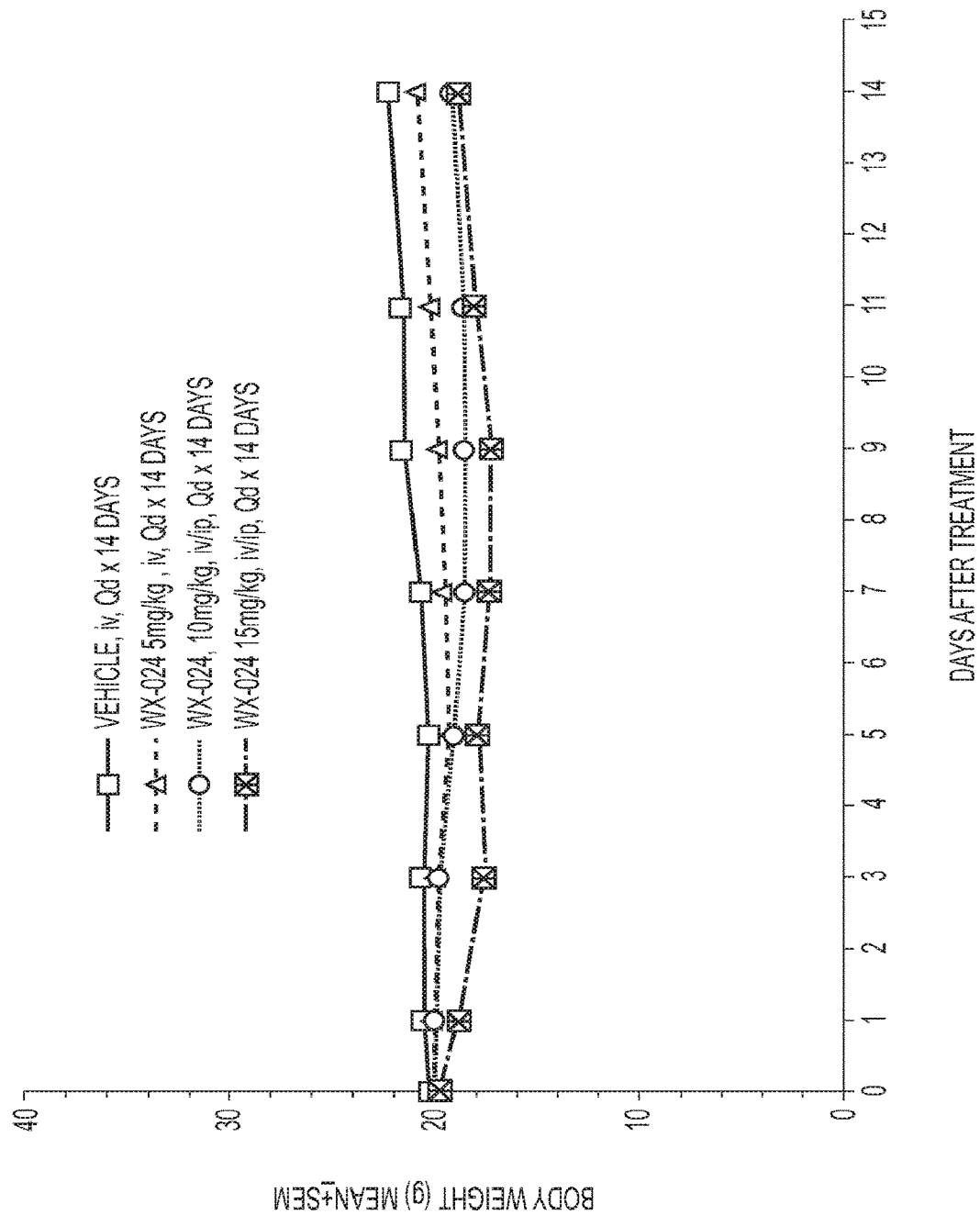
FIG. 11 shows body weight data of female Balb/c nude mice at 6-8 weeks of age inoculated with Colo320DM tumor cells and treated with a vehicle or WX-024. Mice were inoculated with Colo320DM tumor cells (5×10$^6$), and tumors were allowed to develop for 14 days, after which treatments were applied. The vehicle and 5 mg/kg treatment groups were dosed throughout the study by i.v. injection with no apparent change in body weight over the study. After 3 days of i.v. dosing of 15 mg/kg WX-024, mice in this group exhibited body weight loss. Therefore, on Day 7, the 10 and 15 mg/kg groups were switched to i.p. dosing for the rest of the treatment period. Following this switch to i.p. dosing, body weight in the 15 mg/kg group stabilized for the remainder of the study.

All treatments were begun as daily i.v. dosing. It was found during the study that i.v. administration of 15 mg/kg WX-024 caused body weight loss with an average body weight loss of approximately 11% as compared to a vehicle treated group after 3 days of treatment. The injection method was changed to i.p. injection at Day 7 for the 10 mg/kg and 15 mg/kg groups. Dosing via i.p. injection (with the dosing volume adjusted to 0.1 ml/10 g) was maintained for the 10 and 15 mg/kg groups from Day 7 of the treatment period onwards, and the body weight of these animals stabilized. Mice treated with vehicle control or 5 mg/kg WX-024 received i.v. injections throughout the study without an apparent effect on body weight. Body weight changes in mice during the treatment period are shown in FIG. 11.

Tumor volumes were measured in two dimensions using a caliper at Days 0, 3, 5, 7, 9, 11, 14 of the treatment period (all dosing starting after 14 days of tumor development). The volume of the tumor was measured using the equation: $V=0.5\ a\times b^2$, wherein a and b are the long and short diameters of the tumor, respectively. Tumor volumes are expressed in $mm^3$. At the end of the study (i.e., following 22 days of treatment) the tumor mass weight was measured.

Figure 12A:
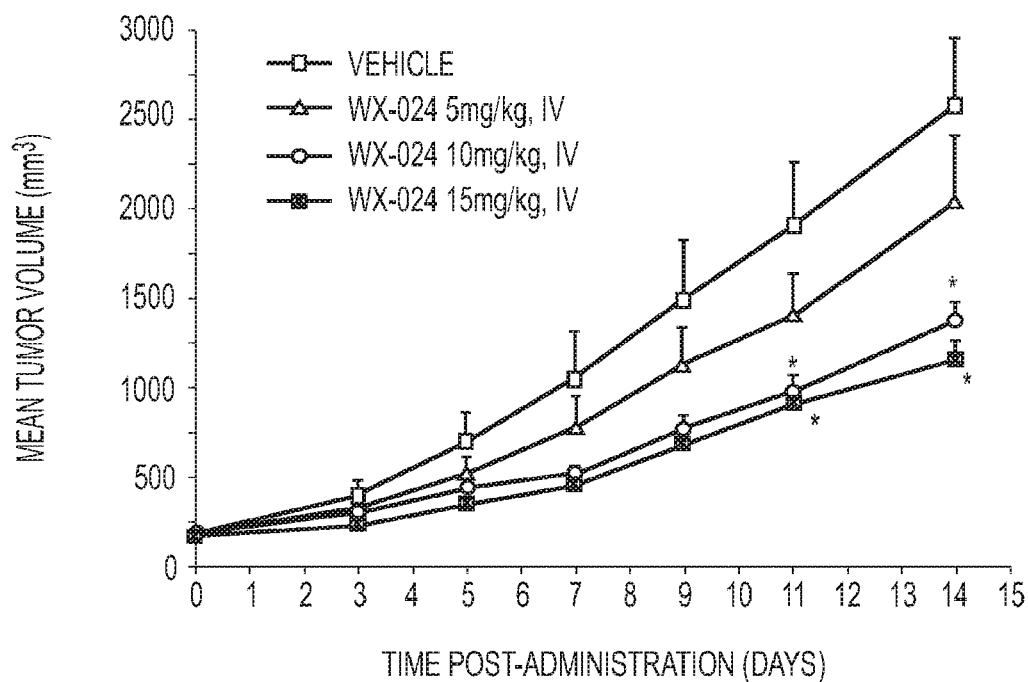
FIG. 12A and FIG. 12B depict tumor growth changes caused by vehicle or WX-024 during the experiment described for FIG. 11.

FIG. 12A shows tumor volumes in the different treatment groups over time. At Day 14, the tumor volume (mean±standard error of mean values) was 2575±382.86 $mm^3$ for vehicle control-treated mice. The tumor volumes for WX-024-treated mice were 2039±373.29, 1370±114.39, and 1157.6±99.04 $mm^3$ for the 5, 10, and 15 mg/kg treatment groups, respectively. The tumor volumes of mice treated with 10 mg/kg or 15 mg/kg WX-024 were significantly smaller at Day 14 of treatment compared with vehicle-treated animals ($P<0.05$, Kruskal-Wallis analysis). Compared to the vehicle-treated group, tumor volumes were 53.2% smaller for the 15 mg/kg WX-024 group and 44.9% smaller for the 10 mg/kg WX-024 group at Day 14 of the treatment period. Significantly smaller tumor volumes for the 10 mg/kg and 15 mg/kg groups compared with the vehicle-control group were also seen on Day 11 of treatment. A preliminary dose-response correlation of WX-024 with predicted tumor size resulted in an $IC_{50}$ value of 12.69 mg/kg.

Figure 12B:
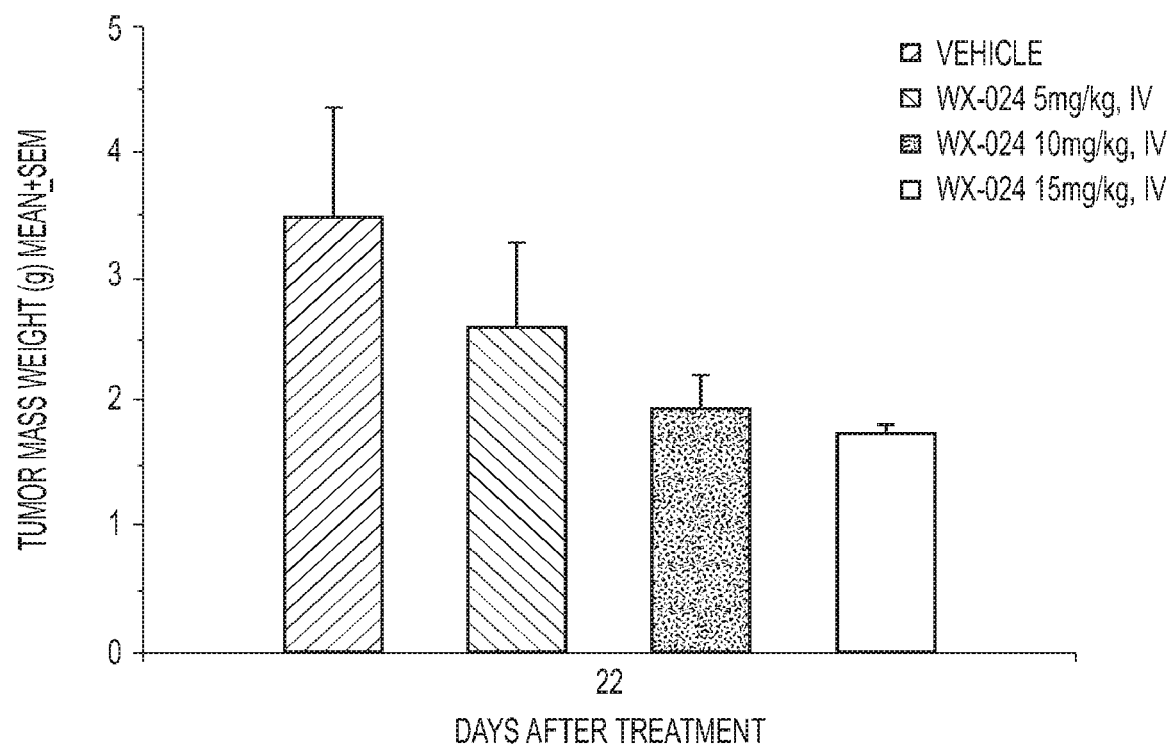

FIG. 12B shows tumor mass weight (measured in grams) at the end of the study following 22 days of treatment with vehicle or WX-024. Tumor mass of mice treated with 10 or 15 mg/kg WX-024 (using the i.v./i.p. protocol described above) was substantially less than tumor mass of vehicle-treated mice. These data confirmed that treatment with either 10 or 15 mg/kg inhibited tumor growth in the Colo320DM colon cancer model in BALB/c nude mice.

At the conclusion of the Colo320DM model, tumor and intestinal samples were collected, fixed in formalin, and imbedded in paraffin using standard techniques. Four μm-thick section of tissue were prepared for immunohistochemistry (IHC) staining. The tissue sections were deparaffinized and rehydrated via sequential washing with xylene, graded ethanol and phosphate-buffered saline (PBS). Following deparaffinization and rehydration, the tissue sections were subjected to high temperature-induced epitope retrieval in target retrieval solution (10 mM citrate buffer; pH 6.0).

Antibody binding was detected using an UltraVision Quanto Detection System (Thermo, Cat #TL-060-QHD) kit following the manufacturer's instructions. The sections were treated with Hydrogen Peroxide Block and Ultra V Block (provided in the kit) and then incubated with primary antibody overnight at 4° C.: CD44 (Abcam, Cat #ab157107 diluted 1:500), Axin (LSBio, Rabbit IgG, Cat #LS-B7029, Lot #51907, Stock Conc.:1000 ug/ml), or VEGFA (VEGFA: LS Bio, Rabbit IgG, Cat #LS-B10263, Lot #65323, Stock Conc.: 1000 ug/ml). Rabbit IgG replaced the primary antibody in the negative control. All sections were counterstained with hematoxylin, dehydrated and mounted. IHC images were taken with an Olympus CKX31SF reverse microscope.

Figure 13A:
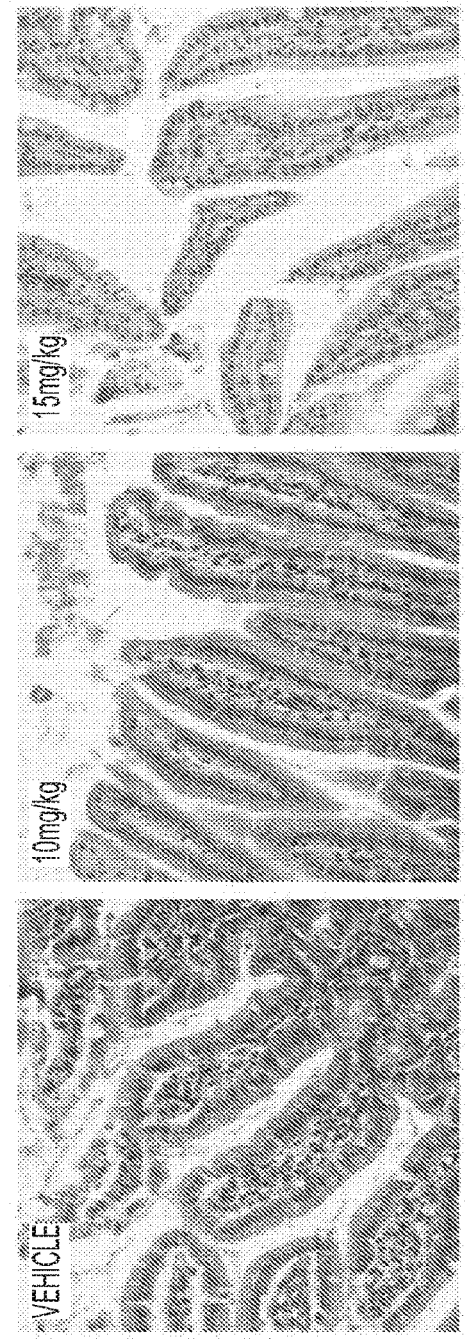
FIG. 13A shows intestinal histology of BALB/c nude mice at the conclusion of the Colo320DM xenograft model after 22 days of treatment, as described for FIG. 11. Samples from vehicle, 10 mg/kg, and 15 mg/kg WX-024 treatment groups are depicted.
Figure 13B:
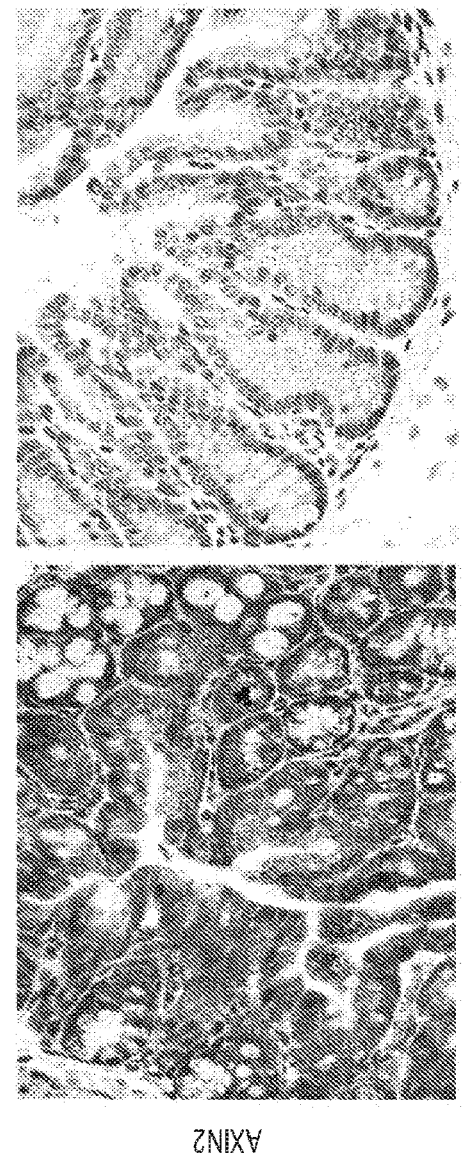
FIG. 13B shows Axin2 staining of the intestine samples collected in FIG. 13A.

FIG. 13A shows that the intestinal morphology was maintained in mice treated with vehicle, 10 mg/kg, or 15 mg/kg WX-024 for 22 days. FIG. 13B shows staining of Axin 2, a downstream protein in the Wnt signaling pathway, indicating that 22 days of treatment with 15 mg/kg WX-024 decreased Axin 2 staining as compared with the vehicle treatment.

Figure 14A:
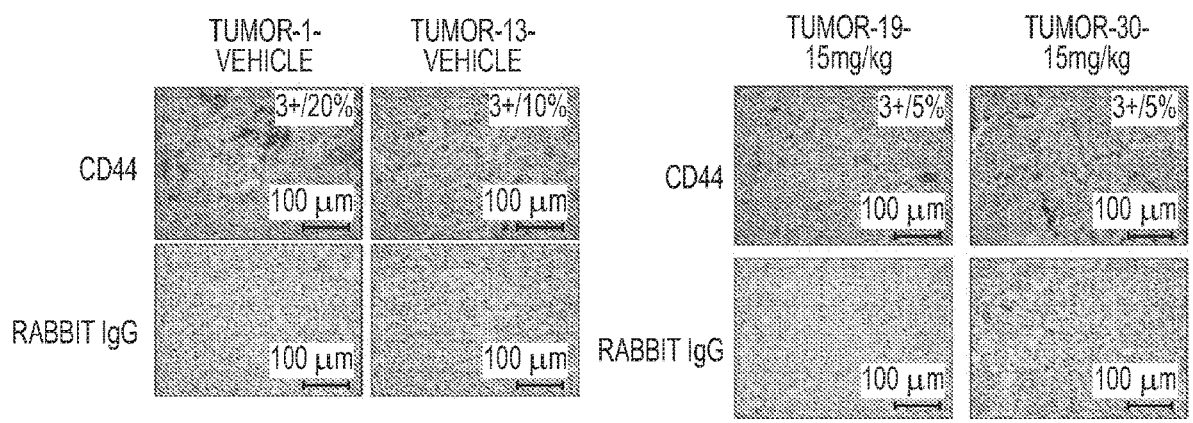
FIG. 14A shows 40×-magnification of CD44 staining of tumor samples collected from the experiment described for FIG. 11. The immunochemistry score of each sample is shown at the upper right corner of each image.
Figure 14B:
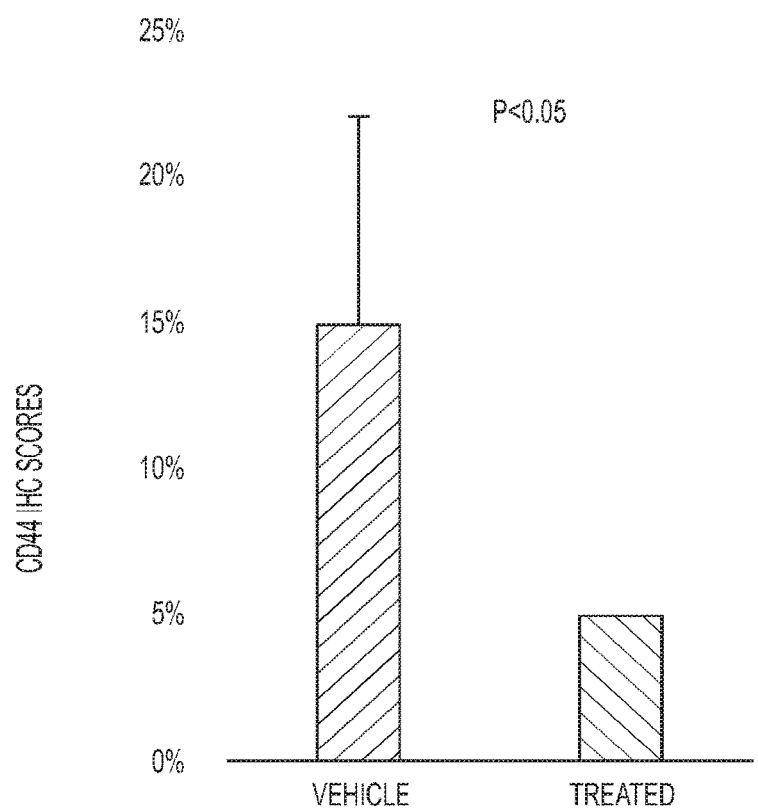
FIG. 14B summarizes the average immunochemistry score of each treatment group.

FIG. 14A shows staining for CD44, another downstream protein in the Wnt signaling pathway, following 22 days of treatment either vehicle or 15 mg/kg WX-024. Immunohistochemistry scores are denoted in the top-right of each CD44 image. FIG. 14B shows the quantitative comparison of the average staining scores calculated from the CD44 staining images. These data indicate that there was also a decrease in CD44 staining following treatment with WX-024.

Figure 15A:
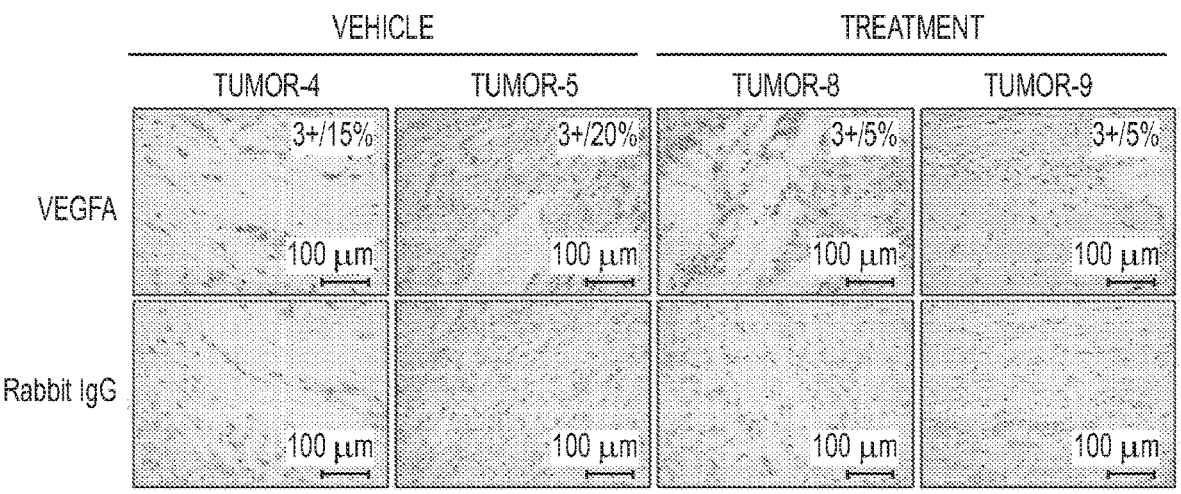
FIG. 15A shows VEGFA staining of tumor samples collected from the experiment described for FIG. 11. The immunochemistry score of each sample is shown at the upper right corner of each image.
Figure 15B:
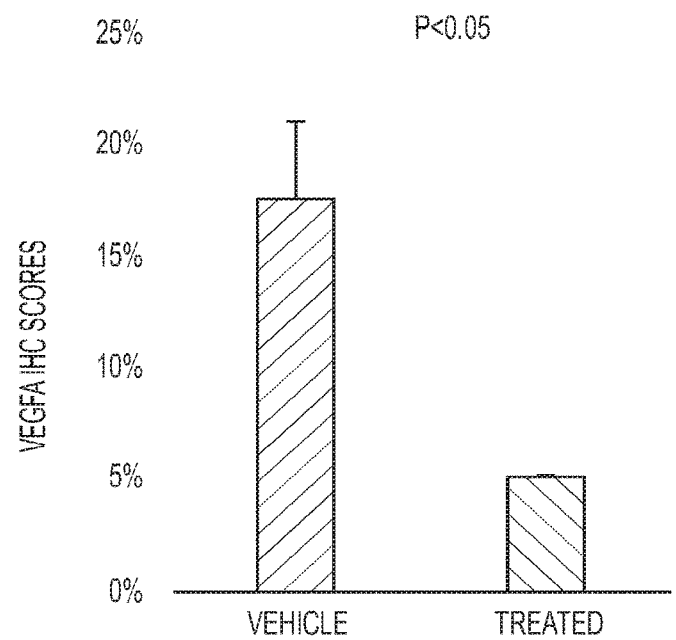
FIG. 15B summarizes the average immunochemistry score of each treatment group.

Likewise, the tumor samples were stained for VEGFA and confirmed that WX-024 was capable of suppressing VEGFA expression in tumors. FIG. 15A shows representative images from two vehicle treated animals and two WX-024 treated animals. The average immunohistochemistry scores calculated from the staining images are summarized in 15B.

Thus, the data from the Colo320DM model indicate that WX-024 is capable of suppressing tumor growth and inhibiting Wnt/β-catenin signaling as compared to a vehicle treatment. The effect of WX-024 on VEGFA also indicates that WX-024 may modulate the immune response via reducing VEGF expression in tumors.

Example 5.3. Efficacy of WX-024 in a Mouse Syngeneic Model of Cancer (CT26)

The CT26 model of colon cancer was used as a model for investigating tumor growth in mice with an intact immune system.

Figure 16A:
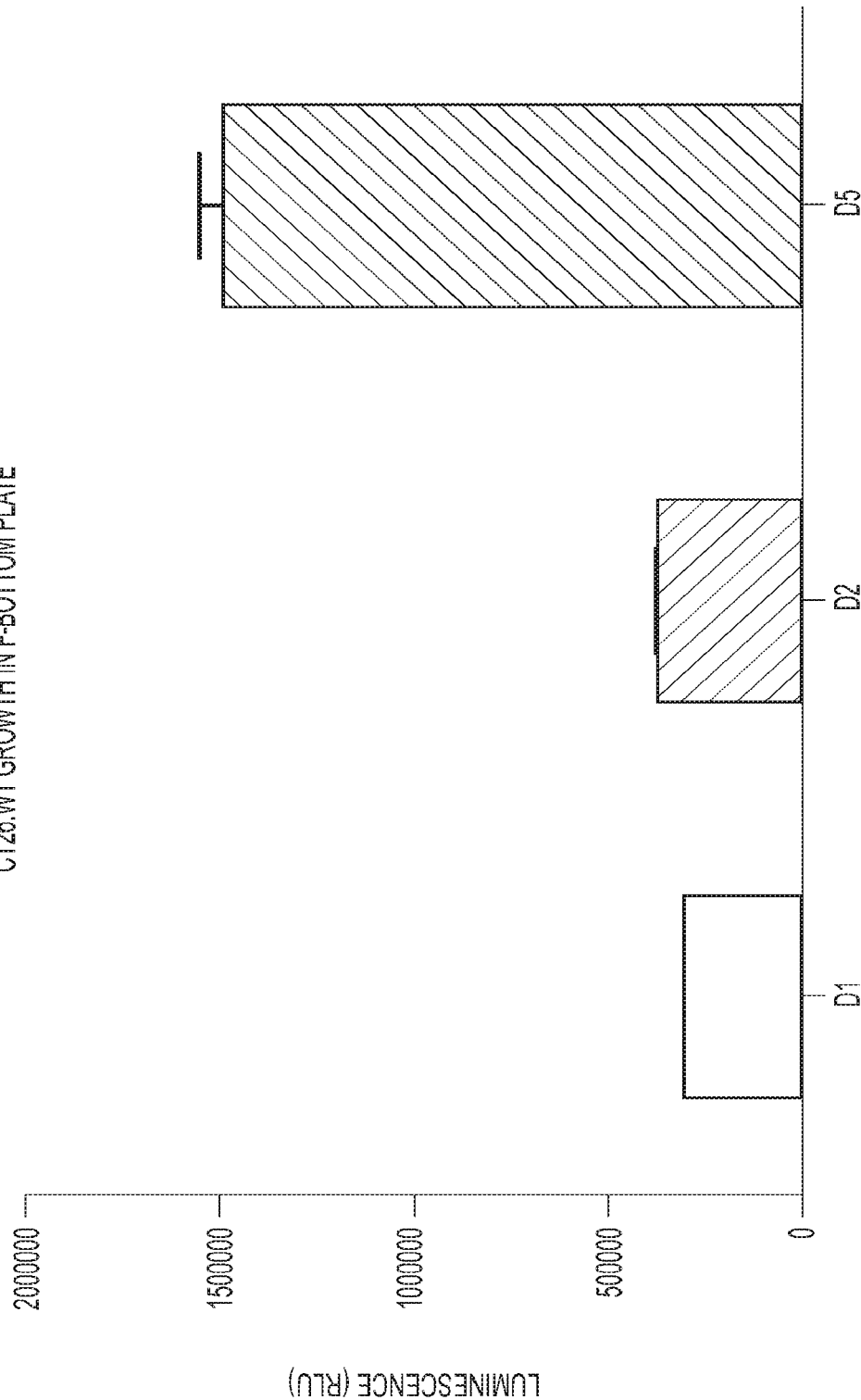
Figure 16B:
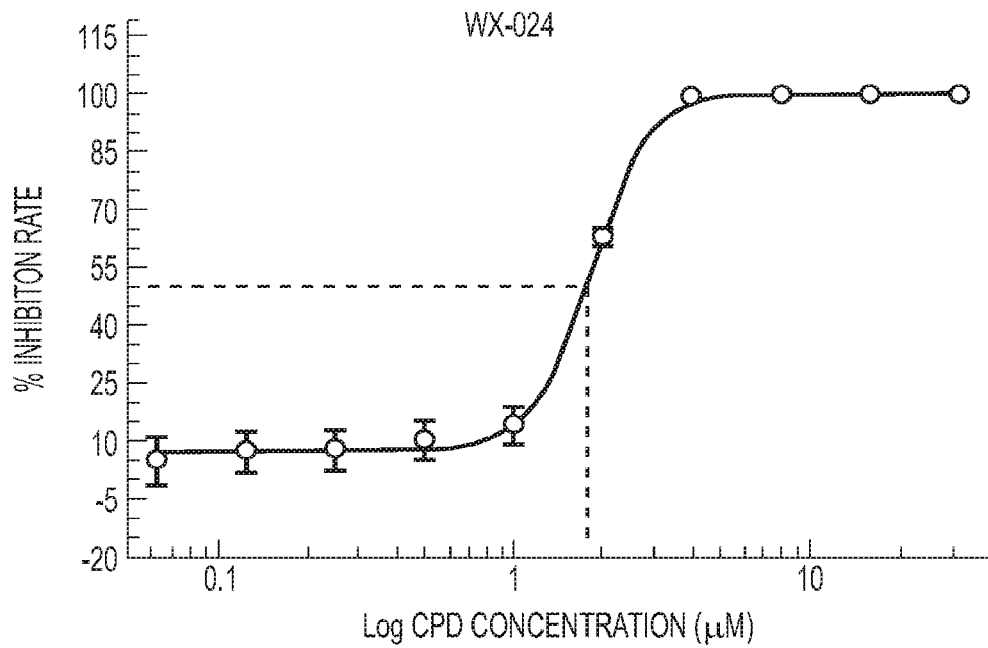
Figure 16C:
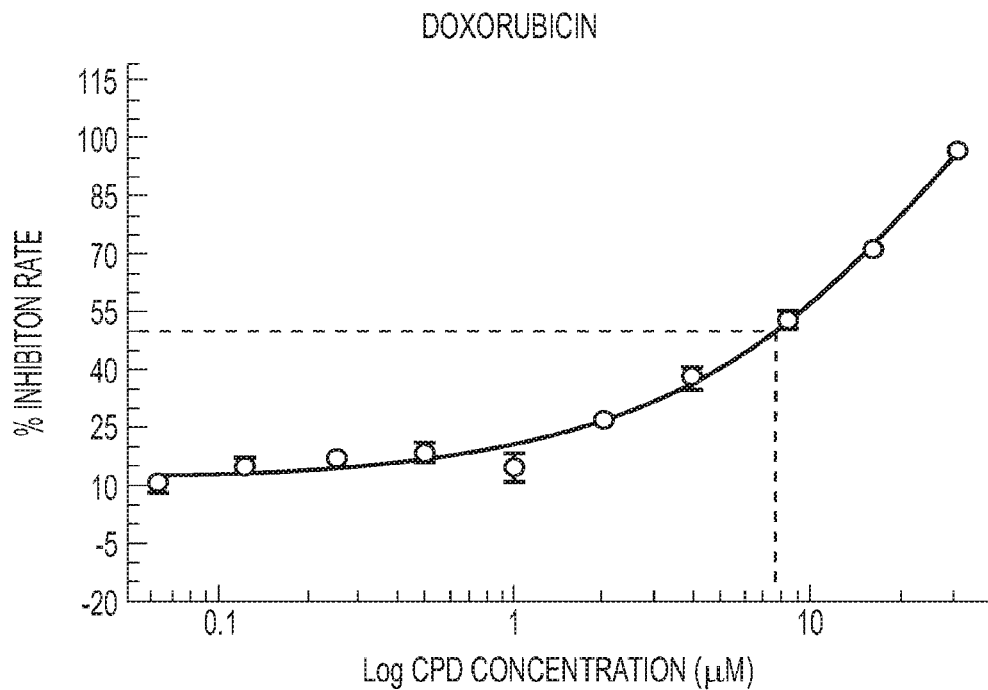

The effect of WX-024 on CT26 cell growth was first investigated in vitro. CT26 cells were grown in F-bottom plates over 5 days. As shown in FIG. 16A, from day 1 (D1) to day 5 (D5), there was substantial growth of CT26 cells, as measured by a luminescence cell viability assay. CellTiterGlo (Promega) cell viability assay. The ability of WX-024 (FIG. 16B) and doxorubicin (FIG. 16C) to inhibit CT26 cell growth was measured. Doxorubicin is a known inhibitor of cell growth and was included as a control. FIG. 16D summarizes the in vitro data in CT26 cells, showing that WX-024 and doxorubicin were both able to inhibit growth of CT26 cells, with WX-024 showing more potent activity. The $IC_{50}$ value of WX-024 was 1.753 µM, much lower than that of doxorubicin, 7.520 µM. The EGFR receptor antagonist, erlotinib, had an $IC_{50}$ greater than 2 µM.

Figure 17A:
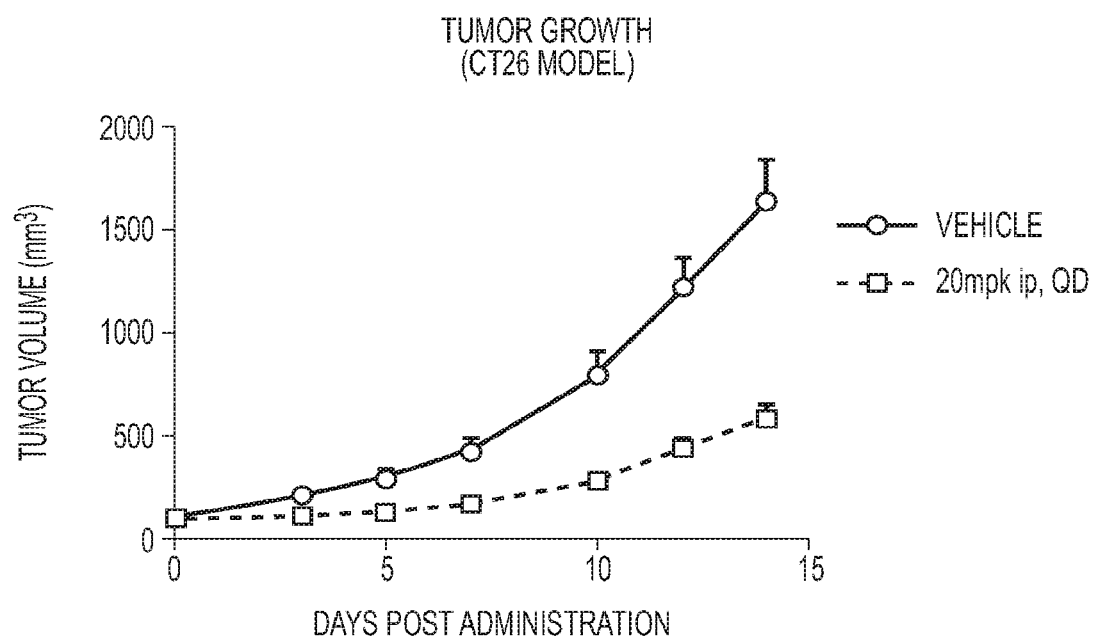
FIG. 17A shows the average tumor growth of two groups of mice treated with either vehicle or 20 mg/kg WX-024. Each mouse received an intraperitoneal injection of its assigned treatment daily for 14 days. A Balb/c syngeneic mouse model bearing CT26 colon cancer cells was used in this experiment. Each data point represents the average of eight mice per group.
Figure 17B:
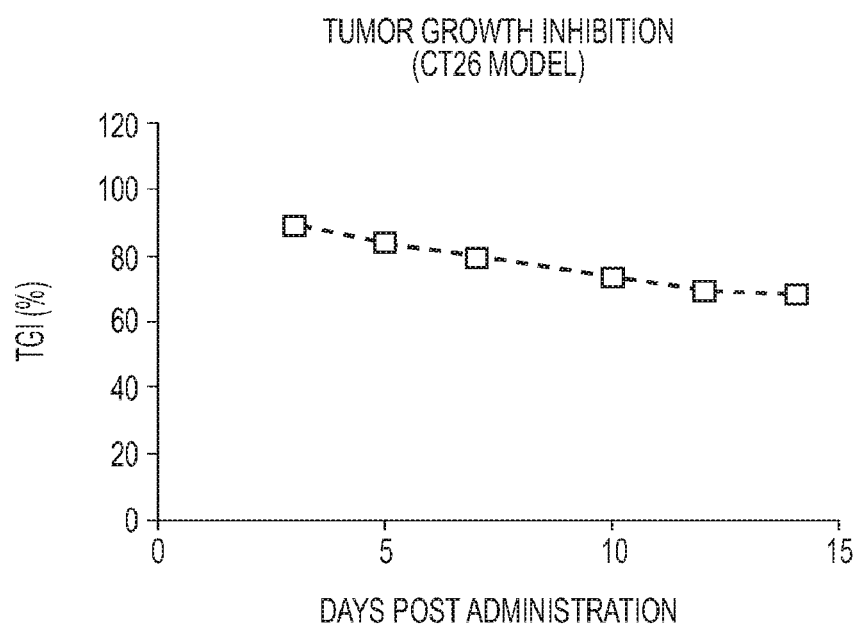
FIG. 17B shows the average tumor growth inhibition (TGI) rate of WX-024 treatment. The TGI at day 3 was 89.2% while the TGI at day 12 was 70.0%.
Figure 18A:
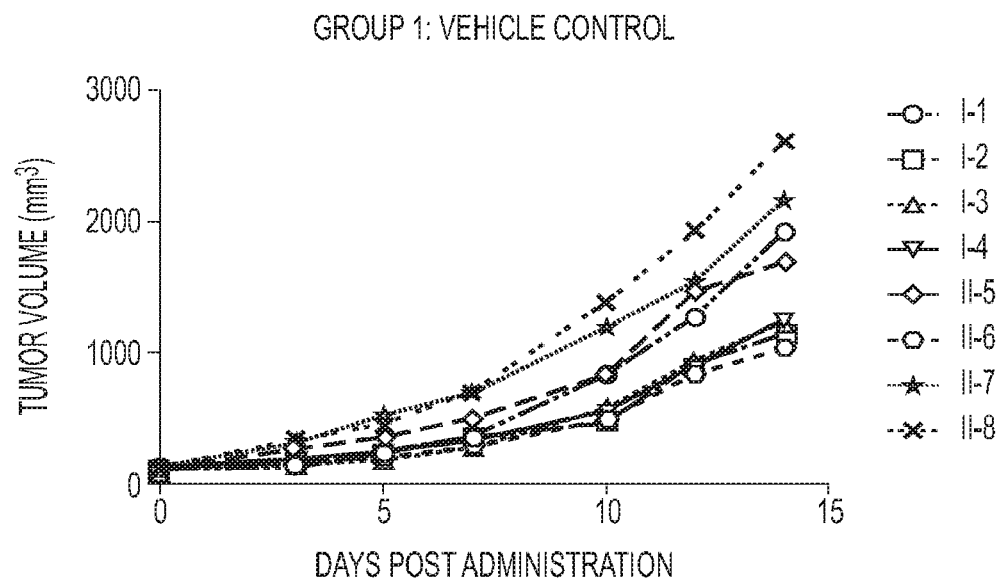
FIG. 18A and FIG. 18B show the tumor growth of individual animals monitored in the experiment described for FIG. 17.
Figure 18B:
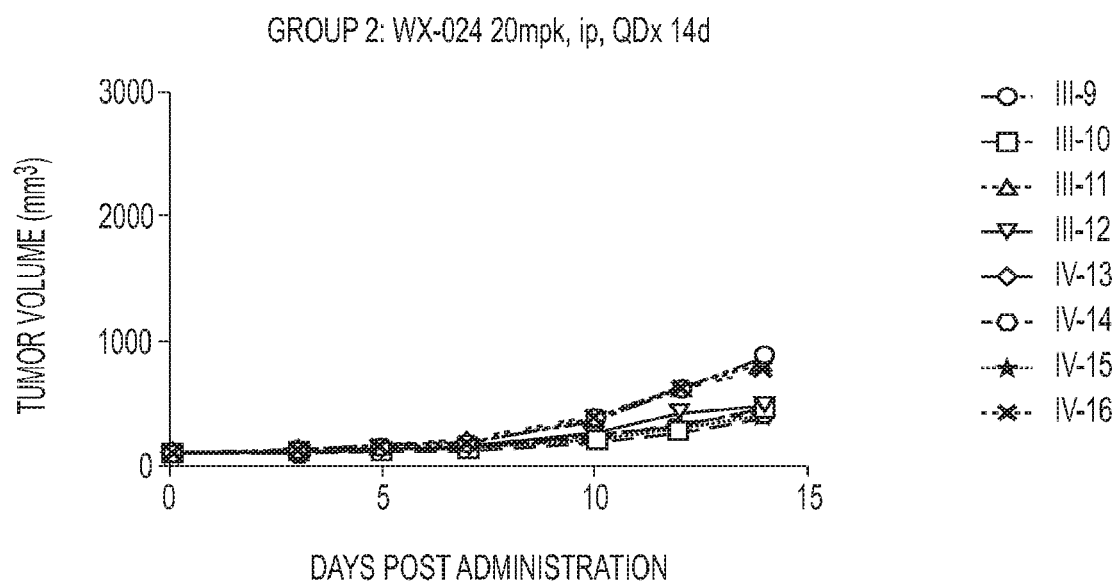

The syngeneic mouse model of colon cancer using CT26 was then assessed. Male Balb/c mice were injected subcutaneously in the right flank with $5 \times 10^4$ CT26 cells each at approximately 5 weeks of age. Mice were then dosed with either vehicle or 20 mg/kg WX-024 i.p. daily. Eight mice were included in each treatment group. Tumor growth was then assessed over 14 days of dosing as shown in FIG. 17A. Tumor volume over time was substantially lower in mice treated with WX-024 compared to vehicle (P<0.001). FIG. 17B summarizes the average tumor growth inhibition rate of WX-024 throughout the experiment. The TGI after 3 days of dosing was 89.2% while the TGI after 12 days of dosing was 70.0%. FIG. 18A shows tumor growth rate of individual animals over 14 days of dosing with vehicle. FIG. 18B shows tumor growth rate of individual animals over 14 days of dosing with 20 mg/kg WX-024. These data indicate that the inhibition of tumor growth seen in the CT26 model was consistent between animals.

Figure 19A:
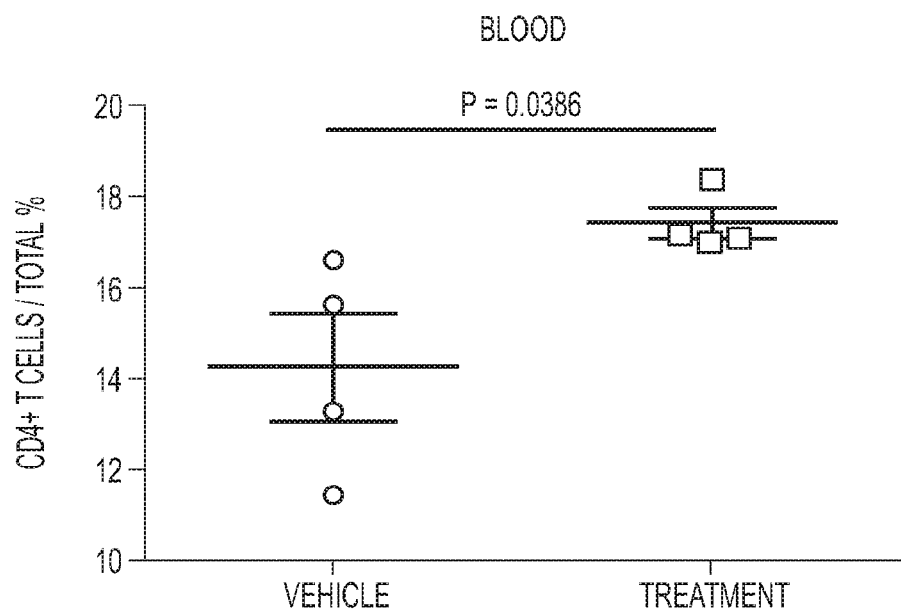
FIGS. 19A and 19B show CD4$^+$ T cell counts in blood samples collected from the mice depicted in FIG. 17. The blood samples were collected at the conclusion of the experiment (day 14).
Figure 19B:
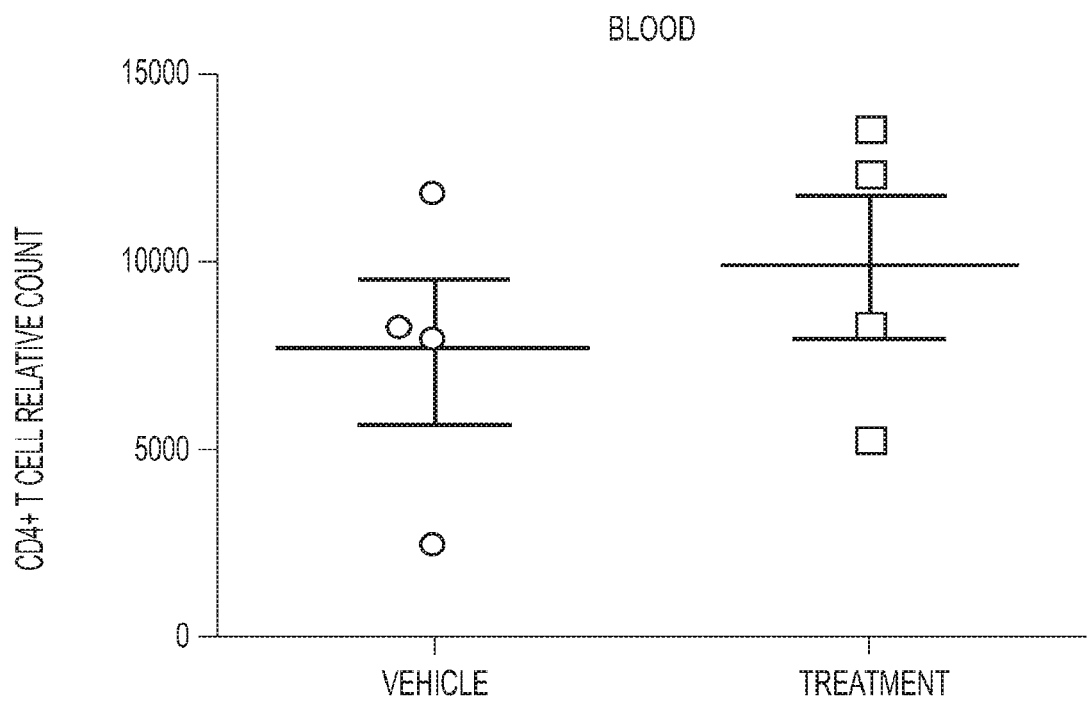

$CD4^+$ T cell counts in the blood after 2 weeks of daily dosing with either vehicle or 20 mg/kg WX-024 were also assessed. The whole blood was taken from each mouse. Lymphocytes were purified from the blood samples by Ficoll, and the cells were stained with fluorescent anti-CD4 antibody. Data were measured by flow cytometry. FIG. 19A shows $CD4^+$ T cell counts presented as the percentage of total cells, indicating an increase with dosing of WX-024. FIG. 19B shows relative T cell count per total cells in the blood sample of one specimen, indicating an increase with dosing of WX-024. These data indicate an increase of T helper cells and activation of the immune system following the treatment with WX-024. These data also indicate that combination therapy of WX-024 with immunotherapy may be appropriate in cancers that do not respond to immunotherapy alone, such as treatment with antibodies directed against PD-1 or CTLA-4.

Figure 20A:
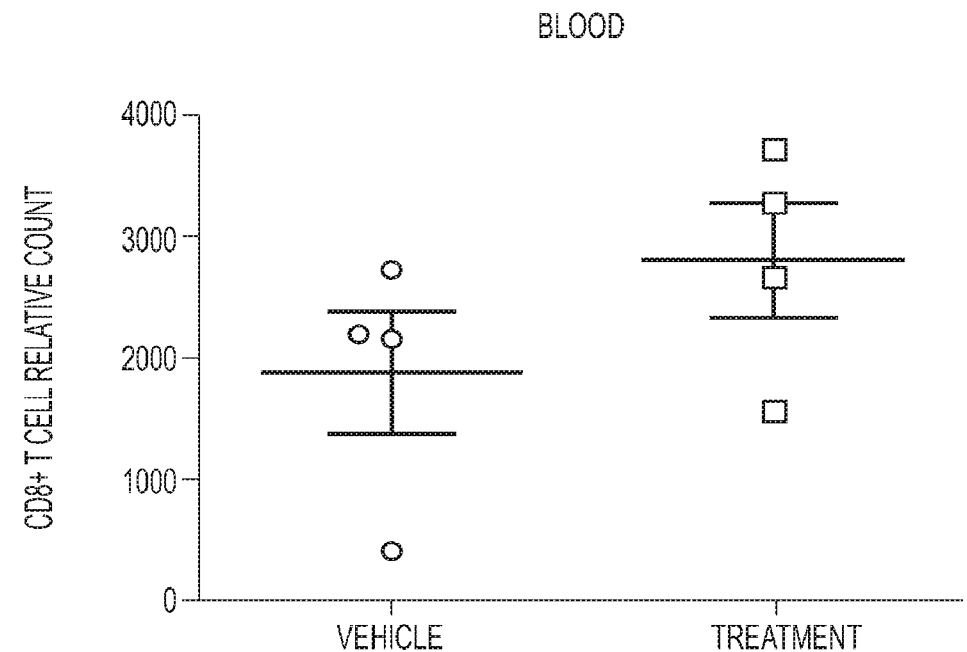
FIG. 20A and FIG. 20B show CD8$^+$ T cell counts in blood samples collected from the mice depicted in FIG. 17. The blood samples were collected at the conclusion of the experiment (day 14).
Figure 20B:
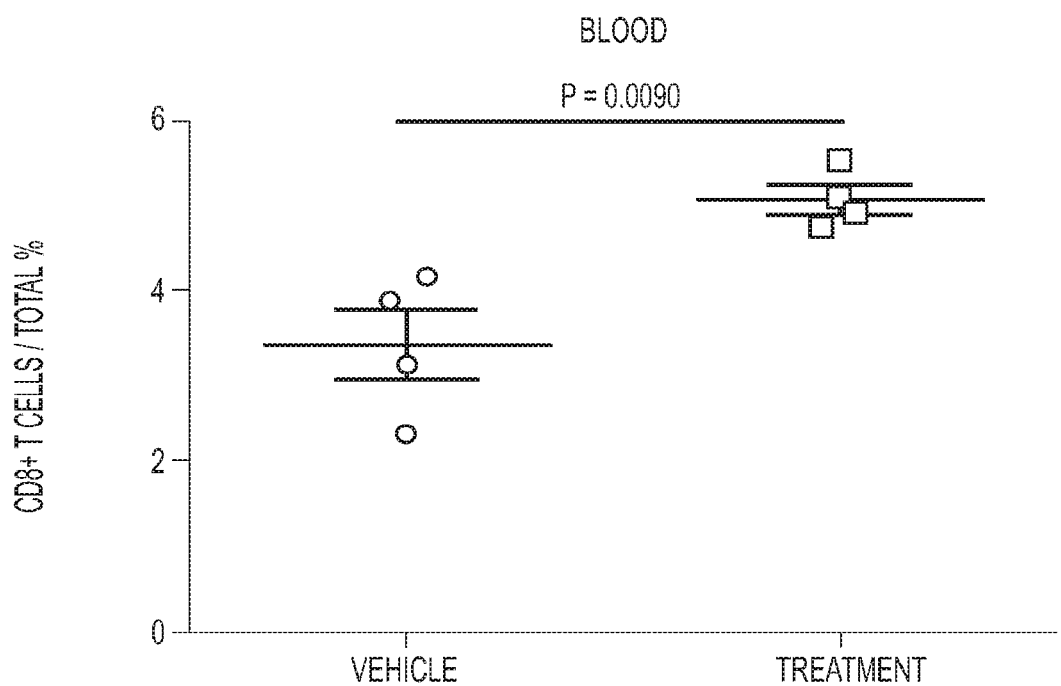

$CD8^+$ T cell counts in the blood after 2 weeks of daily dosing with either vehicle or 20 mg/kg WX-024 were also assessed. As described above, the whole blood was taken from each mouse. Lymphocytes were purified from blood by Ficoll, and the cells were stained with fluorescent anti-CD8 antibody. Data were measured by flow cytometry. FIG. 20A shows $CD8^+$ T cell counts presented as the percentage of total cells, indicating an increase with dosing of WX-024. FIG. 20B shows relative T cell count per total cells in blood samples, indicating an increase with dosing of WX-024. These data indicate an increase in cytotoxic T cells and activation of the immune system following treatment with WX-024, and further support the use of WX-024 together with immunotherapy.

Figure 21A:
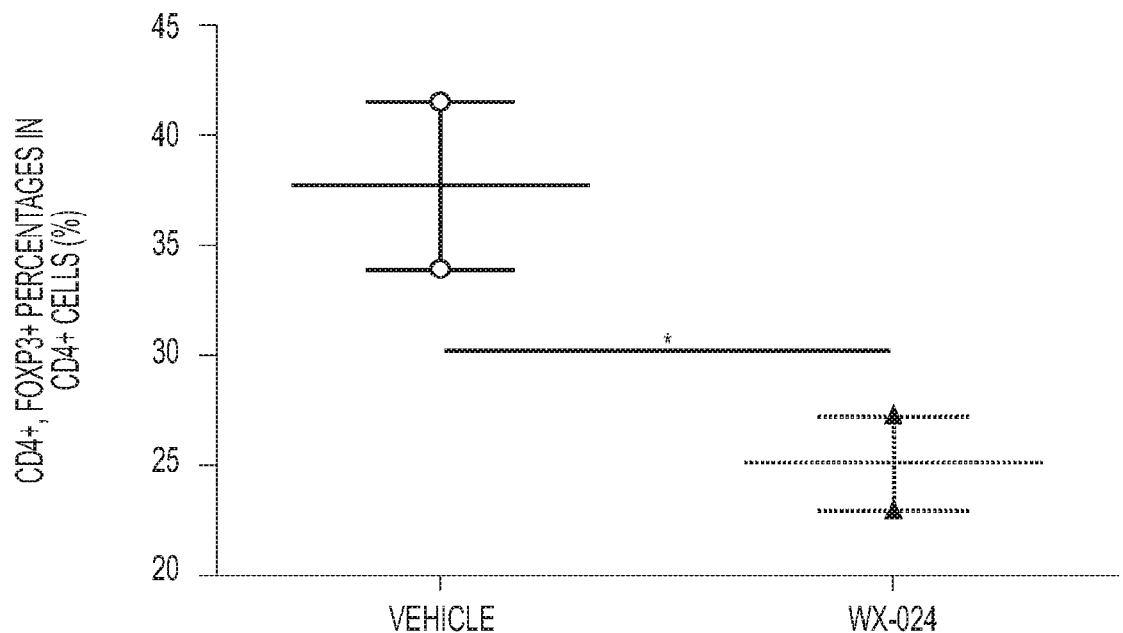
FIG. 21A depicts the percentage of regulatory T cells in CD4$^+$ T cell populations in tumor samples collected from the experiment described in FIG. 17.
Figure 21B:
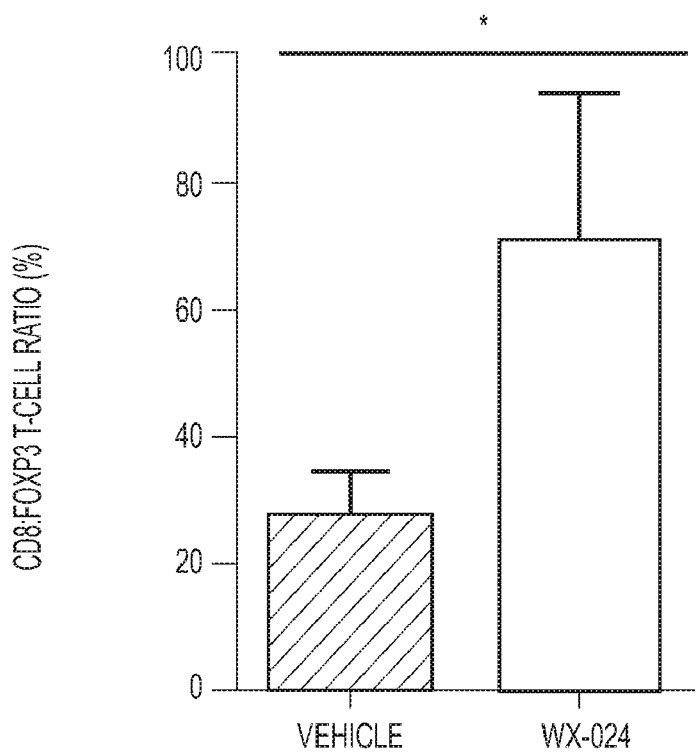
FIG. 21B depicts the ratio between CD8$^+$ T cells and regulatory T cells in the same tumor samples.

To further assess whether WX-024 is capable of modulating a tumor microenvironment, tumor and blood samples were collected in anticoagulation tubes at the end of the study. Single cells separation was performed and then cells were stained for FACS analysis. For cell surface staining, CD45-PerCP-Cy5, CD4-FITC, CD8-PE-Cy7, and CD25-PE were used. For intranuclear staining, cells were permeabilized overnight and then stained with Foxp3-APC for 60 minutes. As shown in FIG. 21A, regulatory T cells in $CD4^+$ T cell populations were significantly reduced in the tumor samples, while the ratio between CD8+ cytotoxic T cells and regulatory T cells was significantly increased (FIG. 21B). A representative FACS analysis for a tumor sample in this experiment is shown in FIG. 21C and FIG. 21D.

Figure 22A:
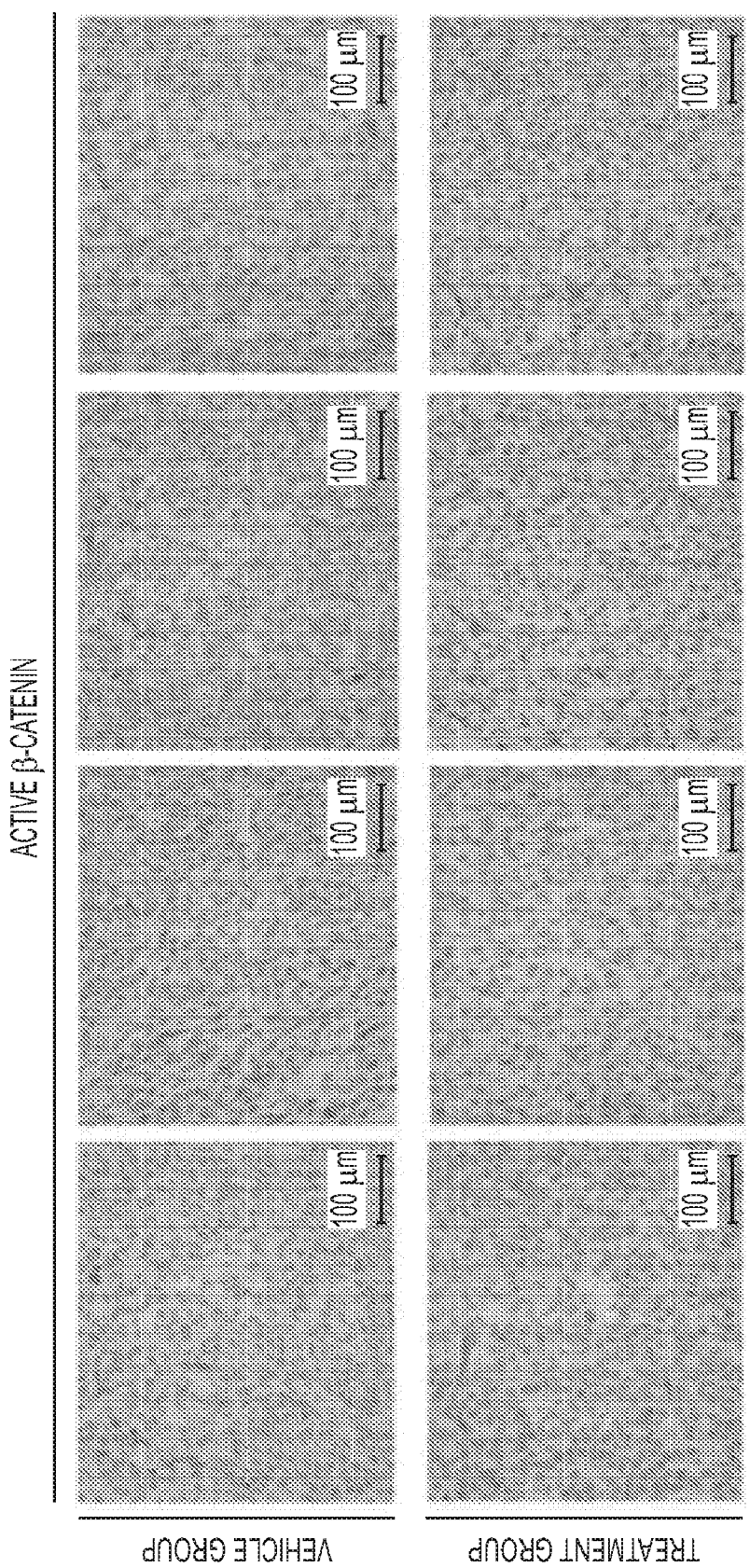
FIG. 22A shows active β-catenin staining of tumor samples collected from the experiment described in FIG. 17. The top four panels show the staining images of four samples collected from a vehicle treated group while the bottom four panels show the staining images of four samples collected from a WX-024 treated group.
Figure 22B:
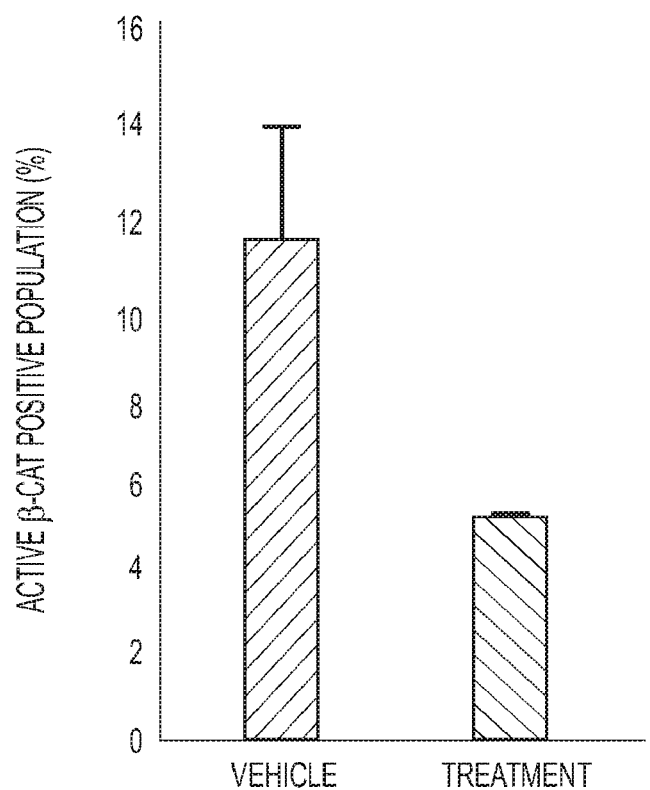
FIG. 22B represents the average immunohistochemical score of each treatment group.
Figure 22C:
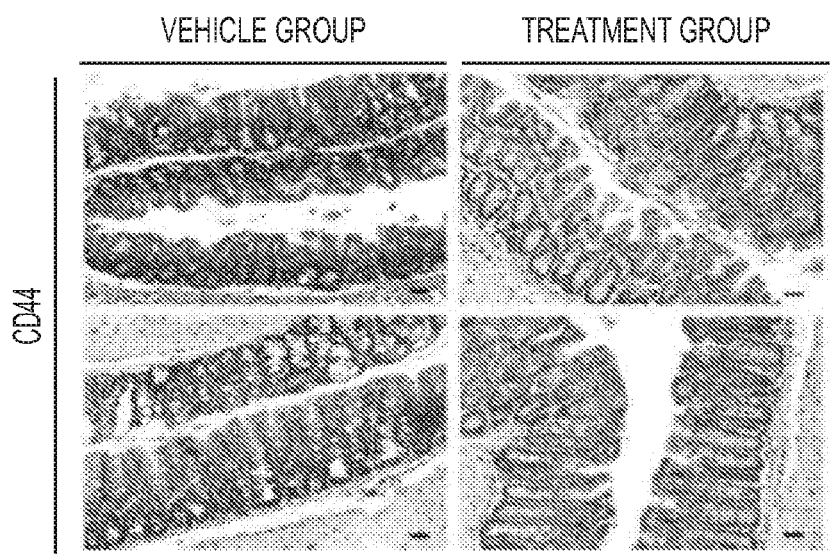
FIG. 22C shows representative staining of CD44 in tumor samples collected from the same experiment.

FIG. 22A shows staining for active β-catenin, following 14 days of treatment with either vehicle or 20 mg/kg WX-024. The average immunohistochemistry scores were calculated based on the staining images. FIG. 22B shows the quantitative comparison of the average staining scores between the vehicle treated group and the WX-024 treated group. FIG. 22C shows staining for CD44, following 14 days of treatment with either vehicle or 20 mg/kg WX-024. These data indicate that WX-024 was capable of suppressing active β-catenin expression in tumors.

Figure 23A:
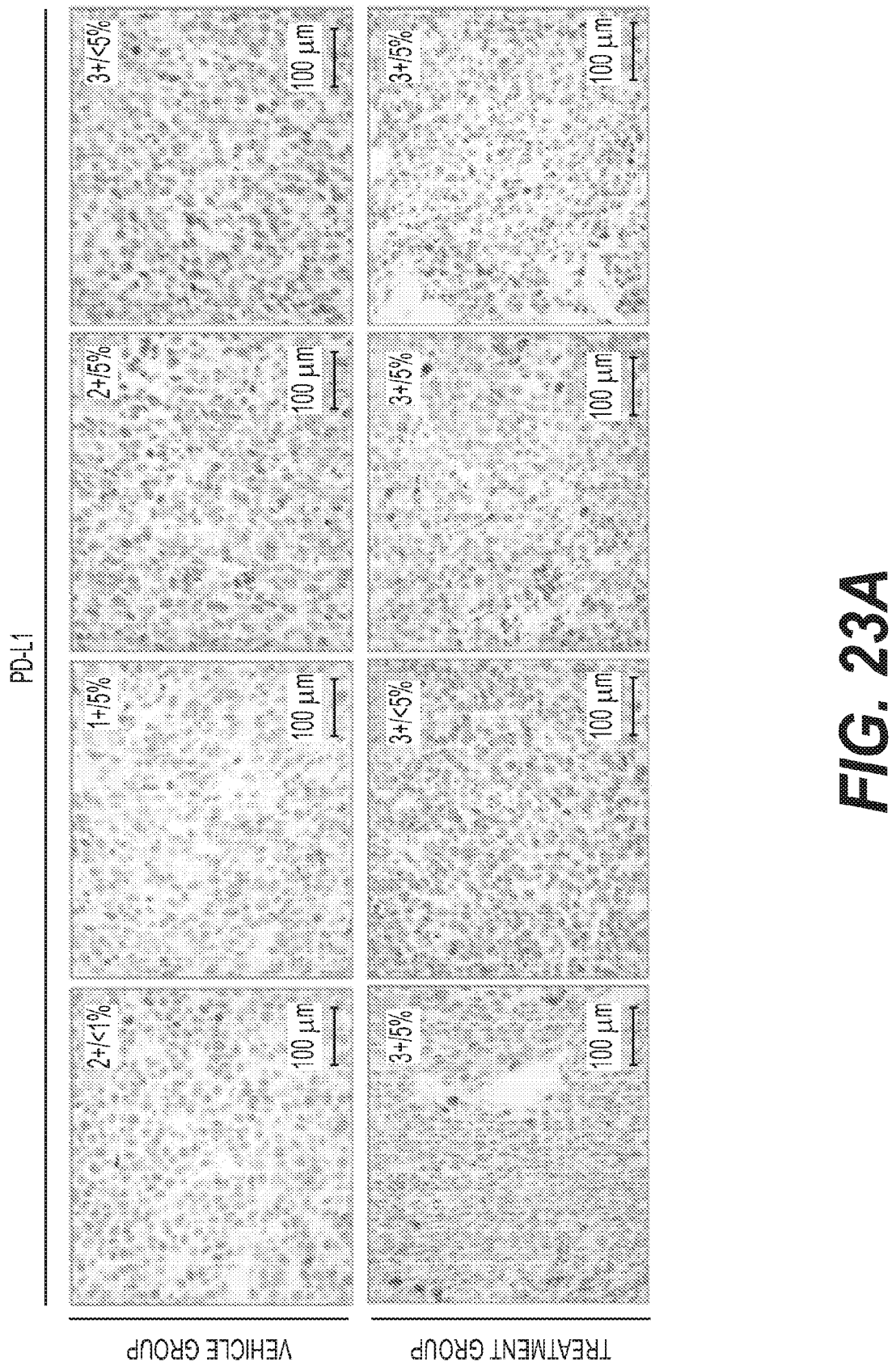
FIG. 23A shows PD-L1 staining of tumor samples collected from the experiment described in FIG. 17. The top four panels show the staining images of four samples collected from a vehicle treated group while the bottom four panels show the staining images of four samples collected from a WX-024 treated group.
Figure 23B:
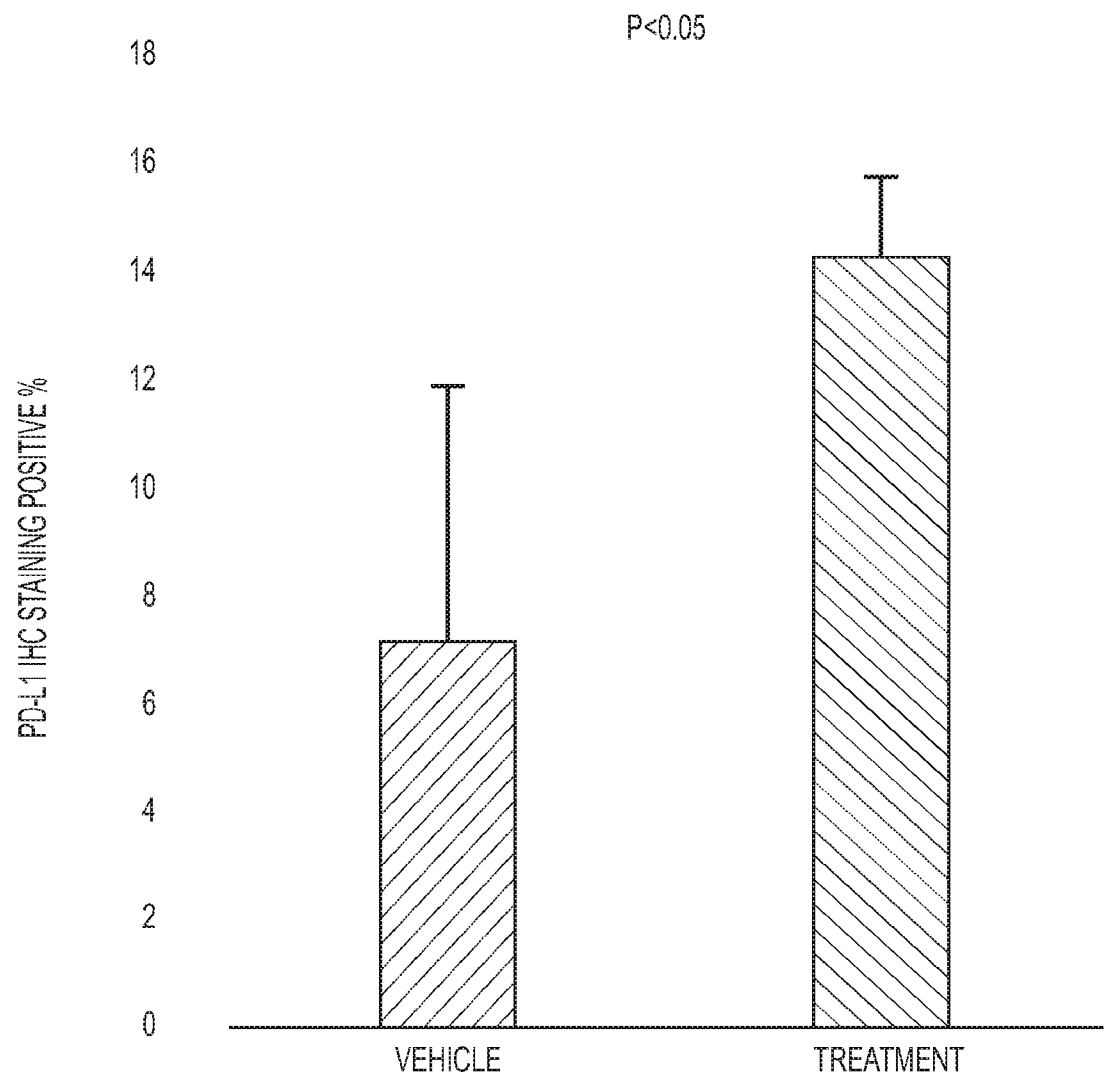
FIG. 23B represents the average immunohistochemical score of each treatment group.

The tumor samples were also stained for PD-L1 and the representative images from four vehicle treated mice and four WX-024 treated mice are shown in FIG. 23A. The quantitative comparison of average immunohistochemistry scores for each treatment group are shown in FIG. 23B.

Overall, these data indicate that WX-024 stimulates T cell infiltration to tumors and stimulates an immune reaction against the tumors. These data also indicate that WX-024 modulates a tumor microenvironment to favor such an immune reaction. Thus, a combination therapy of WX-024 and checkpoint-blocking agents may produce a synergistic effect in stimulating an immune reaction against a tumor through reduction of regulatory T cells or dendritic cells present in the tumor. Furthermore, since WX-024 was capable of increasing $CD8^+$ T cells in blood, it further indicates that WX-024 likely increases T cell infiltration in tumor and immunogenicity against tumor.

Example 5.4. Efficacy of WX-024 in a Mouse Syngeneic Model of Cancer (B16F10)

Figure 24:
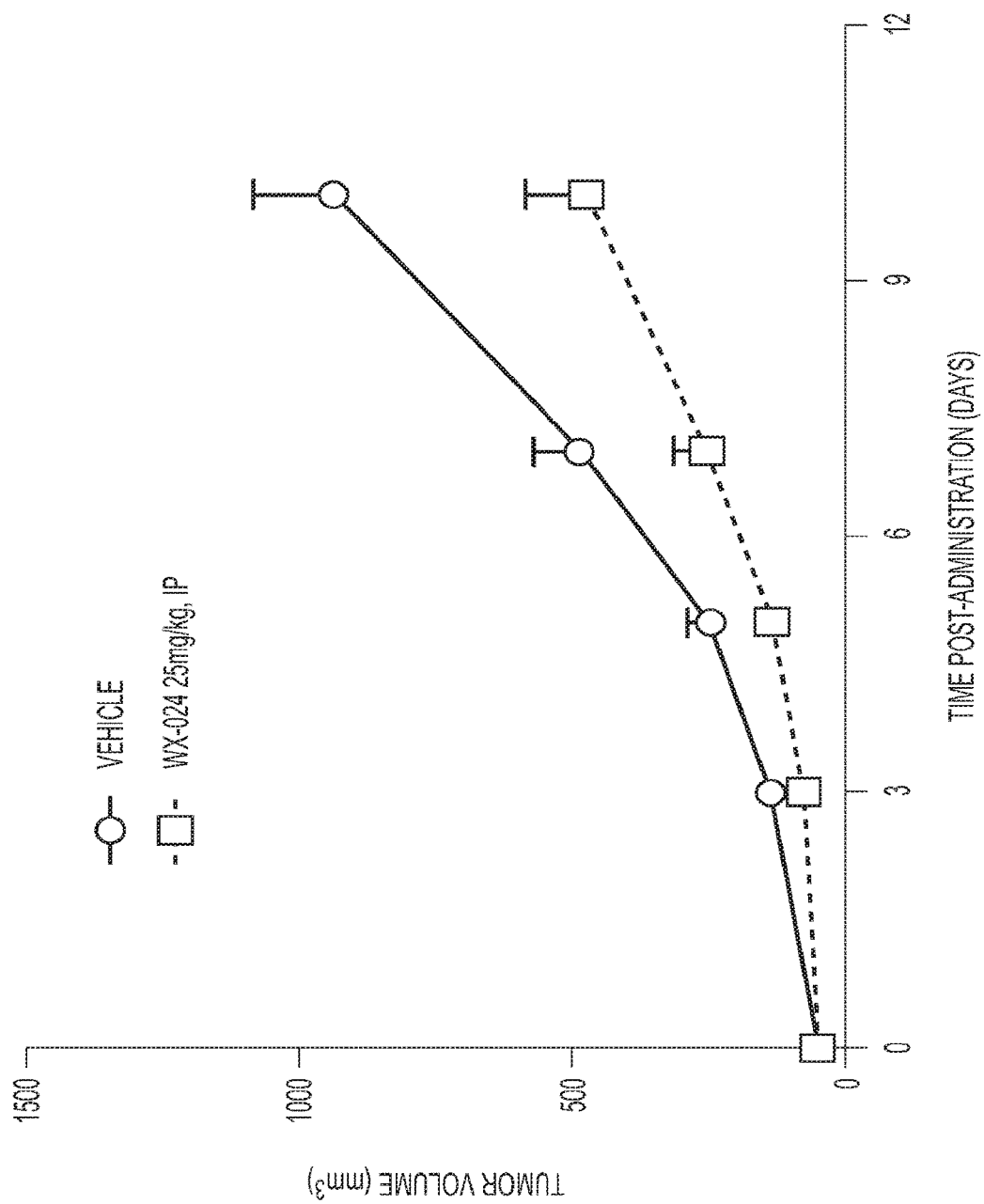
FIG. 24 shows tumor growth changes caused by vehicle or WX-024 in C57BL/6 mice inoculated with B16 cells (1×10$^3$). The mice were intraperitoneally administered with either a vehicle or 25 mg/kg WX-024 daily for 14 consecutive days (n=6 per group).

The ability of WX-024 to suppress other types of tumors was also assessed. C57BL/6 mice were inoculated with B16F10 cells. Female C57BL/6 mice aged 4-5 weeks were inoculated with B16F10 cells ($2 \times 10^5$ cells in 0.05 ml per mouse) in the right flank. When the average tumor size of the mice reached 100 $mm^3$, the mice were divided into two groups (N=6). The first group was administered 25 mg/kg WX-024 while the second group was treated with a vehicle. The treatment was intraperitoneally administered daily for 14 consecutive days. As shown in FIG. 24, WX-024 effectively reduced tumor growth as compared to vehicle treatment, again confirming that WX-024 has a robust efficacy in suppressing tumor growth in vivo.

To further assess whether WX-024 is capable of inducing T cell infiltration into tumors and modulating the tumor microenvironment, C57BL/6 mice were inoculated with B16F10 cells. When the average tumor size of the mice reached 100 $mm^3$, the mice were divided into two groups (N=3) and treated with a vehicle or 25 mg/kg WX-024. The treatment was intraperitoneally administered daily for 12 consecutive days. At the end of the treatment, the mice were sacrificed and tumor and blood samples were collected in anticoagulation tubes. Single cell separation was performed for each sample and then stained for FACS analysis. For cell surface staining, CD45-PerCP-Cy5, CD4-FITC, CD8-PE- Cy7, and CD25-PE were used. The tumor samples were then stained with either an anti-CD4 antibody or an anti-CD8 antibody to assess the presence of T cells in the tumor samples. The tumor samples were also stained with an anti-CD194 antibody and anti-CD196 antibody to assess the presence of T helper 17 cells in the tumor samples.

Figure 25A:
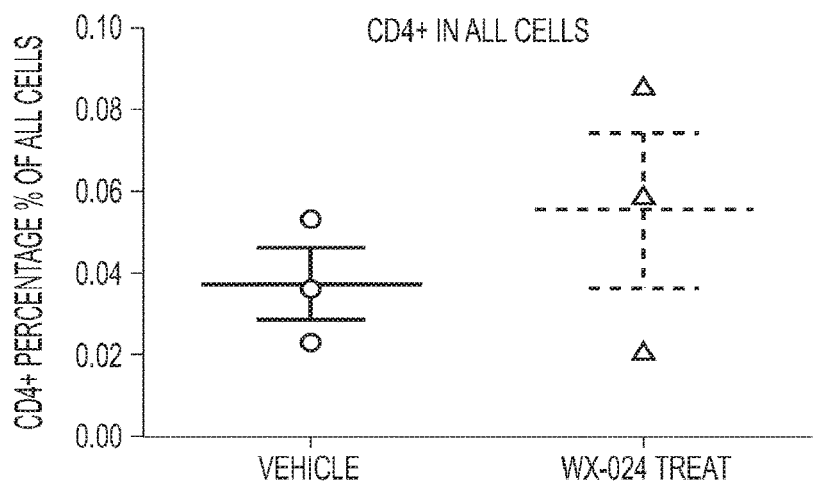
FIGS. 25A, 25B, and 25C depict T cell infiltration into tumor caused by WX-024 treatment. Female 5 weeks of age C57BL/6 mice were inoculated with B16 cells (1×10$^3$). When the average tumor volume of the inoculated mice reached 100 mm$^3$, the mice were divided into two groups and intraperitoneally administered with either a vehicle or 25 mg/kg WX-024 for 12 consecutive days. At the conclusion of the experiment, tumor samples were collected and stained with either CD4 or CD8.
Figure 25B:
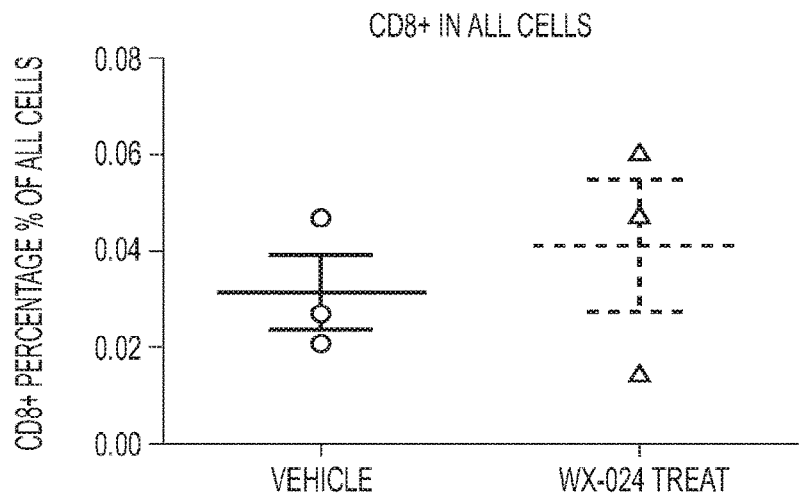
Figure 25C:
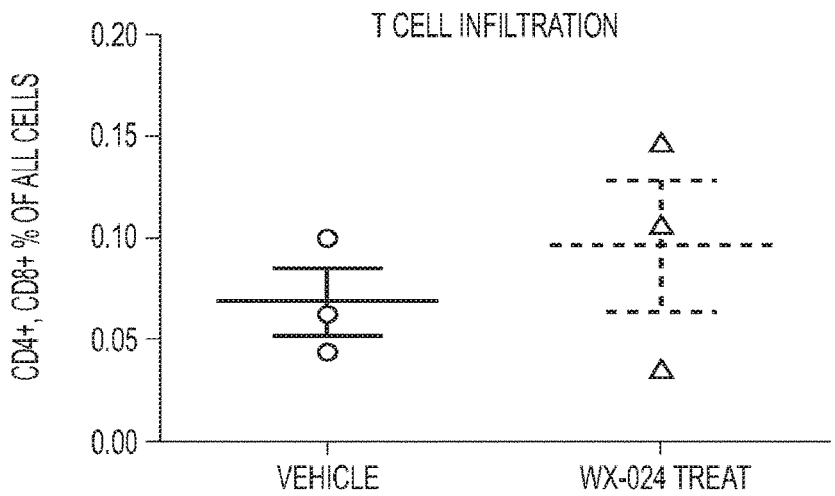

As shown in FIG. 25A, WX-024 increased the CD4$^+$ positive cells present in the tumor samples, as compared to vehicle, indicating that WX-024 induces T helper cell infiltration into tumors. Likewise, FIG. 25B demonstrates that WX-024 increased the CD8$^+$ positive cells present in the tumor samples, indicating that WX-024 induces cytotoxic T cell infiltration into tumors. As summarized in FIG. 25C, these results demonstrate that overall, WX-024 is capable of inducing T cell infiltration into tumors and thereby further elicits beneficial immune reactions specifically targeting the tumor mass. Overall, the data shows a tendency of WX-024 to increase CD8+, and CD4+ lymphocyte infiltration in tumors, indicating that WX-024 induces a tumor microenvironment to favor an immune reaction by altering compositions of T cells in and/or around the tumor.

Figure 26A:
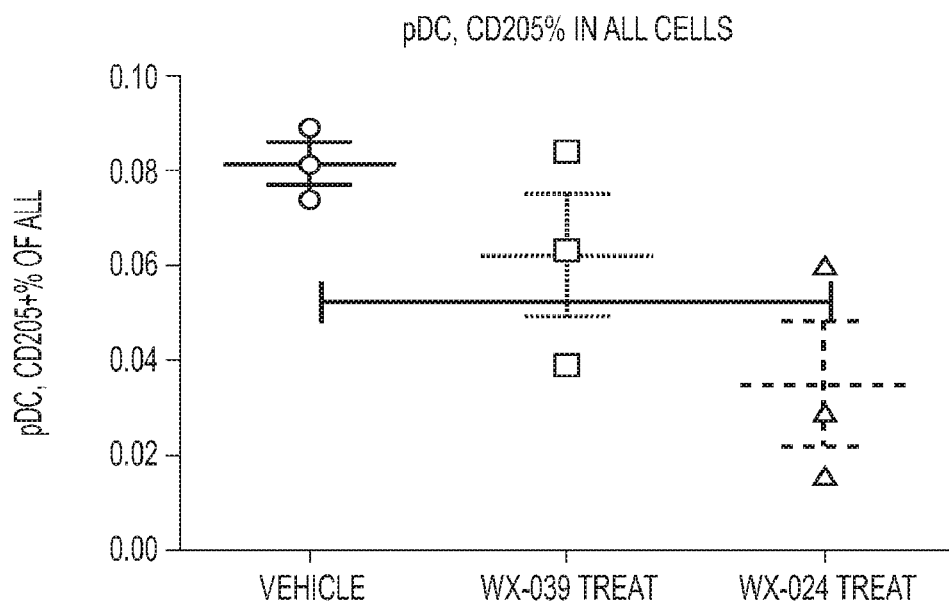
FIG. 26A and FIG. 26B depict the effects of WX-024 and WX-039 on dendritic cells in present in tumor. C57BL/6 mice were inoculated with B16 cells. When the average tumor volume of the inoculated mice reached 100 mm$^3$, the mice were divided into two groups and intraperitoneally administered with a vehicle, 20 mg/kg WX-024, or 60 mg/kg WX-039 for 12 consecutive days. At the conclusion of the experiment, tumor samples were collected and stained for dendritic cell markers and T helper 17 cell markers.
Figure 26B:
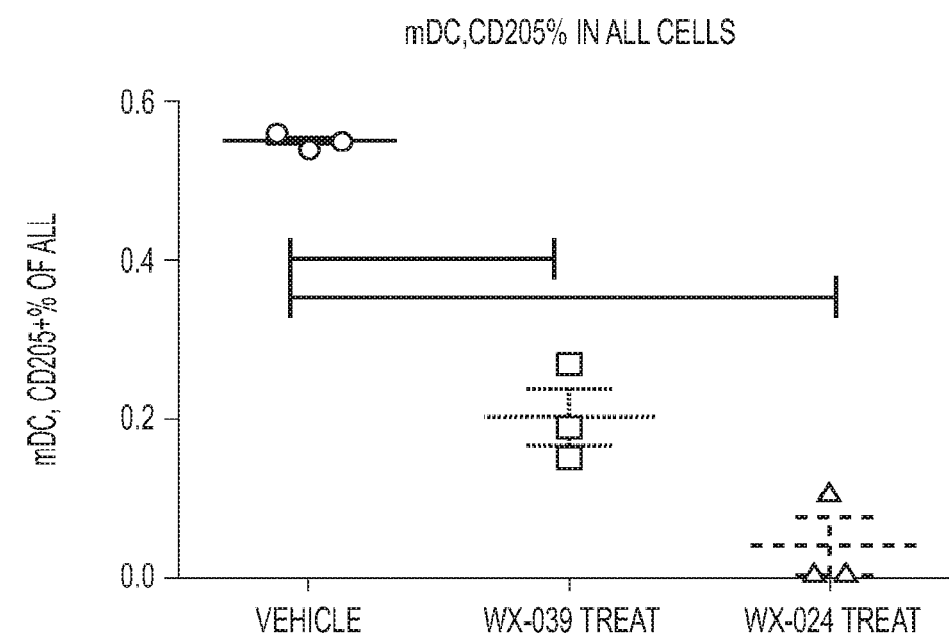
Figure 26C:
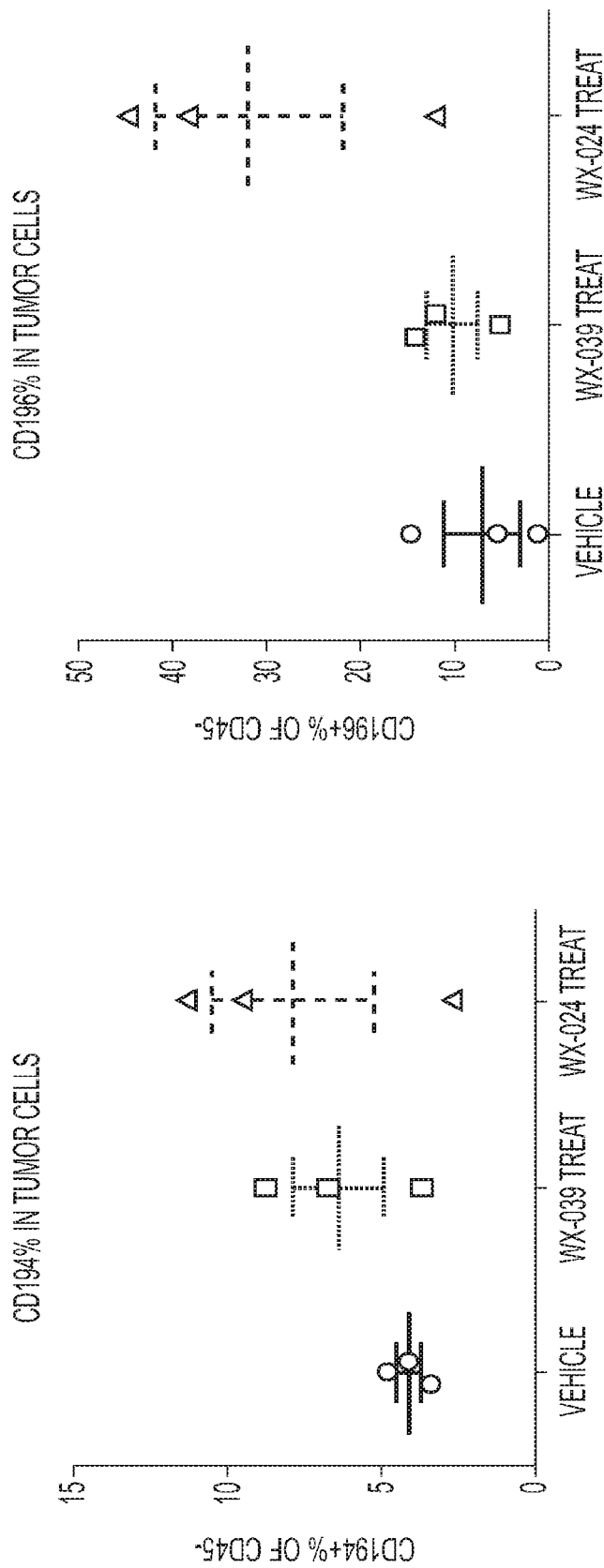
FIG. 26C shows CD194+ or CD196+ T cells presented as a percentage of total tumor cells.
Figure 26D:
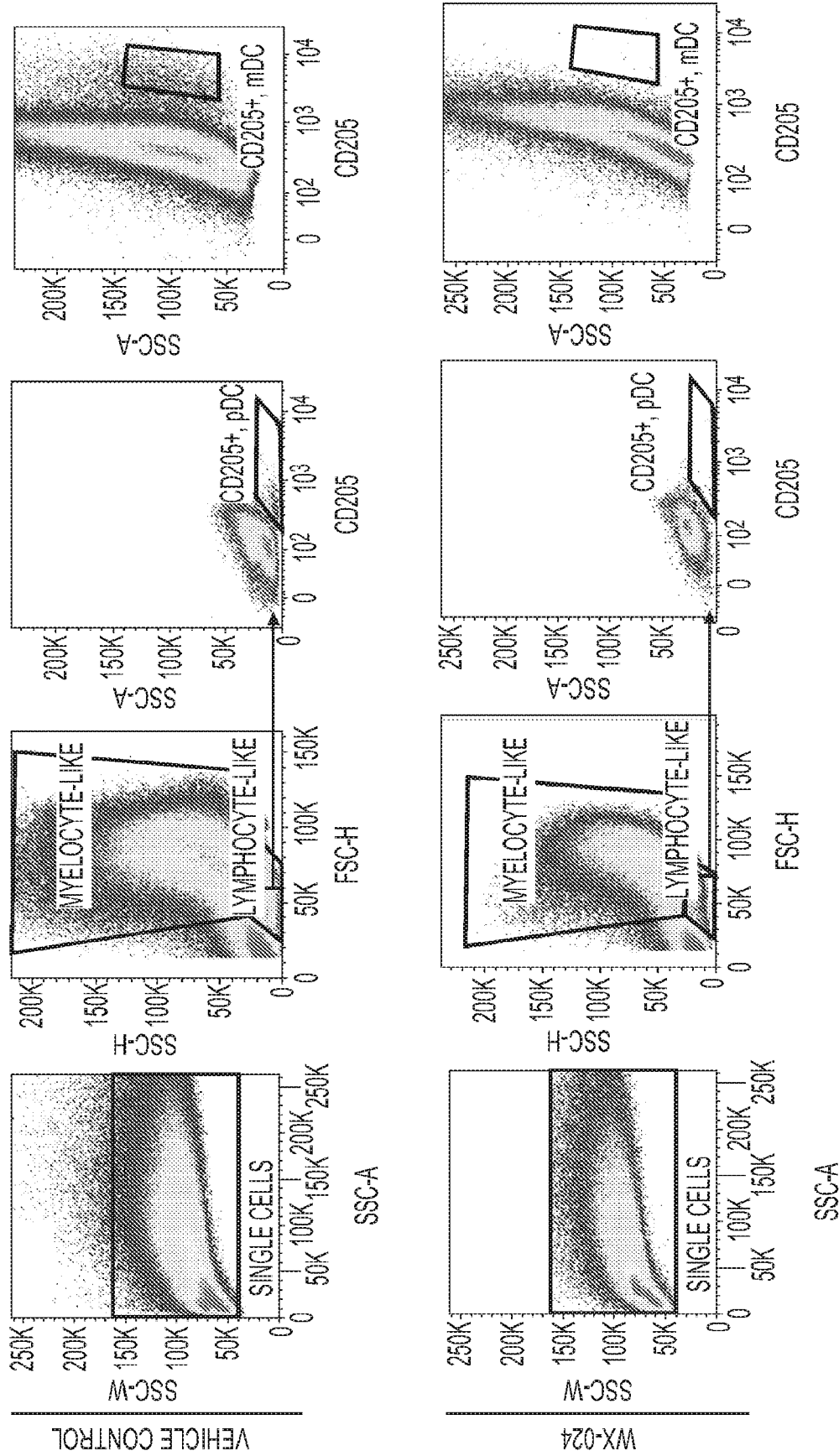
FIG. 26D shows a representative FACS analysis of a tumor sample tested in this experiment.

The effects of WX-024 on a tumor microenvironment were compared with those of WX-039, a variant of WX-024. The process of constructing WX-039 is described in Example 10. C57BL/6 mice were inoculated with B16F10 cells. When the average tumor size of the mice reached 100 mm$^3$, the mice were divided into three groups (N=3) and treated with a vehicle, 20 mg/kg WX-024, or 60 mg/kg WX-039. The treatment was intraperitoneally administered daily for 12 consecutive days. At the end of the treatment, the mice were sacrificed and tumor and blood samples were collected in anticoagulation tubes. Tumor cells collected from the experiment were stained as described above and also with anti-CD205 antibody to assess whether WX compounds are capable of modulating dendritic cells. As shown in FIGS. 26A and 26B, WX-024 significantly reduced CD205$^+$ cells, confirming that WX-024 is capable of suppressing dendritic cells within a tumor. While WX-039 was also capable of suppressing dendritic cells present in tumor, the effect of WX-024 was more pronounced than WX-039. FIG. 26C also shows that while WX-039 increased T helper 17 cells in tumor, WX-024 appeared to be more effective than WX-039. Consistent with CT26 animal model studies, these data indicate that WX-024 is capable of stimulating an immune reaction against tumors and modulating the tumor microenvironment to favor such an immune reaction. A representative FACS analysis for a tumor sample in this experiment is shown in FIG. 26D.

In combination with other immunotherapy agents, such as an anti-PD-L1 antibody or other antibodies that are capable of modulating T cell activation, WX-024 could modulate regulatory T cells and increase the ratio between CD8$^+$ cytotoxic T cells and regulatory T cells. WX-024 in combination with those immunotherapy agents could also further synergistically decrease myeloid dendritic cells in tumor and thereby induce a tumor microenvironment favoring an immune reaction against a tumor.

Example 5.5. Efficacy of WX-024 in a Mouse Orthotopic Model of Cancer

Orthotopic mouse models are useful to visualize the effect of an anti-tumor compound on a tumor implanted in a mouse and to assess the effect of the compound on tumor metastasis. An orthotropic model utilizing the NCI—H1299-Luc cell line (non-small-cell lung carcinoma cell line expressing luciferase) was selected for this experiment. Upon uptake of luciferin substrate, these cells are capable of producing bioluminescence. Proliferation of the NCI—H1299 cell line is dependent on Pygopus (Pygo) 2/β-catenin transcription activity, in which TCF-1 transcription factors (BCL9, β-cat and Pygo) form a transcription complex to initiate transcription.

To assess the effect of WX-024 in an orthotopic animal tumor model, female balb/c nude mice were injected with NCI—H1299-Luc cells. The mice were about 5 weeks of age. NCI—H1299-Luc cells (5×10$^6$) in 50 µL in PBS were injected into each mouse lung with a syringe. After the cells were administered to the mice, the mice were divided into two groups (n=3 each) and a vehicle or 15 mg/kg WX-024 was administered intravenously daily for 10 consecutive days.

Figure 27A:
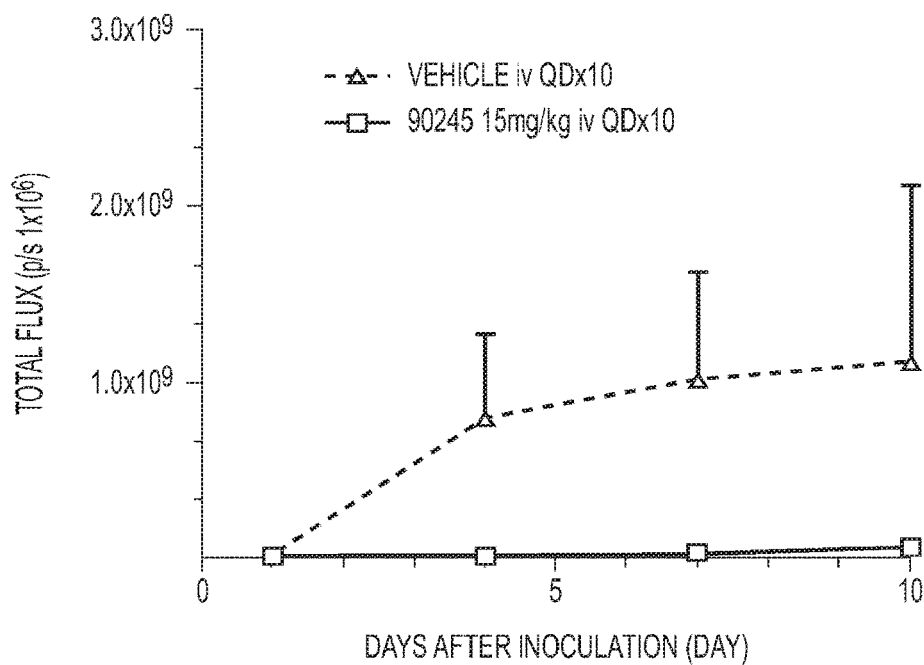
FIG. 27A depicts the average total flux of orthotopic mice treated with either a vehicle or 15 mg/kg WX-024. Balb/c female nude mice were injected with NCI—H1299-Luc cells (5×10$^6$ in 50 μL in PBS) and treated intravenously with a vehicle or WX-024 for 10 consecutive days. 3 mice per group were tested. The total flux indicates the luminescence photon flux signal generated by tumor cells in the mice.
Figure 27B:
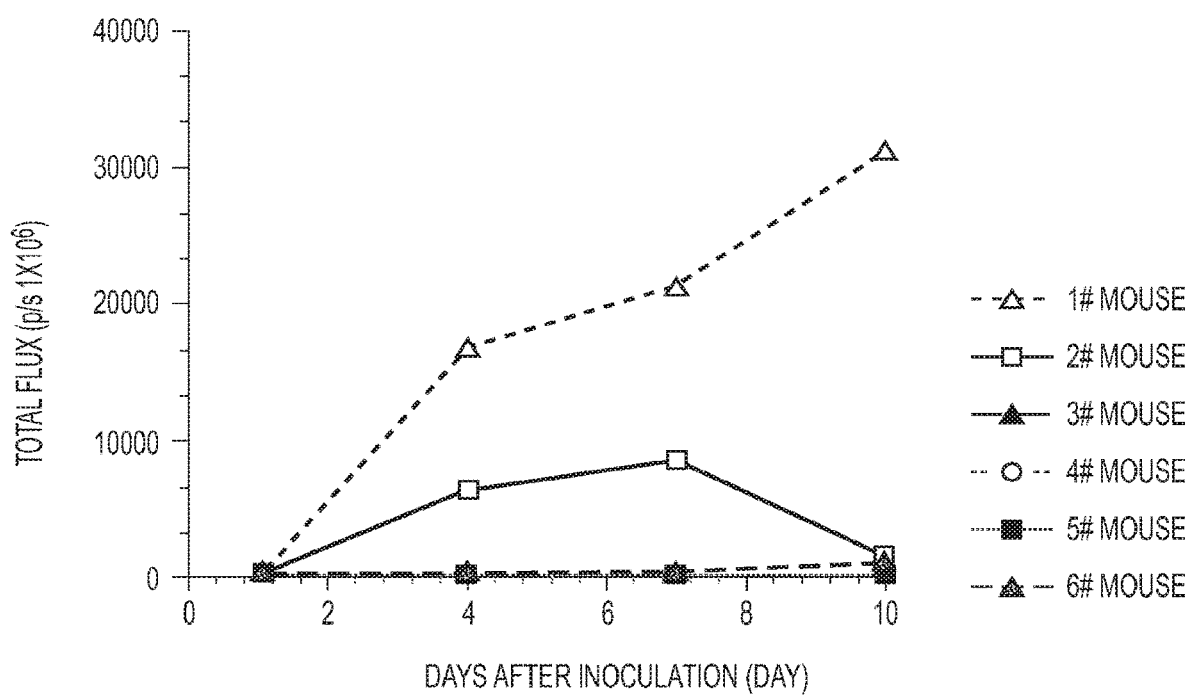
FIG. 27B depicts the total flux of each mouse monitored in the same experiment.
Figure 27C:
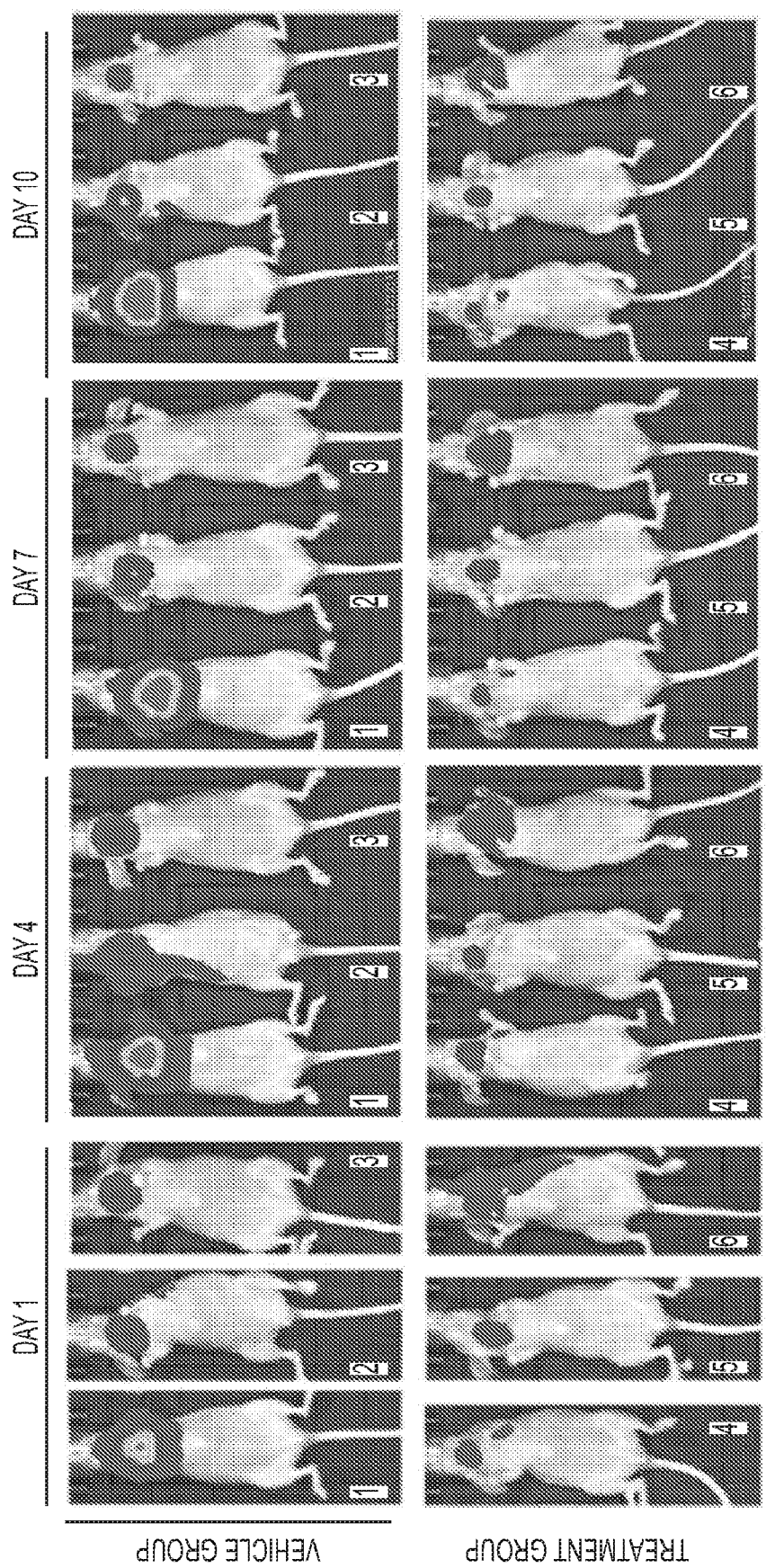
FIG. 27C shows the bioluminescence image of each mouse monitored in this experiment.

The bioluminescence intensity (total Flux [p/s]) of each mouse was measured periodically throughout the study according to manufacturer protocol (Xenogen ivis imaging system, PerkinElmer). The average total flux depicted in FIG. 27A indicates the average bioluminescence photon flux signal generated by tumor cells in the mice treated with the vehicle or WX-024. As shown in FIG. 27A, WX-024 almost completely blocked tumor formation and growth in vivo, demonstrating the in vivo efficacy of WX-024. FIG. 27B shows the total flux of each mouse monitored in this experiment. The data indicate that the inhibitory effect of WX-024 on tumor formation and growth was consistent among the mice. The data also indicate that WX-024 is capable of suppressing tumor metastasis. FIG. 27C shows a bioluminescence image of each mouse, taken throughout the study. Mice #1-3 are from the vehicle treated group while mice #4-6 are from the WX-024 treatment group.

Figure 28A:
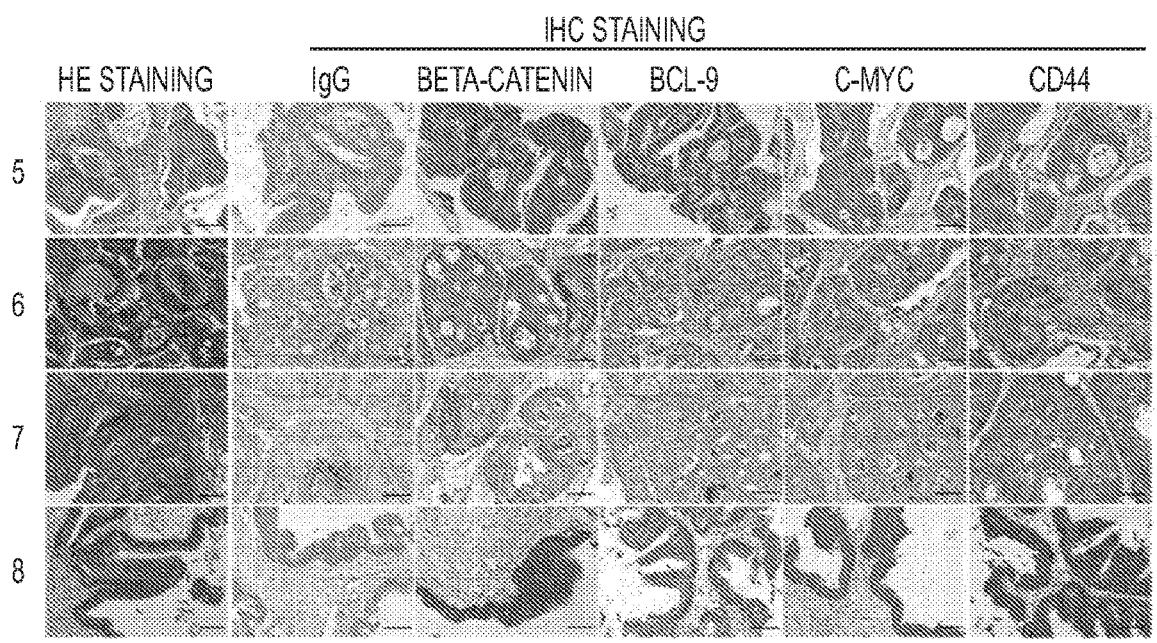
FIG. 28A shows immunohistochemical staining of selective biomarkers in four samples derived from colorectal cancer patients (scale bar: 100 μm). Each sample was stained with H&E (Haemotoxylin and Eosin), IgG, β-catenin, BCL9, c-Myc, and CD44. Colorectal cancer sample #8 was selected for further examination.

Example 5.5. Efficacy of WX-024 in a Patient Derived Xenograft (PDX) Animal Model To assess whether WX-024 is also applicable to tumor derived from human patients, a xenograft animal model inoculated with patient derived colon cancer cells was exposed to WX-024. Samples derived from four different colon cancer patients were screened for biomarkers that indicate an elevated level of canonical Wnt/β-catenin signaling. As shown in FIG. 28A, the samples (#5-#8) were stained for β-catenin, BCL9, c-Myc, and CD44 expression and also stained for IgG as a control. The samples were also stained for nuclear co-localization of BCL9 and β-catenin. The sample derived from patient #8 showed elevated levels of all biomarkers tested in this experiment and therefore was selected for the patient-derived xenograft animal study.

Male NOD/SCID mice at about 5 weeks of age were intravenously injected with colon cancer cells derived from patient #8. Briefly, the selected CRC tumor samples from FIG. 28A were sliced into 3 mm$^3$ fragments and subcutaneously implanted onto the right flank of NOD/SCID mice. When mean tumor size reached about 135 mm$^3$ (about 18 days after transplantation), the mice were divided into two groups (n=8 each) and administered either a vehicle or 15 mg/kg WX-024. Each moue was given a daily intravenous administration for more than 31 days.

Figure 28B:
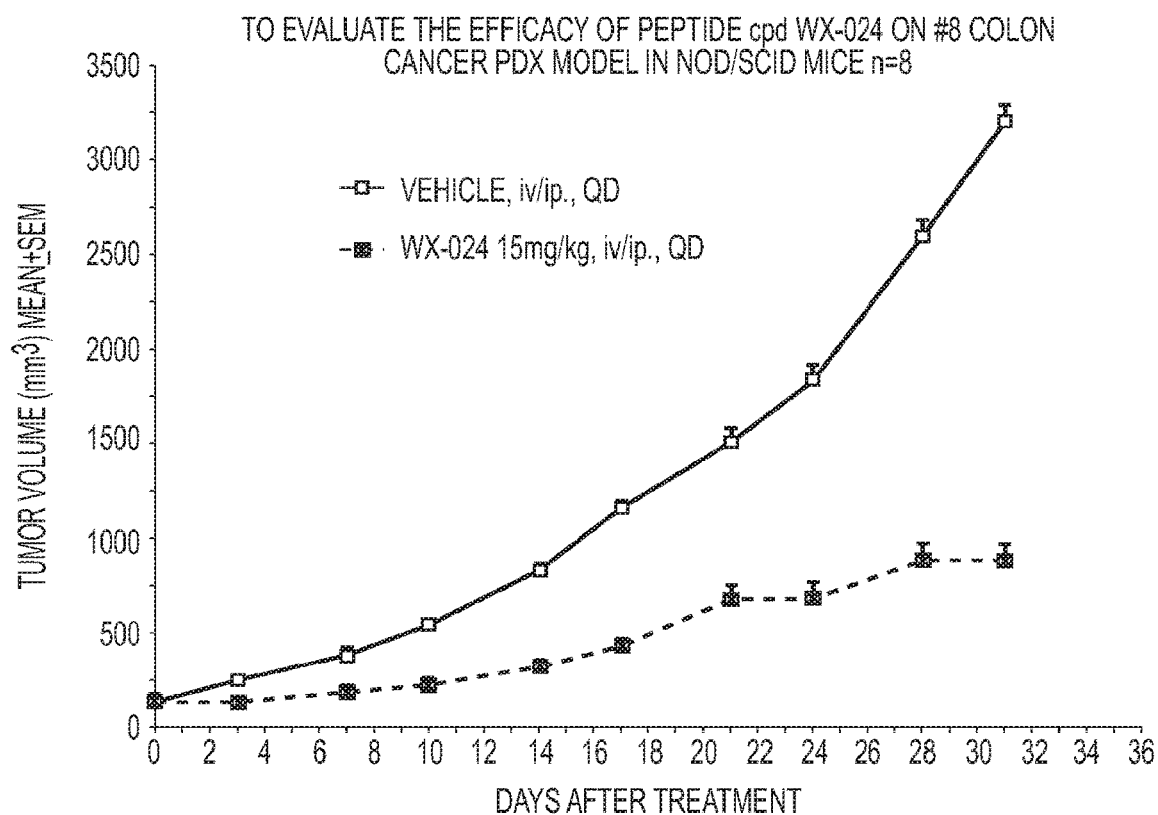
FIG. 28B shows the effect of WX-024 on patient-derived xenograft NOD/SCID mice inoculated with cells derived from patient #8. After two weeks of inoculation, the mice were divided into two groups (N=8 per group) and treated with a vehicle or 15 mg/kg WX-024 intravenously for the following four weeks. The average tumor growth inhibition at day 31 by WX-024 was 75.6%.
Figure 29A:
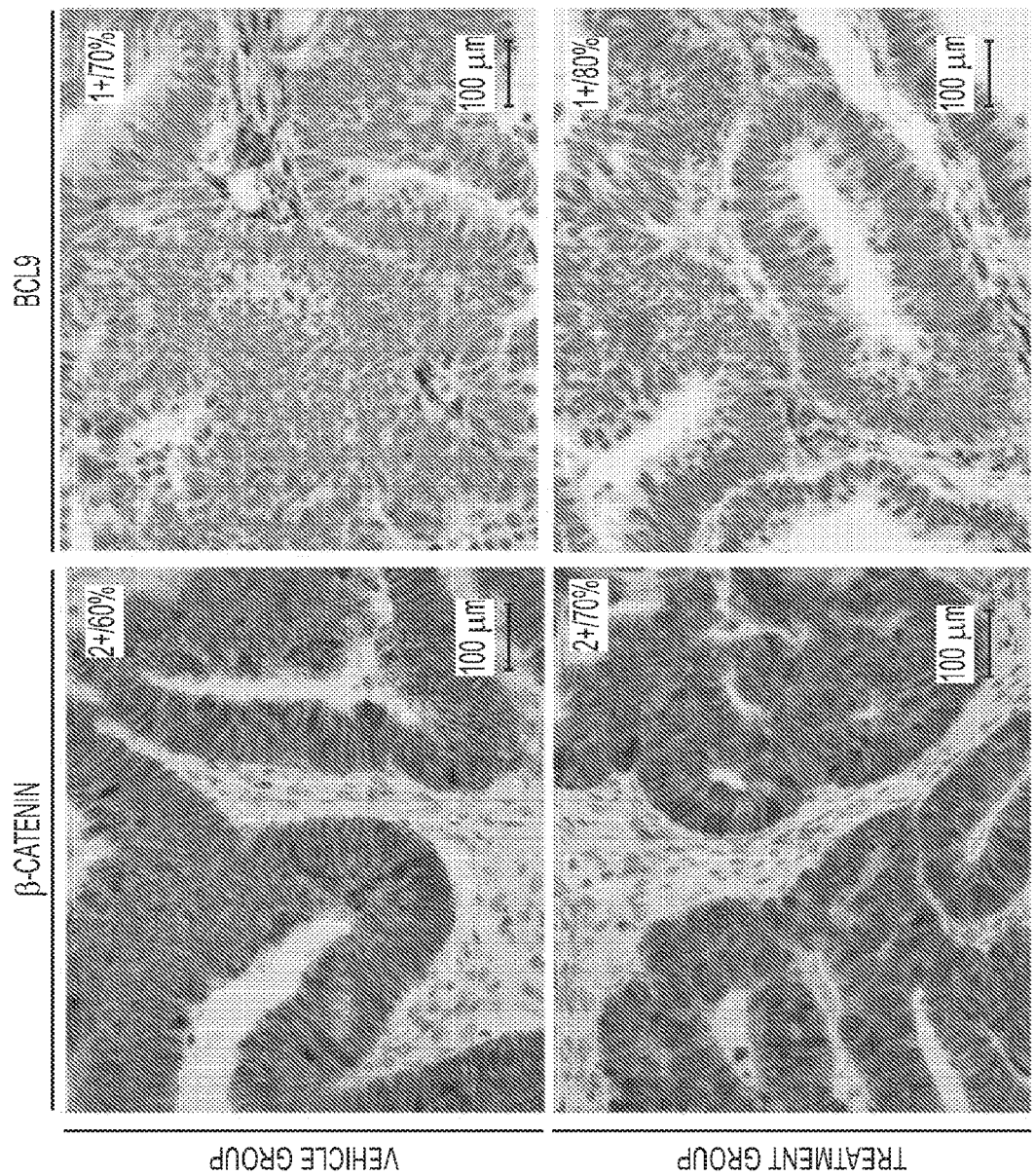
FIG. 29A depict β-catenin and BCL9 staining of tumor samples collected from the experiment described in FIG. 28. The immunohistochemical score of each image is shown at the top right corner of the image.
Figure 29B:
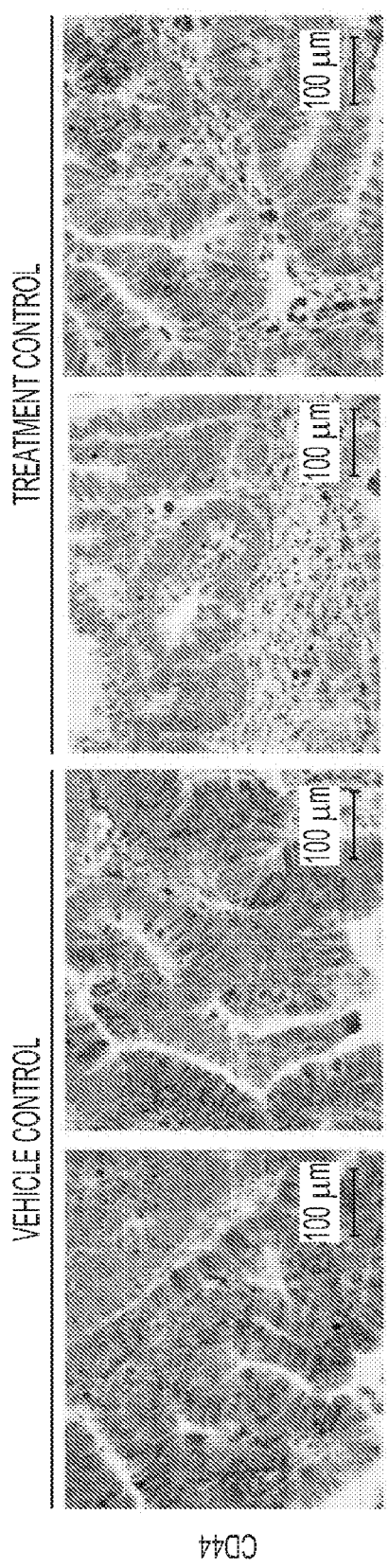
FIG. 29B depict CD44 staining of tumor samples collected from the experiment described in FIG. 28.

As shown in FIG. 28B, WX-024 effectively inhibited the tumor growth as compared to vehicle. The average tumor growth inhibition rate of WX-024 was 75.6% after 31 days of dosing. At the end of the study, the mice were sacrificed and tumor samples were collected. Tissue samples were fixed with 10% formalin and transferred into 70% ethanol, and then processed following deparaffinization, antigen retrieval (190° C., 5 min), endogenous peroxidase quenching (3% H2O2, RT, 5 min), blocking with 5% FBS for 15 minutes at room temperature, primary antibody incubation (room temperature, 1 h), secondary antibody incubation (room temperature, 30 min), color development with DAB (room temperature, 5 min) and dehydration and mounting. Each tumor sample was stained for BCL9, β-catenin, and CD44 expression and the results are shown in FIGS. 29A, and 29B. Of note, WX-024 was capable of reducing CD44 expression in those tumor samples, confirming that WX-024 is capable of inhibiting Wnt/β-catenin signaling.

These data indicate that WX-024 is an effective therapy for human patients. The data also suggest that various biomarkers such as β-catenin, BCL9, c-Myc, and CD44 can be useful to determine whether a given patient is particularly suitable for WX-024 treatment.

Example 5.6. Toxicology Study of WX-024

Figure 30A:
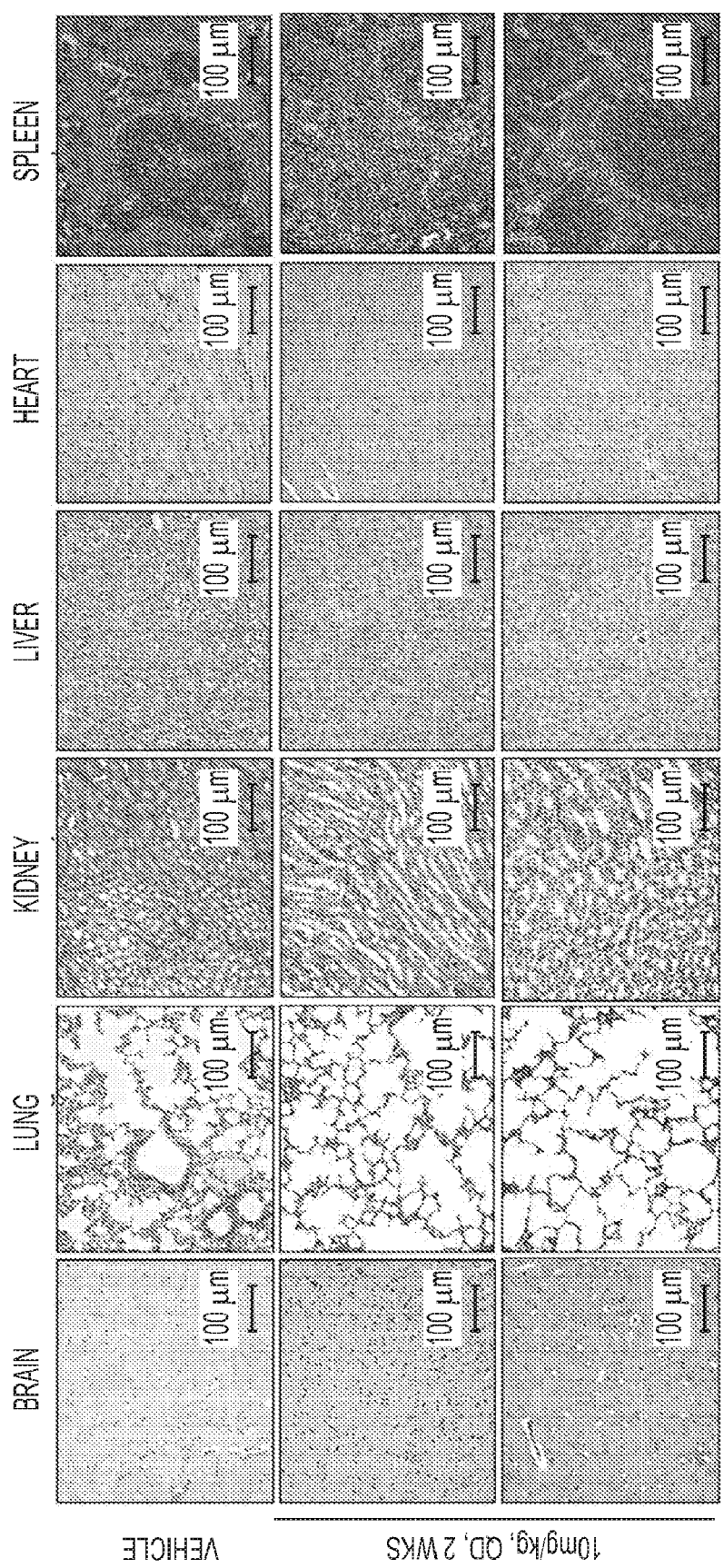

To assess the toxicity effect of WX-024, female balb/c mice of about 5 weeks of age were treated with WX-024 for 14 consecutive days. The mice were divided into four groups (n=6 each) treated intravenously with a daily dose of vehicle, or 10 mg/kg, 15 mg/kg, or 20 mg/kg WX-024. At the end of the study, the mice were sacrificed and various major organs were collected. The tissue samples were treated and processed as described in Example 5.5. The embedded tissue samples were sectioned and stained with H&E. Representative H&E staining images from the vehicle treated group and 10 mg/kg WX-024 treated group are shown in FIG. 30A. The body weight of each moue was monitored throughout the study and the average body weight of each treatment group is shown in FIG. 30B. While there was a slight decrease at the beginning of the study, the average body weight of all three WX-024 treated groups stabilized and was maintained throughout the study. Likewise, while the food consumption of all WX-024 treated groups was slightly decreased at the beginning of the study, it recovered to near baseline levels with continued treatment. At the end of the study, blood from each mouse was also collected for serum chemistry and hematological analysis (complete blood cell count analysis). FIG. 30C shows the blood cell count profiles of the vehicle treatment group and 20 mg/kg WX-024 treatment group. The profiles of these two groups did not differ significantly, indicating that WX-024 induced no significant toxicity in this experimental condition.

Figure 31A:
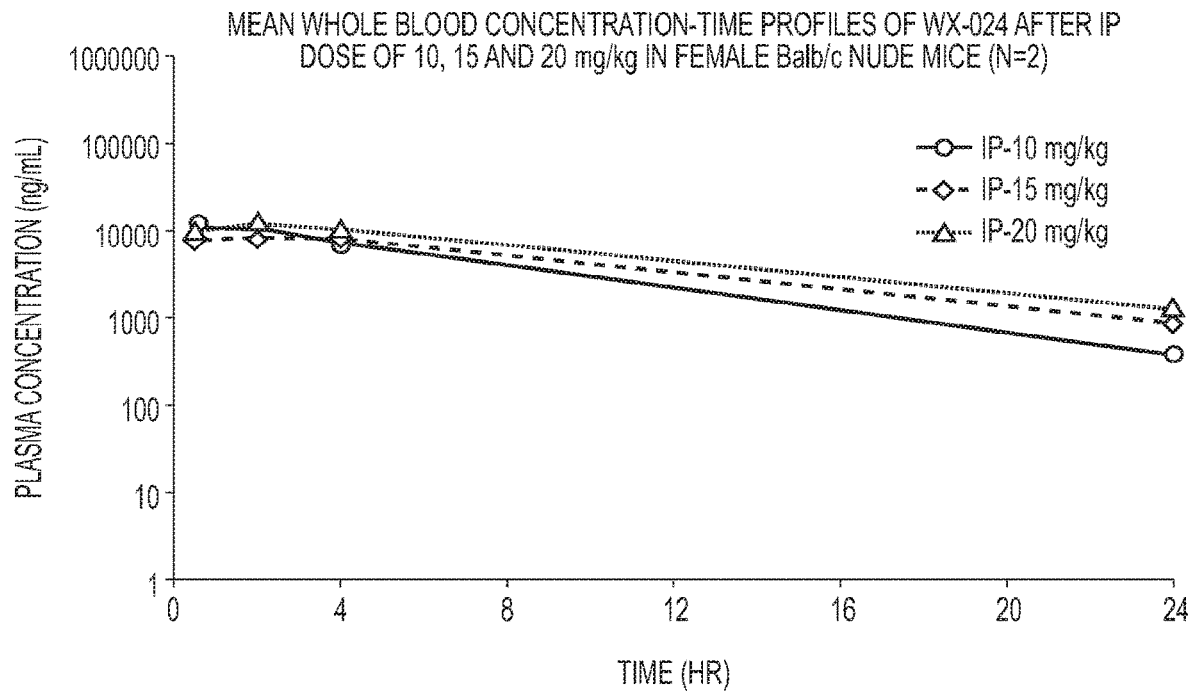
FIG. 31A and FIG. 31B show the toxicokinetic analysis of female balb/c mice intraperitoneally treated with vehicle, 10 mg/kg, 15 mg/kg, or 20 mg/kg WX-024 for 14 consecutive days.

The toxicokinetics of WX-024 were analyzed in female balb/c mice of about 5 weeks of age. The mice were treated intraperitoneally with 10 mg/kg, 15 mg/kg, or 20 mg/kg WX-024 for 14 consecutive days. The mice were administered with WX-024 daily. FIG. 31A shows the plasma concentration change over 24 hrs after the first dosing of the experiment at day 1 (n=2 each group). The mean toxicokinetic parameters calculated at day 1 are summarized in Table 5 below.

TABLE 5

Mean toxicokinetic parameters of WX-024 after the first dosing

| TK parameters | Unit | IP-10 mg/kg | IP-15 mg/kg | IP-20 mg/kg |
| --- | --- | --- | --- | --- |
| $T_{max}$ | hr | 1.50 | 2.17 | 2.67 |
| $C_{max}$ | ng/mL | 11390 | 9767 | 12733 |
| Terminal $t_{1/2}$ | hr | 4.52 | 7.59 | 6.47 |
| $AUC_{last}$ | hr*ng/mL | 114333 | 118033 | 162333 |
| $AUC_{INF}$ | hr*ng/mL | 117000 | 129100 | 175333 |

Figure 31B:
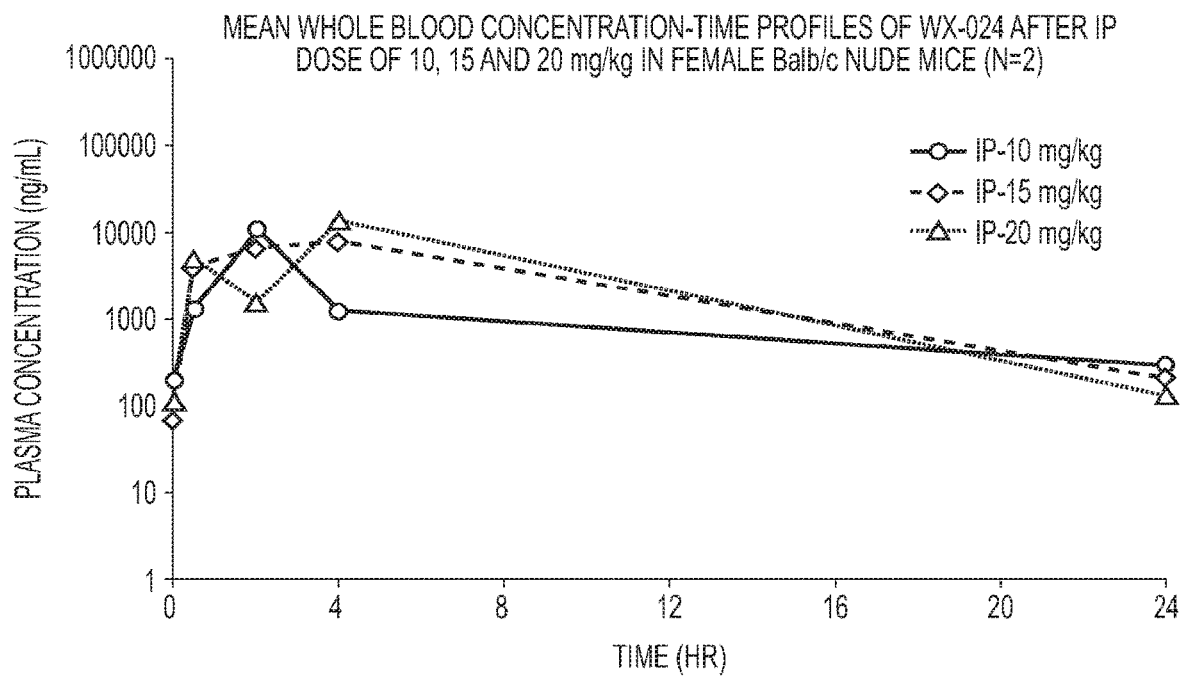

FIG. 31B shows the plasma concentration change over 24 hrs after the last dosing of the experiment at day 14. Table 6 summarizes the mean toxicokinetic parameters calculated at day 14. A toxicokinetic study using IP dosing (15 and 20 mg/kg) displayed comparable AUC values between Day 1 (118,033 and 162,333 hr*ng/mL, respectively) and Day 14 (107,420 and 159,976 hr*ng/m, respectively), indicating that drug-induced immunogenicity caused by WX-024 is unlikely.

TABLE 6

Mean toxicokinetic parameters of WX-024 after the last dosing

| TK parameters | Unit | IP-10 mg/kg | IP-15 mg/kg | IP-20 mg/kg |
| --- | --- | --- | --- | --- |
| $T_{max}$ | hr | 2.00 | 3.33 | 4.00 |
| $C_{max}$ | ng/mL | 11360 | 8748 | 13725 |
| Terminal $t_{1/2}$ | hr | 6.97 | 4.25 | 4.55 |
| $AUC_{last}$ | hr*ng/mL | 37836 | 107420 | 159976 |
| $AUC_{INF}$ | hr*ng/mL | 41091 | 108735 | 160881 |

Example 6. WX-024 Preclinical Study Summary

Overall, WX-024 showed an improved in vitro efficacy as compared other known Wnt inhibitors. For instance, when tested in a cell-based Wnt transcription assay using HCT166 cells, WX-024 exhibited an $IC_{50}$ value of about 200 nM. WX-024 also specifically inhibited Wnt transcription, with the stapled polypeptide showing $IC_{50}$ values greater than 100 μM in other transcription assays such as JAK/STAT, TGF-β, PI3K/AKT/FOXO3, and TNF-αt/JNK reporter assays.

The overall pharmacokinetic profile of WX-024 was also acceptable for producing a physiologically relevant plasma concentration in vivo. For instance, when tested at 10 mg/kg by a subcutaneous administration route, the bioavailability was about 70%. In this condition, $T_{max}$ was 8 hours and $T_{1/2}$ was 13 hours while $C_{max}$ was 7.7 μM.

The in vivo efficacy of WX-024 was confirmed in multiple animal models. For instance, the average tumor growth inhibition rate of WX-024 was about 70-80% in those animal models when administered for 3-6 weeks. When animals were chronically dosed with WX-024, no particular drug-related toxicity was observed.

Example 7. Additional Stabilized Polypeptide Comprising the Core Functional Domain WX-035, comprising the core HD2 functional domain, was constructed according to the protocols described in Example 1. Briefly, a first hydrocarbon crosslinker was generated between $Xaa_1$ and $Xaa_2$ amino acids of SEQ ID NO: 104 and a second hydrocarbon crosslinker was generated between $Xaa_3$ and $Xaa_4$ amino acids of SEQ ID NO: 104, using ruthenium-mediated ring-closing olefin metathesis as outlined in Kim 2011. Following the ring closure metathesis, the polypeptide was deprotected and released. The resulting stabilized polypeptide comprises a first hydrocarbon crosslinker of —CH₂—CH₂—CH₂—CH=CH—CH₂—CH₂—CH₂— with an S-configuration on one end and an R-configuration on the other end and a second hydrocarbon crosslinker of —$CH_2$—$CH_2$—$CH_2$—CH═CH—$CH_2$—$CH_2$—$CH_2$— with an S-configuration on both ends. The chemical structure of WX-035 is shown in FIG. 1B. The polypeptide was further purified according to the protocol described in Example 1.

Example 8. In Vitro Profile of Stabilized Polypeptide

Figure 32:
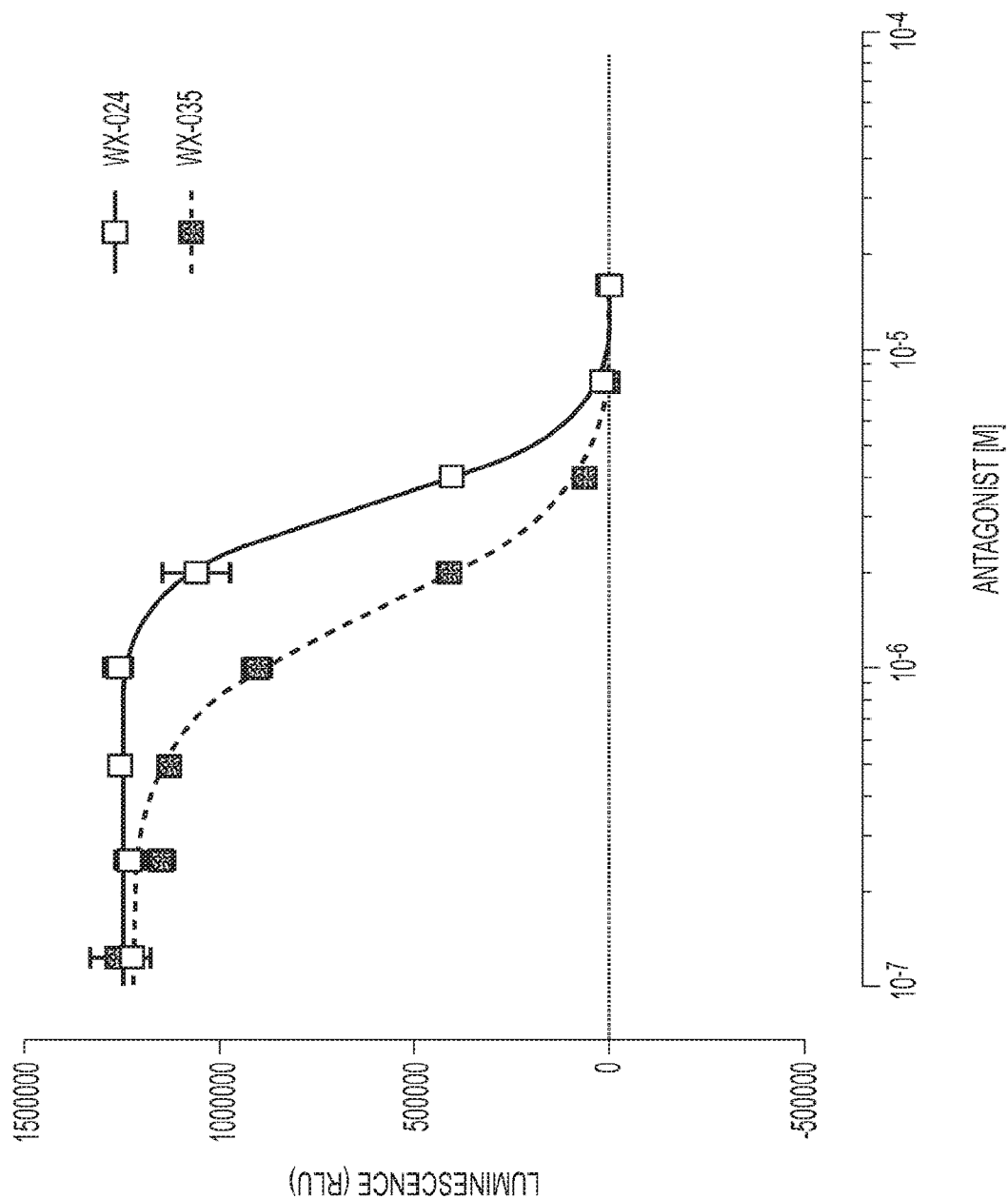
FIG. 32 shows results of a cell viability assay testing WX-024 and WX-035. Colo320DM cells were used in this experiment.

Following the procedure described in Example 2, the ability of WX-035 to inhibit cell growth was tested in a cell viability assay using Colo320DM cells. As shown in FIG. 32, WX-035 exhibited an improved $IC_{50}$ value as compared to WX-024.

Example 9. In Vivo Profile of Stabilized Polypeptide

Example 9.1. Pharmacokinetic Profile of WX-035 in Mice

Figures 33A, 33B:
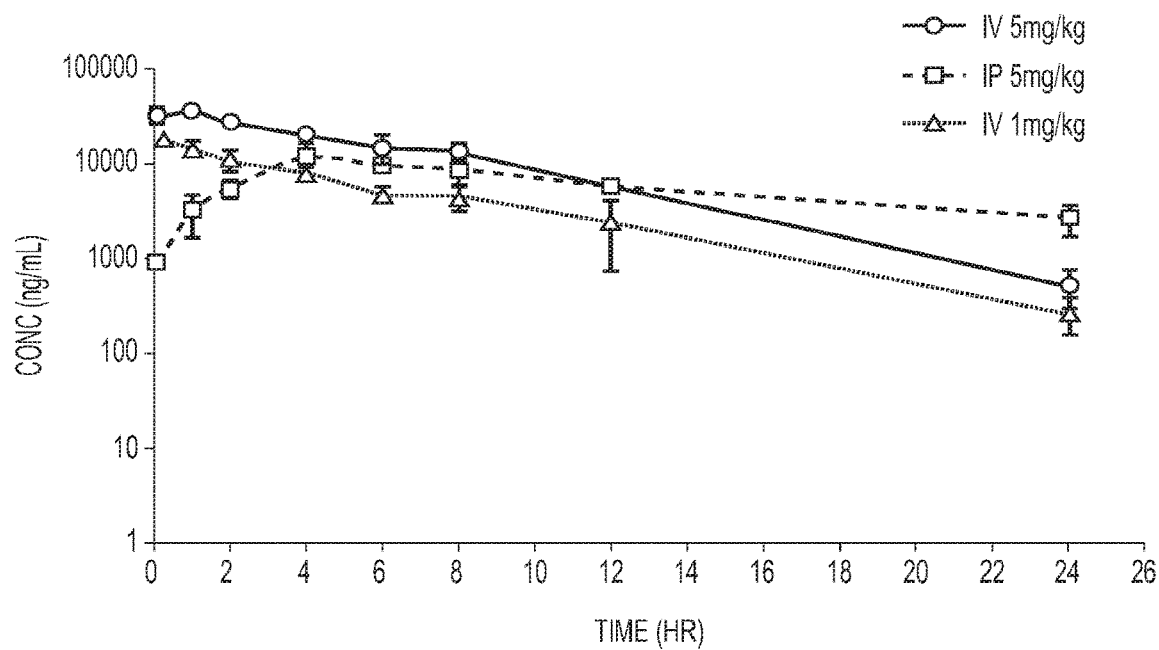
FIG. 33A and FIG. 33B show PK data for WX-035 administered to male ICR mice (an outbred strain). The mice were treated with either 1 mg/kg, or 5 mg/kg WX-035 intravenously or 5 mg/kg WX-035 intraperitoneally. Blood samples from each mouse were collected at 15 min, 1, 2, 4, 6, 8, 12, and 24 hours post administration.

The pharmacokinetic profile of WX-035 was assessed following the procedures described in Example 5.1. Briefly, the mice were administered 1 mg/kg or 5 mg/kg intravenously, or 5 mg/kg intraperitoneally. Blood samples were collected at 15 min, 1, 2, 3, 6, 8, 12, and 24 hours post administration. FIG. 33A shows the plasma concentration of WX-035 in male ICR mice. The maximum observed concentration ($C_{max}$), terminal half-life ($T_{1/2}$), total body clearance (CL), volume of distribution ($V_z$), area under the curve from the time of dosing to the last measurable concentration ($AUC_{0-t}$), area under the curve from the time of dosing extrapolated to infinity ($AUC_{0-inf}$), and bioavailability were determined and are summarized in FIG. 33B. Of note, the half-life measurements for WX-035 indicate improved stability in the blood with $T_{1/2}$ values of greater than 4 hours.

Figures 34A, 34B:
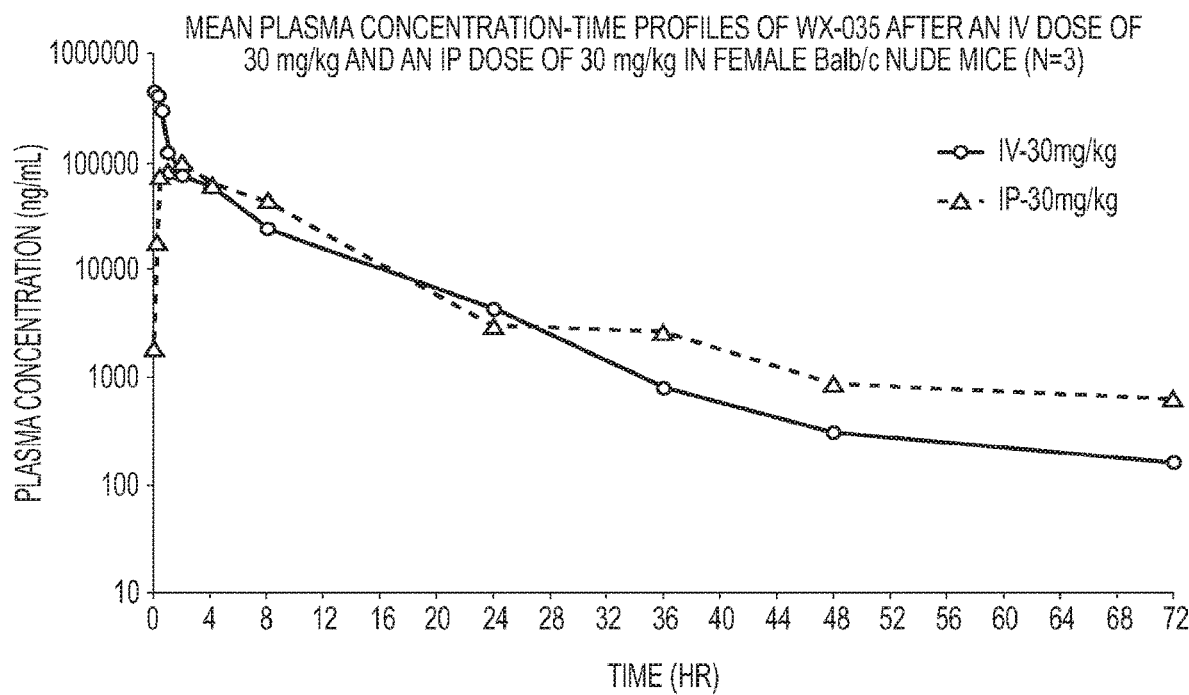
FIG. 34A and FIG. 34B show PK data for WX-035 administered to female balb/c mice (n=3). The mice were either intravenously or intraperitoneally administered with 30 mg/kg WX-035. Blood samples from each mouse were collected at 5 min, 15 min, 30 min, 1, 2, 4, 6, 8, 12, 24, 36, 48, and 72 hours post administration.

As done with WX-024, the pharmacokinetic profile of WX-035 was again analyzed in female balb/c mice (n=3 per treatment). Two different administration routes, intravenous or intraperitoneal, were compared using 30 mg/kg WX-035. As shown in FIG. 34A, the pharmacokinetic profile of WX-035 was similar to that observed with male ICR mice. The mean pharmacokinetic parameters were calculated following the procedures in Example 5.1 and are summarized in FIG. 34B. As observed with male ICR mice, the half-life of WX-035 in this experiment was more than 9 hours.

These data are consistent with the hypothesis that stabilization of BCL9 peptides with multiple crosslinkers may improve PK parameters.

Example 9.2. Efficacy of WX-035 in a Mouse Syngeneic Model of Cancer

The in vivo efficacy of WX-035 in treating a cancer was assessed in a syngeneic mouse model, following the procedures described in Example 5.3. Trametinib, a known MEK inhibitor, was used as a comparison. Briefly, balb/c mice were inoculated with CT26 and treatment started when tumor volume reached to about 100 $mm^3$. The mice were then divided into three groups and began administered with a vehicle, 40 mg/kg WX-035, or 1 mg/kg trametinib for 7 consecutive days.

Figure 35A:
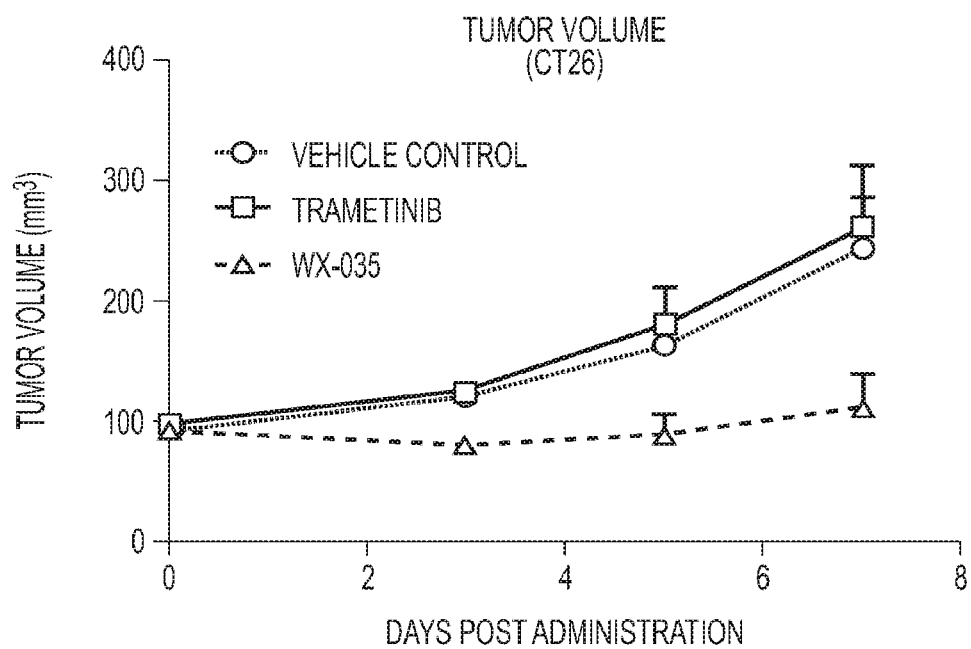
FIG. 35A shows the effect of WX-035 on tumor growth inhibition tested in male balb/c syngeneic animal models. The mice were inoculated with CT26 cells (1×10$^3$). When the average tumor volume reached 100 mm$^3$, the mice were divided into three groups and treated intraperitoneally with a vehicle, 20 mg/kg WX-035, or 1 mg/kg trametinib for 7 consecutive days (n=7).
Figure 35B:
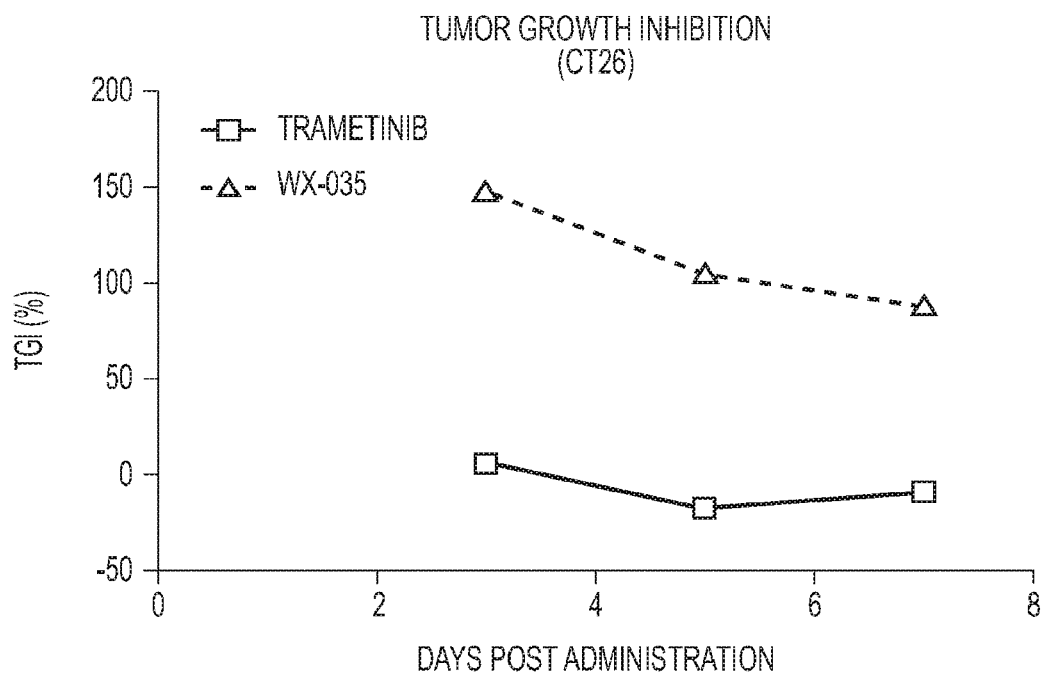
FIG. 35B compares the tumor growth inhibition by WX-035 and by trametinib in this experiment. At day 7, the average tumor growth inhibition by WX-035 was 88.44%.

As shown in FIGS. 35A and 35B, WX-035 was capable of robustly suppressing tumor growth as compared to trametinib and vehicle treatments. The average tumor growth inhibition rate of WX-035 was 88.44% at the end of the study.

Example 9.3. Effect of WX-035 in T Cell Activation

Figure 36A:
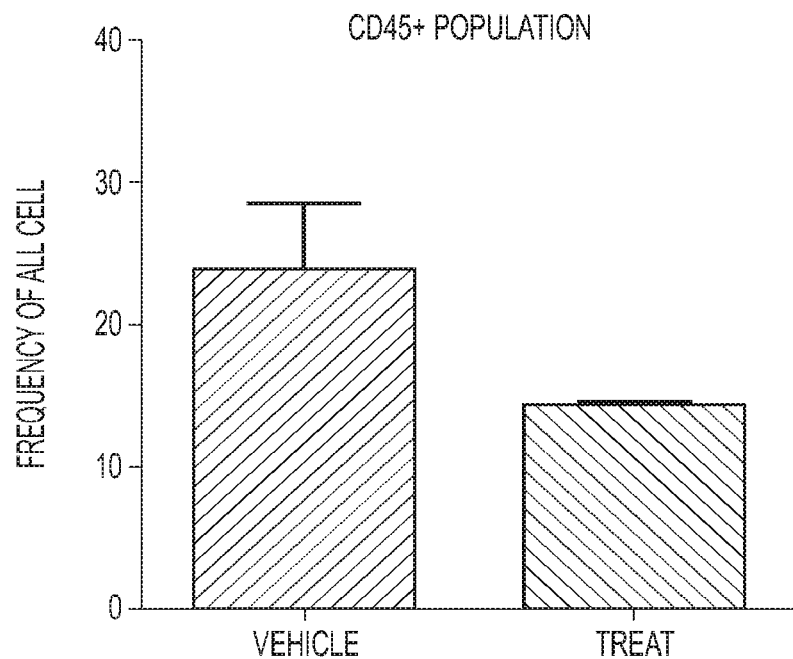
FIGS. 36A, 36B, 36C, and 36D show the in vivo effect of WX-035 on T reg cells and other types of T cell populations. At the conclusion of the experiment depicted in FIG. 35, tumor samples were collected from a vehicle treated group and a WX-035 treated group.
Figure 36B:
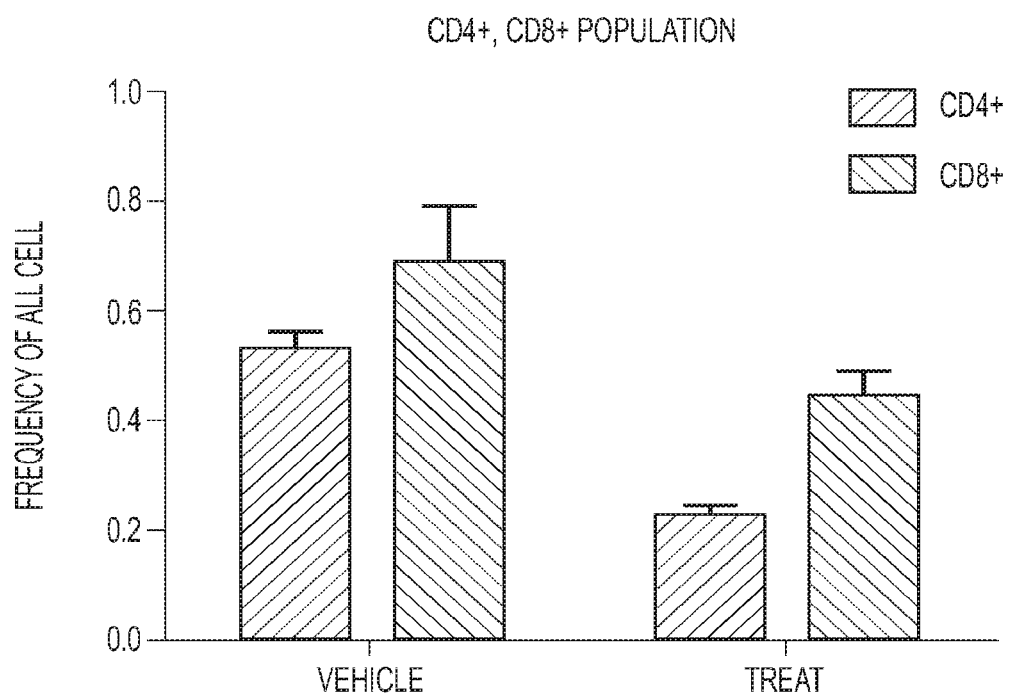
Figure 36C:
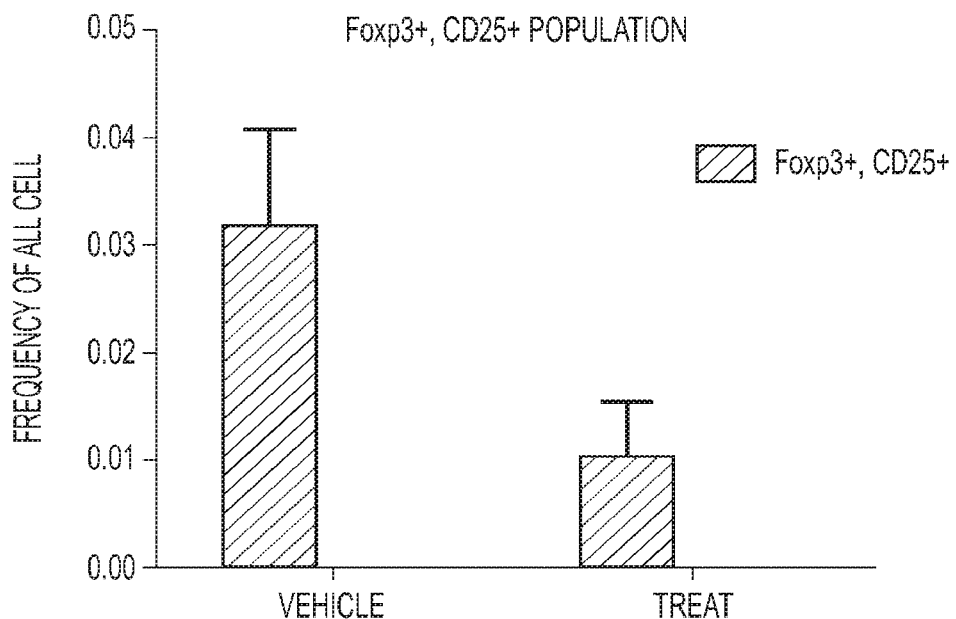
Figure 36D:
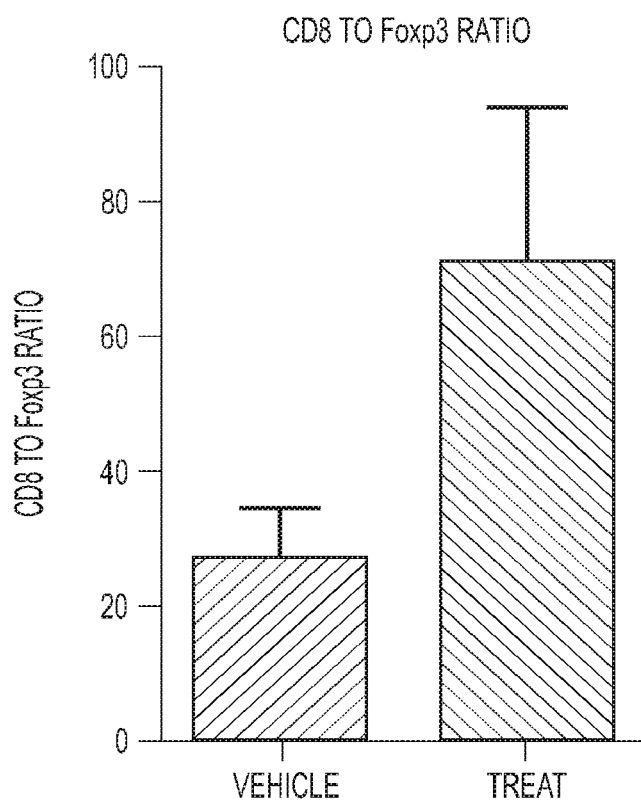

At the end of the study described in Example 9.2, a tumor sample from each mouse was collected to assess the effect of WX-035 in modulating T cell activation. The FACS analysis of each tumor sample was performed following the procedure described in Example 5. A shown in FIG. 36A, treatment with WX-035 reduced the total amount of $CD45^+$ cells. Because the total amount of haematolymphoid cells was reduced, the total amount of $CD4^+$ or $CD8^+$ T cells was also reduced (FIG. 36B). Likewise, $Foxp3^+CD25^+$ T cells were reduced by WX-035 treatment (FIG. 36C). However, as shown in FIG. 36D, WX-035 increased the ratio between cytotoxic T cells ($CD8^+$ T cells) and $Foxp3^+$ T cells (regulatory T cells) as compared to the vehicle treatment. Therefore, these data suggest that WX-035 is capable of reducing regulatory T cells in a syngeneic animal model. Furthermore, by increasing the ratio of cytotoxic T cells over regulatory T cells, WX-035 may induce a microenvironment that favors an immune reaction beneficial for tumor treatment. Of note, the samples collected from this experiment were also assessed for LGR5 expression. As shown in FIG. 36E, WX-035 reduced the expression of LGR5 in intestine samples collected from this experiment, confirming that WX-035 is capable of inhibiting Wnt/β-catenin signaling in vivo.

Example 9.4. Toxicity Effect of WX-035

Figure 37:
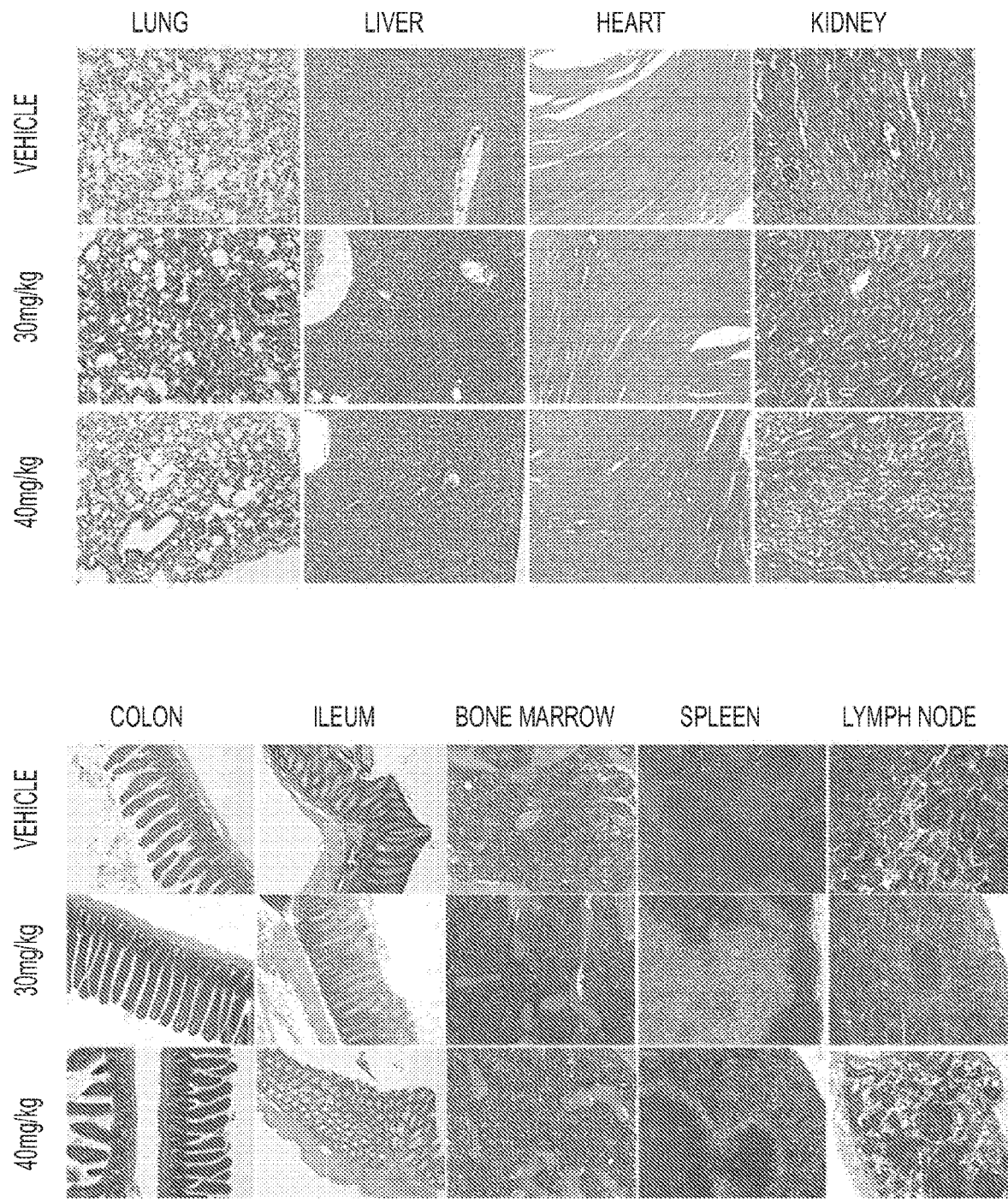
FIG. 37 depicts H&E staining of major organs harvested from female 6 weeks of age balb/c nude mice intravenously treated with vehicle, 30 mg/kg, or 40 mg/kg WX-035 for 7 consecutive days (scale bar: 100 μm).

To assess the toxicity effect of WX-035, balb/c nude mice were administered with a vehicle, or 30 mg/kg, or 40 mg/kg WX-035, following the procedure described in Example 5.6. At the end of the study, the mice were sacrificed and major organs were harvested for H&E staining. As shown in FIG. 37, treatment with WX-035 did not cause any significant abnormality to major organs, indicating that WX-035 did not produce a significant toxic effect.

Example 10. Additional Stabilized Polypeptides

Additional polypeptides derived from the HD2 domain of human BCL9 protein were also constructed and the sequences of those polypeptides are shown in Table 7 below. The polypeptides were constructed and purified according to the protocol described in Example 1. WX-029 comprises a 8-carbon hydrocarbon crosslinker between amino acids $Xaa_1$ and $Xaa_2$. WX-037, WX-038, and WX-039 each comprises two hydrocarbon crosslinkers. In each polypeptide, a first 8-carbon crosslinker was generated between $Xaa_1$ and $Xaa_2$ amino acids of its respective sequence and a second 8-carbon crosslinker was generated between $Xaa_3$ and $Xaa_4$ amino acids of its respective sequence. WX-037 is a polypeptide derived from the HD2 domain of human BCL9 protein, wherein hydrophobic leucine (L) residues have been mutated to charged aspartic acid (D). WX-040 comprises a 11-carbon crosslinker between amino acids $Xaa_1$ and $Xaa_2$.

TABLE 7

Additional stabilized polypeptides derived from the HD domain of BCL9 protein

| SEQ ID NO: | Amino Acid Sequence (WX No.) | Corresponding position within BCL9 | N-terminus Modification | C-terminus Modification |
|---|---|---|---|---|
| 97 | LQTLRXaa$_1$IQRXaa$_2$L (WX-029) | 363-373 | Ac | 2-Nal-β-Ala-β-Ala-GRKKRRQRRRPQ |
| 98 | Xaa$_1$LQXaa$_2$LRXaa$_3$IQRXaa$_4$L (WX-036) | 362-373 | Ac | 2-Nal-β-Ala-β-Ala-GRKKRRQRRRPQ |
| 99 | Xaa$_1$DQXaa$_2$DRXaa$_3$DQRXaa$_4$DH (WX-037) | 362-374 | Ac | β-Ala-β-Ala-NH$_2$ |
| 100 | Xaa$_1$LEXaa$_2$LRXaa$_3$IERXaa$_4$L (WX-038) | 362-373 | Ac | 2-Nal-β-Ala-β-Ala-NH$_2$ |
| 101 | RXaa$_1$LQXaa$_2$LRXaa$_3$IQRXaa$_4$L (WX-039) | 361-373 | Ac | 2-Nal-β-Ala-β-Ala-NH$_2$ |
| 102 | LQXaa$_1$LRDIQRXaa$_2$L (WX-040) | 363-373 | Ac | 2-Nal-β-Ala-β-Ala-NH$_2$ |

Example 11. In Vitro Profile of Stabilized Polypeptides

One of the stabilized polypeptides generated in Example 10 was tested in a cell viability assay and compared against WX-035. WX-037 was selected for this comparison study. The cell viability assay was performed with CT26.WT cells (ATCC), following the procedures described in Example 2. Briefly, 4000 cells per well of each plate were seeded with 50 μL opti-MEM medium. Each polypeptide, WX-035 or WX-037, was diluted with 2% FBS containing opti-MEM medium using 1 μL of 200× concentrated polypeptide in 99 μL of the medium. Each stock solution was diluted for testing a wide range of concentrations. 50 μL of 2× concentrated polypeptide was added to each well of the plate. Three days after the polypeptide addition, the viability of cells was measured using CellTiterGlo assay, according to the manufacturer's protocol.

As shown in FIGS. 38A and 38B, WX-035 more effectively inhibited cell viability in this condition (Ab IC$_{50}$=1.858 μM) than WX-037 (Ab IC$_{50}$>32 μM). The data indicate that hydrophobic leucine residues further increase the efficacy of a polypeptide derived from the HD2 domain of human BCL9 protein. FIG. 38C summarizes the in vitro profiles of each polypeptide.

Example 12. In Vivo Profile of Stabilized Polypeptides

Example 12.1. Pharmacokinetic Profiles of Stabilized Polypeptides in Mice

Figures 39A, 39B:
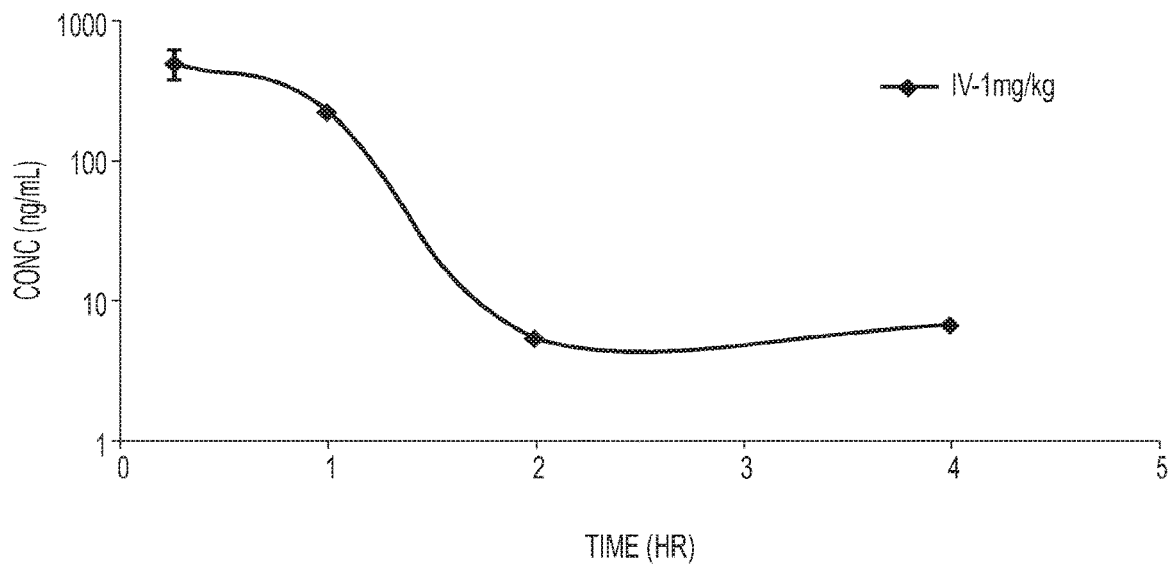
FIG. 39A and FIG. 39B show PK data for WX-029 administered to female balb/c nude mice (N=2). 1 mg/kg of WX-029 was administered to each mouse intravenously.
Figures 40A, 40B:
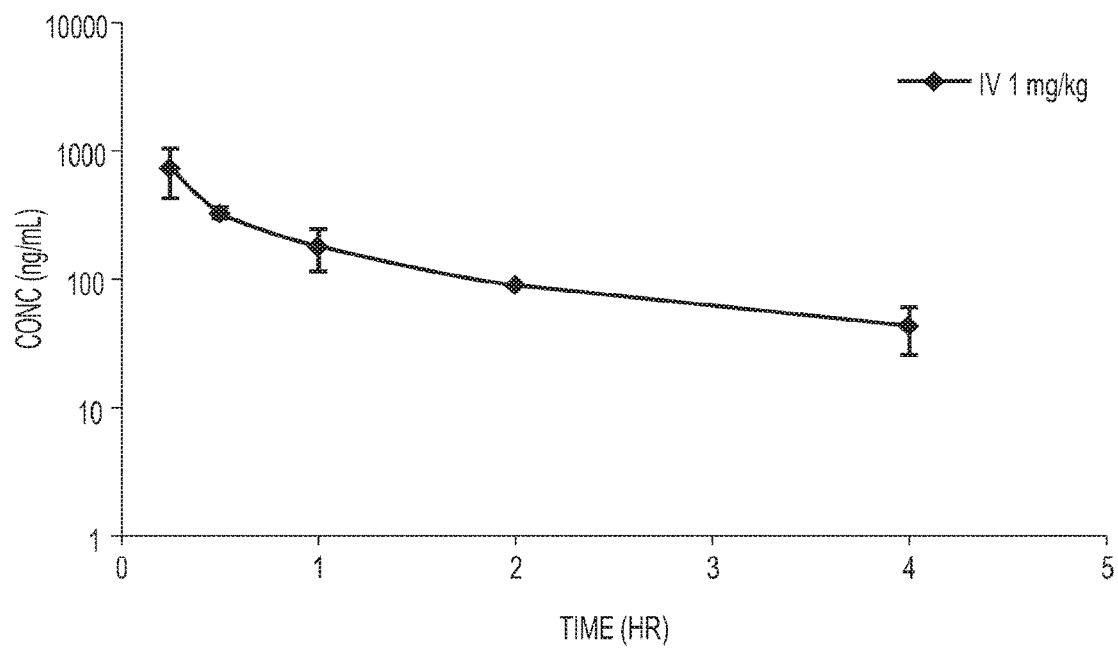
FIG. 40A and FIG. 40B show PK data for WX-036 administered to female balb/c nude mice (N=2). 1 mg/kg WX-036 was administered to each mouse intravenously.

The pharmacokinetic profiles of the four additional polypeptides constructed in Example 10 were assessed following the procedures described in Example 5.1. WX-029 and WX-036 were administered 1 mg/kg intravenously to female balb/c nude mice. Blood samples were collected at 15 min, 1, 2, and 4 hours post administration. FIG. 39A and FIG. 39B summarize the plasma concentration and the pharmacokinetic profiles calculated for WX-029. FIG. 40A and FIG. 40B summarize the plasma concentration and the pharmacokinetic profiles calculated for WX-036.

Figure 41A:
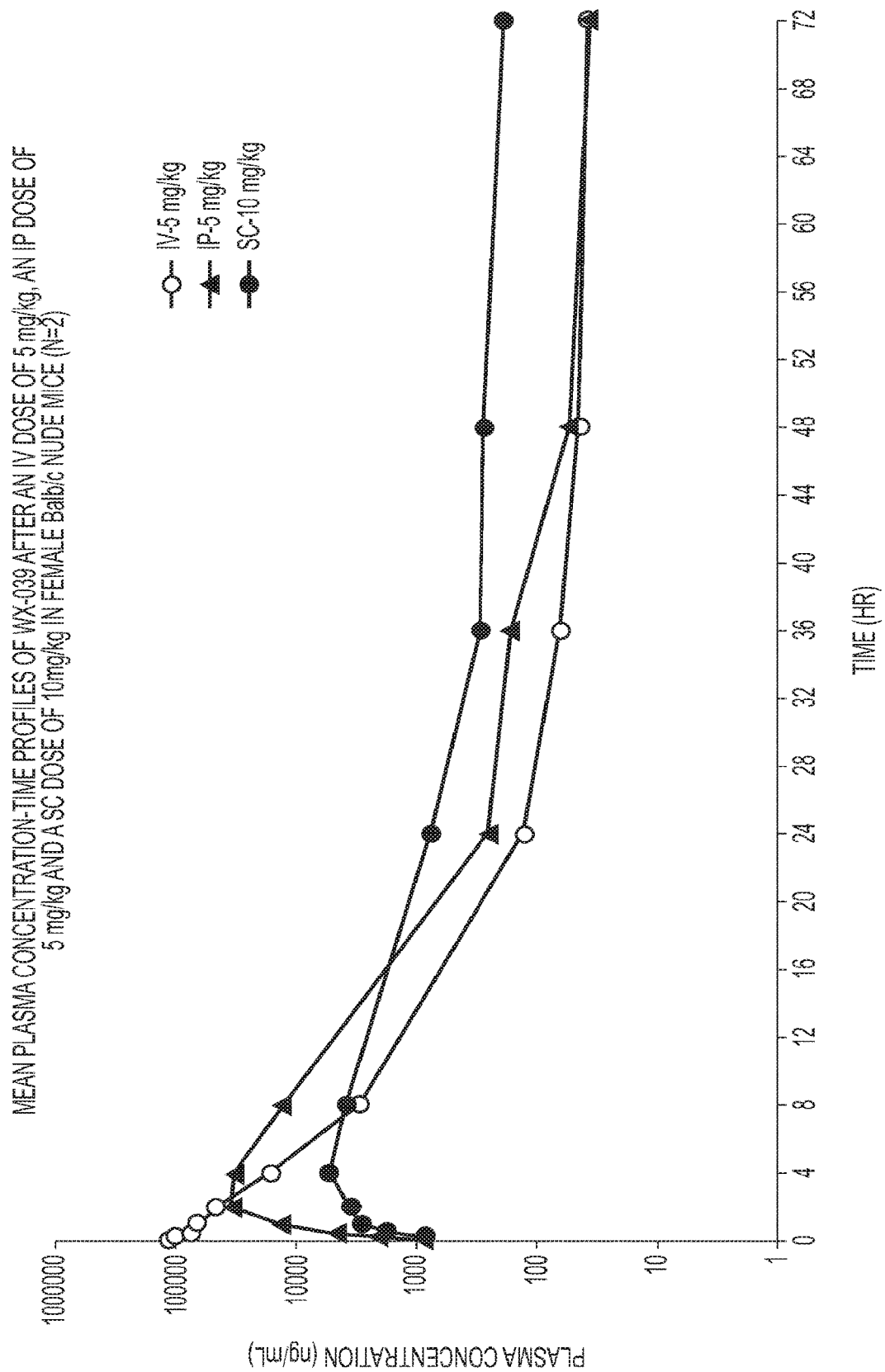
Figure 42A:
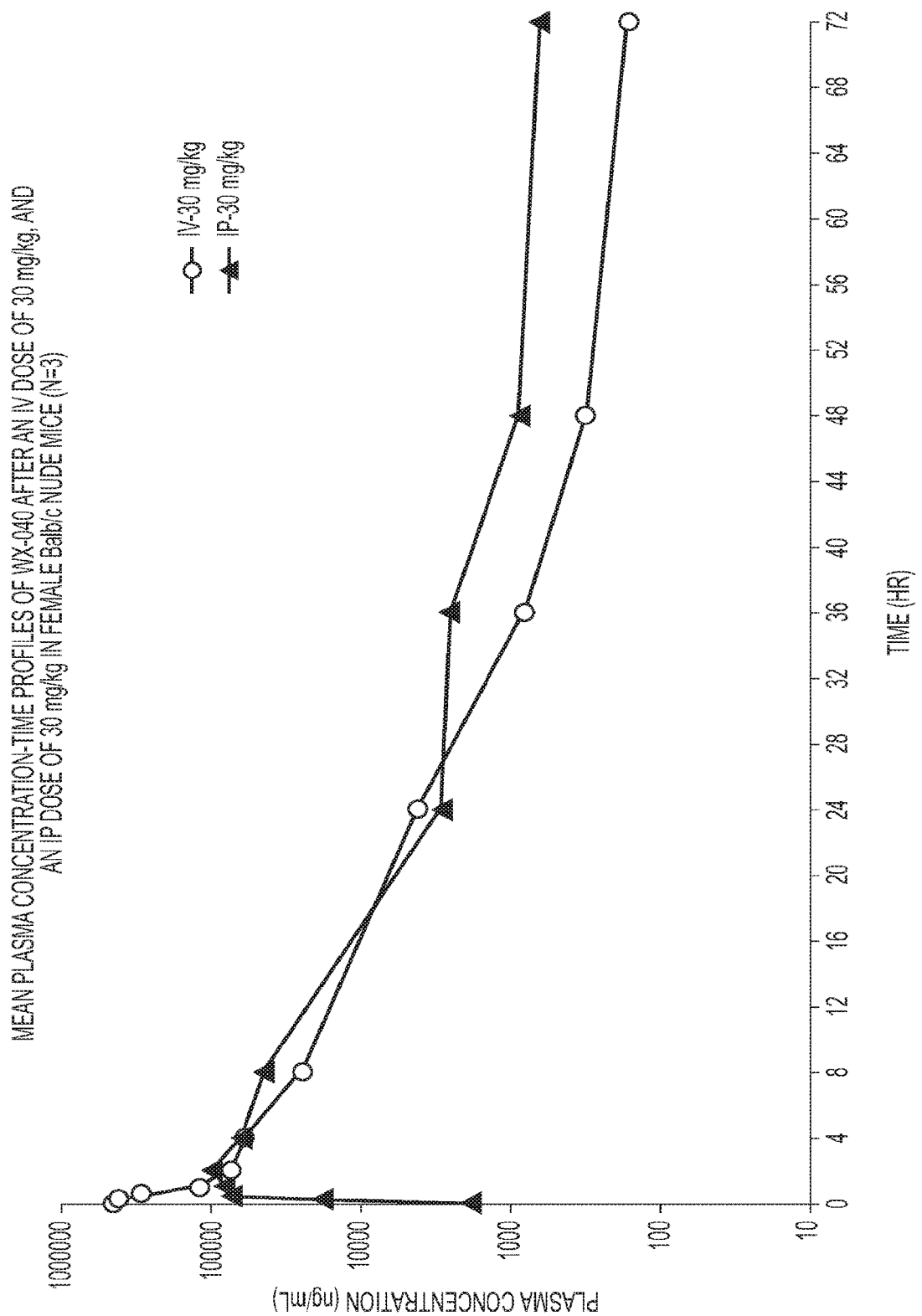

Similarly, WX-039 and WX-040 were also tested in female balb/c nude mice and assessed for their pharmacokinetic profiles. WX-039 was administered at 5 mg/kg intravenously, 5 mg/kg intraperitoneally, or 10 mg/kg subcutaneously. WX-040 was administered at 30 mg/kg intravenously or 30 mg/kg intraperitoneally. Blood samples were collected at 15 min, 1, 2, 4, 8, 24, 36, 48, and 72 hours post administration. FIG. 41A and FIG. 41B summarize the plasma concentration and the pharmacokinetic profiles calculated for WX-039. FIG. 42A and FIG. 42B summarize the plasma concentration and the pharmacokinetic profiles calculated for WX-040. Of note, the half-life of WX-039 calculated in this experiment was about 52 hours, when administered subcutaneously.

Example 12.2. Efficacy of WX-039 in a Mouse Syngeneic Model of Cancer (B16F10)

Figure 43A:
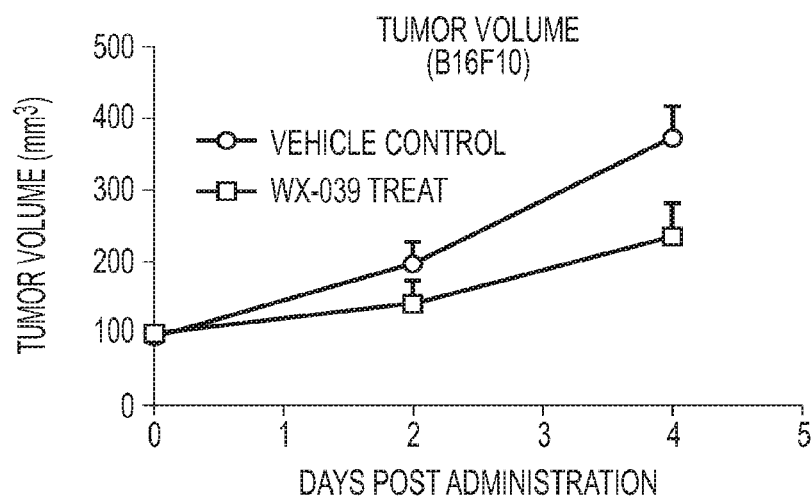
FIG. 43A shows the effect of WX-039 on tumor growth inhibition tested in 5 weeks old female C57BL/6 mice inoculated with B16F10 cells (N=3). The tumor growth inhibition rate assessed during the experiment is shown in FIG. 43B.
Figure 43B:
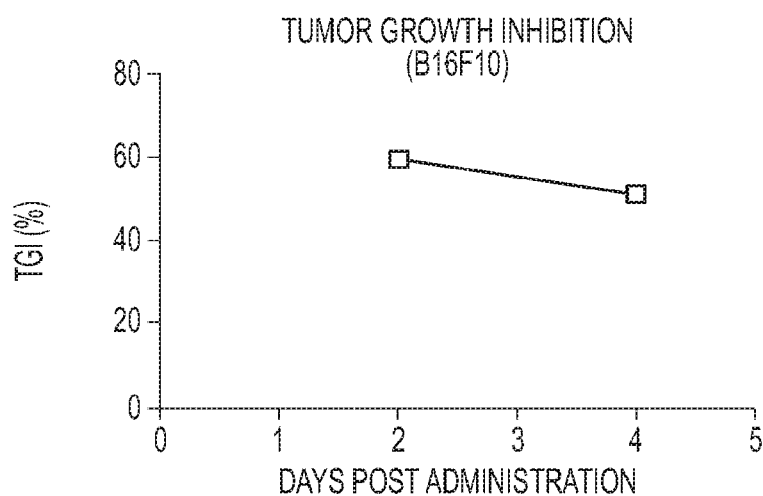
FIG. 43C shows the body weight change during the experiment depicted in FIG. 43A.
Figure 43C:
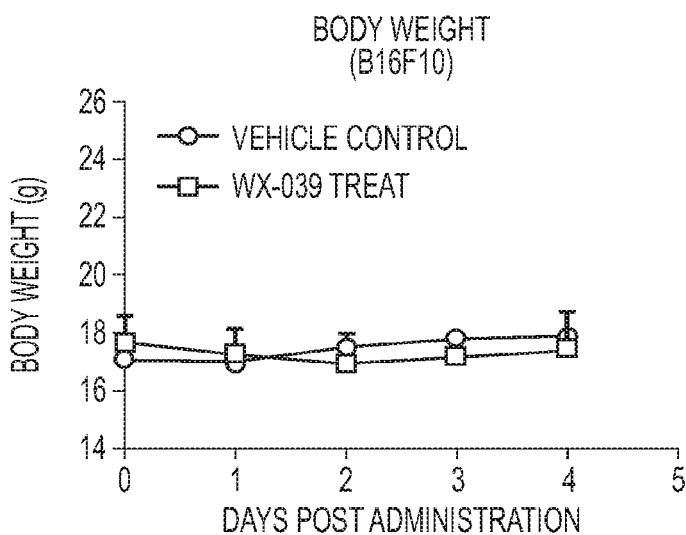

The ability of WX-039 to suppress tumor growth was assessed in the animal model described in Example 5.4. Briefly, C57BL/6 mice were inoculated with B16 cells. Female C57BL/6 mice aged 5 weeks were inoculated with B16F10 cells (2×10$^5$ cells in 0.05 ml per mouse) in the right flank. When the average tumor size of the mice reached 100 mm$^3$, the mice were divided into two groups (N=3). The first group was administered 60 mg/kg WX-039 while the second group was treated with a vehicle. The treatment was intraperitoneally administered daily for 12 consecutive days. As shown in FIG. 43A, WX-039 reduced tumor growth as compared to vehicle treatment, confirming the in vivo efficacy of WX-039. The tumor growth inhibition rate assessed during the experiment is shown in FIG. 43B. As shown in FIG. 43C, there was no substantial body weight change caused by WX-039 during the experiment, indicating that WX-039 has tolerable toxicity.

INCORPORATION BY REFERENCE

The contents of all cited references (including literature references, patents, patent applications, and websites) that may be cited throughout this application are hereby expressly incorporated by reference in their entirety for any purpose, as are the references cited therein. To the extent those references contradict or are inconsistent with any statements in this application, the text of the application will control. The disclosure will employ, unless otherwise indicated, conventional techniques of immunology, molecular biology and cell biology, and pathology, which are well known in the art.

EQUIVALENTS

The invention may be embodied in other specific forms without departing from the spirit or essential characteristics thereof. The foregoing embodiments are therefore to be considered in all respects illustrative rather than limiting of the inventions described herein. Scope of the invention is thus indicated by the appended claims rather than by the foregoing description, and all changes that come within the meaning and range of equivalency of the claims are therefore intended to be embraced herein.

The invention claimed is:

1. A method of inhibiting binding of BCL9 to β-catenin in a subject, the method comprising administering to the subject in need thereof a peptide having a length of 7-14 amino acids, the peptide comprising a hydrocarbon crosslinker and comprising any sequence selected from:

$$\text{LQTLRXaa}_1\text{IQRXaa}_2\text{L;} \quad \text{(SEQ ID NO: 79)}$$
and
$$\text{Xaa}_1\text{LQXaa}_2\text{LRXaa}_3\text{IQRXaa}_4\text{L,} \quad \text{(SEQ ID NO: 82)}$$

wherein:
a) $Xaa_1$, $Xaa_2$, $Xaa_3$, and $Xaa_4$ are each alanine;
b) a first hydrocarbon crosslinker is present between $Xaa_1$ and $Xaa_2$; and/or
c) a second hydrocarbon crosslinker is present between $Xaa_3$ and $Xaa_4$,
or a pharmaceutical composition thereof.

2. The method of claim 1, wherein the hydrocarbon crosslinker is selected from —$CH_2$—$CH_2$—$CH_2$—$CH$=$CH$—$CH_2$—$CH_2$—$CH_2$— and —$CH_2$—$CH_2$—$CH_2$—$CH_2$—$CH_2$—$CH_2$—$CH$=$CH$—$CH_2$—$CH_2$—$CH_2$—.

3. The method of claim 1, wherein the hydrocarbon crosslinker has an S-configuration on at least one end, an R-configuration on at least one end, or has an S-configuration on one end and an R-configuration on the other end.

4. The method of claim 1, wherein:
a) the peptide consists of an amino acid sequence of LQTLRXaa$_1$IQRXaa$_2$L (SEQ ID NO: 79);
b) $Xaa_1$ and $Xaa_2$ are each alanine;
c) a hydrocarbon crosslinker is present between $Xaa_1$ and $Xaa_2$;
d) the hydrocarbon crosslinker is —$CH_2$—$CH_2$—$CH_2$—$CH$=$CH$—$CH_2$—$CH_2$—$CH_2$—; and/or
e) the hydrocarbon crosslinker has an S-configuration at both ends.

5. The method of claim 1, wherein:
a) the peptide consists of an amino acid sequence of $Xaa_1$LQXaa$_2$LRXaa$_3$IQRXaa$_4$L (SEQ ID NO: 82);
b) $Xaa_1$, $Xaa_2$, $Xaa_3$, and $Xaa_4$ are each alanine;
c) a first hydrocarbon crosslinker is present between $Xaa_1$ and $Xaa_2$;
d) a second hydrocarbon crosslinker is present between $Xaa_3$ and $Xaa_4$;
e) the first hydrocarbon crosslinker is —$CH_2$—$CH_2$—$CH_2$—$CH$=$CH$—$CH_2$—$CH_2$—$CH_2$—;
f) the second hydrocarbon crosslinker is —$CH_2$—$CH_2$—$CH_2$—$CH$=$CH$—$CH_2$—$CH_2$—$CH_2$—;
g) the first hydrocarbon crosslinker has an S-configuration at one end and an R-configuration at the other end; and/or h) the second hydrocarbon crosslinker has an S-configuration at both ends.

6. The method of claim 1, wherein the N-terminus is optionally modified with an acetyl group; and C-terminus of the peptide is modified with $NH_2$, two units of β-alanine, 2-Naphthylalanine, or 2-Naphthylalanine linked to two units of β-alanine, wherein the carboxyl group of the C-terminus modification is further modified with $NH_2$.

7. A method of inhibiting canonical Wnt/β-catenin signaling in a subject, the method comprising administering to the subject in need thereof a peptide comprising a hydrocarbon crosslinker and comprising any sequence selected from:

LQTLRXaa$_1$IQRXaa$_2$L; (SEQ ID NO: 79)
and

Xaa$_1$LQXaa$_2$LRXaa$_3$IQRXaa$_4$L, (SEQ ID NO: 82)

wherein:
a) Xaa$_1$, Xaa$_2$, Xaa$_3$, and Xaa$_4$ are each alanine;
b) a first hydrocarbon crosslinker is present between Xaa$_1$ and Xaa$_2$; and/or
c) a second hydrocarbon crosslinker is present between Xaa$_3$ and Xaa$_4$, or a pharmaceutical composition thereof.

8. The method of claim 7, wherein the hydrocarbon crosslinker is selected from —$CH_2$—$CH_2$—$CH_2$—CH=CH—$CH_2$—$CH_2$—$CH_2$— and —$CH_2$—$CH_2$—$CH_2$—$CH_2$—$CH_2$—$CH_2$—CH=CH—$CH_2$—$CH_2$—$CH_2$—.

9. The method of claim 7, wherein the hydrocarbon crosslinker has an S-configuration on at least one end, an R-configuration on at least one end, or has an S-configuration on one end and an R-configuration on the other end.

10. The method of claim 7, wherein:
a) the peptide consists of an amino acid sequence of LQTLRXaa$_1$IQRXaa$_2$L (SEQ ID NO: 79);
b) Xaa$_1$ and Xaa$_2$ are each alanine;
c) a hydrocarbon crosslinker is present between Xaa$_1$ and Xaa$_2$;
d) the hydrocarbon crosslinker is —$CH_2$—$CH_2$—$CH_2$—CH=CH—$CH_2$—$CH_2$—$CH_2$—; and/or
e) the hydrocarbon crosslinker has an S-configuration at both ends.

11. The method of claim 7, wherein:
a) the peptide consists of an amino acid sequence of Xaa$_1$LQXaa$_2$LRXaa$_3$IQRXaa$_4$L (SEQ ID NO: 82);
b) Xaa$_1$, Xaa$_2$, Xaa$_3$, and Xaa$_4$ are each alanine;
c) a first hydrocarbon crosslinker is present between Xaa$_1$ and Xaa$_2$;
d) a second hydrocarbon crosslinker is present between Xaa$_3$ and Xaa$_4$;
e) the first hydrocarbon crosslinker is —$CH_2$—$CH_2$—$CH_2$—CH=CH—$CH_2$—$CH_2$—$CH_2$—;
f) the second hydrocarbon crosslinker is —$CH_2$—$CH_2$—$CH_2$—CH=CH—$CH_2$—$CH_2$—$CH_2$—;
g) the first hydrocarbon crosslinker has an S-configuration at one end and an R-configuration at the other end; and/or
h) the second hydrocarbon crosslinker has an S-configuration at both ends.

12. The method of claim 7, wherein the N-terminus is optionally modified with an acetyl group; and C-terminus of the peptide is modified with $NH_2$, two units of β-alanine, 2-Naphthylalanine, or 2-Naphthylalanine linked to two units of β-alanine, wherein the carboxyl group of the C-terminus modification is further modified with $NH_2$.

13. A method of treating a cancer by inhibiting binding of BCL9 to β-catenin in the cancer, wherein the cancer is selected from familial adenomatous polyposis (FAP), ocular cancer, rectal cancer, colon cancer, colorectal cancer, cervical cancer, prostate cancer, breast cancer, bladder cancer, oral cancer, benign and malignant tumors, stomach cancer, liver cancer, pancreatic cancer, lung cancer, corpus uteri, ovarian cancer, prostate cancer, testicular cancer, renal cancer, brain/CNS cancer, throat cancer, multiple myeloma, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, gastric cancer, ovarian cancer, hepatocellular carcinoma, and lymphangiogenesis in a subject, the method comprising administering to the subject in need thereof a peptide having a length of 7-14 amino acids, the peptide comprising a hydrocarbon crosslinker and comprising any sequence selected from:

LQTLRXaa$_1$IQRXaa$_2$L; (SEQ ID NO: 79)
and

Xaa$_1$LQXaa$_2$LRXaa$_3$IQRXaa$_4$L, (SEQ ID NO: 82)

wherein:
a) Xaa$_1$, Xaa$_2$, Xaa$_3$, and Xaa$_4$ are each alanine;
b) a first hydrocarbon crosslinker is present between Xaa$_1$ and Xaa$_2$; and/or
c) a second hydrocarbon crosslinker is present between Xaa$_3$ and Xaa$_4$,
or a pharmaceutical composition thereof.

14. The method of claim 13, further comprising administering to the subject at least one additional agent selected from: a checkpoint inhibitor, an EGFR inhibitor, a VEGF inhibitor, a chemotherapeutic agent, and a VEGFR inhibitor.

15. The method of claim 14, wherein the checkpoint inhibitor is an anti-PD-1 antibody, an anti-PD-L1 antibody, or an anti-CTLA4 antibody.

16. The method of claim 13, further comprising measuring at least one biomarker to monitor treatment efficacy and/or to select a subject for treatment, wherein the biomarker is selected from: BCL9, CD44, Axin2, cMyc, LGR5, VEGFA, Sox2, Oct4, Nanog, and active β-catenin.

17. The method of claim 13, wherein the hydrocarbon crosslinker is selected from —$CH_2$—$CH_2$—$CH_2$—CH=CH—$CH_2$—$CH_2$—$CH_2$— and —$CH_2$—$CH_2$—$CH_2$—$CH_2$—$CH_2$—$CH_2$—CH=CH—$CH_2$—$CH_2$—$CH_2$—.

18. The method of claim 13, wherein the hydrocarbon crosslinker has an S-configuration on at least one end, an R-configuration on at least one end, or has an S-configuration on one end and an R-configuration on the other end.

19. The method of claim 13, wherein:
a) the peptide consists of an amino acid sequence of LQTLRXaa$_1$IQRXaa$_2$L (SEQ ID NO: 79);
b) Xaa$_1$ and Xaa$_2$ are each alanine;
c) a hydrocarbon crosslinker is present between Xaa$_1$ and Xaa$_2$;

d) the hydrocarbon crosslinker is —CH$_2$—CH$_2$—CH$_2$—CH=CH—CH$_2$—CH$_2$—CH$_2$—; and/or e) the hydrocarbon crosslinker has an S-configuration at both ends.

20. The method of claim 13, wherein:

a) the peptide consists of an amino acid sequence of Xaa$_1$LQXaa$_2$LRXaa$_3$IQRXaa$_4$L (SEQ ID NO: 82);

b) Xaa$_1$, Xaa$_2$, Xaa$_3$, and Xaa$_4$ are each alanine;

c) a first hydrocarbon crosslinker is present between Xaa$_1$ and Xaa$_2$;

d) a second hydrocarbon crosslinker is present between Xaa$_3$ and Xaa$_4$;

e) the first hydrocarbon crosslinker is —CH$_2$—CH$_2$—CH$_2$—CH=CH—CH$_2$—CH$_2$—CH$_2$—;

f) the second hydrocarbon crosslinker is —CH$_2$—CH$_2$—CH$_2$—CH=CH—CH$_2$—CH$_2$—CH$_2$—;

g) the first hydrocarbon crosslinker has an S-configuration at one end and an R-configuration at the other end; and/or h) the second hydrocarbon crosslinker has an S-configuration at both ends.

* * * * *